(12) United States Patent
Albaugh et al.

(10) Patent No.: US 8,202,876 B2
(45) Date of Patent: Jun. 19, 2012

(54) COMPOUNDS AND COMPOSITIONS AS PROTEIN KINASE INHIBITORS

(75) Inventors: Pamela Albaugh, Carlsbad, CA (US); Gregory B. Chopiuk, San Diego, CA (US); Qiang Ding, San Diego, CA (US); Shenlin Huang, San Diego, CA (US); Zuosheng Liu, San Diego, CA (US); Shifeng Pan, San Diego, CA (US); Pingda Ren, San Diego, CA (US); Xia Wang, San Diego, CA (US); Xing Wang, San Diego, CA (US); Yongping Xie, San Diego, CA (US); Chengzhi Zhang, San Diego, CA (US); Qiong Zhang, Union City, CA (US); Guobao Zhang, San Diego, CA (US); Daniel Poon, Oakland, CA (US); Paul Renhowe, Danville, CA (US); Martin Sendzik, San Mateo, CA (US)

(73) Assignees: IRM LLC, Hamilton (BM); Novartis AG, Basel (CH)

( * ) Notice: Subject to any disclaimer, the term of this patent is extended or adjusted under 35 U.S.C. 154(b) by 248 days.

(21) Appl. No.: 12/444,129

(22) PCT Filed: Sep. 24, 2007

(86) PCT No.: PCT/US2007/079340
§ 371 (c)(1),
(2), (4) Date: Jun. 3, 2009

(87) PCT Pub. No.: WO2008/042639
PCT Pub. Date: Apr. 10, 2008

(65) Prior Publication Data
US 2010/0029605 A1    Feb. 4, 2010

Related U.S. Application Data

(60) Provisional application No. 60/827,873, filed on Oct. 2, 2006.

(51) Int. Cl.
| | |
|---|---|
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 231/00* | (2006.01) |
| *C07D 403/02* | (2006.01) |
| *A01N 43/56* | (2006.01) |
| *A61K 31/415* | (2006.01) |

(52) U.S. Cl. ...... 514/256; 514/406; 544/333; 548/364.1
(58) Field of Classification Search .................. 514/256, 514/406; 544/333; 548/364.1
See application file for complete search history.

(56) References Cited

U.S. PATENT DOCUMENTS 6,979,686 B1    12/2005 Naraian et al.

FOREIGN PATENT DOCUMENTS

| WO | WO9852941 | 11/1998 |
|---|---|---|
| WO | WO0130154 | 5/2001 |
| WO | WO2004005282 | 1/2004 |
| WO | WO2004046120 | 6/2004 |
| WO | WO2004046120 A2 * | 6/2004 |
| WO | WO2004050650 | 6/2004 |
| WO | WO 2004050650 A1 * | 6/2004 |
| WO | WO2005013982 | 2/2005 |
| WO | WO2005068452 | 7/2005 |
| WO | WO2005123719 | 12/2005 |
| WO | WO2006084015 | 8/2006 |
| WO | WO2006125101 | 11/2006 |
| WO | WO 2007027842 A1 * | 3/2007 |
| WO | WO2007027855 | 3/2007 |
| WO | WO2007105058 | 9/2007 |
| WO | WO2007129195 | 11/2007 |
| WO | WO20070123892 | 11/2007 |

OTHER PUBLICATIONS

Chou et. al., Bioorganic and Medicinal Chemistry, 2003, Pergamon, vol. 13, pp. 507-511.*
Mortensen et. al., J. Medicinal Chemistry, 2001, American Chemical Society, vol. 44, pp. 3838-3848.*

* cited by examiner

*Primary Examiner* — Sreeni Padmanabhan
*Assistant Examiner* — Sarah Pihonak
(74) *Attorney, Agent, or Firm* — Daniel E. Raymond; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, ARG, BCR-Abl, BRK, EphB, Fms, Fyn, KDR, c-Kit, LCK, PDGF-R, b-Raf, c-Raf, SAPK2, Src, Tie2 and TrkB kinases.

9 Claims, No Drawings

COMPOUNDS AND COMPOSITIONS AS PROTEIN KINASE INHIBITORS

CROSS-REFERENCE TO RELATED APPLICATIONS

This application is a 371 U.S. national phase application of international application number PCT/US2007/079340 filed 24 Sep. 2007, which application claims priority to U.S. provisional patent application No. 60/827,873, filed 2 Oct. 2006. The full disclosure of these applications is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, ARG, BCR-Abl, BRK, EphB, Fms, Fyn, KDR, c-Kit, LCK, PDGF-R, b-Raf, c-Raf, SAPK2, Src, Tie2 and TrkB kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor (trkB), and the fibroblast growth factor receptor (FGFR3); non-receptor tyrosine kinases such Abl and the fusion kinase BCR-Abl, Lck, Bmx and c-src; and serine/threonine kinases such as b-RAF, c-RAF, sgk, MAP kinases (e.g., MKK4, MKK6, etc.) and SAP 2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

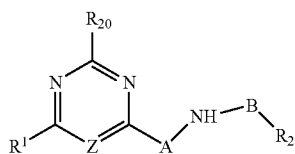

I in which:

A is a 5 member, unsaturated or partially unsaturated, ring containing 1 to 3 heteroatoms selected from —N═, —NR$_3$—, —O— and —S—; wherein R$_3$ is selected from hydrogen, halo, substituted or unsubstituted-C$_{1-6}$alkyl, substituted or unsubstituted C$_{2-6}$alkenyl, substituted or unsubstituted C$_{2-6}$ alkynyl, —XOR$_{4a}$, —XCN, —XC(O)OR$_{4a}$, —XC(O)R$_{4b}$, —XNR$_{4a}$R$_{4a}$, —XNR$_{4a}$XNR$_{4a}$R$_{4a}$, —XC(O)NR$_{4a}$XNR$_{4a}$R$_{4a}$, —XC(O)NR$_{4a}$XR$_{4b}$, —XC(O)NR$_{4a}$XNR$_{4a}$R$_{4b}$, —XC(O)NR$_{4a}$XOR$_{4a}$, —XNR$_{4a}$XNR$_{4a}$R$_{4b}$, —XNR$_{4a}$XOR$_{4a}$, —XNR$_{4a}$XCF$_3$, —XC(O)NR$_{4a}$R$_{4a}$, and —XR$_{4b}$; wherein each X is independently selected from a bond and C$_{1-4}$alkylene; R$_{4a}$ is selected from hydrogen and substituted or unsubstituted C$_{1-6}$alkyl, and two R$_{4a}$ on the same or adjacent atoms can optionally be joined to form a 5-6 membered ring containing up to two heteroatoms selected from N, O and S as ring members; and R$_{4b}$ is selected from C$_{6-10}$aryl, C$_{1-10}$heteroaryl, C$_{3-10}$cycloalkyl and C$_{3-10}$heterocycloalkyl; wherein any cycloalkyl, heterocycloalkyl, aryl or heteroaryl of R$_{4b}$ is optionally substituted with 1 to 3 radicals independently selected from C$_{1-6}$alkyl and —NR$_{4c}$R$_{4d}$; wherein each R$_{4c}$ and R$_{4d}$ is independently selected from hydrogen and substituted or unsubstituted C$_{1-6}$alkyl, and R$_{4c}$ and R$_{4d}$ can optionally be joined together to form a 5-6 membered ring containing N and optionally containing an additional heteroatom selected from N, O and S; with the proviso that ring A is not imidazole;

wherein any ring A can be optionally substituted with one or two R$_3$ radicals, with the proviso that R$_3$ is not halo when attached directly to a nitrogen atom;

B is 5 or 6 member, unsaturated or partially unsaturated, ring containing 0 to 3 heteroatoms selected from —N═, —NR$_{21}$—, —O— and —S—; wherein R$_{21}$ is selected from hydrogen, C$_{1-6}$alkyl, halo-substituted-C$_{1-6}$alkyl and halo; wherein B can be optionally substituted with 1 to 3 radicals independently selected from C$_{1-6}$alkyl, halo-substituted-C$_{1-6}$alkyl and halo;

Z is selected from CH and N;

R$_1$ is selected from —XNR$_5$R$_6$, —XNR$_5$XNR$_5$R$_6$, —XNR$_5$XR$_5$, —XNR$_5$XOR$_6$, —XNR$_6$XC(O)OR$_5$, —XNR$_6$XC(O)NR$_6$R$_6$, —XOR$_5$, —XC(O)R$_5$, —XR$_5$ and —XS(O)$_{0-2}$R$_5$; wherein X is selected from a bond and C$_{1-4}$alkylene optionally substituted by 1 to 2 C$_{1-6}$alkyl radicals; R$_5$ is selected from hydrogen, substituted or unsubstituted C$_{1-6}$alkyl, C$_{6-10}$aryl-C$_{0-4}$alkyl, C$_{1-10}$heteroaryl-C$_{0-4}$alkyl, C$_{3-10}$cycloalkyl-C$_{0-4}$alkyl and C$_{3-10}$heterocycloalkyl-C$_{0-4}$alkyl; and each R$_6$ is independently selected from hydrogen and substituted or unsubstituted C$_{1-6}$alkyl; or R$_5$ and R$_6$ together with the nitrogen to which R$_5$ and R$_6$ are both attached form heteroaryl or heterocycloalkyl that can contain an additional heteroatom selected from N, O and S as a ring member; or R$_1$ together with the N1 of the pyrimidine ring to which R$_1$ is attached forms 2,3-dihydroimidazo[1,2-f]pyrimidine;

wherein any aryl, heteroaryl, cycloalkyl and heterocycloalkyl of R$_5$ or the combination of R$_5$ and R$_6$ can be optionally substituted with 1 to 3 radicals independently selected from halo, nitro, cyano, hydroxy, C$_{1-6}$alkyl, C$_{1-6}$alkoxy, halo-substituted-alkyl, halo-substituted-alkoxy, —XNR$_7$R$_8$, —XOR$_7$, —XNR$_7$S(O)$_2$R$_8$, —XNR$_7$S(O)R$_8$, —XNR$_7$SR$_8$, —XC(O)NR$_7$R$_8$, —XC(O)NR$_7$XNR$_7$R$_8$, —XNR$_7$C(O)NR$_7$R$_8$, —XNR$_7$XNR$_7$R$_8$, —XNR$_7$XOR$_7$, —XNR$_7$C(═NR$_7$)NR$_7$R$_8$, —XS(O)$_2$R$_9$, —XNR$_7$C(O)R$_8$, —XNR$_7$C(O)R$_9$, —XR$_9$, —XC(O)OR$_8$, —XS(O)$_2$NR$_7$R$_8$, —XS(O)NR$_7$R$_8$ and —XSNR$_7$R$_8$; wherein X is a bond or C$_{1-4}$alkylene; R$_7$ and R$_8$ are independently selected from the group consisting of hydrogen and substituted or unsubstituted C$_{1-4}$alkyl, and wherein R$_7$ and R$_8$ on one nitrogen can optionally cyclize to form a 5-6 membered ring that can contain an additional heteroatom selected from N, O and S as a ring member; and R$_9$ is selected from C$_{3-10}$heterocycloalkyl and C$_{1-10}$heteroaryl; wherein said heterocycloalkyl or heteroaryl of R$_9$ is optionally substituted with a radical selected from the group consisting of C$_{1-4}$alkyl, —XNR$_7$XNR$_7$R$_7$, XNR$_7$XOR$_7$ and —XOR$_7$;

$R_2$ is selected from $-R_{11}$, $-CONR_{10}R_{11}$, $SO_2NR_{10}R_{11}$, $-NR_{10}R_{11}$, $-NR_{10}C(O)R_{11}$, $-NR_{10}S(O)_{0-2}R_{11}$ and $-NR_{10}C(O)NR_{10}R_{11}$; wherein $R_{10}$ is selected from hydrogen and substituted or unsubstituted $C_{1-6}$alkyl; $R_{11}$ is selected from $C_{6-10}$aryl, $C_{1-10}$heteroaryl, $C_{3-10}$cycloalkyl and $C_{3-10}$heterocycloalkyl; wherein $R_{10}$ and $R_{11}$ on the same nitrogen can optionally cyclize to form a 5-6 membered ring that can contain an additional heteroatom selected from N, O and S as a ring member, and any aryl, heteroaryl, cycloalkyl or heterocycloalkyl of $R_{11}$ is optionally substituted by 1 to 3 radicals selected from halo, nitro, cyano, hydroxy, substituted or unsubstituted $C_{1-6}$alkyl, $C_{1-6}$alkoxy, halo-substituted-$C_{1-6}$alkyl, cyano-substituted-$C_{1-6}$alkyl, hydroxy-substituted-$C_{1-6}$alkyl, halo-substituted-$C_{1-6}$alkoxy, $-X_2R_{13}$, $-X_2NR_{12}C(O)R_{13}$, $-X_2NR_{12}C(O)NR_{12}R_{13}$, $-X_2NR_{12}R_{12}$, $-X_2NR_{12}R_{13}$, $-X_2NR_{12}X_2R_{13}$, $-X_2NR_{12}NR_{12}R_{12}$, $-X_2NR_{12}X_2OR_{12}$, $-X_2C(O)NR_{12}R_{13}$, $-X_2NR_{12}S(O)_{0-2}R_{13}$ and $-X_2S(O)_{0-2}NR_{12}R_{13}$; wherein $X_2$ is selected from a bond, $C_{1-4}$alkylene and $C_{2-4}$alkenylene; $R_{12}$ is selected from hydrogen, $C_{1-6}$alkyl and hydroxy-substituted-$C_{1-6}$alkyl; $R_{13}$ is selected from substituted or unsubstituted $C_{1-6}$ alkyl, $C_{6-10}$aryl, $C_{1-10}$heteroaryl, $C_{3-10}$cycloalkyl and $C_{3-10}$heterocycloalkyl; wherein two $R_{12}$ groups or $R_{12}$ and $R_{13}$ on the same nitrogen can optionally cyclize to form a 5-6 membered ring that can contain an additional heteroatom selected from N, O and S as a ring member, any aryl, heteroaryl, cycloalkyl or heterocycloalkyl of $R_{13}$ is optionally substituted with 1 to 3 radicals independently selected from halo, cyano, hydroxy, nitro, amino, $C_{1-6}$alkyl, halo-substituted-$C_{1-6}$alkyl, hydroxy-substituted-$C_{1-6}$alkyl, cyano-substituted-$C_{1-6}$alkyl, hydroxy-substituted-$C_{1-6}$alkyl, $C_{1-6}$alkoxy, halo-substituted-$C_{1-6}$alkoxy, $-X_3NR_7R_8$, $-X_3NR_7X_3OR_7$, $C_{6-10}$-aryl-$C_{0-4}$alkyl, $C_{1-10}$heteroaryl-$C_{0-4}$alkyl, $C_{3-10}$cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein $X_3$ is selected from a bond and $C_{1-4}$alkylene; $R_7$ and $R_8$ are as described above and wherein any aryl, heteroaryl, cycloalkyl or heterocycloalkyl substituents of $R_{13}$ is further optionally substituted by 1 to 3 radicals independently selected from halo, hydroxy, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy;

$R_{20}$ is selected from hydrogen, substituted or unsubstituted $C_{1-6}$alkyl, and $N(R_{21})_2$, wherein each $R_{21}$ is independently H or substituted or unsubstituted $C_{1-6}$ alkyl, and wherein two $R_{21}$ on the same nitrogen can cyclize to form a 5-6 membered ring that can contain an additional heteroatom selected from N, O and S;

and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly Abl, ARG, BCR-Abl, BRK, EphB, Fms, Fyn, KDR, c-Kit, LCK, PDGF-R, b-Raf, c-Raf, SAPK2, Src, Tie2 and/or TrkB activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, ARG, BCR-Abl, BRK, EphB, Fms, Fyn, KDR, c-Kit, LCK, PDGF-R, b-Raf, c-Raf, SAPK2, Src, Tie2 and/or TrkB activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

As used herein, the terms "alkyl," "alkenyl" and "alkynyl" have their ordinary meanings and include straight-chain, branched-chain and cyclic monovalent hydrocarbon radicals, and combinations of these, which contain only C and H when they are unsubstituted. "Alkyl" groups are saturated so they contain no carbon-carbon multiple bonds; "alkenyl" groups contain at least one carbon-carbon double bond; and "alkynyl" groups contain at least one carbon-carbon triple bond. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10.

Typically, the alkyl, alkenyl and alkynyl substituents of the invention contain 1-10C (alkyl) or 2-10C (alkenyl or alkynyl). Preferably they contain 1-6C (alkyl) or 2-6C (alkenyl or alkynyl). Sometimes they contain 1-4C (alkyl) or 2-4C (alkenyl or alkynyl). A single alkenyl or alkynyl group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups As used herein, these terms also include rings that contain a double bond or two, as long as the ring is not aromatic.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

Alkyl, alkenyl and alkynyl groups and the corresponding cyclic groups, heteroforms of these groups, and rings formed by joining together two of these groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR, $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Alkoxy" as used herein refers to an alkyl group connected through oxygen. For example, $C_{1-4}$-alkoxy includes, methoxy, ethoxy, and the like. Other substituted alkyl groups are described similarly.

Halosubstituted-$C_{1-6}$alkyl, as used in this application, includes trifluoromethyl, pentafluoroethyl, difluoromethyl, difluoromethyl, and the like, as well as the isomer combinations thereof. Alkylene, as used in this application, is a divalent alkyl radical that can be single chain, branched or cyclized. For example $C_{1-4}$alkylene includes cyclobutyl, and the like.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)—heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Arylene" means a divalent radical derived from an aryl group. A ring described as "unsaturated" contains at least one carbon-carbon multiple bond, and can be aromatic; a ring described as "partially unsaturated" contains at least one carbon-carbon multiple bond but is not aromatic.

"Heteroaryl" is as defined for aryl above where one or more of the ring members is a heteroatom. For example $C_{1-10}$heteroaryl, as used in this application, includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. Heteroaryl may also include partially unsaturated ring systems such as 1,2,3,6-tetrahydropyridin-4-yl, and the like.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, ═O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Substituted" as used herein indicates that the particular group or groups being described will have one or more non-hydrogen substituents. "Optionally substituted" indicates that the group may or may not have non-hydrogen substituents. If not otherwise specified, the total number of such substituents that may be present is equal to the number of H atoms present on the unsubstituted form of the group being described. Where an optional substituent is attached via a double bond, such as a carbonyl oxygen (═O), the group takes up two available valences, so the total number of substituents that may be included is reduced according to the number of available valences.

"Kinase Panel" is a list of kinases comprising Abl(human), Abl(T315I), JAK2, JAK3, ALK, JNK1α1, ALK4, KDR, Aurora-A, Lck, Blk, MAPK1, Bmx, MAPKAP-K2, BRK, MEK1, CaMKII(rat), Met, CDK1/cyclinB, p70S6K, CHK2, PAK2, CK1, PDGFRα, CK2, PDK1, c-kit, Pim-2, c-RAF, PKA(h), CSK, PKBα, cSrc, PKCα, DYRK2, Plk3, EGFR, ROCK-I, Fes, Ron, FGFR3, Ros, Flt3, SAPK2α, Fms, SGK, Fyn, SIK, GSK3β, Syk, IGF-1R, Tie-2, IKKβ, TrKB, IR, WNK3, IRAK4, ZAP-70, ITK, AMPK(rat), LIMK1, Rsk, Ax1, LKB1, SAPK2β, BrSK2, Lyn (h), SAPK3, BTK, MAP-KAP-K3, SAPK4, CaMKIV, MARK1, Snk, CD 2/cyclinA, MINK, SRPK1, CDK3/cyclinE, MKK4(m), TAK1, CDK5/p25, MKK6(h), TBK1, CDK6/cyclinD3, MLCK, TrkA, CDK7/cyclinH/MAT1, MRCKβ, TSSK1, CHK1, MSK1, Yes, CK1d, MST2, ZIPK, c-Kit (D816V), MuSK, DAPK2, NEK2, DDR2, NEK6, DMPK, PAK4, DRAK1, PAR-1Bα, EphA1, PDGFRβ, EphA2, Pim-1, EphA5, PKBβ, EphB2, PKCβ1, EphB4, PKCδ, FGFR1, PKCη, FGFR2, PKCθ, FGFR4, PKD2, Fgr, PKG1β, Flt1, PRK2, Hck, PYK2, HIPK2, Ret, IKKα, RIPK2, IRR, ROCK-II(human), JNK2α2, Rse, JNK3, Rsk1(h), PI3 Kγ, PI3 Kδ and PI3-Kβ. Compounds of the invention are screened against the kinase panel (wild type and/or mutation thereof) and inhibit the activity of at least one of said panel members.

"Mutant forms of BCR-Abl" means single or multiple amino acid changes from the wild-type sequence. Mutations in BCR-ABL act by disrupting critical contact points between protein and inhibitor (for example, Gleevec, and the like), more often, by inducing a transition from the inactive to the active state, i.e. to a conformation to which BCR-ABL and Gleevec is unable to bind. From analyses of clinical samples, the repertoire of mutations found in association with the resistant phenotype has been increasing slowly but inexorably over time. Mutations seem to cluster in four main regions. One group of mutations (G250E, Q252R, Y253F/H, E255K/V) includes amino acids that form the phosphate-binding loop for ATP (also known as the P-loop). A second group (V289A, F311L, T315I, F317L) can be found in the Gleevec binding site and interacts directly with the inhibitor via hydrogen bonds or Van der Waals' interactions. The third group of mutations (M351T, E355G) clusters in close proximity to the catalytic domain. The fourth group of mutations (H396R/P) is located in the activation loop, whose conformation is the molecular switch controlling kinase activation/inactivation. BCR-ABL point mutations associated with Gleevec resistance detected in CML and ALL patients include: M224V, L248V, G250E, G250R, Q252R, Q252H, Y253H, Y253F, E255K, E255V, D276G, T277A, V289A, F311L, T315I, T315N, F317L, M343T, M315T, E355G, F359V, F359A, V3791, F382L, L387M, L387F, H396P, H396R, A397P, S417Y, E459K, and F486S (Amino acid positions, indicated by the single letter code, are those for the GenBank sequence, accession number AAB60394, and correspond to ABL type 1a; Martinelli et al., Haematologica/The Hematology Journal, 2005, April; 90-4). Unless otherwise stated for this invention, Bcr-Abl refers to wild-type and mutant forms of the enzyme.

"Treat", "treating" and "treatment" refer to a method of alleviating or abating a disease and/or its attendant symptoms.

Description Of The Preferred Embodiments

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly Abl, ARG, BCR-Abl, BRK, EphB, Fms, Fyn, KDR, c-Kit, LCK, PDGF-R, b-Raf, c-Raf, SAPK2, Src, Tie2 and TrkB kinase related diseases. For example, leukemia and other proliferation disorders related to BCR-Abl can be treated through the inhibition of wild type and mutant forms of Bcr-Abl.

In one embodiment, with reference to compounds of Formula I, are compounds of Formula Ia:

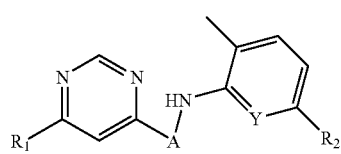

Ia in which: A is a 5 member, unsaturated or partially unsaturated, ring containing 1 to 3 heteroatoms selected from —N=, —NR$_3$—, —O— and —S—; wherein R$_3$ is selected from hydrogen, halo, halo-substituted-C$_{1-6}$alkyl, C$_{1-6}$alkyl, —XOR$_{4a}$, —XCN, —XC(O)OR$_{4a}$, —XC(O)R$_{4b}$, —XNR$_{4a}$R$_{4a}$, —XNR$_{4a}$R$_{4b}$, —XNR$_{4a}$XNR$_{4a}$R$_{4a}$, —XC(O)NR$_{4a}$XNR$_{4a}$R$_{4a}$, —XC(O)NR$_{4a}$XR$_{4b}$, —XC(O)NR$_{4a}$XNR$_{4b}$, —XC(O)NR$_{4a}$XOR$_{4a}$, —XNR$_{4a}$XNR$_{4a}$R$_{4b}$, —XNR$_{4a}$XOR$_{4a}$, —XNR$_{4a}$XCF$_3$, —XC(O)NR$_{4a}$R$_{4a}$, and —XR$_{4b}$; wherein X is selected from a bond and C$_{1-4}$alkylene; R$_{4a}$ is selected from hydrogen and C$_{1-6}$alkyl; and R$_{4b}$ is selected from C$_{6-10}$aryl, C$_{1-10}$heteroaryl, C$_{3-10}$cycloalkyl and C$_{3-10}$heterocycloalkyl; wherein any cycloalkyl, heterocycloalkyl, aryl or heteroaryl of R$_{4b}$ is optionally substituted with 1 to 3 radicals independently selected from C$_{1-6}$alkyl and —NR$_{4c}$R$_{4d}$; wherein each R$_{4c}$ and R$_{4d}$ is independently selected from hydrogen and C$_{1-6}$alkyl; with the proviso that ring A is not imidazole; wherein any ring A can be optionally substituted with an R$_3$ radical;

R$_1$ is selected from —XNR$_5$R$_6$, —XNR$_5$XNR$_5$R$_6$, —XNR$_5$XR$_5$, —XNR$_5$XOR$_5$, —XNR$_6$XC(O)OR$_5$, —XNR$_6$XC(O)NR$_6$R$_6$, —XOR$_5$, —XC(O)R$_5$, —XR$_5$ and —XS(O)$_{0-2}$R$_5$; wherein X is selected from a bond and C$_{1-4}$alkylene optionally substituted by 1 to 2 C$_{1-6}$alkyl radicals; R$_5$ is selected from hydrogen, C$_{1-6}$alkyl, C$_{6-10}$aryl-C$_{0-4}$alkyl, C$_{1-10}$heteroaryl-C$_{0-4}$alkyl, C$_{3-10}$cycloalkyl-C$_{0-4}$alkyl and C$_{3-10}$heterocycloalkyl-C$_{0-4}$alkyl; and each R$_6$ is independently selected from hydrogen and C$_{1-6}$alkyl; or R$_5$ and R$_6$ together with the nitrogen to which R$_5$ and R$_6$ are both attached form heteroaryl or heterocycloalkyl; or R$_1$ together with the N1 of the pyrimidine ring to which R$_1$ is attached forms 2,3-dihydroimidazo[1,2-f]pyrimidine;

wherein any aryl, heteroaryl, cycloalkyl and heterocycloalkyl of R$_5$ or the combination of R$_5$ and R$_6$ can be optionally substituted with 1 to 3 radicals independently selected from halo, nitro, cyano, hydroxy, C$_{1-6}$alkyl, C$_{1-6}$alkoxy, halo-substituted-alkyl, halo-substituted-alkoxy, —XNR$_7$R$_8$, —XOR$_7$, —XNR$_7$S(O)$_2$R$_8$, —XNR$_7$S(O)R$_8$, —XNR$_7$SR$_8$, —XC(O)NR$_7$R$_8$, —XC(O)NR$_7$XNR$_7$R$_8$, —XNR$_7$C(O)NR$_7$R$_8$, —XNR$_7$XNR$_7$R$_8$, —XNR$_7$XOR$_7$, —XNR$_7$C(=NR$_7$)NR$_7$R$_8$, —XS(O)$_2$R$_9$, —XNR$_7$C(O)R$_8$, —XNR$_7$C(O)R$_9$, —XR$_9$, —XC(O)OR$_8$, —XS(O)$_2$NR$_7$R$_8$, —XS(O)NR$_7$R$_8$ and —XSNR$_7$R$_8$; wherein X is a bond or C$_{1-4}$alkylene; R$_7$ and R$_8$ are independently selected from the group consisting of hydrogen and C$_{1-4}$alkyl; and R$_9$ is selected from C$_{3-10}$heterocycloalkyl and C$_{1-10}$heteroaryl; wherein said heterocycloalkyl or heteroaryl of R$_9$ is optionally substituted with a radical selected from the group consisting of C$_{1-4}$alkyl, —XNR$_7$XNR$_7$R$_7$, XNR$_7$XOR$_7$ and —XOR$_7$;

R$_2$ is selected from —R$_{11}$, —CONR$_{10}$R$_{11}$, —SO$_2$NR$_{10}$R$_{11}$, —NR$_{10}$R$_{11}$, —NR$_{10}$C(O)R$_{11}$, —NR$_{10}$S(O)$_{0-2}$R$_{11}$ and —NR$_{10}$C(O)NR$_{10}$R$_{11}$; R$_{10}$ is selected from hydrogen and C$_{1-6}$alkyl; R$_{11}$ is selected from C$_{6-10}$aryl, C$_{1-10}$heteroaryl, C$_{3-10}$cycloalkyl and C$_{3-10}$heterocycloalkyl; wherein any aryl, heteroaryl, cycloalkyl or heterocycloalkyl of R$_{11}$ is optionally substituted by 1 to 3 radicals selected from halo, nitro, cyano, hydroxy, C$_{1-6}$alkyl, C$_{1-6}$alkoxy, halo-substituted-C$_{1-6}$alkyl, cyano-substituted-C$_{1-6}$alkyl, hydroxy-substituted-C$_{1-6}$alkyl, halo-substituted-C$_{1-6}$alkoxy, —X$_2$R$_{13}$, —X$_2$NR$_{12}$C(O)R$_{13}$, —X$_2$NR$_{12}$C(O)NR$_{12}$R$_{13}$, —X$_2$NR$_{12}$R$_{12}$, —X$_2$NR$_{12}$R$_{13}$, —X$_2$NR$_{12}$X$_2$R$_{13}$, —X$_2$NR$_{12}$NR$_{12}$R$_{12}$, —X$_2$NR$_{12}$X$_2$OR$_{12}$, —X$_2$C(O)NR$_{12}$R$_{13}$, —X$_2$NR$_{12}$S(O)$_{0-2}$R$_{13}$ and —X$_2$S(O)$_{0-2}$NR$_{12}$R$_{13}$; wherein R$_{12}$ is selected from hydrogen, C$_{1-6}$alkyl and hydroxy-substituted-C$_{1-6}$alkyl; wherein X$_2$ is selected from a bond, C$_{1-4}$alkylene and C$_{2-4}$alkenylene; R$_{13}$ is selected from C$_{6-10}$aryl, C$_{1-10}$heteroaryl, C$_{3-10}$cycloalkyl and C$_{3-10}$heterocycloalkyl; wherein any aryl, heteroaryl, cycloalkyl or heterocycloalkyl of R$_{13}$ is optionally substituted with 1 to 3 radicals independently selected from halo, cyano, hydroxy, nitro, amino, C$_{1-6}$alkyl, halo-substituted-C$_{1-6}$alkyl, hydroxy-substituted-C$_{1-6}$alkyl, cyano-substituted-C$_{1-6}$alkyl, hydroxy-substituted-C$_{1-6}$alkyl, C$_{1-6}$alkoxy, halo-substituted-C$_{1-6}$alkoxy, —X$_3$NR$_7$R$_8$, —X$_3$NR$_7$X$_3$OR$_7$, C$_{6-10}$aryl-C$_{0-4}$alkyl, C$_{1-10}$heteroaryl-C$_{0-4}$alkyl, C$_{3-10}$cycloalkyl-C$_{0-4}$alkyl, C$_{3-10}$heterocycloalkyl-C$_{0-4}$alkoxy and C$_{3-10}$heterocycloalkyl-C$_{0-4}$alkyl; wherein X$_3$ is selected from a bond and C$_{1-4}$alkyelene; R$_7$ and R$_8$ are as described above and wherein any aryl, heteroaryl, cycloalkyl or heterocycloalkyl substituents of R$_{13}$ is further optionally substituted by 1 to 3 radicals independently selected from halo, hydroxy, C$_{1-6}$alkyl, halo-substituted-C$_{1-6}$alkyl, hydroxy-substituted-C$_{1-6}$alkyl, C$_{1-6}$alkoxy, C$_{3-10}$heterocycloalkyl and halo-substituted-C$_{1-6}$alkoxy; and Y is selected from C and N.

In another embodiment, is a compound selected from Formula Ib, Ic and Id:

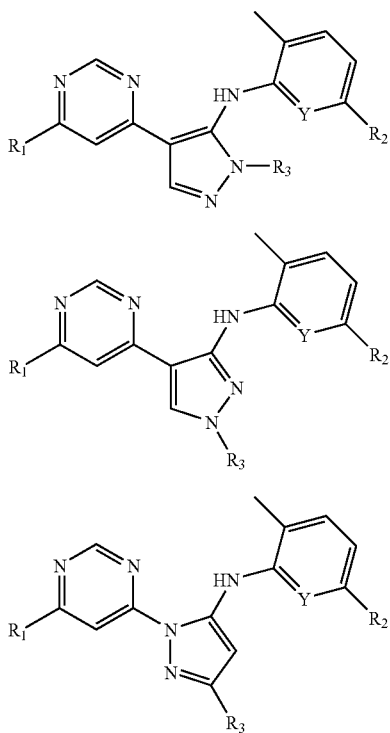

in which:

R₁ is selected from —XNR₅R₆, —XNR₅XNR₅R₆, —XNR₅XR₅, —XNR₅XOR₆, —XNR₆XC(O)OR₅, —XNR₆XC(O)NR₆R₆, —XOR₅, —XC(O)R₅, —XR₅ and —XS(O)₀₋₂R₅; wherein X is selected from a bond and C₁₋₄alkylene optionally substituted by 1 to 2 C₁₋₆alkyl radicals; R₅ is selected from hydrogen, C₁₋₆alkyl, C₆₋₁₀aryl-C₀₋₄alkyl, C₁₋₁₀heteroaryl-C₀₋₄alkyl, C₃₋₁₀cycloalkyl-C₀₋₄alkyl and C₃₋₁₀heterocycloalkyl-C₀₋₄alkyl; and each R₆ is independently selected from hydrogen and C₁₋₆alkyl; or R₅ and R₆ together with the nitrogen to which R₅ and R₆ are both attached form heteroaryl or heterocycloalkyl; or R₁ together with the N1 of the pyrimidine ring to which R₁ is attached forms 2,3-dihydroimidazo[1,2-f]pyrimidine;

wherein any aryl, heteroaryl, cycloalkyl and heterocycloalkyl of R₅ or the combination of R₅ and R₆ can be optionally substituted with 1 to 3 radicals independently selected from halo, nitro, cyano, hydroxy, C₁₋₆alkyl, C₁₋₆alkoxy, halo-substituted-alkyl, halo-substituted-alkoxy, —XNR₇R₈, —XOR₇, —XNR₇S(O)₂R₈, —XNR₇S(O)R₈, —XNR₇SR₈, —XC(O)NR₇R₈, —XC(O)NR₇XNR₇R₈, —XNR₇C(O)NR₇R₈, —XNR₇XNR₇R₈, —XNR₇XOR₇, —XNR₇C(=NR₇)NR₇R₈, —XS(O)₂R₉, —XNR₇C(O)R₈, —XNR₇C(O)R₉, —XR₉, —XC(O)OR₈, —XS(O)₂NR₇R₈, —XS(O)NR₇R₈ and —XSNR₇R₈; wherein X is a bond or C₁₋₄alkylene; each R₇ and R₈ are independently selected from the group consisting of hydrogen and C₁₋₄alkyl, or R₇ and R₈ together with the nitrogen to which R₇ and R₈ are both attached form heteroaryl or heterocycloalkyl; and R₉ is selected from C₃₋₁₀heterocycloalkyl and C₁₋₁₀heteroaryl; wherein said heterocycloalkyl or heteroaryl of R₉ is optionally substituted with a radical selected from the group consisting of C₁₋₄alkyl, —XNR₇XNR₇R₇, XNR₇XOR₇ and —XOR₇;

R₂ is selected from —R₁₁, —CONR₁₀R₁₁, SO₂NR₁₀R₁₁, —NR₁₀R₁₁, —NR₁₀C(O)R₁₁, —NR₁₀S(O)₀₋₂R₁₁ and —NR₁₀C(O)NR₁₀R₁₁; wherein R₁₀ is selected from hydrogen and C₁₋₆alkyl; R₁₁ is selected from C₆₋₁₀aryl, C₁₋₁₀heteroaryl, C₃₋₁₀cycloalkyl and C₃₋₁₀heterocycloalkyl; wherein R₁₀ and R₁, together with the nitrogen to which R₁₀ and R₁₁ are both attached can optionally form heteroaryl or heterocycloalkyl, and any aryl, heteroaryl, cycloalkyl or heterocycloalkyl of R₁₁ is optionally substituted by 1 to 3 radicals selected from halo, nitro, cyano, hydroxy, C₁₋₆alkyl, C₁₋₆alkoxy, halo-substituted-C₁₋₆alkyl, cyano-substituted-C₁₋₆alkyl, hydroxy-substituted-C₁₋₆alkyl, halo-substituted-C₁₋₆alkoxy, —X₂R₁₃, —X₂NR₁₂C(O)R₁₃, —X₂NR₁₂C(O)NR₁₂R₁₃, —X₂NR₁₂R₁₂, —X₂NR₁₂R₁₃, —X₂NR₁₂X₂R₁₃, —X₂NR₁₂NR₁₂R₁₂, —X₂NR₁₂X₂OR₁₂, —X₂C(O)NR₁₂R₁₃, —X₂S(O)₀₋₂R₁₂, —X₂NR₁₂S(O)₀₋₂R₁₃ and —X₂S(O)₀₋₂NR₁₂R₁₃; wherein X₂ is selected from a bond, C₁₋₄alkylene and C₂₋₄alkenylene; R₁₂ is selected from hydrogen, C₁₋₆alkyl and hydroxy-substituted-C₁₋₆alkyl; R₁₃ is selected from C₆₋₁₀aryl, C₁₋₁₀heteroaryl, C₃₋₁₀cycloalkyl and C₃₋₁₀heterocycloalkyl; wherein two R₁₂ of NR₁₂R₁₂ or R₁₂ and R₁₃ of NR₁₂R₁₃ together with the nitrogen to which both are attached optionally form heteroaryl or heterocycloalkyl, and any aryl, heteroaryl, cycloalkyl or heterocycloalkyl of R₁₃ is optionally substituted with 1 to 3 radicals independently selected from halo, cyano, hydroxy, nitro, amino, C₁₋₆alkyl, halo-substituted-C₁₋₆alkyl, hydroxy-substituted-C₁₋₆alkyl, cyano-substituted-C₁₋₆alkyl, hydroxy-substituted-C₁₋₆alkyl, C₁₋₆alkoxy, halo-substituted-C₁₋₆alkoxy, —X₃NR₇R₈, —X₃NR₇X₃OR₇, C₆₋₁₀aryl-C₀₋₄alkyl, C₁₋₁₀heteroaryl-C₀₋₄alkyl, C₃₋₁₀cycloalkyl-C₀₋₄alkyl, C₃₋₁₀heterocycloalkyl-C₀₋₄alkoxy and C₃₋₁₀heterocycloalkyl-C₀₋₄alkyl; wherein X₃ is selected from a bond and C₁₋₄alkyelene; R₇ and R₈ are as described above and wherein any aryl, heteroaryl, cycloalkyl or heterocycloalkyl substituents of R₁₃ is further optionally substituted by 1 to 3 radicals independently selected from halo, hydroxy, C₁₋₆alkyl, halo-substituted-C₁₋₆alkyl, hydroxy-substituted-C₁₋₆alkyl, C₁₋₆alkoxy, C₃₋₁₀heterocycloalkyl and halo-substituted-C₁₋₆alkoxy;

R₃ is selected from hydrogen, halo, halo-substituted-C₁₋₆alkyl, C₁₋₆alkyl, —XOR₄ₐ, —XCN, —XC(O)OR₄ₐ, —XC(O)R₄ᵦ, —XNR₄ₐR₄ₐ, —XNR₄ₐR₄ᵦ, —XNR₄ₐXNR₄ₐR₄ₐ, —XC(O)NR₄ₐXNR₄ₐ, —XC(O)NR₄ₐXR₄ᵦ, —XC(O)NR₄ₐXNR₄ᵦ, —XC(O)NR₄ₐXOR₄ₐ, —XNR₄ₐXNR₄ₐR₄ᵦ, —XNR₄ₐXOR₄ₐ, —XNR₄ₐXCF₃, —XC(O)NR₄ₐR₄ₐ, and —XR₄ᵦ; wherein X is selected from a bond and C₁₋₄alkylene; R₄ₐ is selected from hydrogen and C₁₋₆alkyl; and R₄ᵦ is selected from C₆₋₁₀aryl, C₁₋₁₀heteroaryl, C₃₋₁₀cycloalkyl and C₃₋₁₀heterocycloalkyl; wherein two R₄ₐ of NR₄ₐR₄ₐ, together with the nitrogen to which both are attached optionally form heteroaryl or heterocycloalkyl, and any cycloalkyl, heterocycloalkyl, aryl or heteroaryl of R₄ᵦ is optionally substituted with 1 to 3 radicals independently selected from C₁₋₆alkyl and —NR₄꜀R₄d; wherein each R₄꜀ and R₄d is independently selected from hydrogen and C₁₋₆alkyl, and R₄꜀ and R₄d of NR₄꜀R₄d together with the nitrogen to which R₄꜀ and R₄d are attached optionally form a heteroaryl or heterocycloalkyl; and Y is selected from CH and N.

In another embodiment, R₃ is selected from hydrogen, methyl, morpholino-ethyl, ethoxy-carbonyl, chloro, trifluoromethyl, (methyl-piperidinyl)(methyl)amino-methyl, methyl-amino-carbonyl, hydroxy-methyl, dimethyl-amino-methyl, methyl-amino-methyl, morpholino-methyl, diethyl-amino-ethyl-amino-methyl, methyl-piperazinyl-methyl, methyl-piperazinyl-ethyl-amino-methyl, dimethyl-amino-propyl-amino-methyl, ((2-hydroxyethyl)(methyl)amino)methyl, ethyl-amino-methyl, trifluoromethyl-amino-methyl, dimethyl-amino-ethyl-amino-carbonyl, piperidinyl-ethylamino-carbonyl, morpholino-ethyl-amino-carbonyl, morpholino-carbonyl, amino-carbonyl, dimethyl-amino-carbonyl, dimethyl-amino-pyrrolidinyl-methyl, dimethyl-amino-pyrrolidinyl-carbonyl, thiomorpholino-methyl, methoxy-ethyl-piperazinyl-methyl, methoxy-ethyl-amino-carbonyl, cyano-methyl, (2,6-dimethylmorpholino)methyl, (2,6-dimethyl-piperidinyl)ethyl-amino-carbonyl and cyclopropyl-amino-carbonyl.

In another embodiment, $R_1$ is selected from morpholino-ethyl-amino, methyl-amino, methyl-piperazinyl-ethyl-amino, cyclopropyl-amino, hydroxy-ethyl-piperazinyl-amino, isopropyl-amino, dimethyl-amino-ethyl-amino, methyl-piperazinyl-amino, amino, 2,6-dimethyl-morpholino-ethyl-amino, hydroxy-pyridinyl-ethyl-amino, amino-ethyl-amino, 3-oxopiperazin-1-yl-ethyl-amino, hydroxy-ethyl-amino, hydroxy-propyl-amino, methyl-sulfanyl, methoxy, sulfanyl, pyridinyl-ethyl-amino, pyridinyl-methyl-amino, morpholino-methyl-pyridinyl-amino, carboxy-propyl-amino, carboxy-methyl-amino, azetidin-3-yl-amino, azetidin-3-yl-methyl-amino, carboxy-ethyl-amino and hydroxy-pyrrolidinyl.

In another embodiment, $R_2$ is selected from $-R_{11}$, $-CONHR_{11}$, $SO_2NHR_{11}$, $-NHR_{11}$, $-NHC(O)R_{11}$, $-NHS(O)_{0-2}R_{11}$ and $-NHC(O)NHR_{11}$; wherein $R_{11}$ is selected from phenyl, pyridinyl, thiazolyl, benzimidazolyl, isoxazolyl, 1,2,3,4-tetrahydronaphthyl, benzothiazolyl, benzo[d][1,2,3]triazole, 2,3-dihydrobenzofuran and 2,3-dihydro-3,3-dimethylbenzofuran-5-yl; wherein said phenyl, pyridinyl, thiazolyl, isoxazolyl and 2,3-dihydro-3,3-dimethylbenzofuran-5-yl of $R_2$ are optionally substituted with 1 to 3 radicals independently selected from halo, isopropyl, methyl-sulfonyl, hydroxy, methyl-sulfonyl-amino, 1-(2-hydroxyethylamino) cyclopropyl, 3-(3-hydroxypropylamino)cyclobutyl, isopropyl-amino-cyclobutyl, 2-(2-hydroxyethylamino)propan-2-yl, 3-aminoprop-1-enyl, isopropyl-3-aminoprop-1-enyl, isopropyl-amino-propyl, isopropyl-amino-ethyl, hydroxyethyl-3-aminoprop-1-enyl, methyl-amino, 1,2-dihydroxyethyl, 2-hydroxy-ethyl, (3-hydroxyazetidin-1-yl)methyl, (3-methoxyazetidin-1-yl)methyl, 2-methyl-morpholino-methyl, (3-methoxypyrrolidin-1-yl)methyl, (2-hydroxy-2-methylpropylamino)methyl, 1-methyl-1,2,3,6-tetrahydropyridin-4-yl, 1,2,3,6-tetrahydropyridin-4-yl, piperidin-4-yl, (4-ethylpiperazin-1-yl)methyl, pyrrolidiny-1-yl-methyl, 1-(ethylamino)ethyl, 4-(2-hydroxypropyl)-1-piperazinyl, 3-trifluoromethyl-4-methyl-1-piperazinyl, difluoro-methyl, 4-methyl-1-imidazolyl, methyl-sulfonyl-ethyl-amino-carbonyl, hydroxy-propyl-amino-carbonyl, 4-t-butoxy-carbonyl-1-piperazinyl, 4-(1-carboxyethyl)piperazin-1-yl, 4,7-diazaspiro[2.5]octan-7-yl, ethoxy, 4-(tert-butoxycarbonyl)-2-oxopiperazin-1-yl, 4-methyl-2-oxopiperazin-1-yl, 2-oxopiperazin-1-yl, methoxy, ethyl, pyrazolyl, trifluoromethyl, 2-cyanobutan-2-yl, 1-cyanocyclopropyl, 2-hydroxypropan-2-yl, difluoromethyl, 3-ethylpentan-3-yl, methyl-piperazinyl, ethyl-piperazinyl, t-butyl, t-butoxy, 1,2-dihydroxypropyl, 2-hydroxymethyl-ethyl, cyclopropyl-1-piperazinyl, 4-methyl-sulfonyl-ethyl-1-piperazinyl, 2-hydroxy-propyl-amino-methyl, (tetrahydrofuran-2-ylamino)methyl, (2,3-dihydroxypropylamino) methyl), (1,3-dihydroxypropan-2-ylamino)methyl, (1-hydroxy-2-methylpropan-2-ylamino)methyl, cyclobutyl-amino-methyl, 4-hydroxy-piperidinyl, (1-hydroxypropan-2-ylamino)methyl, dimethyl-amino-amino-methyl, methoxy-amino-methyl, hydroxy-amino-methyl, 2-hydroxy-methyl-pyrrolidin-1-yl-methyl, pyrrolidinyl-ethoxy, 3-hydroxy-pyrrolidinyl, 3-hydroxyazetidin-1-yl, 3-(methoxy-carbonyl)-4-methylpiperazin-1-yl, 4-methylpiperazin-1-yl, 4-methyl-3-hydroxymethyl-piperazin-1-yl, 4-methoxy-carbonyl-piperidinyl, 4-carboxy-piperidinyl, piperazinyl, 4-(2,2,2-trifluoroethyl)piperazin-1-yl, 2-hydroxy-cyclopent-1-yl-amino-methyl, amino-carbonyl-methyl, dimethyl-amino-propyl(methyl)-amino, (2-(dimethylamino)ethyl)(methyl) amino, methoxy-ethyl(methyl)amino, dimethyl-amino-ethoxy, nitro, 1-methyl-4-piperidinyloxy, morpholino, 2-methyl-morpholino, 4-ethyl-piperazin-1-yl-methyl, ethyl-amino-methyl, cyclopropyl-amino-methyl, diethyl-amino-ethyl, azetidin-1-ylmethyl, 3-hydroxy-pyrrolidin-1-yl-methyl, hydroxy-ethyl-amino-methyl, propyl-amino-methyl, 3-hydroxy-azetidin-1-ylmethyl, 4-methoxyethyl-1-piperazinyl, methoxy-ethyl-amino-methyl, butyl-amino-ethyl, t-butyl-amino-methyl, hydroxy-cyclohexyl-amino-methyl, amino-methyl, hydroxy-propyl-amino-methyl, hydroxy-ethyl(methyl)amino-methyl, 4-hydroxypropyl-1-piperazinyl, 4-carboxy-methyl-piperazinyl, dimethyl-amino-methyl, isopropyl-amino-methyl, 4-dimethyl-amino-carbonyl-methyl-1-piperazinyl, 4-(2-hydroxypropyl)piperazin-1-yl, hydroxy-ethyl-piperazinyl, methyl, cyclopropyl, halo, trifluoromethoxy, difluoromethoxy, 2-fluoropropan-2-yl, 2-methoxy-propan-2-yl, 1,1-difluoroethyl, 1-methyl-1-fluoroethyl, 1-methyl-1-methoxy-ethyl, 2-hydroxypropan-2-yl, 2-methoxypropan-2-yl, 2-cyanopropan-2-yl, 3-cyanopropan-2-yl, 2,3-difluoropropan-2-yl and cyano-cyclopropyl.

Preferred compounds are selected from N-(4-Methyl-3-{2-methyl-4-[6-(2-morpholin-4-yl-ethylamino)-pyrimnidin-4-yl]-2H-pyrazol-3-ylamino}-phenyl)-3-trifluoromethyl-benzamide, N-(4-Methyl-3-{1-methyl-4-[6-(2-morpholin-4-yl-ethylamino)-pyrimnidin-4-yl]-1H-pyrazol-3-ylamino}-phenyl)-3-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-{4-Methyl-3-[2-(6-methylamino-pyrimidin-4-yl)-2H-pyrazol-3-ylamino]phenyl}-3-(4-methyl-piperazin-1-yl)-5-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-[4-Methyl-3-(5-methyl-2-{6-[2-(4-methyl-piperazin-1-yl)-ethylamino]-pyrimidin-4-yl}-2H-pyrazol-3-ylamino)-phenyl]-3-trifluoromethyl-benzamide, N-{3-[2-(6-Cyclopropylamino-pyrimidin-4-yl)-5-methyl-2H-pyrazol-3-ylamino]-4-methyl-phenyl}-3-trifluoromethyl-benzamide, N-{3-[4-(6-Cyclopropylamino-pyrimidin-4-yl)-2-methyl-2H-pyrazol-3-ylamino]-4-methyl-phenyl}-3-trifluoromethyl-benzamide, N-[4-Methyl-3-(2-methyl-4-{6-[2-(4-methyl-piperazin-1-yl)-ethylamino]-pyrimnidin-4-yl}-2H-pyrazol-3-ylamino)-phenyl]-3-trifluoromethyl-benzamide, N-(4-Methyl-3-{2-methyl-4-[6-(2-morpholin-4-yl-ethylamino)-pyrimnidin-4-yl]-2H-pyrazol-3-ylamino}-phenyl)-3-trifluoromethyl-benzamide, N-{3-[4-(6-Cyclopropylamino-pyrimidin-4-yl)-1-methyl-1H-pyrazol-3-ylamino]-4-methyl-phenyl}-3-trifluoromethyl-benzamide, N-[4-Methyl-3-(1-methyl-4-{6-[2-(4-methyl-piperazin-1-yl)-ethylamino]-pyrimnidin-4-yl}-1H-pyrazol-3-ylamino)-phenyl]-3-trifluoromethyl-benzamide, N-(4-Methyl-3-{1-methyl-4-[6-(2-morpholin-4-yl-ethylamino)-pyrimidin-4-yl]-1H-pyrazol-3-ylamino}-phenyl)-3-trifluoromethyl-benzamide, N-{3-[2-(6-Cyclopropylamino-pyrimidin-4-yl)-5-methyl-2H-pyrazol-3-ylamino]-4-methyl-phenyl}-3-(4-methyl-piperazin-1-yl)-5-trifluoromethyl-benzamide, N-{4-Methyl-3-[5-methyl-2-(6-methylamino-pyrimidin-4-yl)-2H-pyrazol-3-ylamino]-phenyl}-3-(4-methyl-piperazin-1-yl)-5-trifluoromethyl-benzamide, N-{3-[2-(6-Cyclopropylamino-pyrimidin-4-yl)-5-methyl-2H-pyrazol-3-ylamino]-4-methyl-phenyl}-3-(4-ethyl-piperazin-1-yl)-5-trifluoromethyl-benzamide, 3-(4-Ethyl-piperazin-1-yl)-N-{4-methyl-3-[5-methyl-2-(6- methylamino-pyrimidin-4-yl)-2H-pyrazol-3-ylamino]-phenyl}-5-trifluoromethyl-benzamide, 3-(4-Ethyl-piperazin-1-yl)-N-(4-methyl-3-{5-methyl-2-[6-(4-methyl-piperazin-1-ylamino)-pyrimnidin-4-yl]-2H-pyrazol-3-ylamino}-phenyl)-5-trifluoromethyl-benzamide, N-(4-Methyl-3-{5-methyl-2-[6-(4-methyl-piperazin-1-ylamino)-pyrimnidin-4-yl]-2H-pyrazol-3-ylamino}-phenyl)-3-(4-methyl-piperazin-1-yl)-5-trifluoromethyl-benzamide, N-{4-Methyl-3-[2-(6-methylamino-pyrimidin-4-yl)-2H-pyrazol-3-ylamino]-phenyl}-3-(4-methyl-piperazin-1-yl)-5-trifluoromethyl-benzamide, 3-(4-Ethyl-piperazin-1-yl)-N-{4-methyl-3-[2-(6-methylamino-pyrimidin-4-yl)-2H-pyrazol-3-ylamino]-phenyl}-5-trifluoromethyl-benzamide, N-(4-Methyl-3-{5-methyl-2-[6-(4-methyl-piperazin-1-ylamino)-pyrimidin-4-yl]-2H-pyrazol-3-ylamino}-phenyl)-3-trifluoromethyl-benzamide, 5-Methyl-6-[2-(6-methylamino-pyrimidin-4-yl)-2H-pyrazol-3-ylamino]-pyridine-2-carboxylic acid (3-trifluoromethyl-phenyl)-amide, 5-Methyl-6-[5-methyl-2-(6-methylamino-pyrimidin-4-yl)-2H-pyrazol-3-ylamino]-pyridine-2-carboxylic acid (3-trifluoromethyl-phenyl)-amide, 5-Methyl-6-{2-[6-(2-morpholin-4-yl-ethylamino)-pyrimidin-4-yl]-2H-pyrazol-3-ylamino}-pyridine-2-carboxylic acid (3-trifluoromethyl-phenyl)-amide, N-(4-Methyl-3-{2-[6-(2-morpholin-4-yl-ethylamino)-pyrimidin-4-yl]-2H-pyrazol-3-ylamino}-phenyl)-3-trifluoromethyl-benzamide, N-{3-[2-(6-Cyclopropylamino-pyrimidin-4-yl)-2H-pyrazol-3-ylamino]-4-methyl-phenyl}-3-trifluoromethyl-benzamide, N-{3-[2-(6-Amino-pyrimnidin-4-yl)-2H-pyrazol-3-ylamino]-4-methyl-phenyl}-3-trifluoromethyl-benzamide, N-{3-[2-(6-Cyclopropylamino-pyrimidin-4-yl)-2H-pyrazol-3-ylamino]-4-methyl-phenyl}-3-(4-methyl-piperazin-1-yl)-5-trifluoromethyl-benzamide, N-[3-(2-{6-[2-(2,6-Dimethyl-morpholin-4-yl)-ethylamino]-pyrimnidin-4-yl}-5-methyl-2H-pyrazol-3-ylamino)-4-methyl-phenyl]-3-trifluoromethyl-benzamide, N-[3-(2-{6-[2-(4-Hydroxy-piperidin-1-yl)-ethylamino]-pyrimnidin-4-yl}-5-methyl-2H-pyrazol-3-ylamino)-4-methyl-phenyl]-3-trifluoromethyl-benzamide, N-[4-Methyl-3-(5-methyl-2-{6-[2-(3-oxo-piperazin-1-yl)-ethylamino]-pyrimnidin-4-yl}-2H-pyrazol-3-ylamino)-phenyl]-3-trifluoromethyl-benzamide, N-(3-{2-[6-(2-Amino-ethylamino)-pyrimidin-4-yl]-5-methyl-2H-pyrazol-3-ylamino}-4-methyl-phenyl)-3-trifluoromethyl-benzamide, 2-tert-Butyl-N-(4-methyl-3-{2-[6-(2-morpholin-4-yl-ethylamino)-pyrimidin-4-yl]-2H-pyrazol-3-ylamino}-phenyl)-isonicotinamide, 2-tert-Butyl-N-(4-methyl-3-{5-methyl-2-[6-(2-morpholin-4-yl-ethylamino)-pyrimidin-4-yl]-2H-pyrazol-3-ylamino}-phenyl)-isonicotinamide, N-{4-Methyl-3-[4-(6-methylamino-pyrimidin-4-yl)-1H-pyrazol-3-ylamino]-phenyl}-3-trifluoromethyl-benzamide, N-{4-Methyl-3-[4-(6-methylamino-pyrimidin-4-yl)-1-(2-morpholin-4-yl-ethyl)-1H-pyrazol-3-ylamino]-phenyl}-3-trifluoromethyl-benzamide, N-{4-Methyl-3-[1-methyl-4-(6-methylamino-pyrimidin-4-yl)-1H-pyrazol-3-ylamino]-phenyl}-3-(4-methyl-piperazin-1-yl)-5-trifluoromethyl-benzamide, 3-[4-(2-Hydroxy-ethyl)-piperazin-1-yl]-N-{4-methyl-3-[1-methyl-4-(6-methylamino-pyrimidin-4-yl)-1H-pyrazol-3-ylamino]-phenyl}-5-trifluoromethyl-benzamide, N-{3-[4-(6-Cyclopropylamino-pyrimidin-4-yl)-1-methyl-1H-pyrazol-3-ylamino]-4-methyl-phenyl}-3-(4-methyl-piperazin-1-yl)-5-trifluoromethyl-benzamide, N-{3-[4-(6-Cyclopropylamino-pyrimidin-4-yl)-1-methyl-1H-pyrazol-3-ylamino]-4-methyl-phenyl}-3-[4-(2-hydroxy-ethyl)-piperazin-1-yl]-5-trifluoromethyl-benzamide, N-(3-{2-[6-(2-Hydroxy-ethylamino)-pyrimidin-4-yl]-5-methyl-2H-pyrazol-3-ylamino}-4-methyl-phenyl)-3-trifluoromethyl-benzamide, N-{4-Methyl-3-[5-methyl-2-(6-methylsulfanyl-pyrimidin-4-yl)-2H-pyrazol-3-ylamino]-phenyl}-3-trifluoromethyl-benzamide, N-{3-[2-(2,3-Dihydro-imidazo[1,2-c]pyrimidin-7-yl)-5-methyl-2H-pyrazol-3-ylamino]-4-methyl-phenyl}-3-trifluoromethyl-benzamide, 2-tert-Butyl-N-(4-methyl-3-{5-methyl-2-[6-(4-methyl-piperazin-1-ylamino)-pyrimidin-4-yl]-2H-pyrazol-3-ylamino}-phenyl)-isonicotinamide, N-{3-[2-(6-Methoxy-pyrimidin-4-yl)-5-methyl-2H-pyrazol-3-ylamino]-4-methyl-phenyl}-3-trifluoromethyl-benzamide, N-{4-Methyl-3-[5-methyl-2-(6-methylamino-pyrimidin-4-yl)-2H-pyrazol-3-ylamino]-phenyl}-3-trifluoromethyl-benzamide, N-{3-[2-(6-Amino-pyrimidin-4-yl)-5-methyl-2H-pyrazol-3-ylamino]-4-methyl-phenyl}-3-trifluoromethyl-benzamide, N-{4-Methyl-3-[2-(6-methylamino-pyrimidin-4-yl)-2H-pyrazol-3-ylamino]-phenyl}-3-trifluoromethyl-benzamide, N-{3-[2-(6-Mercapto-pyrimidin-4-yl)-5-methyl-2H-pyrazol-3-ylamino]-4-methyl-phenyl}-3-trifluoromethyl-benzamide, N-(4-Methyl-3-{5-methyl-2-[6-(2-pyridin-3-yl-ethylamino)-pyrimidin-4-yl]-2H-pyrazol-3-ylamino}-phenyl)-3-trifluoromethyl-benzamide, 4-(6-{3-Methyl-5-[2-methyl-5-(3-trifluoromethyl-benzoylamino)-phenylamino]-pyrazol-1-yl}-pyrimidin-4-ylamino)-butyric acid, (6-{3-Methyl-5-[2-methyl-5-(3-trifluoromethyl-benzoylamino)-phenylamino]-pyrazol-1-yl}-pyrimidin-4-ylamino)-acetic acid, N-(3-{2-[6-(Azetidin-3-ylamino)-pyrimidin-4-yl]-5-methyl-2H-pyrazol-3-ylamino}-4-methyl-phenyl)-3-trifluoromethyl-benzamide, 3-(6-{3-Methyl-5-[2-methyl-5-(3-trifluoromethyl-benzoylamino)-phenylamino]-pyrazol-1-yl}-pyrimidin-4-ylamino)-propionic acid, N-(3-{2-[6-(3-Hydroxy-pyrrolidin-1-yl)-pyrimidin-4-yl]-5-methyl-2H-pyrazol-3-ylamino}-4-methyl-phenyl)-3-trifluoromethyl-benzamide, N-[3-(2-{6-[(Azetidin-3-ylmethyl)-amino]-pyrimidin-4-yl}-5-methyl-2H-pyrazol-3-ylamino)-4-methyl-phenyl]-3-trifluoromethyl-benzamide, N-[4-Methyl-3-(5-methyl-2-{6-[(pyridin-2-ylmethyl)-amino]-pyrimidin-4-yl}-2H-pyrazol-3-ylamino)-phenyl]-3-trifluoromethyl-benzamide, 4-Methyl-3-[5-methyl-2-(6-methylamino-pyrimidin-4-yl)-2H-pyrazol-3-ylamino]-N-[3-(4-methyl-piperazin-1-yl)-5-trifluoromethyl-phenyl]-benzamide, (4-Methyl-3-{5-methyl-2-[6-(5-morpholin-4-ylmethyl-pyridin-2-ylamino)-pyrimidin-4-yl]-2H-pyrazol-3-ylamino}-phenyl)-carbamic acid tert-butyl ester, 5-Methyl-N-(4-methyl-3-{5-methyl-2-[6-(5-morpholin-4-ylmethyl-pyridin-2-ylamino)-pyrimidin-4-yl]-2H-pyrazol-3-ylamino}-phenyl)-nicotinamide, 3-Cyclopropyl-isoxazole-5-carboxylic acid (4-methyl-3-{5-methyl-2-[6-(5-morpholin-4-ylmethyl-pyridin-2-ylamino)-pyrimidin-4-yl]-2H-pyrazol-3-ylamino}-phenyl)-amide, 3,4-Dichloro-N-(4-methyl-3-{5-methyl-2-[6-(2-morpholin-4-yl-ethylamino)-pyrimidin-4-yl]-2H-pyrazol-3-ylamino}-phenyl)-benzamide, 3-Fluoro-N-(4-methyl-3-{5-methyl-2-[6-(2-morpholin-4-yl-ethylamino)-pyrimidin-4-yl]-2H-pyrazol-3-ylamino}-phenyl)-5-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-4-trifluoromethyl-benzamide, 3,5-Dichloro-N-(4-methyl-3-{5-methyl-2-[6-(2-morpholin-4-yl-ethylamino)-pyrimidin-4-yl]-2H-pyrazol-3-ylamino}-phenyl)-benzamide, 4-Fluoro-N-(4-methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethoxy-benzamide, 3-Bromo-4-chloro-N-(4-methyl-3-{5-methyl-2-[6-(2-morpholin-4-yl-ethylamino)-pyrimidin-4-yl]-2H-pyrazol-3-ylamino}-phenyl)-benzamide, 3-Difluoromethoxy-N-(4-methyl-3-{5-methyl- 2-[6-(2-morpholin-4-yl-ethylamino)-pyrimidin-4-yl]-2H-pyrazol-3-ylamino}-phenyl)-benzamide, 3-Chloro-N-(4-methyl-3-{5-methyl-2-[6-(2-morpholin-4-yl-ethylamino)-pyrimnidin-4-yl]-2H-pyrazol-3-ylamino}-phenyl)-benzamide, 3-(1-Hydroxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1-Methoxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 2-(Cyano-dimethyl-methyl)-N-(4-methyl-3-{5-methyl-2-[6-(2-morpholin-4-yl-ethylamino)-pyrimnidin-4-yl]-2H-pyrazol-3-ylamino}-phenyl)-isonicotinamide, 3-(Cyano-dimethyl-methyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1,1-Difluoro-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1-Cyano-cyclopropyl)-N-(4-methyl-3-{5-methyl-2-[6-(2-morpholin-4-yl-ethylamino)-pyrimnidin-4-yl]-2H-pyrazol-3-ylamino}-phenyl)-benzamide, 3,3-Dimethyl-2,3-dihydro-benzofuran-5-carboxylic acid (4-methyl-3-{5-methyl-2-[6-(2-morpholin-4-yl-ethylamino)-pyrimidin-4-yl]-2H-pyrazol-3-ylamino}-phenyl)-amide, 4-Methyl-N-(4-methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, 2-(Cyano-dimethyl-methyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 3-(Cyano-dimethyl-methyl)-N-(4-methyl-3-{5-methyl-2-[6-(4-methyl-piperazin-1-ylamino)-pyrimidin-4-yl]-2H-pyrazol-3-ylamino}-phenyl)-benzamide, 3-(1-Cyano-cyclopropyl)-N-(4-methyl-3-{5-methyl-2-[6-(4-methyl-piperazin-1-ylamino)-pyrimidin-4-yl]-2H-pyrazol-3-ylamino}-phenyl)-benzamide, 2-(1-Cyano-cyclopropyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 3-(1,1-Difluoro-ethyl)-N-(4-methyl-3-{5-methyl-2-[6-(4-methyl-piperazin-1-ylamino)-pyrimnidin-4-yl]-2H-pyrazol-3-ylamino}-phenyl)-benzamide, 3-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-benzamide, 3-(1-Methoxy-1-methyl-ethyl)-N-(4-methyl-3-{5-methyl-2-[6-(4-methyl-piperazin-1-ylamino)-pyrimnidin-4-yl]-2H-pyrazol-3-ylamino}-phenyl)-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid ethyl ester, 1-(6-Cyclopropylamino-pyrimidin-4-yl)-5-[2-methyl-5-(3-trifluoromethyl-benzoylamino)-phenylamino]-1H-pyrazole-3-carboxylic acid methylamide, N-{3-[2-(6-Cyclopropylamino-pyrimidin-4-yl)-5-hydroxymethyl-2H-pyrazol-3-ylamino]-4-methyl-phenyl}-3-trifluoromethyl-benzamide, N-{3-[2-(6-Cyclopropylamino-pyrimidin-4-yl)-5-dimethylaminomethyl-2H-pyrazol-3-ylamino]-4-methyl-phenyl}-3-trifluoromethyl-benzamide, N-{3-[2-(6-Cyclopropylamino-pyrimidin-4-yl)-5-methylaminomethyl-2H-pyrazol-3-ylamino]-4-methyl-phenyl}-3-trifluoromethyl-benzamide, N-{3-[2-(6-Cyclopropylamino-pyrimidin-4-yl)-5-morpholin-4-ylmethyl-2H-pyrazol-3-ylamino]-4-methyl-phenyl}-3-trifluoromethyl-benzamide, N-(3-{2-(6-Cyclopropylamino-pyrimidin-4-yl)-5-[(2-di-ethylamino-ethylamino)-methyl]-2H-pyrazol-3-ylamino}-4-methyl-phenyl)-3-trifluoromethyl-benzamide, N-{3-[2-(6-Cyclopropylamino-pyrimidin-4-yl)-5-(4-methyl-piperazin-1-ylmethyl)-2H-pyrazol-3-ylamino]-4-methyl-phenyl}-3-trifluoromethyl-benzamide, N-[3-(2-(6-Cyclopropylamino-pyrimidin-4-yl)-5-{[2-(4-methyl-piperazin-1-yl)-ethylamino]-methyl}-2H-pyrazol-3-ylamino)-4-methyl-phenyl]-3-trifluoromethyl-benzamide, N-(3-{2-(6-Cyclopropylamino-pyrimidin-4-yl)-5-[(3-dimethylamino-propylamino)-methyl]-2H-pyrazol-3-ylamino}-4-methyl-phenyl)-3-trifluoromethyl-benzamide, N-{3-[2-(6-Cyclopropylamino-pyrimidin-4-yl)-5-ethylaminomethyl-2H-pyrazol-3-ylamino]-4-methyl-phenyl}-3-trifluoromethyl-benzamide, N-(3-{2-(6-Cyclopropylamino-pyrimidin-4-yl)-5-[(2,2,2-trifluoro-ethylamino)-methyl]-2H-pyrazol-3-ylamino}-4-methyl-phenyl)-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-dimethylamino-ethyl)-amide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-piperidin-1-yl-ethyl)-amide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-morpholin-4-yl-ethyl)-amide, N-{3-[2-(6-Cyclopropylamino-pyrimidin-4-yl)-5-(morpholine-4-carbonyl)-2H-pyrazol-3-ylamino]-4-methyl-phenyl}-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid amide, 1-(6-Cyclopropylamino-pyrimidin-4-yl)-5-[2-methyl-5-(3-trifluoromethyl-benzoylamino)-phenylamino]-1H-pyrazole-3-carboxylic acid dimethylamide, N-{3-[2-(6-Cyclopropylamino-pyrimidin-4-yl)-5-(3-dimethylamino-pyrrolidine-1-carbonyl)-2H-pyrazol-3-ylamino]-4-methyl-phenyl}-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-methoxy-ethyl)-amide, 1-(6-Methylamino-pyrimidin-4-yl)-5-[2-methyl-5-(3-trifluoromethyl-benzoylamino)-phenylamino]-1H-pyrazole-3-carboxylic acid methylamide, N-{4-Methyl-3-[5-methylaminomethyl-2-(6-methylamino-pyrimidin-4-yl)-2H-pyrazol-3-ylamino]-phenyl}-3-trifluoromethyl-benzamide, N-{4-Methyl-3-[2-(6-methylamino-pyrimidin-4-yl)-5-morpholin-4-ylmethyl-2H-pyrazol-3-ylamino]-phenyl}-3-trifluoromethyl-benzamide, 1-(6-Methylamino-pyrimidin-4-yl)-5-{2-methyl-5-[3-(4-methyl-piperazin-1-yl)-5-trifluoromethyl-benzoylamino]-phenylamino}-1H-pyrazole-3-carboxylic acid methylamide, 1-(6-Methylamino-2-morpholin-4-yl-pyrimidin-4-yl)-5-[2-methyl-5-(3-trifluoromethyl-benzoylamino)-phenylamino]-1H-pyrazole-3-carboxylic acid methylamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5{-5-[3-(Cyano-dimethyl-methyl)-benzoylamino]-2-methyl-phenylamino}-1-(6-methylamino-pyrimidin-4-yl)-1H-pyrazole-3-carboxylic acid methylamide, 5-{5-[3-(1-Cyano-cyclopropyl)-benzoylamino]-2-methyl-phenylamino}-1-(6-methylamino-pyrimidin-4-yl)-1H-pyrazole-3-carboxylic acid methylamide, N-{3-[5-Cyanomethyl-2-(6-methylamino-pyrimidin-4-yl)-2H-pyrazol-3-ylamino]-4-methyl-phenyl}-3-trifluoromethyl-benzamide, 1-(6-Methylamino-pyrimidin-4-yl)-5-[2-methyl-5-(3-trifluoromethyl-benzoylamino)-phenylamino]-1H-pyrazole-3-carboxylic acid (2-morpholin-4-yl-ethyl)-amide, 1-(6-Methylamino-pyrimidin-4-yl)-5-[2-methyl-5-(3-trifluoromethyl-benzoylamino)-phenylamino]-1H-pyrazole-3-carboxylic acid cyclopropylamide, 5-tert-Butyl-N-(4-methyl-3-{5-methyl-2-[6-(2-morpholin-4-yl-ethylamino)- pyrimidin-4-yl]-2H-pyrazol-3-ylamino}-phenyl)-nicotinamide, 5-tert-Butyl-N-(4-methyl-3-{2-[6-(2-morpholin-4-yl-ethylamino)-pyrimidin-4-yl]-2H-pyrazol-3-ylamino}-phenyl)-nicotinamide, 5-tert-Butyl-N-(4-methyl-3-{5-methyl-2-[6-(4-methyl-piperazin-1-ylamino)-pyrimidin-4-yl]-2H-pyrazol-3-ylamino}-phenyl)-nicotinamide, N-[5-(1-Fluoro-1-methyl-ethyl)-pyridin-3-yl]-4-methyl-3-[5-methyl-2-(6-methylamino-pyrimidin-4-yl)-2H-pyrazol-3-ylamino]-benzamide, N-[5-(1-Methoxy-1-methyl-ethyl)-pyridin-3-yl]-4-methyl-3-[5-methyl-2-(6-methylamino-pyrimidin-4-yl)-2H-pyrazol-3-ylamino]-benzamide, N-[5-(1-Fluoro-1-methyl-ethyl)-pyridin-3-yl]-4-methyl-3-{5-methyl-2-[6-(4-methyl-piperazin-1-ylamino)-pyrimnidin-4-yl]-2H-pyrazol-3-ylamino}-benzamide, N-[5-(1-Methoxy-1-methyl-ethyl)-pyridin-3-yl]-4-methyl-3-{5-methyl-2-[6-(4-methyl-piperazin-1-ylamino)-pyrimidin-4-yl]-2H-pyrazol-3-ylamino}-benzamide, 4-Methyl-3-{5-methyl-2-[6-(4-methyl-piperazin-1-ylamino)-pyrimnidin-4-yl]-2H-pyrazol-3-ylamino}-N-(4-trifluoromethyl-pyridin-2-yl)-benzamide, N-(3-tert-Butyl-phenyl)-4-methyl-3-{5-methyl-2-[6-(4-methyl-piperazin-1-ylamino)-pyrimnidin-4-yl]-2H-pyrazol-3-ylamino}-benzamide, N-(2-tert-Butyl-pyridin-4-yl)-4-methyl-3-[5-methyl-2-(6-methylamino-pyrimidin-4-yl)-2H-pyrazol-3-ylamino]-benzamide, N-(3-tert-Butyl-phenyl)-4-methyl-3-[5-methyl-2-(6-methylamino-pyrimidin-4-yl)-2H-pyrazol-3-ylamino]-benzamide, N-[3-(Cyano-dimethyl-methyl)-phenyl]-4-methyl-3-[5-methyl-2-(6-methylamino-pyrimidin-4-yl)-2H-pyrazol-3-ylamino]-benzamide, 4-Methyl-3-[5-methyl-2-(6-methylamino-pyrimidin-4-yl)-2H-pyrazol-3-ylamino]-N-(4-trifluoromethyl-pyridin-2-yl)-benzamide, (6{-5-[5-(6-tert-Butyl-1H-benzoimidazol-2-yl)-2-methyl-phenylamino]-3-methyl-pyrazol-1-yl}-pyrimnidin-4-yl)-(4-methyl-piperazin-1-yl)-amine, (6-{3-Methyl-5-[2-methyl-5-(6-trifluoromethyl-1H-benzoimidazol-2-yl)-phenylamino]-pyrazol-1-yl}-pyrimnidin-4-yl)-(4-methyl-piperazin-1-yl)-amine, N-[3-(1,1-Difluoro-ethyl)-phenyl]-4-methyl-3-{5-methyl-2-[6-(4-methyl-piperazin-1-ylamino)-pyrimidin-4-yl]-2H-pyrazol-3-ylamino}-benzamide, N-[3-(1,1-Difluoro-ethyl)-phenyl]-4-methyl-3-{5-methyl-2-[6-(4-methyl-piperazin-1-ylamino)-pyrimidin-4-yl]-2H-pyrazol-3-ylamino}-benzamide, 4-Fluoro-N-{4-methyl-3-[2-(6-methylamino-pyrimidin-4-yl)-5-morpholin-4-ylmethyl-2H-pyrazol-3-ylamino]-phenyl}-3-trifluoromethyl-benzamide, 4-Fluoro-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethyl-benzamide, 5-[5-(4-Fluoro-3-trifluoromethyl-benzoylamino)-2-methyl-phenylamino]-1-[6-(2-morpholin-4-yl-ethylamino)-pyrimidin-4-yl]-1H-pyrazole-3-carboxylic acid methylamide, 5-[5-(4-Fluoro-3-trifluoromethyl-benzoylamino)-2-methyl-phenylamino]-1-[6-(4-methyl-piperazin-1-ylamino)-pyrimidin-4-yl]-1H-pyrazole-3-carboxylic acid methylamide, 5-[5-(4-Fluoro-3-trifluoromethyl-benzoylamino)-2-methyl-phenylamino]-1-(6-methylamino-pyrimidin-4-yl)-1H-pyrazole-3-carboxylic acid (2-morpholin-4-yl-ethyl)-amide, 5-[5-(2-tert-Butyl-pyridin-4-ylcarbamoyl)-2-methyl-phenylamino]-1-[6-(4-methyl-piperazin-1-ylamino)-pyrimidin-4-yl]-1H-pyrazole-3-carboxylic acid methylamide, 5-{5-[3-(1,1-Difluoro-ethyl)-benzoylamino]-2-methyl-phenylamino}-1-[6-(4-methyl-piperazin-1-ylamino)-pyrimidin-4-yl]-1H-pyrazole-3-carboxylic acid (2-morpholin-4-yl-ethyl)-amide, N-(4-Methyl-3-{2-[6-(4-methyl-piperazin-1-ylamino)-pyrimidin-4-yl]-5-morpholin-4-ylmethyl-2H-pyrazol-3-ylamino}-phenyl)-3-trifluoromethyl-benzamide, 3-(1,1-Difluoro-ethyl)-N-(4-methyl-3-{2-[6-(4-methyl-piperazin-1-ylamino)-pyrimnidin-4-yl]-5-morpholin-4-ylmethyl-2H-pyrazol-3-ylamino}-phenyl)-benzamide, 3-(Cyano-dimethyl-methyl)-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-benzamide, 2-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-isonicotinamide, 5-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-nicotinamide, 2-(Cyano-dimethyl-methyl)-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-isonicotinamide, 2-(Cyano-dimethyl-methyl)-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-isonicotinamide, 3-(Cyano-dimethyl-methyl)-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-benzamide, 2-tert-Butyl-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-isonicotinamide, 2-tert-Butyl-N-{3-[5-[2-(2,6-dimethyl-piperidin-1-yl)-ethylcarbamoyl]-2-(6-methylamino-pyrimidin-4-yl)-2H-pyrazol-3-ylamino]-4-methyl-phenyl}-isonicotinamide, 2-(Cyano-dimethyl-methyl)-N-{4-methyl-3-[5-methyl-2-(6-methylamino-pyrimidin-4-yl)-2H-pyrazol-3-ylamino]-phenyl}-isonicotinamide, 3-(Cyano-dimethyl-methyl)-N-{4-methyl-3-[5-methyl-2-(6-methylamino-pyrimidin-4-yl)-2H-pyrazol-3-ylamino]-phenyl}-benzamide, 3-(1-Cyano-cyclopropyl)-N-{4-methyl-3-[5-methyl-2-(6-methylamino-pyrimidin-4-yl)-2H-pyrazol-3-ylamino]-phenyl}-benzamide, 2-(1-Cyano-cyclopropyl)-N-{4-methyl-3-[5-methyl-2-(6-methylamino-pyrimidin-4-yl)-2H-pyrazol-3-ylamino]-phenyl}-isonicotinamide, 3-(1-Cyano-1-methyl-propyl)-N-{4-methyl-3-[5-methyl-2-(6-methylamino-pyrimidin-4-yl)-2H-pyrazol-3-ylamino]-phenyl}-benzamide, 2-tert-Butyl-N-{4-methyl-3-[5-methyl-2-(6-methylamino-pyrimidin-4-yl)-2H-pyrazol-3-ylamino]-phenyl}-isonicotinamide, 3-(1,1-Difluoro-ethyl)-N-{4-methyl-3-[5-methyl-2-(6-methylamino-pyrimidin-4-yl)-2H-pyrazol-3-ylamino]-phenyl}-benzamide, 3-(1-Hydroxy-1-methyl-ethyl)-N-{4-methyl-3-[5-methyl-2-(6-methylamino-pyrimidin-4-yl)-2H-pyrazol-3-ylamino]-phenyl}-benzamide, 3-(1-Methoxy-1-methyl-ethyl)-N-{4-methyl-3-[5-methyl-2-(6-methylamino-pyrimidin-4-yl)-2H-pyrazol-3-ylamino]-phenyl}-benzamide, 5-tert-Butyl-N-{4-methyl-3-[5-methyl-2-(6-methylamino-pyrimidin-4-yl)-2H-pyrazol-3-ylamino]-phenyl}-nicotinamide, 2-tert-Butyl-N-{4-methyl-3-[5-methyl-2-(6-methylamino-pyrimidin-4-yl)-2H-pyrazol-3-ylamino]-phenyl}-isonicotinamide, 2,2-Dimethyl-2,3-dihydro-benzofuran-7-carboxylic acid {4-methyl-3-[5-methyl-2-(6-methylamino-pyrimidin-4-yl)-2H-pyrazol-3-ylamino]-phenyl}-amide, 2-(1-Fluoro-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 2-(1-Fluoro-1-methyl-ethyl)-N-{4-methyl-3-[5-methyl-2-(6-methylamino-pyrimidin-4-yl)-2H-pyrazol-3-ylamino]-phenyl}-isonicotinamide, 2-(1-Fluoro-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 2-(1-Methoxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 2-(1-Methoxy-ethyl)-N-{4-methyl-3-[5-methyl-2-(6-methylamino-pyrimidin-4-yl)-

2H-pyrazol-3-ylamino]-phenyl}-isonicotinamide, 2-(1-Methoxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 2-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 2-(1-Hydroxy-1-methyl-ethyl)-N-{4-methyl-3-[5-methyl-2-(6-methylamino-pyrimidin-4-yl)-2H-pyrazol-3-ylamino]-phenyl}-isonicotinamide, 2-(1-Hydroxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 3-(1-Cyano-cyclopropyl)-N-{4-methyl-3-[2-(6-methylamino-pyrimidin-4-yl)-2H-pyrazol-3-ylamino]-phenyl}-benzamide, 3-(Cyano-dimethyl-methyl)-N-{4-methyl-3-[2-(6-methylamino-pyrimidin-4-yl)-2H-pyrazol-3-ylamino]-phenyl}-benzamide, 2-(Cyano-dimethyl-methyl)-N-{4-methyl-3-[2-(6-methylamino-pyrimidin-4-yl)-2H-pyrazol-3-ylamino]-phenyl}-isonicotinamide, 2-(1-Cyano-cyclopropyl)-N-{4-methyl-3-[2-(6-methylamino-pyrimidin-4-yl)-2H-pyrazol-3-ylamino]-phenyl}-isonicotinamide, 3-(1,1-Difluoro-ethyl)-N-{4-methyl-3-[2-(6-methylamino-pyrimidin-4-yl)-2H-pyrazol-3-ylamino]-phenyl}-benzamide, 3-(1-Methoxy-1-methyl-ethyl)-N-{4-methyl-3-[2-(6-methylamino-pyrimidin-4-yl)-2H-pyrazol-3-ylamino]-phenyl}-benzamide, 3-(1-Hydroxy-1-methyl-ethyl)-N-{4-methyl-3-[2-(6-methylamino-pyrimidin-4-yl)-2H-pyrazol-3-ylamino]-phenyl}-benzamide, 2-(1-Fluoro-1-methyl-ethyl)-N-{4-methyl-3-[2-(6-methylamino-pyrimidin-4-yl)-2H-pyrazol-3-ylamino]-phenyl}-isonicotinamide, 2-(1-Methoxy-1-methyl-ethyl)-N-{4-methyl-3-[2-(6-methylamino-pyrimidin-4-yl)-2H-pyrazol-3-ylamino]-phenyl}-isonicotinamide, 2-(1-Hydroxy-1-methyl-ethyl)-N-{4-methyl-3-[2-(6-methylamino-pyrimidin-4-yl)-2H-pyrazol-3-ylamino]-phenyl}-isonicotinamide, 5-tert-Butyl-N-{4-methyl-3-[2-(6-methylamino-pyrimidin-4-yl)-2H-pyrazol-3-ylamino]-phenyl}-nicotinamide, N-[3-(Cyano-dimethyl-methyl)-phenyl]-4-methyl-3-{5-methyl-2-[6-(4-methyl-piperazin-1-ylamino)-pyrimidin-4-yl]-2H-pyrazol-3-ylamino}-benzamide, N-(2-tert-Butyl-pyridin-4-yl)-4-methyl-3-{5-methyl-2-[6-(4-methyl-piperazin-1-ylamino)-pyrimidin-4-yl]-2H-pyrazol-3-ylamino}-benzamide, 5-(1-Fluoro-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 5-(1-Methoxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 5-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 2-(1,1-Difluoro-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, N-{3-[2-(6-Amino-pyrimidin-4-yl)-5-methyl-2H-pyrazol-3-ylamino]-4-methyl-phenyl}-3-(1,1-difluoro-ethyl)-benzamide, 3-(1,1-Difluoro-ethyl)-N-(4-methyl-3-{5-methyl-2-[6-(5-morpholin-4-ylmethyl-pyridin-2-ylamino)-pyrimidin-4-yl]-2H-pyrazol-3-ylamino}-phenyl)-benzamide, 3-(1,1-Difluoro-ethyl)-N-(4-methyl-3-{5-methyl-2-[6-(4-morpholin-4-ylmethyl-pyridin-2-ylamino)-pyrimidin-4-yl]-2H-pyrazol-3-ylamino}-phenyl)-benzamide, N-{3-[2-(6-Amino-pyrimidin-4-yl)-2H-pyrazol-3-ylamino]-4-methyl-phenyl}-2-tert-butyl-isonicotinamide, 2-tert-Butyl-N-{4-methyl-3-[2-(6-methylamino-pyrimidin-4-yl)-2H-pyrazol-3-ylamino]-phenyl}-isonicotinamide, 2-tert-Butyl-N-[3-(2-{6-[4-(2-hydroxy-ethyl)-piperazin-1-ylamino]-pyrimidin-4-yl}-5-methyl-2H-pyrazol-3-ylamino)-4-methyl-phenyl]-isonicotinamide, 5-tert-Butyl-N-[3-(2-{6-[4-(2-hydroxy-ethyl)-piperazin-1-ylamino]-pyrimidin-4-yl}-5-methyl-2H-pyrazol-3-ylamino)-4-methyl-phenyl]-nicotinamide, N-(2-tert-Butyl-pyridin-4-yl)-3-(2-{6-[4-(2-hydroxy-ethyl)-piperazin-1-ylamino]-pyrimidin-4-yl}-5-methyl-2H-pyrazol-3-ylamino)-4-methyl-benzamide, N-(5-tert-Butyl-pyridin-3-yl)-4-methyl-3-{5-methyl-2-[6-(4-methyl-piperazin-1-ylamino)-pyrimidin-4-yl]-2H-pyrazol-3-ylamino}-benzamide, N-[2-(1-Methoxy-1-methyl-ethyl)-pyridin-4-yl]-4-methyl-3-{5-methyl-2[6-(4-methyl-piperazin-1-ylamino)-pyrimidin-4-yl]-2H-pyrazol-3-ylamino}-benzamide, N-[3-(1,1-Difluoro-ethyl)-phenyl]-4-methyl-3-[5-methyl-2-(6-methylamino-pyrimidin-4-yl)-2H-pyrazol-3-ylamino]-benz amide, N-[2-(Cyano-dimethyl-methyl)-pyridin-4-yl]-4-methyl-3-[5-methyl-2-(6-methylamino-pyrimidin-4-yl)-2H-pyrazol-3-ylamino]-benzamide, 5-(1-Fluoro-1-methyl-ethyl)-N-{4-methyl-3-[2-(6-methylamino-pyrimidin-4-yl)-2H-pyrazol-3-ylamino]-phenyl}-nicotinamide, N-{3-[2-(6-Amino-pyrimidin-4-yl)-2H-pyrazol-3-ylamino]-4-methyl-phenyl}-2-tert-butyl-isonicotinamide, 3-(1,1-Difluoro-ethyl)-N-{4-methyl-3-[2-(6-methylamino-pyrimidin-4-yl)-5-morpholin-4-ylmethyl-2H-pyrazol-3-ylamino]-phenyl}-benzamide, 2-tert-Butyl-N-(3-{2-[6-(2-dimethylamino-acetylamino)-pyrimidin-4-yl]-2H-pyrazol-3-ylamino}-4-methyl-phenyl)-isonicotinamide, N-[2-(1,1-Difluoro-ethyl)-pyridin-4-yl]-4-methyl-3-{5-methyl-2-[6-(2-morpholin-4-yl-ethylamino)-pyrimidin-4-yl]-2H-pyrazol-3-ylamino}-benzamide, 5{-5-[3-(1,1-Difluoro-ethyl)-benzoylamino]-2-methyl-phenylamino}-1-(6-methylamino-pyrimidin-4-yl)-1H-pyrazole-3-carboxylic acid (2-morpholin-4-yl-ethyl)-amide, 5-tert-Butyl-N-{4-methyl-3-[2-(6-methylamino-pyrimidin-4-yl)-5-(2-morpholin-4-yl-ethylcarbamoyl)-2H-pyrazol-3-ylamino]-phenyl}-nicotinamide, 5-tert-Butyl-N-(4-methyl-3-{5-methylcarbamoyl-2-[6-(4-methyl-piperazin-1-ylamino)-pyrimidin-4-yl]-2H-pyrazol-3-ylamino}-phenyl)-nicotinamide, 1-(6-Methylamino-pyrimidin-4-yl)-5-{2-methyl-5-[3-(4-methyl-piperazin-1-yl)-5-trifluoromethyl-benzoylamino]-phenylamino}-1H-pyrazole-3-carboxylic acid methylamide, 1-(6-Methylamino-2-morpholin-4-yl-pyrimidin-4-yl)-5-[2-methyl-5-(3-trifluoromethyl-benzoylamino)-phenylamino]-1H-pyrazole-3-carboxylic acid methylamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5{-5-[3-(Cyano-dimethyl-methyl)-benzoylamino]-2-methyl-phenylamino}-1-(6-methylamino-pyrimidin-4-yl)-1H-pyrazole-3-carboxylic acid methylamide, 5{-5-[3-(1-Cyano-cyclopropyl)-benzoylamino]-2-methyl-phenylamino}-1-(6-methylamino-pyrimidin-4-yl)-1H-pyrazole-3-carboxylic acid methylamide, 1-(6-Methylamino-pyrimidin-4-yl)-5-[2-methyl-5-(3-trifluoromethyl-benzoylamino)-phenylamino]-1H-pyrazole-3-carboxylic acid cyclopropylamide, 2-(Cyano-dimethyl-methyl)-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-(Cyano-dimethyl-methyl)-N-(4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, 5{-5-[3-(Cyano-dimethyl-methyl)-benzoylamino]-2-methyl-phenylamino}-1-[6-(2-morpholin-4-yl-ethylamino)-pyrimidin-4-yl]-1H-pyrazole-3-carboxylic acid methylamide, 5{-5-[3-(Cyano-dimethyl-methyl)-benzoylamino]-2-methyl-phenylamino}-1-[6-(4-methyl-piperazin-1-ylamino)-pyrimnidin-4-yl]-1H-pyrazole-3-carboxylic acid methylamide, 2-tert-Butyl-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-tert-Butyl-N-(4-methyl-3-{2-[6-(2-morpholin-4-yl-ethylamino)-pyrimnidin-4-yl]-5-morpholin-4-ylmethyl-2H-pyrazol-3-ylamino}-phenyl)-isonicotinamide, 2-tert-Butyl-N-{4-methyl-3-[2-[6-(2-morpholin-4-yl-ethylamino)-pyrimidin-4-yl]-5-(2-morpholin-4-yl-ethylcarbamoyl)-2H-pyrazol-3-ylamino]-phenyl}-isonicotinamide, 2-tert-Butyl-N-{4-methyl-3-[2-(6-methylamino-pyrimnidin-4-yl)-5-methylcarbamoyl-2H-pyrazol-3-ylamino]-phenyl}-isonicotinamide, 2-tert-Butyl-N-{4-methyl-3-[2-(6-methylamino-pyrimnidin-4-yl)-5-(2-morpholin-4-yl-ethylcarbamoyl)-2H-pyrazol-3-ylamino]-phenyl}-isonicotinamide, 5-[5-(3-tert-Butyl-benzoylamino)-2-methyl-phenylamino]-1-[6-(4-methyl-piperazin-1-ylamino)-pyrimnidin-4-yl]-1H-pyrazole-3-carboxylic acid methylamide, 2-Chloro-6-methoxy-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-Chloro-6-methoxy-N-(4-methyl-3-{2-[6-(2-morpholin-4-yl-ethylamino)-pyrimnidin-4-yl]-5-morpholin-4-ylmethyl-2H-pyrazol-3-ylamino}-phenyl)-isonicotinamide, 2-Chloro-6-methoxy-N-{4-methyl-3-[2-[6-(2-morpholin-4-yl-ethylamino)-pyrimnidin-4-yl]-5-(2-morpholin-4-yl-ethylcarbamoyl)-2H-pyrazol-3-ylamino]-phenyl}-isonicotinamide, 2-Chloro-6-methoxy-N-{4-methyl-3-[2-[6-(2-morpholin-4-yl-ethylamino)-pyrimnidin-4-yl]-5-(2-morpholin-4-yl-ethylcarbamoyl)-2H-pyrazol-3-ylamino]-phenyl}-isonicotinamide, 2-Chloro-6-methoxy-N-{4-methyl-3-[2-(6-methylamino-pyrimidin-4-yl)-5-(2-morpholin-4-yl-ethylcarbamoyl)-2H-pyrazol-3-ylamino]-phenyl}-isonicotinamide, 2-Chloro-6-methoxy-N-(4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, N-(4-Methyl-3-{5-methylcarbamoyl-2-[6-(2-morpholin-4-yl-ethylamino)-pyrimnidin-4-yl]-2H-pyrazol-3-ylamino}-phenyl)-6-pyrazol-1-yl-nicotinamide, N-{4-Methyl-3-[2-(6-methylamino-pyrimidin-4-yl)-5-methylcarbamoyl-2H-pyrazol-3-ylamino]-phenyl}-6-pyrazol-1-yl-nicotinamide, N-{4-Methyl-3-[2-(6-methylamino-pyrimnidin-4-yl)-5-(2-morpholin-4-yl-ethylcarbamoyl)-2H-pyrazol-3-ylamino]-phenyl}-6-pyrazol-1-yl-nicotinamide, N-(4-Methyl-3-{5-methylcarbamoyl-2-[6-(4-methyl-piperazin-1-ylamino)-pyrimnidin-4-yl]-2H-pyrazol-3-ylamino}-phenyl)-6-pyrazol-1-yl-nicotinamide, 5-[2-Methyl-5-(3-trifluoromethyl-benzoylamino)-phenylamino]-1-[6-(2-morpholin-4-yl-ethylamino)-pyrimidin-4-yl]-1H-pyrazole-3-carboxylic acid methylamide, N-(4-Methyl-3-{2-[6-(2-morpholin-4-yl-ethylamino)-pyrimnidin-4-yl]-5-morpholin-4-ylmethyl-2H-pyrazol-3-ylamino}-phenyl)-3-trifluoromethyl-benzamide, 5-[2-Methyl-5-(3-trifluoromethyl-benzoylamino)-phenylamino]-1-[6-(2-morpholin-4-yl-ethylamino)-pyrimidin-4-yl]-1H-pyrazole-3-carboxylic acid (2-morpholin-4-yl-ethyl)-amide, 1-[6-(4-Methyl-piperazin-1-ylamino)-pyrimidin-4-yl]-5-[2-methyl-5-(3-trifluoromethyl-benzoylamino)-phenylamino]-1H-pyrazole-3-carboxylic acid methylamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-6-trifluoromethoxy-nicotinamide, N-{4-Methyl-3-[2-[6-(2-morpholin-4-yl-ethylamino)-pyrimidin-4-yl]-5-(2-morpholin-4-yl-ethylcarbamoyl)-2H-pyrazol-3-ylamino]-phenyl}-6-trifluoromethoxy-nicotinamide, N-{4-Methyl-3-[2-(6-methylamino-pyrimidin-4-yl)-5-methylcarbamoyl-2H-pyrazol-3-ylamino]-phenyl}-6-trifluoromethoxy-nicotinamide, N-{4-Methyl-3-[2-(6-methylamino-pyrimidin-4-yl)-5-(2-morpholin-4-yl-ethylcarbamoyl)-2H-pyrazol-3-ylamino]-phenyl}-6-trifluoromethoxy-nicotinamide, N-(4-Methyl-3-{5-methylcarbamoyl-2-[6-(4-methyl-piperazin-1-ylamino)-pyrimidin-4-yl]-2H-pyrazol-3-ylamino}-phenyl)-6-trifluoromethoxy-nicotinamide, 2-(Cyano-dimethyl-methyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-isonicotinamide, 5{-5-[3-(1-Cyano-1-methyl-propyl)-benzoylamino]-2-methyl-phenylamino}-1-[6-(2-morpholin-4-yl-ethylamino)-pyrimidin-4-yl]-1H-pyrazole-3-carboxylic acid methylamide, 3-(1-Cyano-1-methyl-propyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5{-5-[3-(1-Cyano-1-methyl-propyl)-benzoylamino]-2-methyl-phenylamino}-1-[6-(2-morpholin-4-yl-ethylamino)-pyrimidin-4-yl]-1H-pyrazole-3-carboxylic acid methylamide, 5{-5-[3-(1-Cyano-1-methyl-propyl)-benzoylamino]-2-methyl-phenylamino}-1-[6-(4-methyl-piperazin-1-ylamino)-pyrimidin-4-yl]-1H-pyrazole-3-carboxylic acid methylamide, 5{-5-[3-(1-Methoxy-1-methyl-ethyl)-benzoylamino]-2-methyl-phenylamino}-1-[6-(2-morpholin-4-yl-ethylamino)-pyrimidin-4-yl]-1H-pyrazole-3-carboxylic acid methylamide, 3-(1-Methoxy-1-methyl-ethyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 3-(Cyano-dimethyl-methyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5-tert-Butyl-N-(4-methyl-3-{5-methylcarbamoyl-2-[6-(2-morpholin-4-yl-ethylamino)-pyrimidin-4-yl]-2H-pyrazol-3-ylamino}-phenyl)-nicotinamide, 5-tert-Butyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-nicotinamide, 5{-5-[3-(1,1-Difluoro-ethyl)-benzoylamino]-2-methyl-phenylamino}-1-[6-(2-morpholin-4-yl-ethylamino)-pyrimnidin-4-yl]-1H-pyrazole-3-carboxylic acid methylamide, 3-(1,1-Difluoro-ethyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5{-5-[3-(1,1-Difluoro-ethyl)-benzoylamino]-2-methyl-phenylamino}-1-[6-(4-methyl-piperazin-1-ylamino)-pyrimidin-4-yl]-1H-pyrazole-3-carboxylic acid methylamide, 2-tert-Butyl-N-(4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, 4-tert-Butyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 4-Methanesulfonyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 4-Chloro-3-methanesulfonyl-N-(4-methyl-3-{2-[6-(2-morpholin-4-yl-ethylamino)-pyrimnidin-4-yl]-5-morpholin-4-ylmethyl-2H-pyrazol-3-ylamino}-phenyl)-benzamide, 4-tert-Butoxy-N-(4-methyl-3-{2-[6-(2-morpholin-4-yl-ethylamino)-pyrimnidin-4-yl]-5-morpholin-4-ylmethyl-2H-pyrazol-3-ylamino}-phenyl)-benzamide, 4-Methoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethyl-benzamide, 3-tert-Butoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 3-Methanesulfonyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-4-trifluoromethoxy-benzamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethoxy-benzamide, 5{-5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5{-5-[3-(Cyano-dimethyl-methyl)-benzoylamino]-2-methyl-phenylamino}-1-(6-methylamino-pyrimidin-4-yl)-1H-pyrazole-3-carboxylic acid (2-morpholin-4-yl-ethyl)-amide, 5-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-nicotinamide, 2-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}phenyl)-isonicotinamide, 5-tert-Butyl-N-{4-methyl-3-[2-(6-methylamino-pyrimidin-4-yl)-5-morpholin-4-ylmethyl-2H-pyrazol-3-ylamino]-phenyl}-nicotinamide, 1-Isopropyl-1H-benzotriazole-5-carboxylic acid {4-methyl-3-[2-(6-methylamino-pyrimidin-4-yl)-5-morpholin-4-ylmethyl-2H-pyrazol-3-ylamino]-phenyl}-amide, 5,5,8,8-Tetramethyl-5,6,7,8-tetrahydro-naphthalene-2-carboxylic acid {4-methyl-3-[2-(6-methylamino-pyrimidin-4-yl)-5-morpholin-4-ylmethyl-2H-pyrazol-3-ylamino]-phenyl}-amide, 2-Methyl-benzothiazole-5-carboxylic acid {4-methyl-3-[2-(6-methylamino-pyrimidin-4-yl)-5-morpholin-4-ylmethyl-2H-pyrazol-3-ylamino]-phenyl}-amide, 3-(1,1-Diethyl-propyl)-N-{4-methyl-3-[2-(6-methylamino-pyrimidin-4-yl)-5-morpholin-4-ylmethyl-2H-pyrazol-3-ylamino]-phenyl}-benzamide, N-{3-[5-(3-Dimethylamino-pyrrolidin-1-ylmethyl)-2-(6-methylamino-pyrimidin-4-yl)-2H-pyrazol-3-ylamino]-4-methyl-phenyl}-3-trifluoromethyl-benzamide, N-{3-[5-[4-(2-Methoxy-ethyl)-piperazin-1-ylmethyl]-2-(6-methylamino-pyrimidin-4-yl)-2H-pyrazol-3-ylamino]-4-methyl-phenyl}-3-trifluoromethyl-benzamide, N-{3-[5-(2,6-Dimethyl-morpholin-4-ylmethyl)-2-(6-methylamino-pyrimidin-4-yl)-2H-pyrazol-3-ylamino]-4-methyl-phenyl}-3-trifluoromethyl-benzamide, N-{3-[5-(2,6-Dimethyl-morpholin-4-ylmethyl)-2-(6-methylamino-pyrimidin-4-yl)-2H-pyrazol-3-ylamino]-4-methyl-phenyl}-3-trifluoromethyl-benzamide, N-[4-Methyl-3-(2-(6-methylamino-pyrimidin-4-yl)-5-{[methyl-(1-methyl-piperidin-4-yl)-amino]-methyl}-2H-pyrazol-3-ylamino)-phenyl]-3-trifluoromethyl-benzamide, N-{3-[5-(1,1-Dioxo-1l6-thiomorpholin-4-ylmethyl)-2-(6-methylamino-pyrimidin-4-yl)-2H-pyrazol-3-ylamino]-4-methyl-phenyl}-3-trifluoromethyl-benzamide, N-{4-Methyl-3-[2-(6-methylamino-pyrimidin-4-yl)-5-thiomorpholin-4-ylmethyl-2H-pyrazol-3-ylamino]-phenyl}-3-trifluoromethyl-benzamide, 5-tert-butyl-N-(3-(3-(((2-hydroxyethyl)(methyl)amino)methyl)-1-(6-(methylamino)pyrimidin-4-yl)-1H-pyrazol-5-ylamino)-4-methylphenyl)nicotinamide, -(2-(2-fluoropropan-2-yl)pyridin-4-yl)-4-methyl-3-(3-methyl-1-(6-(methylamino)pyrimidin-4-yl)-1H-pyrazol-5-ylamino)benzamide, 5-tert-butyl-N-(3-(3-(((2-hydroxyethyl)(methyl)amino)methyl)-1-(6-(methylamino)pyrimidin-4-yl)-1H-pyrazol-5-ylamino)-4-methylphenyl)nicotinamide, 5-tert-butyl-N-(3-(3-(2-(2,6-dimethylpiperidin-1-yl)ethylcarbamoyl)-1-(6-(methylamino)pyrimidin-4-yl)-1H-pyrazol-5-ylamino)-4-methylphenyl)nicotinamide, 5-(2-methoxypropan-2-yl)-N-(4-methyl-3-(3-methyl-1-(6-(methylamino)pyrimidin-4-yl)-1H-pyrazol-5-ylamino)phenyl)nicotinamide, 5-(2-fluoropropan-2-yl)-N-(4-methyl-3-(3-methyl-1-(6-(methylamino)pyrimidin-4-yl)-1H-pyrazol-5-ylamino)phenyl)nicotinamide, N-(4-tert-butylthiazol-2-yl)-4-methyl-3-(3-methyl-1-(6-(methylamino)pyrimidin-4-yl)-1H-pyrazol-5-ylamino)benzamide, N-(4-(2-fluoropropan-2-yl)pyridin-2-yl)-4-methyl-3-(3-methyl-1-(6-(4-methylpiperazin-1-ylamino)pyrimidin-4-yl)-1H-pyrazol-5-ylamino)benzamide, 5-(5-(2-tert-butylpyridin-4-ylcarbamoyl)-2-methylphenylamino)-1-(6-(isopropylamino)pyrimidin-4-yl)-N-methyl-1H-pyrazole-3-carboxamide, 5-(5-(2-tert-butylpyridin-4-ylcarbamoyl)-2-methylphenylamino)-N-methyl-1-(6-(methylamino)pyrimidin-4-yl)-1H-pyrazole-3-carboxamide, N-(2-tert-butylpyridin-4-yl)-4-methyl-3-(1-(6-(methylamino)pyrimidin-4-yl)-3-(morpholinomethyl)-1H-pyrazol-5-ylamino)benzamide, N-(2-tert-Butyl-pyridin-4-yl)-3-[5-(1,1-dioxo-1 lambda*6*-thiomorpholin-4-ylmethyl)-2-(6-methylamino-pyrimidin-4-yl)-2H-pyrazol-3-ylamino]-4-methyl-benzamide (see example 295), 2-tert-butyl-N-(3-(1-(6-(isopropylamino)pyrimidin-4-yl)-3-(methylcarbamoyl)-1H-pyrazol-5-ylamino)-4-methylphenyl)isonicotinamide, N-(2-tert-butylpyridin-4-yl)-3-(1-(6-(isopropylamino)pyrimidin-4-yl)-3-(morpholinomethyl)-1H-pyrazol-5-ylamino)-4-methylbenzamide, N-(2-tert-Butyl-pyridin-4-yl)-3-[5-(1,1-dioxo-1 lambda*6*-thiomorpholin-4-ylmethyl)-2-(6-isopropylamino-pyrimidin-4-yl)-2H-pyrazol-3-ylamino]-4-methyl-benzamide (see example 298), 2-tert-butyl-N-(3-(1-(6-(isopropylamino)pyrimidin-4-yl)-3-(morpholinomethyl)-1H-pyrazol-5-ylamino)-4-methylphenyl)isonicotinamide, N-(4-(2-fluoropropan-2-yl)pyridin-2-yl)-4-methyl-3-(3-methyl-1-(6-(methylamino)pyrimidin-4-yl)-1H-pyrazol-5-ylamino)benzamide, N-(5-tert-butyl-4-methylthiazol-2-yl)-4-methyl-3-(3-methyl-1-(6-(methylamino)pyrimidin-4-yl)-1H-pyrazol-5-ylamino)benzamide, N-(5-tert-butyl-4-methylthiazol-2-yl)-4-methyl-3-(3-methyl-1-(6-(4-methylpiperazin-1-ylamino)pyrimidin-4-yl)-1H-pyrazol-5-ylamino)benzamide, N-(4-(2-cyanopropan-2-yl)pyridin-2-yl)-4-methyl-3-(3-methyl-1-(6-(methylamino)pyrimidin-4-yl)-1H-pyrazol-5-ylamino)benzamide, N-(2-(2-methoxypropan-2-yl)pyridin-4-yl)-4-methyl-3-(3-methyl-1-(6-(methylamino)pyrimidin-4-yl)-1H-pyrazol-5-ylamino)benzamide, N-(4-tert-butylthiazol-2-yl)-4-methyl-3-(3-methyl-1-(6-(2-morpholinoethylamino)pyrimidin-4-yl)-1H-pyrazol-5-ylamino)benzamide, N-(5-tert-butyl-4-methylthiazol-2-yl)-4-methyl-3-(3-methyl-1-(6-(2-morpholinoethylamino)pyrimidin-4-yl)-1H-pyrazol-5-ylamino)benzamide, -(4-(1,1-difluoroethyl)pyridin-2-yl)-4-methyl-3-(3-methyl-1-(6-(methylamino)pyrimidin-4-yl)-1H-pyrazol-5-ylamino)benzamide, N-(4-(1,1-difluoroethyl)pyridin-2-yl)-4-methyl-3-(3-methyl-1-(6-(4-methylpiperazin-1-ylamino)pyrimidin-4-yl)-1H-pyrazol-5-ylamino)benzamide, N-(4-tert-butylpyridin-2-yl)-4-methyl-3-(3-methyl-1-(6-(methylamino)pyrimidin-4-yl)-1H-pyrazol-5-ylamino)benzamide, N-(4-tert-butylpyridin-2-yl)-4-methyl-3-(3-methyl-1-(6-(4-methylpiperazin-1-ylamino)pyrimidin-4-yl)-1H-pyrazol-5-ylamino)benzamide, 3-(1-(6-aminopyrimidin-4-yl)-1H-pyrazol-5-ylamino)-N-(5-tert-butyl-4-methylthiazol-2-yl)-4-methylbenzamide, 3-(1-(6-aminopyrimidin-4-yl)-1H-pyrazol-5-ylamino)-N-(4-tert-butylthiazol-2-yl)-4-methylbenzamide, N-(4-(2-methoxypropan-2-yl)pyridin-2-yl)-4-methyl-3-(3-methyl-1-(6-(methylamino)pyrimidin-4-yl)-1H-pyrazol-5-ylamino)benzamide, N-(4-(2-methoxypropan-2-yl)pyridin-2-yl)-4-methyl-3-(3-methyl-1-(6-(4-methylpiperazin-1-ylamino)pyrimidin-4-yl)-1H-pyrazol-5-ylamino)benzamide, N-(6-methyl-5-(3-methyl-1-(6-(4-methylpiperazin-1-ylamino)pyrimidin-4-yl)-1H-pyrazol-5-ylamino)pyridin-3-yl)-3-(trifluoromethyl)benzamide, N-(6-methyl-5-(3-methyl-1-(6-(methylamino)pyrimidin-4-yl)-1H-pyrazol-5-ylamino)pyridin-3-yl)-3-(trifluoromethyl)benzamide, 2-tert-butyl-N-(6-methyl-5-(3-methyl-1-(6-(methylamino)pyrimidin-4-yl)-

1H-pyrazol-5-ylamino)pyridin-3-yl)isonicotinamide, 2-tert-butyl-N-(6-methyl-5-(3-methyl-1-(6-(4-methylpiperazin-1-ylamino)pyrimidin-4-yl)-1H-pyrazol-5-ylamino)pyridin-3-yl)isonicotinamide, N-(4-methyl-3-(1-(6-(methylamino)pyrimidin-4-yl)-3-(1-oxo-thiomorpholinomethyl)-1H-pyrazol-5-ylamino)phenyl)-3-(trifluoromethyl)benzamide, N-(3-(1-(6-aminopyrimidin-4-yl)-3-methyl-1H-pyrazol-5-ylamino)-4-methylphenyl)-3-(4-hydroxypiperidin-1-yl)-5-(trifluoromethyl)benzamide, 3-(4-hydroxypiperidin-1-yl)-N-(4-methyl-3-(1-(6-(methylamino)pyrimidin-4-yl)-1H-pyrazol-5-ylamino)phenyl)-5-(trifluoromethyl)benzamide, 3-(4-hydroxypiperidin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(1-methylpiperidin-4-yloxy)-5-(trifluoromethyl)benzamide, 3-(4-(2-hydroxyethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-morpholino-5-(trifluoromethyl)benzamide, (S)—N-(4-methyl-3-(3-methyl-1-(6-(methylamino)pyrimidin-4-yl)-1H-pyrazol-5-ylamino)phenyl)-3-(2-methylmorpholino)-5-(trifluoromethyl)benzamide, (R)—N-(4-methyl-3-(3-methyl-1-(6-(methylamino)pyrimidin-4-yl)-1H-pyrazol-5-ylamino)phenyl)-3-(2-methylmorpholino)-5-(trifluoromethyl)benzamide, 1-(4-methyl-3-(3-methyl-1-(6-(methylamino)pyrimidin-4-yl)-1H-pyrazol-5-ylamino)phenyl)-3-(3-(trifluoromethyl)phenyl)urea, 1-(4-fluoro-3-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(4-methyl-3-(3-methyl-1-(6-(methylamino)pyrimidin-4-yl)-1H-pyrazol-5-ylamino)phenyl)urea, 1-(3-(4-ethylpiperazin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, N-(4-methyl-3-(3-methyl-1-(6-(methylamino)pyrimidin-4-yl)-1H-pyrazol-5-ylamino)phenyl)-3-(1,1-dioxo-thiomorpholino)-5-(trifluoromethyl)benzamide, (R)-3-(3,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(3,4-dimethylpiperazin-1-yl)-N-(4-methyl-3-(1-(6-(methylamino)pyrimidin-4-yl)-1H-pyrazol-5-ylamino)phenyl)-5-(trifluoromethyl)benzamide, N-(3-(4-hydroxypiperidin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-(2-(dimethylamino)ethoxy)-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-(2-(pyrrolidin-1-yl)ethoxy)-5-(trifluoromethyl)phenyl)benzamide, N-(3-(3-hydroxypyrrolidin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-(3-hydroxyazetidin-1-yl)-5-(trifluoromethyl)phenyl)-4-methyl-3-(3-methyl-1-(6-(methylamino)pyrimidin-4-yl)-1H-pyrazol-5-ylamino)benzamide, 2-(1,1-difluoroethyl)-N-(4-methyl-3-(3-methyl-1-(6-(methylamino)pyrimidin-4-yl)-1H-pyrazol-5-ylamino)phenyl)isonicotinamide, methyl 1-methyl-4-(3-(4-methyl-3-(3-methyl-1-(6-(methylamino)pyrimidin-4-yl)-1H-pyrazol-5-ylamino)benzamido)-5-(trifluoromethyl)phenyl)piperazine-2-carboxylate, N-(3-((2-methoxyethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide, N-(3-((2-(dimethylamino)ethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide, 3-(1,1-difluoroethyl)-N-(3-(3-(hydroxymethyl)-1-(6-(methylamino)pyrimidin-4-yl)-1H-pyrazol-5-ylamino)-4-methylphenyl)benzamide, N-(3-(3-(hydroxymethyl)-1-(6-(methylamino)pyrimidin-4-yl)-1H-pyrazol-5-ylamino)-4-methylphenyl)-3-(4-hydroxypiperidin-1-yl)-5-(trifluoromethyl)benzamide, 4-methyl-3-(1-(6-(methylamino)pyrimidin-4-yl)-3-(trifluoromethyl)-1H-pyrazol-5-ylamino)-N-(3-(4-methylpiperazin-1-yl)-5-(trifluoromethyl)phenyl)benzamide, methyl 1-(3-(4-methyl-3-(3-methyl-1-(6-(methylamino)pyrimidin-4-yl)-1H-pyrazol-5-ylamino)benzamido)-5-(trifluoromethyl)phenyl)piperidine-4-carboxylate, 1-(3-(4-methyl-3-(3-methyl-1-(6-(methylamino)pyrimidin-4-yl)-1H-pyrazol-5-ylamino)benzamido)-5-(trifluoromethyl)phenyl)piperidine-4-carboxylic acid, N-(3-(3-(hydroxymethyl)-4-methylpiperazin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-((2-hydroxyethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide, N-(3-(4-(hydroxymethyl)piperidin-1-yl)-5-(trifluoromethyl)phenyl)-4-methyl-3-(3-methyl-1-(6-(methylamino)pyrimidin-4-yl)-1H-pyrazol-5-ylamino)benzamide, 1-(3-(1,1-difluoroethyl)phenyl)-3-(4-methyl-3-(3-methyl-1-(6-(methylamino)pyrimidin-4-yl)-1H-pyrazol-5-ylamino)phenyl)urea, 1-(2-(1,1-difluoroethyl)pyridin-4-yl)-3-(4-methyl-3-(3-methyl-1-(6-(methylamino)pyrimidin-4-yl)-1H-pyrazol-5-ylamino)phenyl)urea, 1-(3-(4-hydroxypiperidin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, N-(3-fluoro-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-(methylsulfonamido)-5-(trifluoromethyl)phenyl)benzamide, 2-methoxy-N-(4-methyl-3-(3-methyl-1-(6-(methylamino)pyrimidin-4-yl)-1H-pyrazol-5-ylamino)phenyl)-6-(trifluoromethyl)isonicotinamide, 4-methyl-3-(3-methyl-1-(6-(methylamino)pyrimidin-4-yl)-1H-pyrazol-5-ylamino)-N-(3-(trifluoromethyl)phenyl)benzamide, N-(4-chloro-3-(trifluoromethyl)phenyl)-4-methyl-3-(3-methyl-1-(6-(methylamino)pyrimidin-4-yl)-1H-pyrazol-5-ylamino)benzamide, N-(4-fluoro-3-(trifluoromethyl)phenyl)-4-methyl-3-(3-methyl-1-(6-(methylamino)pyrimidin-4-yl)-1H-pyrazol-5-ylamino)benzamide, 3-((3-(dimethylamino)propyl)(methyl)amino)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-nitro-5-(trifluoromethyl)benzamide, 3-amino-N-(4-methyl-3-(3-methyl-1-(6-(methylamino)pyrimidin-4-yl)-1H-pyrazol-5-ylamino)phenyl)-5-(trifluoromethyl)benzamide, 3-((2-methoxyethyl)(methyl)amino)-N-(4-methyl-3-(3-methyl-1-(6-(methylamino)pyrimidin-4-yl)-1H-pyrazol-5-ylamino)phenyl)-5-(trifluoromethyl)benzamide, 1-(4-bromo-3-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(6-methyl-5-(3-methyl-1-(6-(methylamino)pyrimidin-4-yl)-1H-pyrazol-5-ylamino)pyridin-3-yl)urea, 3-((2-(dimethylamino)ethyl)(methyl)

amino)-N-(4-methyl-3-(3-methyl-1-(6-(methylamino) pyrimidin-4-yl)-1H-pyrazol-5-ylamino)phenyl)-5-(trifluoromethyl)benzamide, 1-(3-(4-(2-hydroxyethyl) piperazin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl) phenyl)-3-(3-(3-(hydroxymethyl)-1-(6-(methylamino) pyrimidin-4-yl)-1H-pyrazol-5-ylamino)-4-methylphenyl) urea, methyl 3-(4-methyl-3-(3-methyl-1-(6-(methylamino) pyrimidin-4-yl)-1H-pyrazol-5-ylamino)benzamido)-5-(trifluoromethyl)benzoate, 3-(2-(dimethylamino)ethoxy)-N-(4-methyl-3-(3-methyl-1-(6-(methylamino)pyrimidin-4-yl)-1H-pyrazol-5-ylamino)phenyl)-5-(trifluoromethyl) benzamide, 3-(3-(dimethylamino)propoxy)-N-(4-methyl-3-(3-methyl-1-(6-(methylamino)pyrimidin-4-yl)-1H-pyrazol-5-ylamino)phenyl)-5-(trifluoromethyl)benzamide, 3-hydroxy-N-(4-methyl-3-(3-methyl-1-(6-(methylamino) pyrimidin-4-yl)-1H-pyrazol-5-ylamino)phenyl)-5-(trifluoromethyl)benzamide, 3-(1-(6-(2-(dimethylamino)ethylamino)pyrimidin-4-yl)-3-methyl-1H-pyrazol-5-ylamino)-4-methyl-N-(3-(trifluoromethyl)phenyl)benzamide, 1-(4-chloro-3-(trifluoromethyl)phenyl)-3-(3-(1-(6-(2-(dimethylamino)ethylamino)pyrimidin-4-yl)-3-methyl-1H-pyrazol-5-ylamino)-4-methylphenyl)urea, 1-(4-chloro-3-(trifluoromethyl)phenyl)-3-(4-methyl-3-(3-methyl-1-(6-(2-morpholinoethylamino)pyrimidin-4-yl)-1H-pyrazol-5-ylamino)phenyl)urea, 3-(1-(6-(3-hydroxypropylamino) pyrimidin-4-yl)-3-methyl-1H-pyrazol-5-ylamino)-4-methyl-N-(3-(trifluoromethyl)phenyl)benzamide, 3-(difluoromethyl)-N-(4-methyl-3-(3-methyl-1-(6-(methylamino)pyrimidin-4-yl)-1H-pyrazol-5-ylamino)phenyl)benzamide, 3-(difluoromethyl)-N-(3-(3-(hydroxymethyl)-1-(6-(methylamino)pyrimidin-4-yl)-1H-pyrazol-5-ylamino)-4-methylphenyl)benzamide, 1-(3-(4-methyl-1H-imidazol-1-yl)-5-(trifluoromethyl)phenyl)-3-(4-methyl-3-(3-methyl-1-(6-(methylamino)pyrimidin-4-yl)-1H-pyrazol-5-ylamino) phenyl)urea, 3-(4-methyl-1H-imidazol-1-yl)-N-(4-methyl-3-(3-methyl-1-(6-(methylamino)pyrimidin-4-yl)-1H-pyrazol-5-ylamino)phenyl)-5-(trifluoromethyl)benzamide, 4-methyl-3-(3-methyl-1-(6-(methylamino)pyrimidin-4-yl)-1H-pyrazol-5-ylamino)-N-(3-(4-methyl-1H-imidazol-1-yl)-5-(trifluoromethyl)phenyl)benzamide, N-(3-methoxy-5-(trifluoromethyl)phenyl)-4-methyl-3-(3-methyl-1-(6-(methylamino)pyrimidin-4-yl)-1H-pyrazol-5-ylamino) benzamide, 4-methyl-3-(3-methyl-1-(6-(methylamino) pyrimidin-4-yl)-1H-pyrazol-5-ylamino)-N-(2-methyl-5-(trifluoromethyl)phenyl)benzamide, 1-(3-(1,1-difluoroethyl) phenyl)-3-(3-(3-(hydroxymethyl)-1-(6-(methylamino) pyrimidin-4-yl)-1H-pyrazol-5-ylamino)-4-methylphenyl) urea, 4-methyl-3-(3-methyl-1-(6-(methylamino)pyrimidin-4-yl)-1H-pyrazol-5-ylamino)-N-(3-(2-(methylsulfonyl) ethylcarbamoyl)-5-(trifluoromethyl)phenyl)benzamide, N-(3-(3-hydroxypropylcarbamoyl)-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-methyl-5-(trifluoromethyl)phenyl) benzamide, 1-(3-((2-methoxyethyl)(methyl)amino)-5-(trifluoromethyl)phenyl)-3-(4-methyl-3-(3-methyl-1-(6-(methylamino)pyrimidin-4-yl)-1H-pyrazol-5-ylamino) phenyl)urea, 1-(3-((2-(dimethylamino)ethyl)(methyl) amino)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl) phenyl)-3-(4-methyl-3-(1-(6-(methylamino)pyrimidin-4-yl)-3-(morpholinomethyl)-1H-pyrazol-5-ylamino)phenyl) urea, 1-(4-chloro-3-(trifluoromethyl)phenyl)-3-(3-(3-((dimethylamino)methyl)-1-(6-(methylamino)pyrimidin-4-yl)-1H-pyrazol-5-ylamino)-4-methylphenyl)urea, 3-bromo-5-(1,1-difluoroethyl)-N-(4-methyl-3-(3-methyl-1-(6-(methylamino)pyrimidin-4-yl)-1H-pyrazol-5-ylamino) phenyl)benzamide, (R)-1-(4-chloro-3-(trifluoromethyl) phenyl)-3-(4-methyl-3-(1-(6-(methylamino)pyrimidin-4-yl)-3-((2-methylmorpholino)methyl)-1H-pyrazol-5-ylamino)phenyl)urea, tert-butyl 4-(3-(4-methyl-3-(3-methyl-1-(6-(methylamino)pyrimidin-4-yl)-1H-pyrazol-5-ylamino) phenylcarbamoyl)-5-(trifluoromethyl)phenyl)piperazine-1-carboxylate, N-(4-methyl-3-(3-methyl-1-(6-(methylamino) pyrimidin-4-yl)-1H-pyrazol-5-ylamino)phenyl)-3-(piperazin-1-yl)-5-(trifluoromethyl)benzamide, N-(4-methyl-3-(3-methyl-1-(6-(methylamino)pyrimidin-4-yl)-1H-pyrazol-5-ylamino)phenyl)-3-(4-(2,2,2-trifluoroethyl) piperazin-1-yl)-5-(trifluoromethyl)benzamide, 3-(4-(2-amino-2-oxoethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-(2-methoxyethyl)piperazin-1-yl)-N-(4-methyl-3-(3-methyl-1-(6-(methylamino)pyrimidin-4-yl)-1H-pyrazol-5-ylamino) phenyl)-5-(trifluoromethyl)benzamide, 3-(4-(3-hydroxypropyl)piperazin-1-yl)-N-(4-methyl-3-(3-methyl-1-(6-(methylamino)pyrimidin-4-yl)-1H-pyrazol-5-ylamino) phenyl)-5-(trifluoromethyl)benzamide, 2-(4-(3-(4-methyl-3-(3-methyl-1-(6-(methylamino)pyrimidin-4-yl)-1H-pyrazol-5-ylamino)phenylcarbamoyl)-5-(trifluoromethyl)phenyl) piperazin-1-yl)acetic acid, 3-(4-(2-(dimethylamino)-2-oxoethyl)piperazin-1-yl)-N-(4-methyl-3-(3-methyl-1-(6-(methylamino)pyrimidin-4-yl)-1H-pyrazol-5-ylamino) phenyl)-5-(trifluoromethyl)benzamide, 3-(4-(2-hydroxypropyl)piperazin-1-yl)-N-(4-methyl-3-(3-methyl-1-(6-(methylamino)pyrimidin-4-yl)-1H-pyrazol-5-ylamino) phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(4-(2-(methylsulfonyl)ethyl)piperazin-1-yl)-5-(trifluoromethyl)benzamide, 3-(4-cyclopropylpiperazin-1-yl)-N-(4-methyl-3-(3-methyl-1-(6-(methylamino)pyrimidin-4-yl)-1H-pyrazol-5-ylamino) phenyl)-5-(trifluoromethyl)benzamide, (S)-2-(4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)piperazin-1-yl)propanoic acid, N-(4-methyl-3-(3-methyl-1-(6-(methylamino)pyrimidin-4-yl)-1H-pyrazol-5-ylamino)phenyl)-3-(4,7-diazaspiro[2.5] octan-7-yl)-5-(trifluoromethyl)benzamide, 2-ethoxy-N-(4-methyl-3-(3-methyl-1-(6-(methylamino)pyrimidin-4-yl)-1H-pyrazol-5-ylamino)phenyl)-6-(trifluoromethyl) isonicotinamide, N-(4-methyl-3-(3-methyl-1-(6-(methylamino)pyrimidin-4-yl)-1H-pyrazol-5-ylamino) phenyl)-3-(trifluoromethyl)-5-(3-(trifluoromethyl) piperazin-1-yl)benzamide, N-(4-methyl-3-(3-methyl-1-(6-(methylamino)pyrimidin-4-yl)-1H-pyrazol-5-ylamino) phenyl)-3-(4-methyl-4,7-diazaspiro[2.5]octan-7-yl)-5-(trifluoromethyl)benzamide, tert-butyl 4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)-3-oxopiperazine-1-carboxylate, N-(4-methyl-3-(3-methyl-1-(6-(methylamino)pyrimidin-4-yl)-1H-pyrazol-5-ylamino) phenyl)-3-(2-oxopiperazin-1-yl)-5-(trifluoromethyl) benzamide, 3-(4-methyl-2-oxopiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-2-(methylamino)-6-(trifluoromethyl)isonicotinamide, N-(4-methyl-3-(3-methyl-1-(6-(methylamino)pyrimidin-4-yl)-1H-pyrazol-5-ylamino)

phenyl)-3-(4-methyl-3-(trifluoromethyl)piperazin-1-yl)-5-(trifluoromethyl)benzamide, 2-(2-(dimethylamino) ethylamino)-N-(4-methyl-3-(3-methyl-1-(6-(methylamino) pyrimidin-4-yl)-1H-pyrazol-5-ylamino)phenyl)-6-(trifluoromethyl)isonicotinamide, 2-(2-hydroxyethylamino)-N-(4-methyl-3-(3-methyl-1-(6-(methylamino)pyrimidin-4-yl)-1H-pyrazol-5-ylamino)phenyl)-6-(trifluoromethyl) isonicotinamide, 3-(4-hydroxypiperidin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(4-(2-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(3-((4-ethylpiperazin-1-yl)methyl)-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-(pyrrolidin-1-ylmethyl)-5-(trifluoromethyl)phenyl) benzamide, N-(3-((dimethylamino)methyl)-5-(trifluoromethyl)phenyl)-4-methyl-3-(3-methyl-1-(6-(methylamino)pyrimidin-4-yl)-1H-pyrazol-5-ylamino) benzamide, 3-((dimethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(pyrrolidin-1-ylmethyl)-5-(trifluoromethyl)benzamide, 3-((isopropylamino)methyl)-N-(4-methyl-3-(3-methyl-1-(6-(methylamino)pyrimidin-4-yl)-1H-pyrazol-5-ylamino)phenyl)-5-(trifluoromethyl) benzamide, N-(4-methyl-3-(3-methyl-1-(6-(methylamino) pyrimidin-4-yl)-1H-pyrazol-5-ylamino)phenyl)-3-((methylamino)methyl)-5-(trifluoromethyl)benzamide, 1-(3-((dimethylamino)methyl)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-methyl-3-(3-methyl-1-(6-(methylamino)pyrimidin-4-yl)-1H-pyrazol-5-ylamino)phenyl)-3-(3-(pyrrolidin-1-ylmethyl)-5-(trifluoromethyl)phenyl)urea, 1-(3-((4-ethylpiperazin-1-yl) methyl)-5-(trifluoromethyl)phenyl)-3-(4-methyl-3-(3-methyl-1-(6-(methylamino)pyrimidin-4-yl)-1H-pyrazol-5-ylamino)phenyl)urea, 3-((ethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((cyclopropylamino)methyl)-N-(4-methyl-3-(3-methyl-1-(6-(methylamino)pyrimidin-4-yl)-1H-pyrazol-5-ylamino) phenyl)-5-(trifluoromethyl)benzamide, 3-(1,1-difluoroethyl)-5-((isopropylamino)methyl)-N-(4-methyl-3-(1-(6-(methylamino)pyrimidin-4-yl)-1H-pyrazol-5-ylamino) phenyl)benzamide, 3-(1,1-difluoroethyl)-5-((isopropylamino)methyl)-N-(4-methyl-3-(3-methyl-1-(6-(methylamino)pyrimidin-4-yl)-1H-pyrazol-5-ylamino) phenyl)benzamide, 3-((diethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-azetidin-1-ylmethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(azetidin-1-ylmethyl)-N-(4-methyl-3-(1-(6-(methylamino)pyrimidin-4-yl)-1H-pyrazol-5-ylamino)phenyl)-5-(trifluoromethyl)benzamide, 3-((3-hydroxyazetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3-hydroxypyrrolidin-1-yl)methyl)-N-(4-methyl-3-(3-methyl-1-(6-(methylamino)pyrimidin-4-yl)-1H-pyrazol-5-ylamino) phenyl)-5-(trifluoromethyl)benzamide, 3-((2-hydroxyethylamino)methyl)-N-(4-methyl-3-(3-methyl-1-(6-(methylamino)pyrimidin-4-yl)-1H-pyrazol-5-ylamino) phenyl)-5-(trifluoromethyl)benzamide, N-(4-methyl-3-(3-methyl-1-(6-(methylamino)pyrimidin-4-yl)-1H-pyrazol-5-ylamino)phenyl)-3-((propylamino)methyl)-5-(trifluoromethyl)benzamide, 3-(1,1-difluoroethyl)-5-((dimethylamino)methyl)-N-(4-methyl-3-(3-methyl-1-(6-(methylamino)pyrimidin-4-yl)-1H-pyrazol-5-ylamino) phenyl)benzamide, 3-((cyclopropylamino)methyl)-5-(1,1-difluoroethyl)-N-(4-methyl-3-(3-methyl-1-(6-(methylamino)pyrimidin-4-yl)-1H-pyrazol-5-ylamino) phenyl)benzamide, 3-((3-hydroxypropylamino)methyl)-N-(4-methyl-3-(3-methyl-1-(6-(methylamino)pyrimidin-4-yl)-1H-pyrazol-5-ylamino)phenyl)-5-(trifluoromethyl) benzamide, 3-(1,1-difluoroethyl)-5-((ethylamino)methyl)-N-(4-methyl-3-(3-methyl-1-(6-(methylamino)pyrimidin-4-yl)-1H-pyrazol-5-ylamino)phenyl)benzamide, 3-((2-methoxyethylamino)methyl)-N-(4-methyl-3-(3-methyl-1-(6-(methylamino)pyrimidin-4-yl)-1H-pyrazol-5-ylamino) phenyl)-5-(trifluoromethyl)benzamide, 3-((butylamino) methyl)-N-(4-methyl-3-(3-methyl-1-(6-(methylamino) pyrimidin-4-yl)-1H-pyrazol-5-ylamino)phenyl)-5-(trifluoromethyl)benzamide, 3-((tert-butylamino)methyl)-N-(4-methyl-3-(3-methyl-1-(6-(methylamino)pyrimidin-4-yl)-1H-pyrazol-5-ylamino)phenyl)-5-(trifluoromethyl) benzamide, 3-(1,1-difluoroethyl)-5-((4-hydroxycyclohexylamino)methyl)-N-(4-methyl-3-(3-methyl-1-(6-(methylamino)pyrimidin-4-yl)-1H-pyrazol-5-ylamino)phenyl)benzamide, 3-((cyclopropylamino)methyl)-5-(1,1-difluoroethyl)-N-(4-methyl-3-(1-(6-(methylamino) pyrimidin-4-yl)-1H-pyrazol-5-ylamino)phenyl)benzamide, 3-(aminomethyl)-N-(4-methyl-3-(3-methyl-1-(6-(methylamino)pyrimidin-4-yl)-1H-pyrazol-5-ylamino)phenyl)-5-(trifluoromethyl)benzamide, 2-((dimethylamino)methyl)-N-(4-methyl-3-(3-methyl-1-(6-(methylamino)pyrimidin-4-yl)-1H-pyrazol-5-ylamino)phenyl)-6-(trifluoromethyl) isonicotinamide, 3-(((2-hydroxyethyl)(methyl)amino) methyl)-N-(4-methyl-3-(3-methyl-1-(6-(methylamino) pyrimidin-4-yl)-1H-pyrazol-5-ylamino)phenyl)-5-(trifluoromethyl)benzamide, 3-(1,2-dihydroxyethyl)-N-(4-methyl-3-(3-methyl-1-(6-(methylamino)pyrimidin-4-yl)-1H-pyrazol-5-ylamino)phenyl)-5-(trifluoromethyl) benzamide, 3-((1-hydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl) benzamide, 3-((1-hydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl) benzamide, 3-((2,2-dimethylhydrazinyl)methyl)-N-(4-methyl-3-(3-methyl-1-(6-(methylamino)pyrimidin-4-yl)-1H-pyrazol-5-ylamino)phenyl)-5-(trifluoromethyl) benzamide, 3-((methoxyamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((hydroxyamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-((2-(hydroxymethyl)pyrrolidin-1-yl)methyl)-N-(4-methyl-3-(3-methyl-1-(6-(methylamino)pyrimidin-4-yl)-1H-pyrazol-5-ylamino) phenyl)-5-(trifluoromethyl)benzamide, (S)-3-((2-hydroxypropylamino)methyl)-N-(4-methyl-3-(3-methyl-1-(6-(methylamino)pyrimidin-4-yl)-1H-pyrazol-5-ylamino) phenyl)-5-(trifluoromethyl)benzamide, (R)—N-(4-methyl-3-(3-methyl-1-(6-(methylamino)pyrimidin-4-yl)-1H-pyrazol-5-ylamino)phenyl)-3-(((tetrahydrofuran-2-yl) methylamino)methyl)-5-(trifluoromethyl)benzamide, (R)-3-

((2,3-dihydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-((2,3-dihydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1,3-dihydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1-hydroxy-2-methylpropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((cyclobutylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((dimethylamino)methyl)-N-(4-methyl-3-(1-(6-(methylamino)pyrimidin-4-yl)-1H-pyrazol-5-ylamino)phenyl)-5-(trifluoromethyl)benzamide, 3-(((2-methoxyethyl)(methyl)amino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(((1S,2R)-2-hydroxycyclopentylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)—N-(4-methyl-3-(3-methyl-1-(6-(methylamino)pyrimidin-4-yl)-1H-pyrazol-5-ylamino)phenyl)-3-(((tetrahydrofuran-2-yl)methylamino)methyl)-5-(trifluoromethyl)benzamide, (R)-3-((2-hydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(morpholinomethyl)-5-(trifluoromethyl)benzamide, 3-((3-methoxyazetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide 3-((3-methoxypyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3-hydroxyazetidin-1-yl)methyl)-N-(4-methyl-3-(1-(6-(methylamino)pyrimidin-4-yl)-1H-pyrazol-5-ylamino)phenyl)-5-(trifluoromethyl)benzamide, N-(4-chloro-3-(3-methyl-1-(6-(methylamino)pyrimidin-4-yl)-1H-pyrazol-5-ylamino)phenyl)-3-((dimethylamino)methyl)-5-(trifluoromethyl)benzamide, N-(4-chloro-3-(3-methyl-1-(6-(methylamino)pyrimidin-4-yl)-1H-pyrazol-5-ylamino)phenyl)-3-((isopropylamino)methyl)-5-(trifluoromethyl)benzamide, N-(4-chloro-3-(3-methyl-1-(6-(methylamino)pyrimidin-4-yl)-1H-pyrazol-5-ylamino)phenyl)-3-(pyrrolidin-1-ylmethyl)-5-(trifluoromethyl)benzamide, 3-((isopropylamino)methyl)-N-(4-methyl-3-(1-(6-(methylamino)pyrimidin-4-yl)-1H-pyrazol-5-ylamino)phenyl)-5-(trifluoromethyl)benzamide, N-(4-methyl-3-(1-(6-(methylamino)pyrimidin-4-yl)-1H-pyrazol-5-ylamino)phenyl)-3-(pyrrolidin-1-ylmethyl)-5-(trifluoromethyl)benzamide, 3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)—N-(4-methyl-3-(3-methyl-1-(6-(methylamino)pyrimidin-4-yl)-1H-pyrazol-5-ylamino)phenyl)-3-((2-methylmorpholino)methyl)-5-(trifluoromethyl)benzamide, (R)—N-(4-methyl-3-(3-methyl-1-(6-(methylamino)pyrimidin-4-yl)-1H-pyrazol-5-ylamino)phenyl)-3-((2-methylmorpholino)methyl)-5-(trifluoromethyl)benzamide, 3-((2-hydroxy-2-methylpropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(1,2,3,6-tetrahydropyridin-4-yl)-5-(trifluoromethyl)benzamide, N-(4-methyl-3-(3-methyl-1-(6-(methylamino)pyrimidin-4-yl)-1H-pyrazol-5-ylamino)phenyl)-3-(piperidin-4-yl)-5-(trifluoromethyl)benzamide, 3-(1-methyl-1,2,3,6-tetrahydropyridin-4-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,2-dihydroxyethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1-hydroxyethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(2-hydroxyethylamino)cyclobutyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(isopropylamino)cyclobutyl)-N-(4-methyl-3-(3-methyl-1-(6-(methylamino)pyrimidin-4-yl)-1H-pyrazol-5-ylamino)phenyl)-5-(trifluoromethyl)benzamide, (E)-3-(3-aminoprop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, (E)-3-(3-(isopropylamino)prop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, (E)-3-(3-(2-hydroxyethylamino)prop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(isopropylamino)propyl)-N-(4-methyl-3-(3-methyl-1-(6-(methylamino)pyrimidin-4-yl)-1H-pyrazol-5-ylamino)phenyl)-5-(trifluoromethyl)benzamide, 3-(2-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(2-(2-hydroxyethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(dimethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(1-(dimethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)—N-(4-methyl-3-(3-methyl-1-(6-(methylamino)pyrimidin-4-yl)-1H-pyrazol-5-ylamino)phenyl)-3-(1-(pyrrolidin-1-yl)ethyl)-5-(trifluoromethyl)benzamide, (R)—N-(4-methyl-3-(3-methyl-1-(6-(methylamino)pyrimnidin-4-yl)-1H-pyrazol-5-ylamino)phenyl)-3-(1-(pyrrolidin-1-yl)ethyl)-5-(trifluoromethyl)benzamide, (S)-3-(1-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-(2,2-difluoroethyl)piperazin-1-yl)-N-(4-methyl-3-(3-methyl-1-(6-(methylamino)pyrimnidin-4-yl)-1H-pyrazol-5-ylamino)phenyl)-5-(trifluoromethyl)benzamide, 3-chloro-5-(4-(2-methoxyethyl)piperazin-1-yl)-N-(4-methyl-3-(3-methyl-1-(6-(methylamino)pyrimnidin-4-yl)-1H-pyrazol-5-ylamino)phenyl)benzamide, 3-chloro-5-(4-(2-ethoxyethyl)piperazin-1-yl)-N-(4-methyl-3-(3-methyl-1-(6-(methylamino)

pyrimidin-4-yl)-1H-pyrazol-5-ylamino)phenyl)benzamide, 3-chloro-N-(4-methyl-3-(3-methyl-1-(6-(methylamino)pyrimnidin-4-yl)-1H-pyrazol-5-ylamino)phenyl)-5-(4-methylpiperazin-1-yl)benzamide, (S)-3-(4-(2-methoxyethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2-methoxyethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(2,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(2,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-((3,3-difluoroazetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3,3-difluoropyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2,2-difluoroethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, rac-3-(2-(3,3-difluoropyrrolidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide, rac-3-(2-(3,3-difluoroazetidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide, and 3-((2,2-difluoroethyl)methyl)-N-(4-methyl-3-(3-methyl-1-(6-(methylamino)pyrimidin-4-yl)-1H-pyrazol-5-ylamino)phenyl)-5-(trifluoromethyl)benzamide.

Further preferred compounds of the invention are detailed in the Examples and Table I, infra.

Pharmacology and Utility

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, Abl, BCR-Abl (wild-type and mutant forms), ARG, BRK, EphB, Fms, Fyn, KDR, c-Kit, LCK, PDGF-R, b-Raf, c-Raf, SAPK2, Src, Tie2 and TrkB.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

Malaria is caused by protozoan parasites of the genus *Plasmodium*. Four species of *Plasmodium* can produce the disease in its various forms: *Plasmodium falciparum*; *Plasmodium vivax*; *Plasmodium ovale*; and *Plasmodium malaria*. *P. falciparum*, the most widespread and dangerous, can lead to fatal cerebral malaria if left untreated. Protein tyrosine kinase activity is distributed in all the stages of *P. falciparum* parasite maturation and kinase inhibitors of the present invention can be used for treating *Plasmodium* related diseases. The in vitro assay, infra, is used as a means to determine the activity of compounds of the invention against a variety of malarial parasite strains.

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949-954 (1 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

The compounds of the present invention also inhibit cellular processes involving c-Raf kinase. c-Raf is activated by the ras oncogene, which is mutated in a wide number of human cancers. Therefore inhibition of the kinase activity of c-Raf may provide a way to prevent ras mediated tumor growth [Campbell, S. L., Oncogene, 17, 1395 (1998)].

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The Tec family kinase, Bmx, a non-receptor protein-tyrosine kinase, controls the proliferation of mammary epithelial cancer cells.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers. Inhibitors of FGFR3 activity are useful in the treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

The activity of serum and glucocorticoid-regulated kinase (SGK), is correlated to perturbed ion-channel activities, in particular, those of sodium and/or potassium channels and compounds of the invention can be useful for treating hypertension.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter. Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000; 65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage.

BTK plays a role in autoimmune and/or inflammatory disease such as systemic lupus erythematosus (SLE), rheumatoid arthritis, multiple vasculitides, idiopathic thrombocytopenic purpura (ITP), myasthenia gravis, and asthma. Because of BTK's role in B-cell activation, inhibitors of BTK are useful as inhibitors of B-cell mediated pathogenic activity, such as autoantibody production, and are useful for the treatment of B-cell lymphoma and leukemia.

CHK2 is a member of the checkpoint kinase family of serine/threonine protein kinases and is involved in a mechanism used for surveillance of DNA damage, such as damage caused by environmental mutagens and endogenous reactive oxygen species. As a result, it is implicated as a tumor suppressor and target for cancer therapy.

CSK influences the metastatic potential of cancer cells, particularly colon cancer.

Fes is a non-receptor protein tyrosine kinase that has been implicated in a variety of cytokine signal transduction pathways, as well as differentiation of myeloid cells. Fes is also a key component of the granulocyte differentiation machinery.

Flt3 receptor tyrosine kinase activity is implicated in leukemias and myelodysplastic syndrome. In approximately 25% of AML the leukemia cells express a constitutively active form of auto-phosphorylated (p) FLT3 tyrosine kinase on the cell surface. The activity of p-FLT3 confers growth and survival advantage on the leukemic cells. Patients with acute leukemia, whose leukemia cells express p-FLT3 kinase activity, have a poor overall clinical outcome. Inhibition of p-FLT3 kinase activity induces apoptosis (programmed cell death) of the leukemic cells.

Inhibitors of IKKα and IKKβ (1 & 2) are therapeutics for diseases which include rheumatoid arthritis, transplant rejection, inflammatory bowel disease, osteoarthritis, asthma, chronic obstructive pulmonary disease, atherosclerosis, psoriasis, multiple sclerosis, stroke, systemic lupus erythematosus, Alzheimer's disease, brain ischemia, traumatic brain injury, Parkinson's disease, amyotrophic lateral sclerosis, subarachnoid hemorrhage or other diseases or disorders associated with excessive production of inflammatory mediators in the brain and central nervous system.

Met is associated with most types of the major human cancers and expression is often correlated with poor prognosis and metastasis. Inhibitors of Met are therapeutics for diseases which include cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), cancers of the blood such as acute myeloid leukemia, chronic myeloid leukemia, etc, Barrett's esophagus (pre-malignant syndrome) neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

The Nima-related kinase 2 (Nek2) is a cell cycle-regulated protein kinase with maximal activity at the onset of mitosis that localizes to the centrosome. Functional studies have implicated Nek2 in regulation of centrosome separation and spindle formation. Nek2 protein is elevated 2- to 5-fold in cell lines derived from a range of human tumors including those of cervical, ovarian, prostate, and particularly breast.

p70S6K-mediated diseases or conditions include, but are not limited to, proliferative disorders, such as cancer and tuberous sclerosis.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41 g. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Schemes I-V:

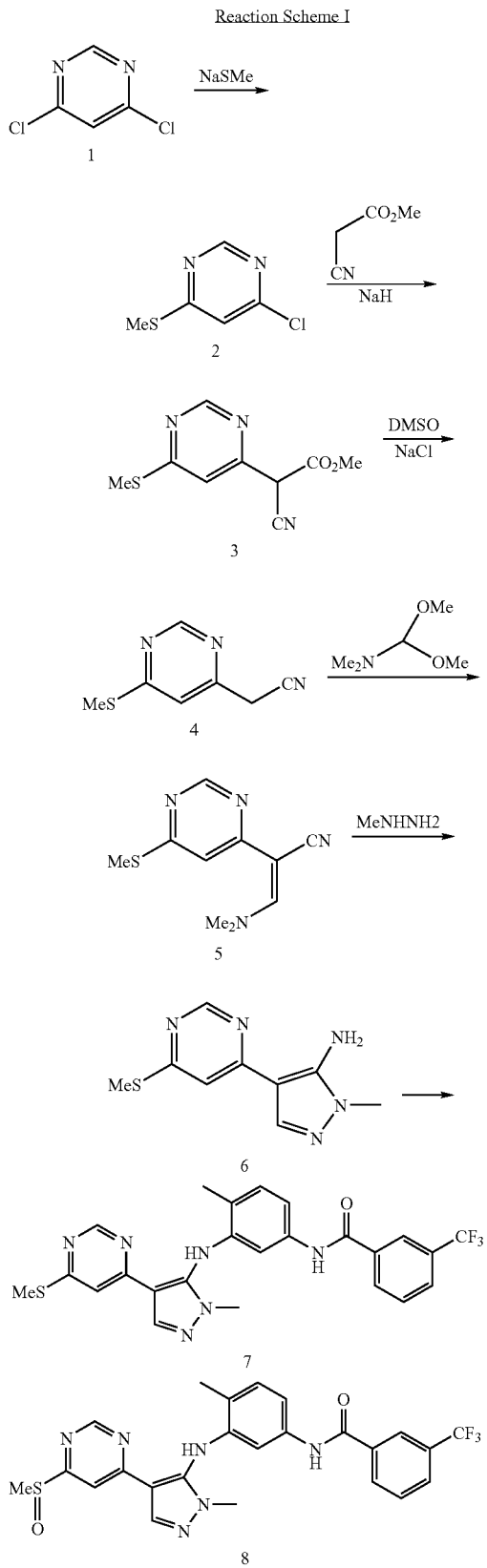

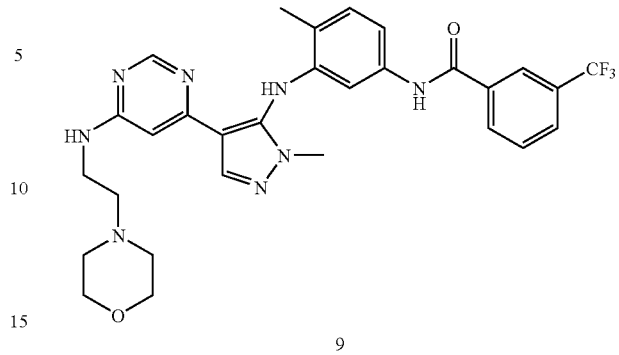

A compound of Formula 2 can be prepared by reacting of a compound of formula 1 with NaSMe in the presence of a suitable solvent (e.g., THF). A compound of formula 3 can be prepared by reacting of a compound of formula 2 and methyl cyanoacetate in the presence of a solvent (e.g., DMSO, DMF and the like) using an appropriate base (e.g., sodium hydride (NaH)).

A compound of formula 4 can be prepared by decarboxylation of a compound of formula 3 with NaCl in a suitable solvent (e.g., a mixture of DMSO and water) and in a temperature range of about 120 to about 180° C. can take up to 4 hours to complete. A compound of formula 4 can be converted to give a compound of formula 5 with a suitable eneamine formation reagent (e.g., N,N-dimethylformamide dimethyl acetal) and can take up to 24 hours to complete. The reaction of the resulting eneamine 5 with an appropriate hydrazine affords a compound of formula 6. A compound of formula 7 can be prepared by reacting a compound of formula 6 with an appropriate halide (e.g., N-(3-bromo-4-methyl-phenyl)-3-trifluoromethyl-benzamide). The reaction proceeds in the presence of a suitable catalyst (e.g., Pd (II) salt, or the like), a suitable ligand (e.g., Xantphos, or the like) and a suitable solvent (e.g., 1,4-dioxane, or the like), in a temperature range of about 80 to about 150° C. and can take up to about 20 hours to complete. A compound of formula 7 can be further oxidized to give a compound of formula 8 with a suitable oxidizing agent (e.g., m-chloroperoxybenzoic acid (mCPBA), or the like) and can take up to 6 hours to complete. A compound of formula 9 can be prepared by reacting a compound of formula 8 with an appropriate amine or aniline. The reaction is carried out in a temperature range of 100-150° C. and can take up to 10 hours to complete. The reaction conditions for alkyl amine displacement involves heating a compound of formula 9 with 5-10 equivalents of amine in a suitable solvent (e.g. DMSO, DMF, or the like).

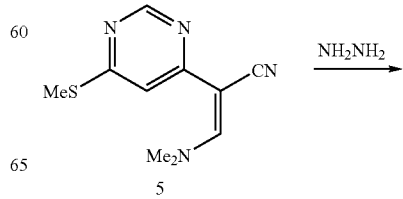

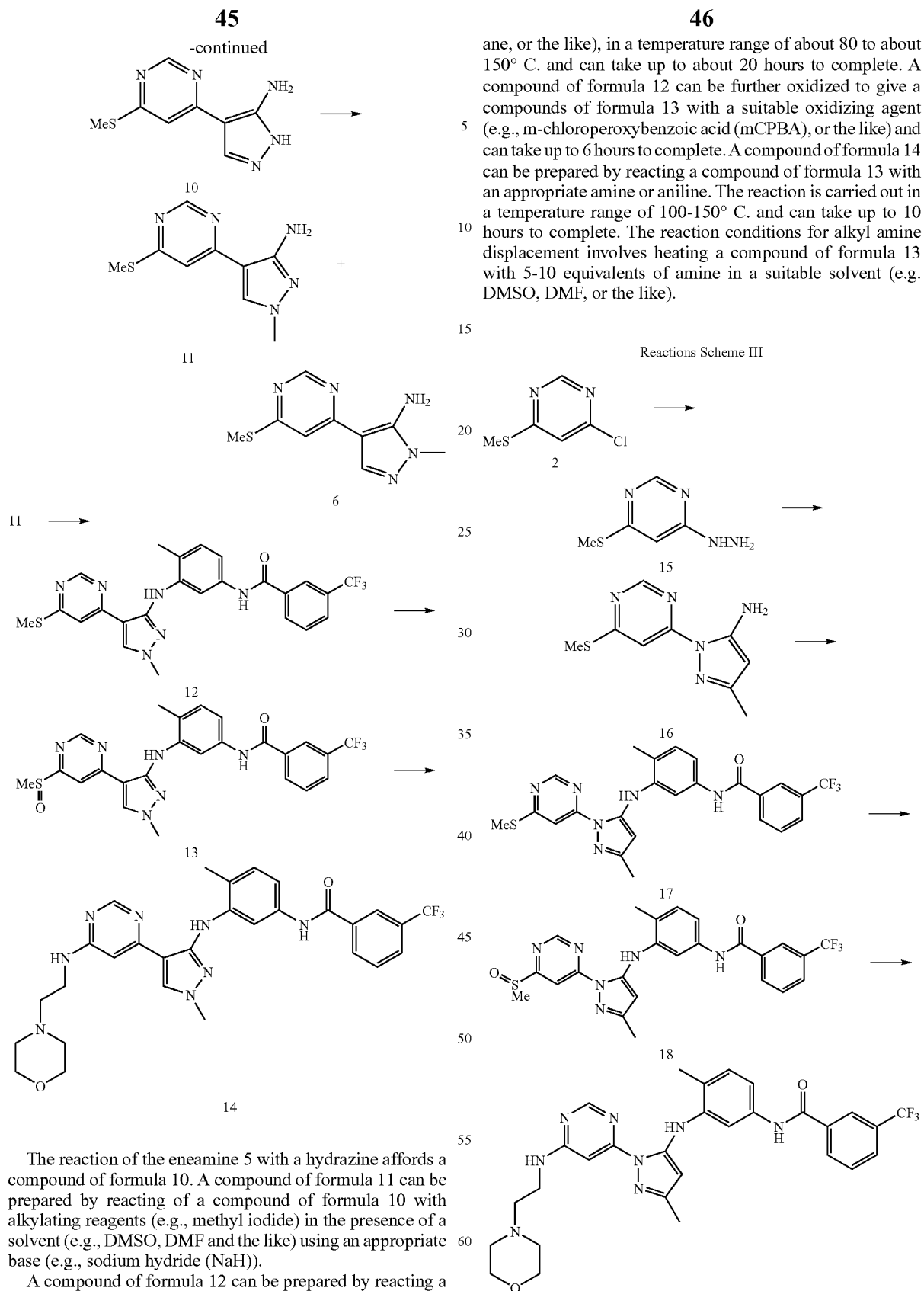

ane, or the like), in a temperature range of about 80 to about 150° C. and can take up to about 20 hours to complete. A compound of formula 12 can be further oxidized to give a compounds of formula 13 with a suitable oxidizing agent (e.g., m-chloroperoxybenzoic acid (mCPBA), or the like) and can take up to 6 hours to complete. A compound of formula 14 can be prepared by reacting a compound of formula 13 with an appropriate amine or aniline. The reaction is carried out in a temperature range of 100-150° C. and can take up to 10 hours to complete. The reaction conditions for alkyl amine displacement involves heating a compound of formula 13 with 5-10 equivalents of amine in a suitable solvent (e.g. DMSO, DMF, or the like).

The reaction of the eneamine 5 with a hydrazine affords a compound of formula 10. A compound of formula 11 can be prepared by reacting of a compound of formula 10 with alkylating reagents (e.g., methyl iodide) in the presence of a solvent (e.g., DMSO, DMF and the like) using an appropriate base (e.g., sodium hydride (NaH)).

A compound of formula 12 can be prepared by reacting a compound of formula 11 with an appropriate halide (e.g., N-(3-bromo-4-methyl-phenyl)-3-trifluoromethyl-benzamide). The reaction proceeds in the presence of a suitable catalyst (e.g., Pd (II) salt, or the like), a suitable ligand (e.g., Xantphos, or the like) and a suitable solvent (e.g., 1,4-diox- A compound of formula 15 can be prepared by reacting of a compound of formula 2 and hydrazine in the presence of a solvent (e.g., ethanol, DMSO, DMF and the like). Cyclization of a compound of formula 15 with an appropriate nitrile (e.g. 3-aminocrotononitrile) affords a compound of formula 16. A compound of formula 17 can be prepared by reacting a compound of formula 16 with an appropriate halide (e.g., N-(3-bromo-4-methyl-phenyl)-3-trifluoromethyl-benzamide). The reaction proceeds in the presence of a suitable catalyst (e.g., Pd (II) salt, or the like), a suitable ligand (e.g., Xantphos, or the like) and a suitable solvent (e.g., 1,4-dioxane, or the like), in a temperature range of about 80 to about 150° C. and can take up to about 20 hours to complete. A compound of formula 17 can be further oxidized to give a compound of formula 18 with a suitable oxidizing agent (e.g., m-chloroperoxybenzoic acid (mCPBA), or the like) and can take up to 6 hours to complete. A compound of formula 19 can be prepared by reacting a compound of formula 18 with an appropriate amine or aniline. The reaction is carried out in a temperature range of 100-150° C. and can take up to 10 hours to complete. The reaction conditions for alkyl amine displacement involves heating a compound of formula 18 with 5-10 equivalents of amine in a suitale solvent (e.g. DMSO, DMF, or the like).

Reactions Scheme IV

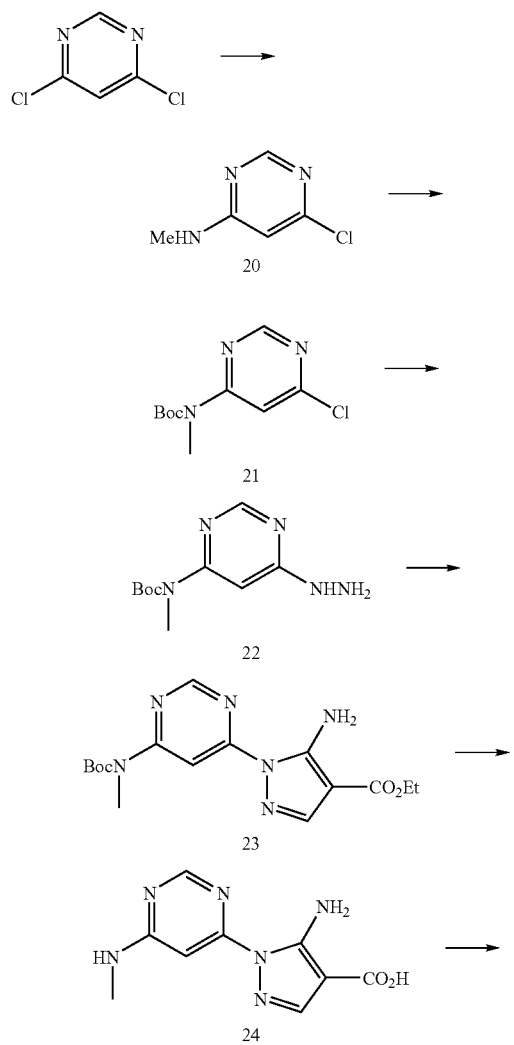

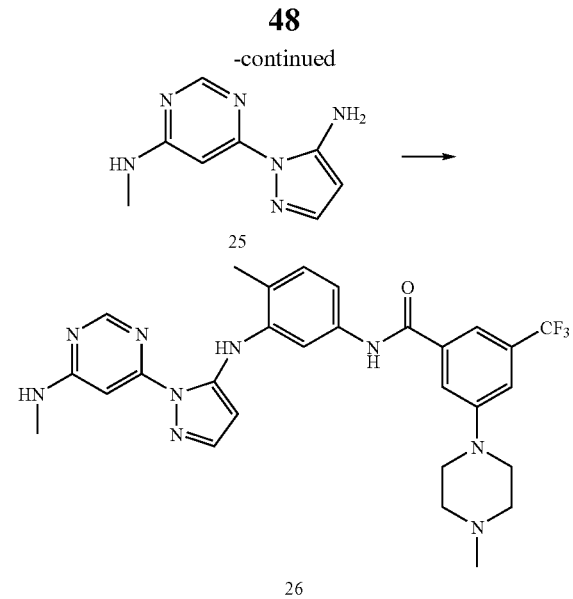

A compound of Formula 20 can be prepared by reacting of 4,6-dichloro pyrimidine with an appropriate amine (e.g. methyl amine) in the presence of a suitable solvent (e.g., ethanol, THF and the like). A compound of formula 21 can be prepared by reacting of a compound of formula 20 and Boc$_2$O in the presence of a solvent (e.g., THF, DCM and the like) using an appropriate base (e.g., DMAP). A compound of formula 22 can be prepared by reacting of a compound of formula 21 and hydrazine in the presence of a solvent (e.g., ethanol, THF, DMF and the like). Cyclization of a compound of formula 22 with an appropriate nitrile (e.g. ethyl(ethoxymethylene)cyanoacetate) affords a compound of formula 23. Cyclization of a compound of formula 22 with an appropriate nitrile (e.g. ethyl(ethoxymethylene)cyanoacetate) affords a compound of formula 23. Hydrolysis of compound of formula 23 with an appropriate base (e.g. NaOH) affords a compound of formula 24. A compound of formula 25 can be prepared by decarboxylation of a compound of formula 24 in a temperature range of about 150 to about 180° C. can take up to 4 hours to complete. A Compound of formula 26 can be prepared by reacting a compound of formula 25 with an appropriate halide (e.g., N-(3-bromo-4-methyl-phenyl)-3-(4-methyl-piperazin-1-yl)-5-trifluoromethyl-benzamide). The reaction proceeds in the presence of a suitable catalyst (e.g., Pd (II) salt, or the like), a suitable ligand (e.g., Xantphos, or the like) and a suitable solvent (e.g., 1,4-dioxane, or the like), in a temperature range of about 80 to about 150° C. and can take up to about 20 hours to complete.

Reactions Scheme V

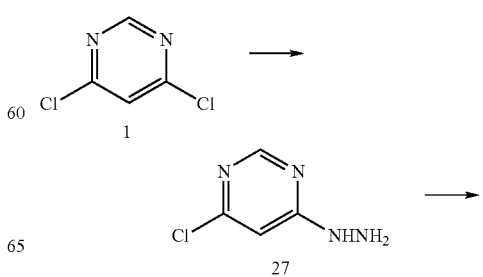

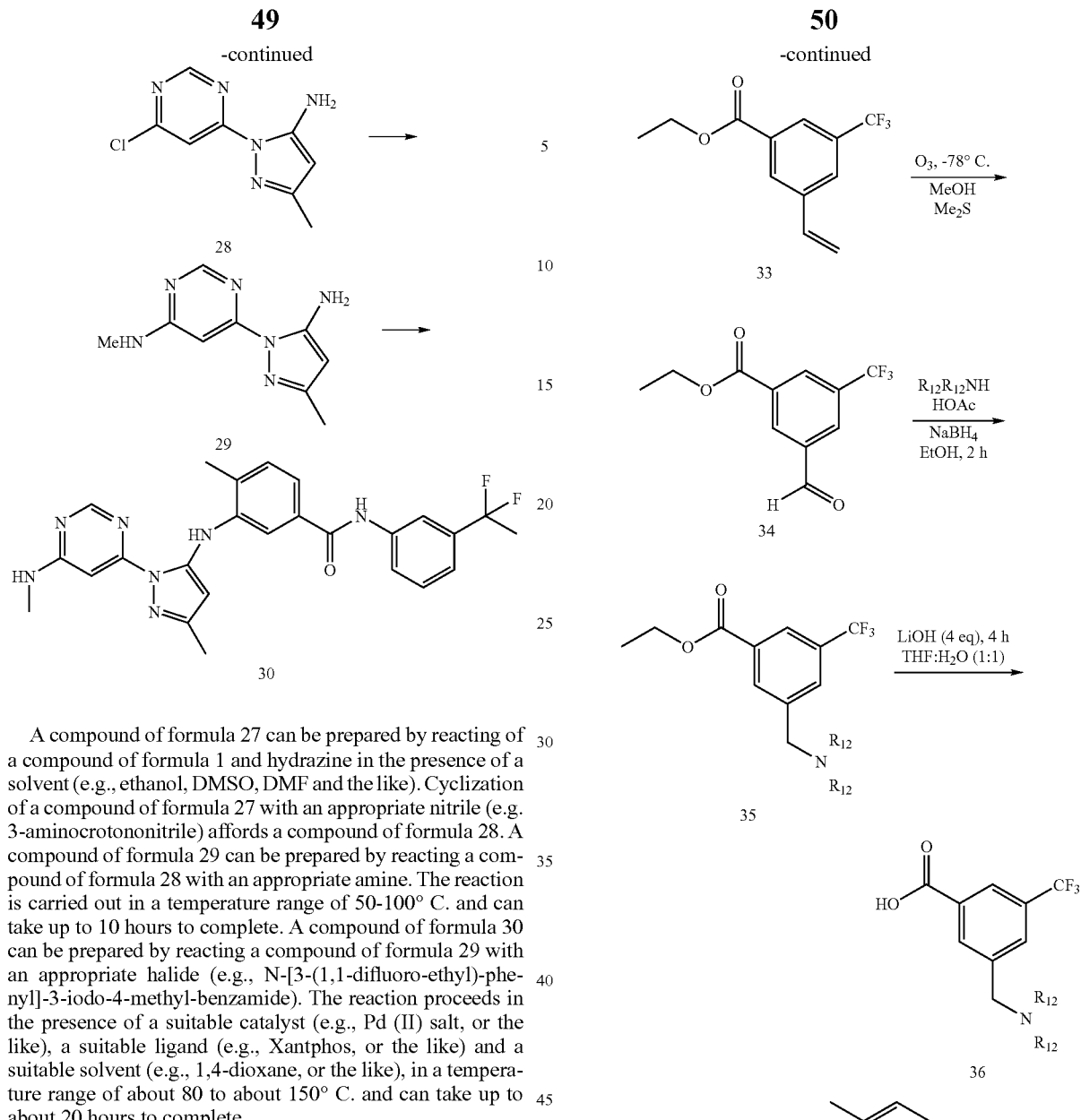

A compound of formula 27 can be prepared by reacting of a compound of formula 1 and hydrazine in the presence of a solvent (e.g., ethanol, DMSO, DMF and the like). Cyclization of a compound of formula 27 with an appropriate nitrile (e.g. 3-aminocrotononitrile) affords a compound of formula 28. A compound of formula 29 can be prepared by reacting a compound of formula 28 with an appropriate amine. The reaction is carried out in a temperature range of 50-100° C. and can take up to 10 hours to complete. A compound of formula 30 can be prepared by reacting a compound of formula 29 with an appropriate halide (e.g., N-[3-(1,1-difluoro-ethyl)-phenyl]-3-iodo-4-methyl-benzamide). The reaction proceeds in the presence of a suitable catalyst (e.g., Pd (II) salt, or the like), a suitable ligand (e.g., Xantphos, or the like) and a suitable solvent (e.g., 1,4-dioxane, or the like), in a temperature range of about 80 to about 150° C. and can take up to about 20 hours to complete.

Reactions Scheme VI

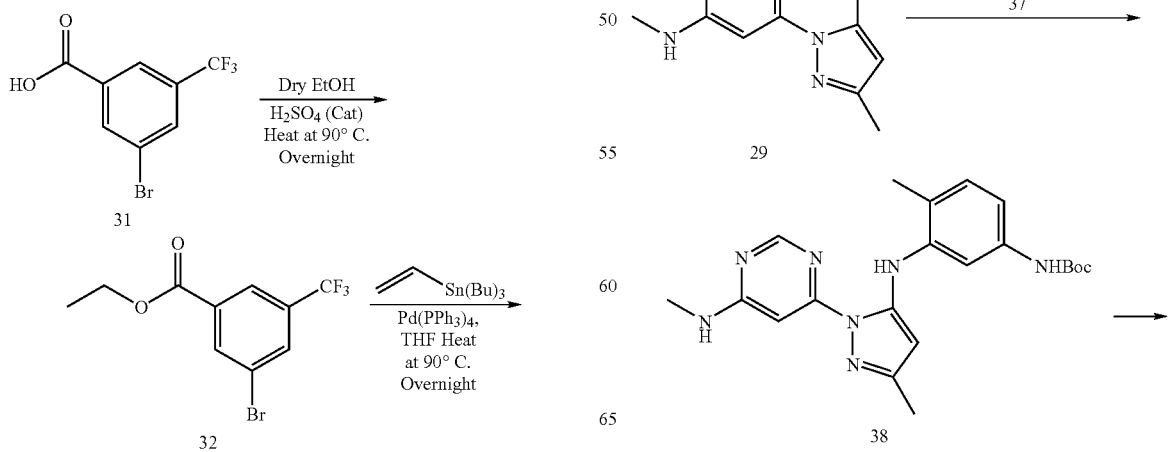

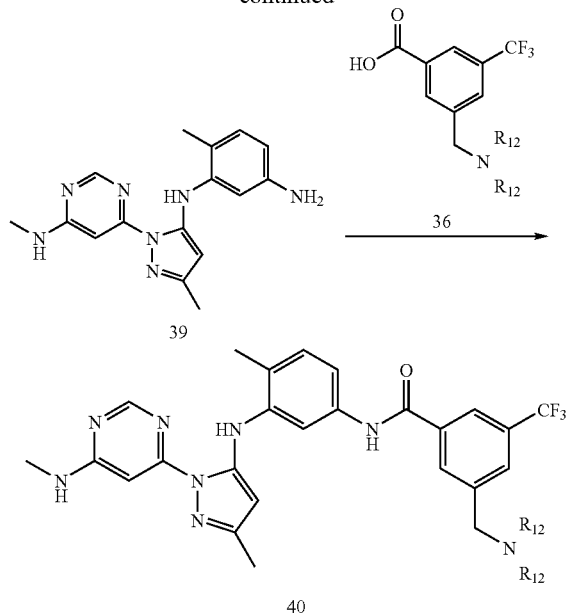

In which $R_{12}$ is as defined in the Summary of the Invention. A compound of formula 33 can be prepared by reacting of a compound of formula 32 and trialkyyl(vinyl)stannane in the presence of a suitable catalyst (e.g., Pd(0) complex or Pd (II) salt, or the like), a suitable phosphor-ligand (or the like), and a solvent (e.g., 1,4-dioxane, THF or the like). Cleavage of the vinyl group using conditions well known in the fields (Ozonolysis, $OsO_4/NaIO_4$, or the like) provides compound of formula 34. Reductive amination using primary or secondary amines in the presence of a reducing reagent ($NaBH_4$, $Na(OAc)_3BH$, $Na(CN)BH_3$, or the like) and suitable solvent (ethanol, 1,2-dichloroethane, DMF, or the like) affords compound of formula 35. Saponification of compound of formula 35 then gives the carboxylic acid of formula 36. Reacting of compound of formula 29 with compound of formula 37 in the presence of a suitable catalyst (e.g., Pd (II) salt, or the like), a suitable ligand (e.g., Xantphos, or the like) and a suitable solvent (e.g., 1,4-dioxane, or the like), in a temperature range of about 80 to about 150° C., provides compound of formula 38. De-protection of the Boc group under acidic conditions such as trifluoroacetic acid/DCM affords compound of formula 39. Amide bond formation between carboxylic acid of formula 36 and the amine of formula 39 under the standard peptide coupling reaction conditions (HATU/DIEA, EDCI/HOBT, or the like) yields compound of formula 40.

A detailed example of the synthesis of a compound of formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction schemes I to V, and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

N-(4-Methyl-3-{2-methyl-4-[6-(2-morpholin-4-yl-ethylamino)-pyrimidin-4-yl]-2H-pyrazol-3-ylamino}-phenyl)-3-trifluoromethyl-benzamide

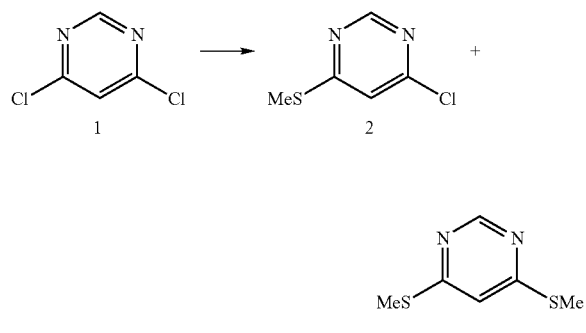

A mixture of 4,6-dichrolo-pyrimidine 1 (20.93 g, 140 mmol), sodium thiomethoxide (10.34 g, 147 mmol) in THF (100 mL) is stirred at room temperature, overnight. The reaction mixture is concentrated. The residue is partitioned between ethyl acetate and brine. The organic layer is separated and washed with brine, dried over $Na_2SO_4$. The crude product is purified by recrystallization from hexanes (60 mL) to afford 4-chloro-6-methylsulfanyl-pyrimidine. The mother liquor is concentrated and the residue is purified by silica gel flash chromatography eluting with ethyl acetate in hexanes from 0% to 10% to give 4-chloro-6-methylsulfanyl-pyrimidine containing and a small amount of byproduct 4,6-bis methylthio-pyrimidine, which is easily removed in the next step. $^1$H NMR 400 MHz ($CDCl_3$) δ 8.72 (s, 1H), 7.21 (s, 1H), 2.58 (s, 3H).

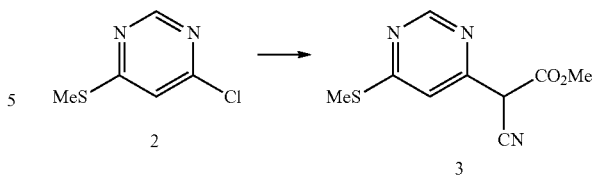

To the suspension of NaH (2.19 g, 55 mmol, 60% in oil) in DMSO (20 mL) is added methyl cyanoacetate (4.88 mL, 51 mmol) at 23° C. (cooled by ice-water if necessary). After the evolution of hydrogen has ceased, 4-chloro-6-methylsulfanyl-pyrimidine (3.56 g, 22 mmol) is added. The reaction is heated at 80° C. for 5 hours. The reaction mixture is then cooled to room temperature and quenched with ice-cooled saturated $NH_4Cl$ (50 mL). The solid is filtered and washed with water. 100 mL of hexanes is added to the solid and heated at 60° C. for 1 hour and then cooled to room temperature. The solid is filtered and washed with hexanes to afford cyano-(6-methylsulfanyl-pyrimidin-4-yl)-acetic acid methyl ester. $^1$H NMR 400 MHz (d6-DMSO) δ 8.42 (d, 1H), 6.64 (s, 1H), 3.71 (s, 3H), 2.55 (s, 3H). MS m/z 224.10 (M+1).

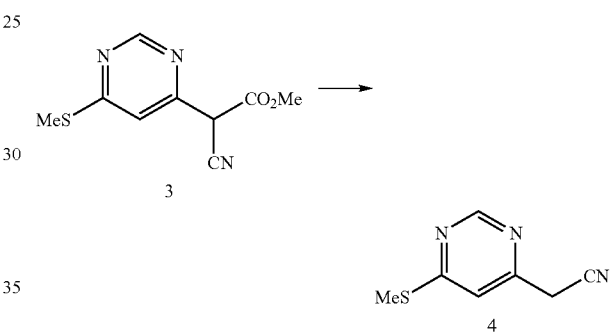

A Smith vial (10-20 mL) is charged with cyano-(6-methylsulfanyl-pyrimidin-4-yl)-acetic acid methyl ester (0.83 g, 3.72 mmol), NaCl (1.0 g), water (1 mL) and DMSO. The vial is sealed and irradiated at 160° C. for 50 minutes in Smith Synthesizer. The reaction mixture is partitioned between ethyl acetate and brine, and then filtered through a pad of celite and washed with ethyl acetate. The organic layer is separated and washed with brine, dried over $Na_2SO_4$, filtered and concentrated. The crude product is purified by silica gel flash chromatography eluting with ethyl acetate in hexanes from 10% to 100% to afford (6-methylsulfanyl-pyrimidin-4-yl)-acetonitrile: $^1$H NMR 400 MHz ($CDCl_3$) δ 8.93 (s, 1H), 7.47 (s, 1H), 4.20 (s, 2H), 2.56 (s, 3H); MS m/z 166.00 (M+1).

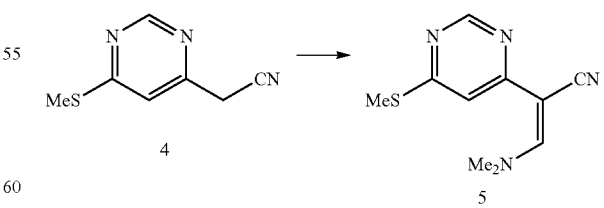

tert-butoxy-bis(dimethylamino)methane (0.60 mL, 2.9 mmol.) is added to a mixture of (6-methylsulfanyl-pyrimidin-4-yl)-acetonitrile (0.397 g, 2.4 mmol) in DMF (10 mL) at 0° C. After 2 hours, the reaction mixture is concentrated, and the residue is used for next reaction without further purification.

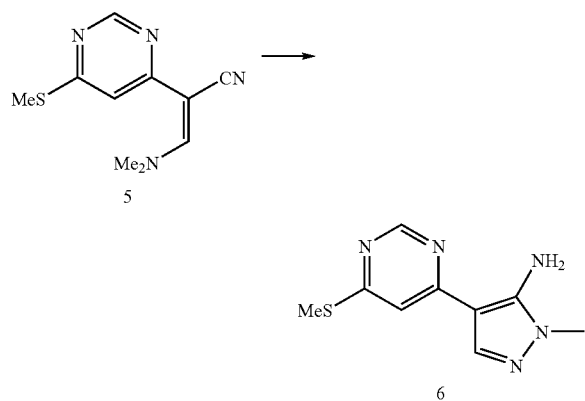

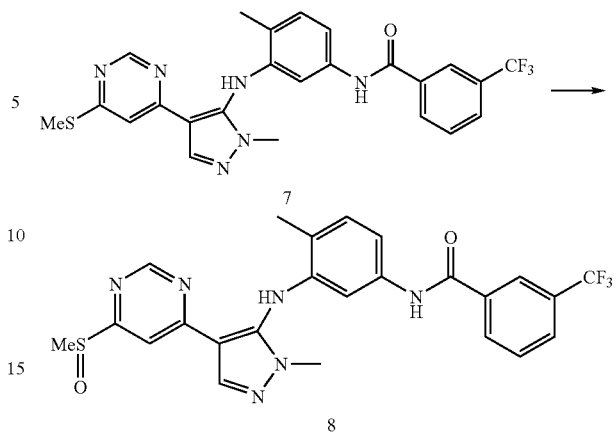

A mixture of crude 5 and methyl hydrazine (0.414 mL, 8.53 mmol) in ethanol (15 ml) is heated at 80° C. for 16 hours. The reaction mixture is cooled to room temperature and concentrated. The reaction mixture is partitioned between ethyl acetate and brine. The organic layer is separated and washed with brine, dried over Na₂SO₄, filtered and concentrated. The crude product is purified by silica gel flash chromatography eluting with ethyl acetate in hexanes from 10% to 100% to afford 2-methyl-4-(6-methylsulfanyl-pyrimidin-4-yl)-2H-pyrazol-3-ylamine: ¹H NMR 400 MHz (d6-DMSO) δ 8.70 (s, 1H), 7.93 (s, 1H), 7.43 (s, 1H), 6.69 (s, br 2H), 3.57 (s, 3H), 2.53 (s, 3H); MS m/z 222.00 (M+1).

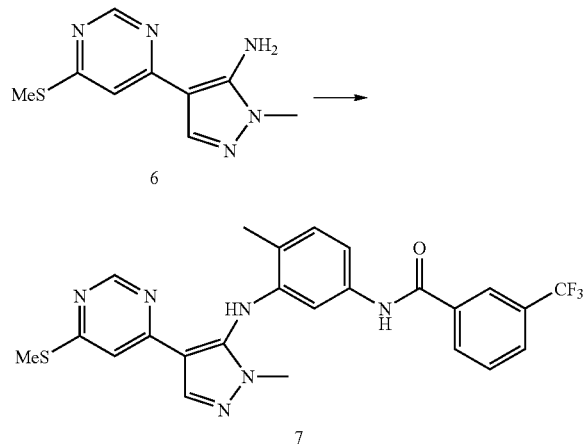

2-Methyl-4-(6-methylsulfanyl-pyrimidin-4-yl)-2H-pyrazol-3-ylamine (120 mg, 0.54 mmol) is mixed with N-(3-Bromo-4-methyl-phenyl)-3-trifluoromethyl-benzamide (290 mg, 0.81 mmol), palladium acetate (25 mg, 0.1 mmol), Xantophos (100 mg, 0.17 mmol) and cesium carbonate (530 mg, 1.63 mmol). 10 mL of anhydrous 1,4-dioxane is added under a nitrogen environment and the mixture is subjected to microwave irradiation to 150° C. for one hour. The reaction mixture is then cooled to room temperature, treated with 100 mL THF, passed through a celite column and concentrated. The crude product is purified by ISCO chromatography eluting with ethyl acetate in hexanes from 10% to 100% to afford N-{4-Methyl-3-[2-methyl-4-(6-methylsulfanyl-pyrimidin-4-yl)-2H-pyrazol-3-ylamino]-phenyl}-3-trifluoromethyl-benzamide: MS m/z 499.1 (M+1).

A suspension of N-{4-Methyl-3-[2-methyl-4-(6-methylsulfanyl-pyrimidin-4-yl)-2H-pyrazol-3-ylamino]-phenyl}-3-trifluoromethyl-benzamide (175 mg, 0.35 mmol) in 40 mL CH₂Cl₂ is treated with 3-choloroperoxybenzoic acid (77% max, 150 mg, 0.67 mmol, 1.9 eq) at 0° C. The reaction mixture is allowed to warm to room temperature with stirring for 3 hours. After oxidation is complete, the reaction mixture is quenched with saturated sodium thiosulfate solution 15 mL and vigorously stirred for 30 minutes, then treated with 100 mL dichloromethane. The reaction mixture is partitioned between dichloromethane and the aqueous layer. The organic layer is washed with saturated NaHCO₃ solution, water, and brine sequentially, then dried over Na₂SO₄, concentrated to give N-{3-[4-(6-Methanesulfinyl-pyrimidin-4-yl)-2-methyl-2H-pyrazol-3-ylamino]-4-methyl-phenyl}-3-trifluoromethyl-benzamide as yellow solid. The crude product is used directly in the next step: MS m/z 515.1 (M+1).

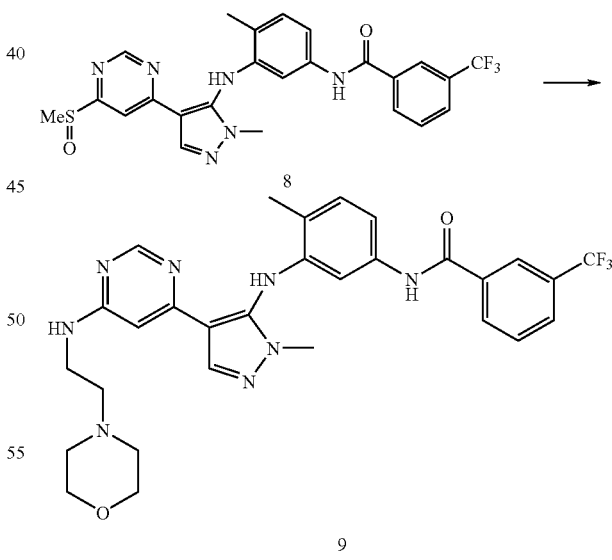

The mixture of N-{3-[4-(6-Methanesulfinyl-pyrimidin-4-yl)-2-methyl-2H-pyrazol-3-ylamino]-4-methyl-phenyl}-3-trifluoromethyl-benzamide (40 mg, 0.078 mmol) and 2-Morpholin-4-yl-ethylamine (100 µL) in 2-propanol is heated to 80° C. for 3 hours. The reaction mixture is cooled to room temperature and concentrated. The crude product is then treated with 1 mL DMSO and purified by LC/MS to afford N-(4-Methyl-3-{2-methyl-4-[6-(2-morpholin-4-yl-ethylamino)-pyrimidin-4-yl]-2H-pyrazol-3-ylamino}-phenyl)-3-trifluoromethyl-benzamide.

Example 2

N-(4-Methyl-3-{1-methyl-4-[6-(2-morpholin-4-yl-ethylamino)-pyrimidin-4-yl]-1H-pyrazol-3-ylamino}-phenyl)-3-trifluoromethyl-benzamide

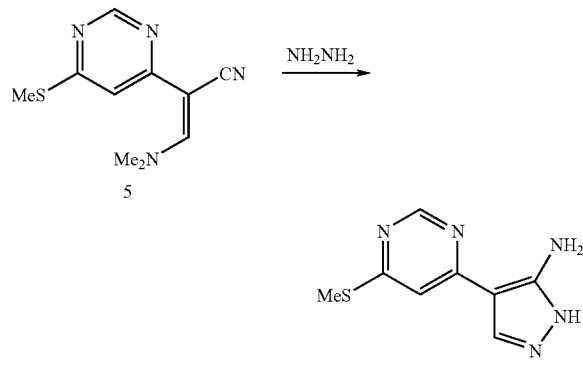

Tert-butoxybis(dimethylamino)methane (0.665 mL, 3.22 mmol.) is added to a mixture of (6-methylsulfanyl-pyrimidin-4-yl)-acetonitrile (0.484 g, 2.93 mmol) in DMF (10 mL) 0° C. After 2 hours, the reaction mixture is concentrated, and the residue is used for the next reaction without further purification.

A mixture of the above crude mixture and hydrazine monohydrate (0.426 mL, 8.78 mmol) in ethanol (15 ml) is heated at 80° C. for 3 hours. The reaction mixture is cooled to room temperature and concentrated. The reaction mixture is partitioned between ethyl acetate and brine. The organic layer is separated and washed with brine, dried over $Na_2SO_4$, filtered and concentrated. The crude product is purified by silica gel flash chromatography eluting with ethyl acetate in hexanes from 10% to 100% to afford 2-methyl-4-(6-methylsulfanyl-pyrimidin-4-yl)-2H-pyrazol-3-ylamine: $^1$H NMR 400 MHz (d6-DMSO) δ 8.70 (s, 1H), 7.92 (bs, 1H), 7.44 (bs, 1H), 6.45 (bs, 2H), 5.78 (bs, 1H), 2.53 (s, 3H); MS m/z 208.06 (M+1).

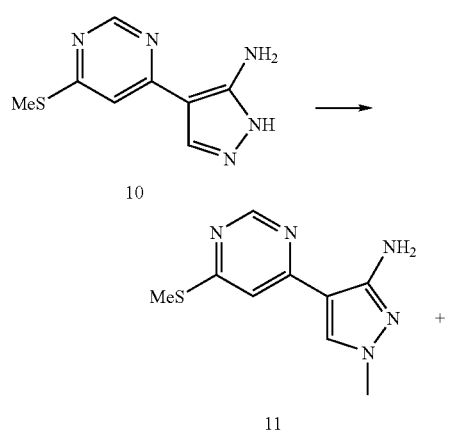

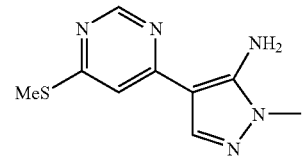

To the solution of 4-(6-Methylsulfanyl-pyrimidin-4-yl)-2H-pyrazol-3-ylamine (245 mg, 1.18 mmol) is added with NaOMe solution (25 wt % in MeOH, 425 μL, 1.53 mmol) dropwise. The reaction mixture is kept stirring for 30 minutes. Then Iodomethane (110 uL, 1.76 mmol) is added into the reaction mixture drop wise. After stirring overnight at room temperature, the reaction mixture is concentrated, treated with 75 mL ethyl acetate, and washed with water. Filtration removes the undissolved solid. The obtained filtrate is separated, and the collected organic layer is dried over sodium sulfate, and concentrated. The crude product is purified by ISCO chromatography eluting with ethyl acetate in hexanes from 25% to 100% to afford 1-Methyl-4-(6-methylsulfanyl-pyrimidin-4-yl)-1H-pyrazol-3-ylamine: $^1$H NMR 400 MHz (d6-DMSO) δ 8.73 (s, 1H), 8.27 (s, 1H), 7.44 (s, 1H), 5.81 (s, 1H), 3.65 (s, 3H), 2.53 (s, 3H); MS m/z 222.07 (M+1).

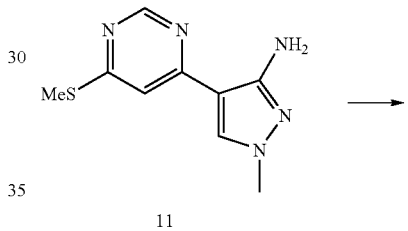

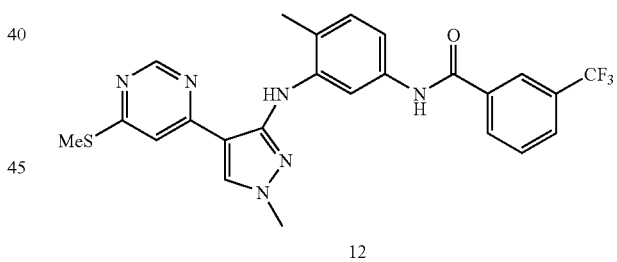

Methyl-4-(6-methylsulfanyl-pyrimidin-4-yl)-1H-pyrazol-3-ylamine (61 mg, 0.27 mmol) is mixed with N-(3-Bromo-4-methyl-phenyl)-3-trifluoromethyl-benzamide (161 mg, 0.45 mmol), palladium acetate (20 mg, 0.089 mmol), Xantophos (78 mg, 0.135 mmol) and cesium carbonate (280 mg, 0.86 mmol). 2 mL anhydrous 1,4-dioxane is added under nitrogen environment and the mixture is subjected to microwave irradiation to 150° C. for 45 minutes. The reaction mixture is then cooled to room temperature, treated with 100 mL THF, passed through a celite column and concentrated. The crude product is purified by ISCO chromatography eluting with ethyl acetate in hexanes from 10% to 100% to afford N-{4-Methyl-3-[1-methyl-4-(6-methylsulfanyl-pyrimidin-4-yl)-1H-pyrazol-3-ylamino]-phenyl}-3-trifluoromethyl-benzamide.

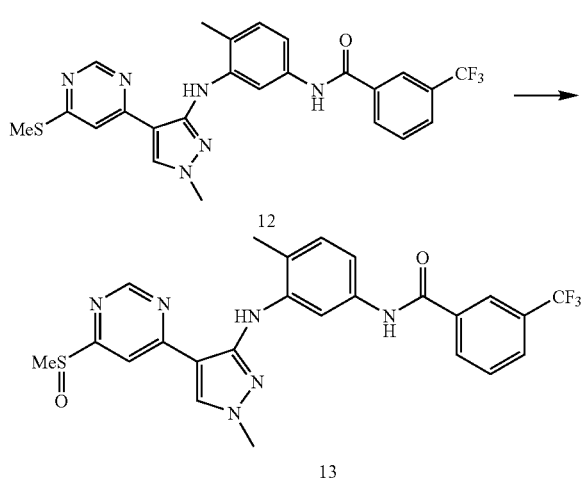

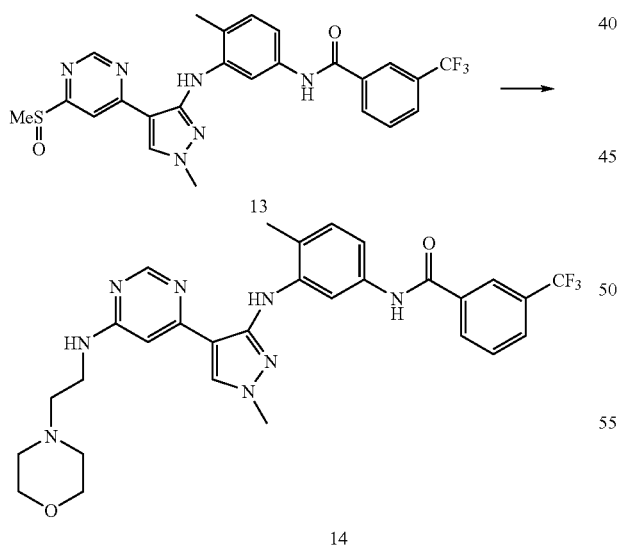

To the suspension of N-{4-Methyl-3-[1-methyl-4-(6-methylsulfanyl-pyrimidin-4-yl)-1H-pyrazol-3-ylamino]-phenyl}-3-trifluoromethyl-benzamide (128 mg, 0.26 mmol) in 25 mL CH$_2$Cl$_2$ is treated with 3-choloroperoxybenzoic acid (77% max, 86 mg, 0.38 mmol) at 0° C. The reaction mixture is allowed to warm to room temperature and kept stirring for 3 hours. After oxidation is complete, the reaction mixture is quenched with saturated sodium thiosulfate solution 10 mL and vigorously stirred for 30 minutes, then treated with 75 mL dichloromethane. The reaction mixture is partitioned between dichloromethane and aqueous layer. The organic layer is washed with saturated NaHCO$_3$ solution, water, and brine sequentially, then dried over Na$_2$SO$_4$, concentrated to give N-{3-[4-(6-Methanesulfinyl-pyrimidin-4-yl)-1-methyl-1H-pyrazol-3-ylamino]-4-methyl-phenyl}-3-trifluoromethyl-benzamide as yellow solid. The crude product is directly used in the next step.

The mixture of N-{3-[4-(6-Methanesulfinyl-pyrimidin-4-yl)-1-methyl-1H-pyrazol-3-ylamino]-4-methyl-phenyl}-3-trifluoromethyl-benzamide (30 mg, 0.058 mmol) and 2-Morpholin-4-yl-ethylamine (100 uL) in 2-propanol is heated to 80° C. for 3 hours. The reaction mixture is cooled to room temperature and condensed. The crude product is then treated with 1 mL DMSO and purified by LC/MS to afford N-(4-Methyl-3-{1-methyl-4-[6-(2-morpholin-4-yl-ethylamino)-pyrimidin-4-yl]-1H-pyrazol-3-ylamino}-phenyl)-3-trifluoromethyl-benzamide.

Example 3

N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-enzamide

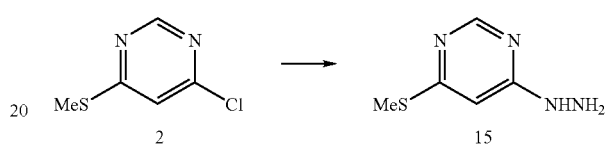

A mixture of 4-Chloro-6-methylsulfanyl-pyrimidine (1.1 g, 6.85 mmol), hydrazine monohydrate (1.2 g, 23.5 mmol), and 2-propanol (10 mL) is heated to 90° C. for 4 hours. The reaction mixture is then cooled to room temperature, concentrated, triturated with water, and filtered. The undissolved solid is washed with water, air-dried to give (6-Methylsulfanyl-pyrimidin-4-yl)-hydrazine as light yellow solid: $^1$H NMR 400 MHz (d6-DMSO) δ 8.29 (s, 1H), 8.16 (s, 1H), 6.55 (s, 1H), 4.34 (s, 2H), 2.43 (s, 3H); MS m/z 157.05 (M+1).

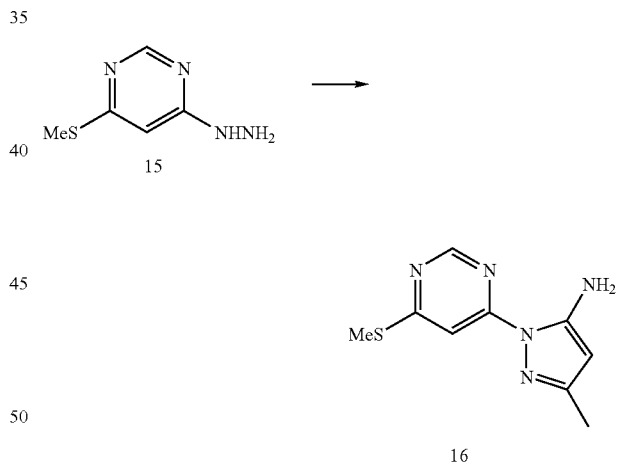

The mixture of (6-Methylsulfanyl-pyrimidin-4-yl)-hydrazine (1.0 g, 6.4 mmol), 3-Imino-butyronitrile (1.1 g, 12.8 mmol), and ethanol (30 mL) is heated to 85° C. for overnight. The reaction mixture is then cooled to room temperature, condensed, and treated with 75 mL ethyl acetate. The reaction mixture is partitioned between ethyl acetate and aqueous layer. The organic layer is dried over Na$_2$SO$_4$ and concentrated. The crude product is purified by ISCO chromatography eluting with ethyl acetate in hexanes from 10% to 80% to afford 5-Methyl-2-(6-methylsulfanyl-pyrimidin-4-yl)-2H-pyrazol-3-ylamine: $^1$H NMR 400 MHz (d6-DMSO) δ 8.72 (s, 1H), 7.53 (s, 1H), 6.90 (s, 1H), 5.26 (s, 1H), 2.57 (s, 3H), 2.08 (s, 3H); MS m/z 222.07 (M+1).

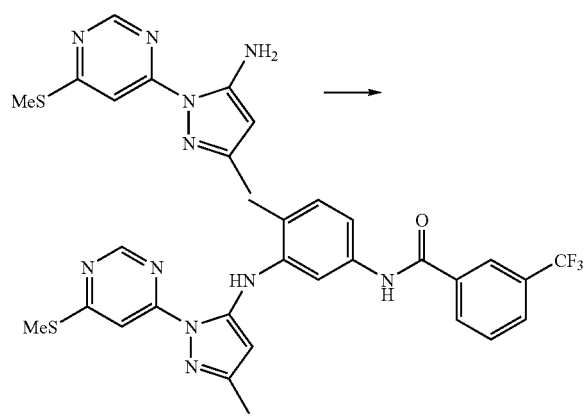

5-Methyl-2-(6-methylsulfanyl-pyrimidin-4-yl)-2H-pyrazol-3-ylamine (90 mg, 0.40 mmol) is mixed with N-(3-Bromo-4-methyl-phenyl)-3-trifluoromethyl-benzamide (228 mg, 0.64 mmol), palladium acetate (20 mg, 0.089 mmol), Xantophos (75 mg, 0.13 mmol) and cesium carbonate (420 mg, 1.28 mmol). 4 mL anhydrous 1,4-dioxane is added under a nitrogen environment and the mixture is subjected to microwave irradiation to 150° C. for 30 minutes. The reaction mixture is then cooled to room temperature, treated with 100 mL THF, passed through a celite column and concentrated. The crude product is purified by ISCO chromatography eluting with ethyl acetate in hexanes from 0% to 40% to afford N-{4-Methyl-3-[5-methyl-2-(6-methylsulfanyl-pyrimidin-4-yl)-2H-pyrazol-3-ylamino]-phenyl}-3-trifluoromethyl-benzamide: $^1$H NMR 400 MHz (d6-DMSO) δ 10.65 (s, 1H), 10.46 (s, 1H), 8.89 (s, 1H), 8.30-8.25 (m, 2H), 7.98 (d, J=7.5 Hz, 1H), 7.89 (s, 1H), 7.80 (t, J=7.5 Hz, 1H), 7.67 (s, 1H), 7.40 (d, J=7.5 Hz, 1H), 7.25 (d, J=8.2 Hz, 1H), 6.12 (s, 1H), 2.61 (s, 3H), 2.34 (s, 3H), 2.25 (s, 3H); MS m/z 499.14 (M+1).

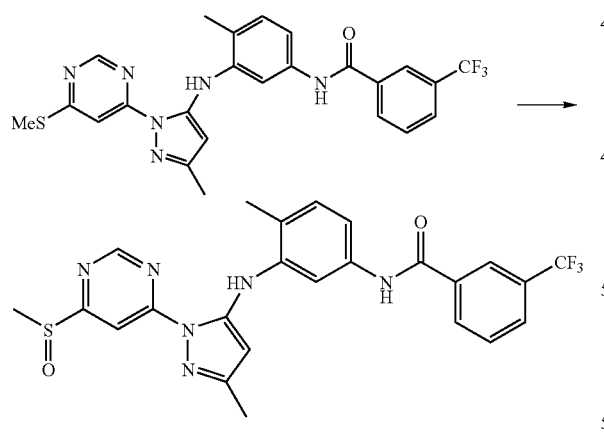

To the suspension of N-{4-Methyl-3-[5-methyl-2-(6-methylsulfanyl-pyrimidin-4-yl)-2H-pyrazol-3-ylamino]-phenyl}-3-trifluoromethyl-benzamide (240 mg, 0.48 mmol) in 25 mL CH$_2$Cl$_2$ is treated with 3-choloroperoxybenzoic acid (77% max, 162 mg, 0.72 mmol, 1.5 eq) at 0° C. The reaction mixture is allowed to warm to room temperature with stirring for 3 hours. After oxidation is complete, the reaction mixture is quenched with saturated sodium thiosulfate solution 10 mL and vigorously stirred for 30 minutes, then treated with 75 mL dichloromethane. The reaction mixture is partitioned between dichloromethane and aqueous layer. The organic layer is washed with saturated NaHCO$_3$ solution, water, and brine sequentially, then dried over Na$_2$SO$_4$, concentrated to give N-{3-[2-(6-Methanesulfinyl-pyrimidin-4-yl)-5-methyl-2H-pyrazol-3-ylamino]-4-methyl-phenyl}-3-trifluoromethyl-benzamide as a green solid. The crude product is directly used in the next step. MS m/z 515.1 (M+1).

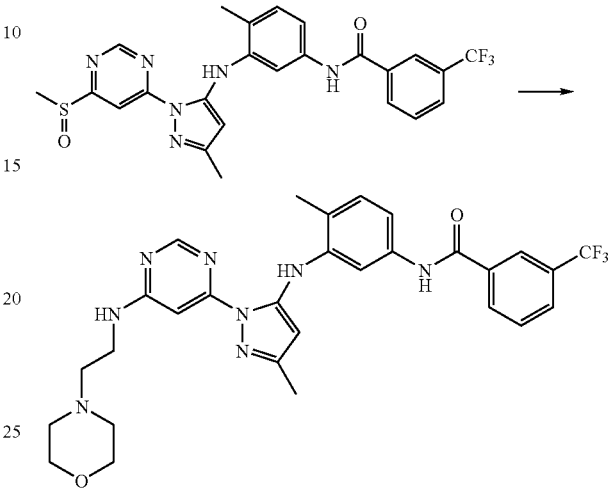

The mixture of N-{3-[2-(6-Methanesulfinyl-pyrimidin-4-yl)-5-methyl-2H-pyrazol-3-ylamino]-4-methyl-phenyl}-3-trifluoromethyl-benzamide (20 mg, 0.04 mmol) and 2-Morpholin-4-yl-ethylamine (100 uL) in 2-propanol is heated to 80° C. for 3 hours. The reaction mixture is cooled to room temperature and condensed. The crude product is then treated with 1 mL DMSO and purified by LC/MS to afford N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-benzamide.

Example 4

N-{4-Methyl-3-[2-(6-methylamino-pyrimidin-4-yl)-2H-pyrazol-3-ylamino]-phenyl}-3-(4-methyl-piperazin-1-yl)-5-trifluoromethyl-benzamide

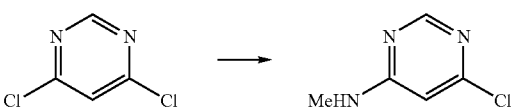

A mixture of 4,6-dichloro-pyrimidine (3.53 g, 23.7 mmol) and methylamine (33 wt % in ethanol, 10 ml, 80 mmol) in ethanol is kept stirring overnight at room temperature. The reaction mixture is concentrated, triturated with water and filtered. The crude product is washed with water, a small amount of ethanol and ethyl ether sequentially, and air-dried to give (6-Chloro-pyrimidin-4-yl)-methyl-amine as white powder: $^1$H NMR 400 MHz (d6-DMSO) δ 8.36-8.16 (m, 1H), 7.69 (s, 1H), 6.50 (s, 1H), 2.90-2.68 (m, 3H); MS m/z 144.00 (M+1).

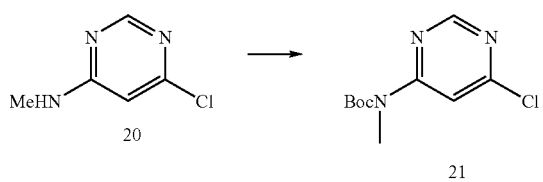

A mixture of (6-chloro-pyrimidin-4-yl)-methyl-amine (10 g, 69.7 mmol), triethylamine (15 mL, 106.7 mmol), and dimethylaminopyridine (8.5 g, 69.5 mmol) in 100 mL dichloromethane is added di-t-butyl dicarbonate (18.75 g, 85.9 mmol) potion wise. The reaction mixture is kept stirring at room temperature for 4 hours and concentrated. The resultant crude product is treated with water and filtered. The obtained solid is dried under vacuum to give (6-Chloro-pyrimidin-4-yl)-methyl-carbamic acid tert-butyl ester: $^1$H NMR 400 MHz (d6-DMSO) δ 8.80 (s, 1H), 8.04 (s, 1H), 3.37 (s, 3H), 1.52 (s, 9H); MS m/z 244.10 (M+1).

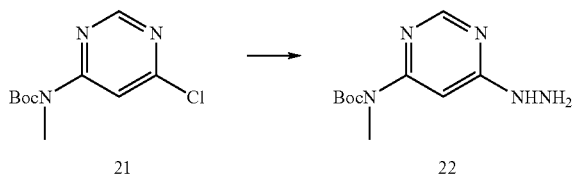

A mixture of (6-Chloro-pyrimidin-4-yl)-methyl-carbamic acid tert-butyl ester (10 g, 41.1 mmol), hydrazine monohydrate (6.5 g, 130.0 mmol), and 2-propanol (50 mL) is heated to 90° C. for 4 hours. The reaction mixture is then cooled to room temperature, and concentrated. The resultant crude product is treated with a mixture of water (80 mL) and ethanol (15 mL), heated for 30 minutes, and slowly cooled to room temperature. White precipitate forms. After filtration, the undissolved solid is washed with water, dried under vacuum overnight to give (6-Hydrazino-pyrimidin-4-yl)-methyl-carbamic acid tert-butyl ester as white powder in needle form: $^1$H NMR 400 MHz (d6-DMSO) δ 8.23 (s, 1H), 8.19 (s, 1H), 7.14 (s, 1H), 4.29 (s, 2H), 3.23 (s, 3H), 1.49 (s, 9H); MS m/z 240.10 (M+1).

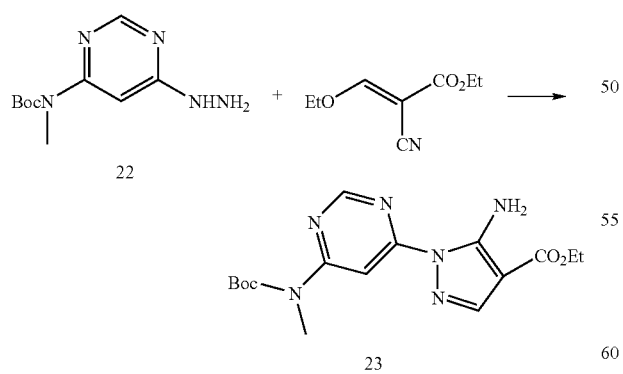

A mixture of (6-hydrazino-pyrimidin-4-yl)-methyl-carbamic acid tert-butyl ester (4.0 g, 16.7 mmol), 2-cyano-3-ethoxy-acrylic acid ethyl ester (3.02 g, 17.5 mmol) and ethanol (25 mL) is heated to reflux for 4 hours. The reaction mixture is then concentrated and triturated with water (10 mL). White precipitate forms. After filtration, the undissolved solid is further washed with water, then air-dried to give 5-amino-1-[6-(tert-butoxycarbonyl-methyl-amino)-pyrimidin-4-yl]-1H-pyrazole-4-carboxylic acid ethyl ester as white powder.

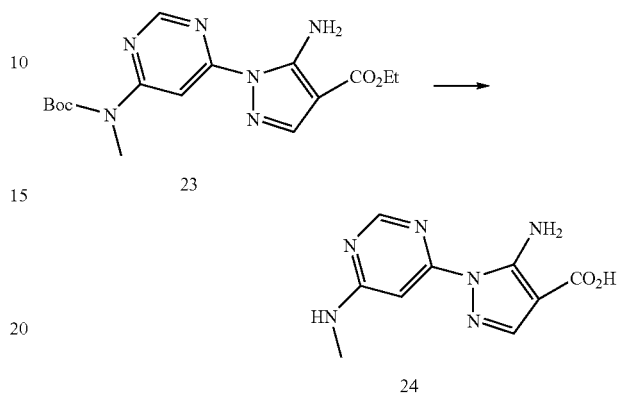

A mixture of 5-amino-1-[6-(tert-butoxycarbonyl-methyl-amino)-pyrimidin-4-yl]-1H-pyrazole-4-carboxylic acid ethyl ester (5.5 g, 15.2 mmol), lithium hydroxide (1.82 g, 75.8 mmol) dissolved in a mixture of 1,4-Dioxane (20 mL) and water (5 mL) is heated to 85° C. for 8 hours. The reaction mixture is then neutralized with 2 M HCl aqueous solution until pH~4-5 causing a white precipitate to form. After filtration, the undissolved solid is washed with small amount of water, air-dried to give 5-amino-1-[6-(tert-butoxycarbonyl-methyl-amino)-pyrimidin-4-yl]-1H-pyrazole-4-carboxylic acid as white powder: $^1$H NMR 400 MHz (d6-DMSO) δ 8.41 (s, 1H), 8.00-7.40 (m, 4H), 6.86-6.58 (m, 1H), 2.86 (s, 3H); MS m/z 235.10 (M+1).

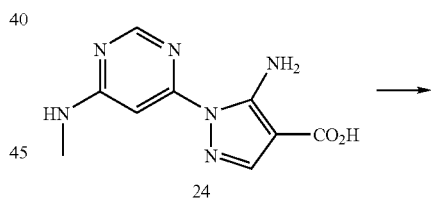

The 5-amino-1-[6-(tert-butoxycarbonyl-methyl-amino)-pyrimidin-4-yl]-1H-pyrazole-4-carboxylic acid (230 mg, 0.98 mmol) is heated to 160° C. for 1.5 hours on a hot plate in powder form. The crude product is purified by ISCO chromatography eluting with ethyl acetate in hexanes from 20% to 100% to afford [6-(5-Amino-pyrazol-1-yl)-pyrimidin-4-yl]-methyl-amine: $^1$H NMR 400 MHz (d6-DMSO) δ 8.33 (s, 1H), 7.53 (s, 1H), 7.35 (s, 1H), 7.00-6.60 (m, 3H), 5.34 (s, 1H), 2.83 (bs, 3H); MS m/z 191.10 (M+1).

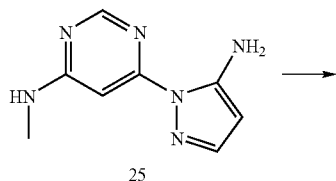

25

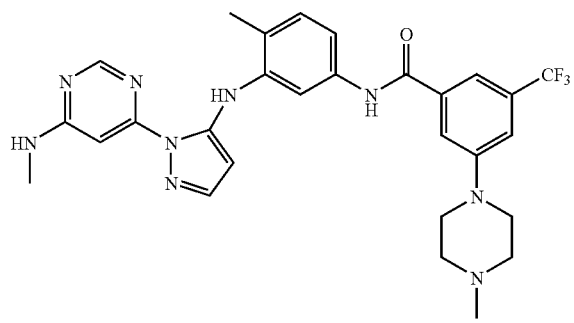

26

[6-(5-Amino-pyrazol-1-yl)-pyrimidin-4-yl]-methyl-amine (200 mg, 1.05 mmol) is mixed with N-(3-bromo-4-methyl-phenyl)-3-(4-methyl-piperazin-1-yl)-5-trifluoromethyl-benzamide (640 mg, 1.40 mmol), palladium acetate (60 mg, 0.27 mmol), Xantophos (235 mg, 0.41 mmol) and cesium carbonate (1.03 g, 3.15 mmol). 10 mL of anhydrous 1,4-dioxane is added under nitrogen environment and the mixture is subjected to microwave irradiation to 160° C. for 25 minutes. The reaction mixture is treated with 150 mL THF, passed through a celite column and condensed. The crude product is purified by ISCO chromatography eluting with THF and methanol (v/v=1:1) in methylene chloride from 0% to 10% to afford N-{4-Methyl-3-[2-(6-methylamino-pyrimidin-4-yl)-2H-pyrazol-3-ylamino]-phenyl}-3-(4-methyl-piperazin-1-yl)-5-trifluoromethyl-benzamide.

Example 5

N-[5-(1-Fluoro-1-methyl-ethyl)-pyridin-3-yl]-4-methyl-3-[5-methyl-2-(6-methylamino-pyrimidin-4-yl)-2H-pyrazol-3-ylamino]-benzamide

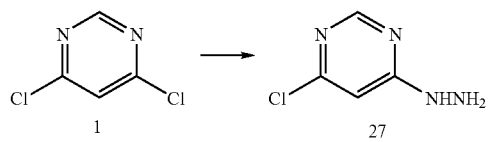

A mixture of 4,6-dichloro-pyrimidine (18.68 g, 125 mmol), hydrazine monohydrate (18.28 mL, 376 mmol), and 2-propanol (300 mL) was stirred at room temperature for 3 hours. The reaction mixture was concentrated, triturated with water, and filtered. The solid was washed with water, air-dried to give (6-chloro-pyrimidin-4-yl)-hydrazine (16.97 g, Yield 94%): $^1$H NMR 400 MHz (d6-DMSO) δ 8.83 (s, 1H), 8.17 (s, 1H), 6.76 (s, 1H), 4.50 (s, 2H); MS m/z 145.02 (M+1).

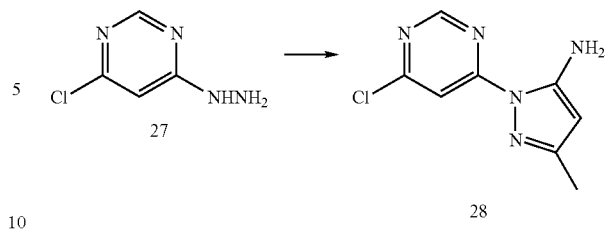

The mixture of (6-chloro-pyrimidin-4-yl)-hydrazine (16.97 g, 117 mmol), 3-imino-butyronitrile (28.88 g, 352 mmol), and 2-propanol (500 mL) was heated to 85° C. for 5 h. The reaction mixture was then cooled to room temperature, condensed, and recrystallized from ethanol/water (1:1, 400 mL). The solid was filtered and washed with water (200 mL), then ethanol/water (1:1, 100 mL), dried to afford the desired product 20 0.66 g. An additional product (0.9 g) was isolated from the filtrate after standing overnight at room temperature. MS m/z 210.05 (M+1).

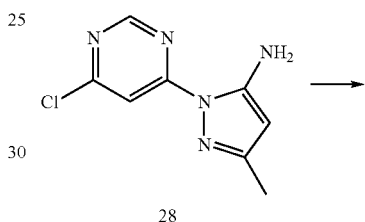

28

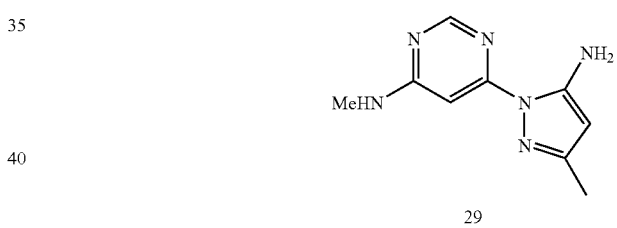

29

5-Methyl-2-(6-chloro-pyrimidin-4-yl)-2H-pyrazol-3-ylamine (2.09 g, 10 mmol) was mixed with methyl amine (40% in water, 9 mL) and 2-propanol (30 mL). The mixture was heated at 50° C. in a sealed tube. After 4 h, the reaction mixture was cooled to room temperature and condensed, triturated with water, and filtered. The solid was washed with water, air-dried to give [6-(5-amino-3-methyl-pyrazol-1-yl)-pyrimidin-4-yl]-methyl-amine (2.08 g, Yield 97%): $^1$H NMR 400 MHz (d6-DMSO) δ 8.80 (s, 1H), 7.44 (s, 1H), 6.82-6.74 (m, 3H), 5.19 (s, 1H), 2.83 (s, 3H), 2.06 (s, 3H); MS m/z 210.64 (M+1).

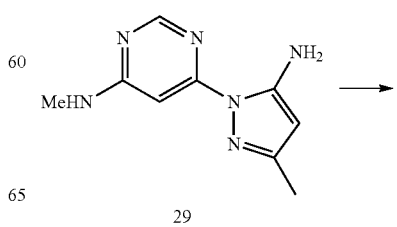

29

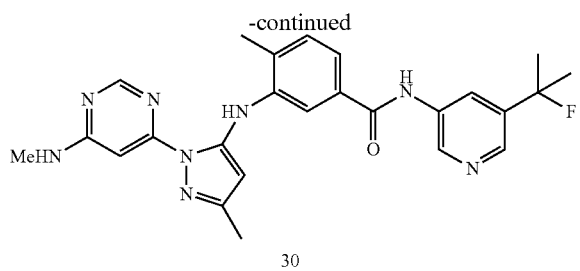

30

A suspension of [6-(5-amino-3-methyl-pyrazol-1-yl)-pyrimidin-4-yl]-methyl-amine (17 mg, 0.083 mmol), N-[5-(1-fluoro-1-methyl-ethyl)-pyridin-3-yl]-3-iodo-4-methyl-benzamide (41 mg, 0.104 mmol), Pd(OAc)$_2$ (2 mg, 0.009 mmol), Xantphos (9 mg, 0.0166 mmol) and Cs$_2$CO$_3$ (54 mg, 0.166 mmol) in anhydrous 1,4-dioxane (2 mL) in a pressure vial was degassed by a stream of argon and sealed. The reaction was stirred at 150° C. for 1 hour. LCMS showed completion of the reaction. A solution of 5% diethyl dithiocarbomic acid sodium salt (3 mL) was added to the reaction. A light yellow precipitate was collected by filtration, washed with water and dried. The crude was purified by column (SiO$_2$, EtOAc/hexanes: 30 to 100%) to give a white solid (25 mg, 64%): m/z 475.2 (M+1).

Example 426

3-((isopropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide

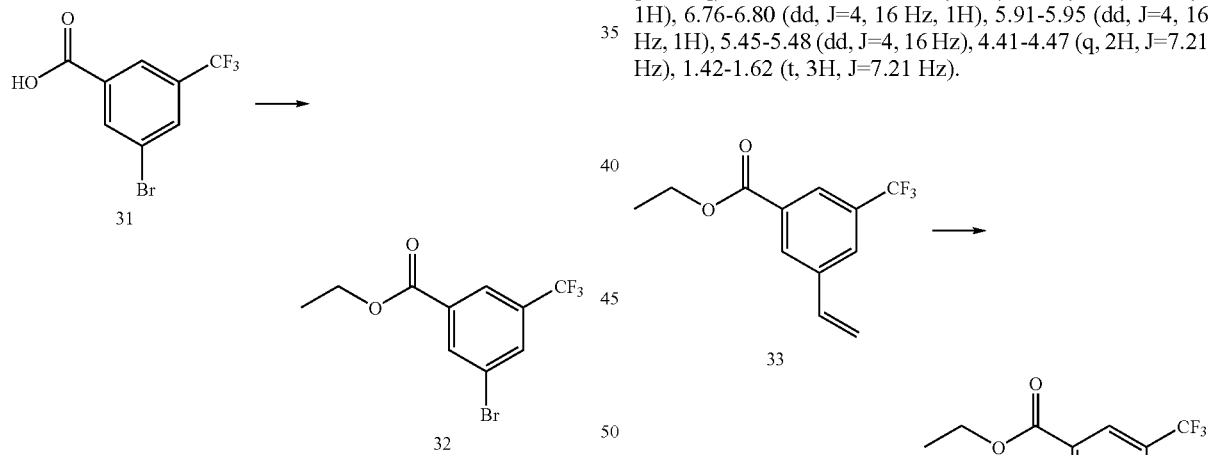

100 g (371.71 mmol) of 3-bromo-5-(trifluoromethyl)benzoic acid 31 is dissolved in dry ethanol (300 mL) and 19 mL of conc. H$_2$SO$_4$ (Catalytic) is added drop by drop over a 15 minutes time period at room temperature. The reaction mixture is stirred at 90° C. overnight. An aliquot is taken out and checked via LC/MS and a big product peak is observed and no starting material is detected. The reaction mixture is poured into ice-cold water (200 mL) and is extracted with ethyl acetate (3×100 mL). The organic layers are combined and dried over magnesium sulfate and is pure enough to be carried over to the next step without further purification. Product is ethyl 3-bromo-5-(trifluoromethyl)-benzoate 32. MS: m/z [M+H+]) 296.80, $^1$H NMR: 8.36 (s, 1H), 8.24, (s, 1H), 7.95, (s, 1H), 4.41-4.47 (q, 2H, J=7.21 Hz), 1.42-1.45 (t, 3H, J=7.21 Hz).

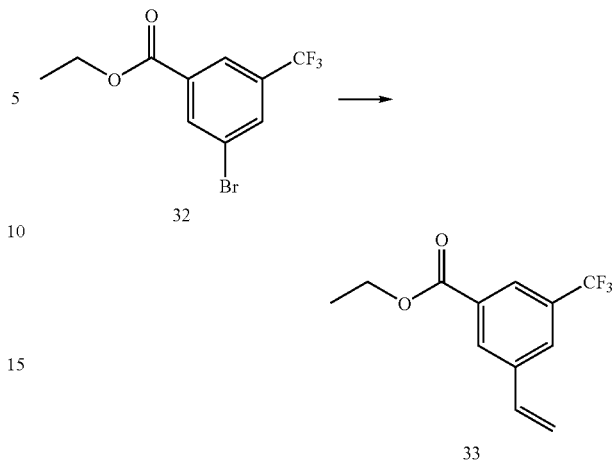

50 g of ethyl 3-bromo-5-(trifluoromethyl)benzoate 32 is dissolved in dry THF (100 mL), and tributyl vinyl tin (56.85 g, 185.14 mmol, 1.09 eq) is added followed by tetrakistriphenylphosphine palladium (0) (2.5 g, 2.16 mmol, 0.013 eq). The reaction is heated at 90° C. for 18 hours. Next day the reaction mixture is tested via LC/MS and only product peak is detected without any trace of starting materials. The reaction mixture is filtered over celite to remove the palladium and then extra solvent is removed under vacuo. The desired compound is then isolated via flash column chromatography using straight hexane followed by 10% EtoAc/Hex) to afford ethyl 3-(trifluoromethyl)-5-vinylbenzoate 33. MS: m/z [M+H+]) 245.10, $^1$H NMR 8.26 (s, 1H), 8.19 (s, 1H), 7.82 (s, 1H), 6.76-6.80 (dd, J=4, 16 Hz, 1H), 5.91-5.95 (dd, J=4, 16 Hz, 1H), 5.45-5.48 (dd, J=4, 16 Hz), 4.41-4.47 (q, 2H, J=7.21 Hz), 1.42-1.62 (t, 3H, J=7.21 Hz).

25.39 g (103.96 mmol) of ethyl 3-(trifluoromethyl)-5-vinylbenzoate 33 is dissolved in dry MeOH (200 mL) and reaction vessel Is cooled down to −78° C. Then O$_3$ is bubbled through for 1.5 hours until the reaction mixture turned dark blue. Then ozone is turned off and nitrogen is bubbled through the reaction mixture to remove extra ozone from the solution. 9.6 g of dimethyl sufide (155.95 mmol, 1.5 eq) is added and the reaction mixture is stirred at −78° C. for 2 hours followed by at room temperature for another hour. All the solvents are removed and ethyl 3-formyl-5-(trifluoromethyl)benzoate 34 is isolated via flash column chromatography (5-10% EtOAc/Hex). MS: m/z [M+H+]) 247.18, $^1$H NMR 10.16 (s, 1H), 8.73 (s, 1H), 8.56, (s, 1H), 8.35 (s, 1H), 4.46-4.51 (q, 2H, J=7.21 Hz), 1.45-1.49 (t, 3H, J=7.21 Hz).

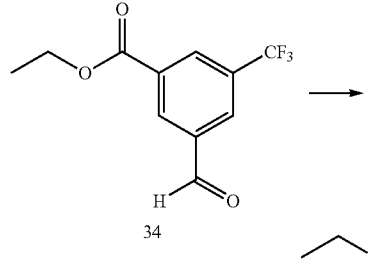

1 g (4.06 mmol, 1 eq) of 3-formyl-5-(trifluoromethyl)benzoate 34 is dissolved in dry EtOH (20 mL). To this reaction flask 287 mg isopropyl amine (4.87 mmol, 1.2 eq) and acetic acid (5 drops) are added. This reaction mixture is heated at 50° C. for 2 hours under sealed condition. The reaction mixture is then cooled down to 0° C. and sodium borohydride (184 mg, 4.87 mmol, 1.2 eq) is added in one portion. The reaction vessel is sealed once again and the mixture is stirred at 0° C. for half an hour followed by at room temperature for another 2 hours. The reaction mixture is checked by LC/MS and a single product peak is found without any trace of starting materials. The reaction mixture is poured into ice-cold NaHCO$_3$ solution and extracted with Ethyl Acetate (3×20 mL). The organic layers are combined and dried over magnesium sulfate. After purification using a flash column chromatography (5-20% Ethyl Acetate/Hex) the pure compound ethyl 3-((isopropylamino)-methyl)-5-(trifluoromethyl)benzoate is isolated as a light yellow oil. MS: m/z [M+H+]) 290.20. $^1$H NMR: 8.10 (m, 2H), 7.74 (s, 1H), 4.31-4.37 (q, 2H, J=7.20 Hz), 3.88 (s, 2H), 2.75-2.82 (m, 1H), 1.33-1.38 (t, 3H, J=7.20 Hz), 1.03-1.05 (m, 6H).

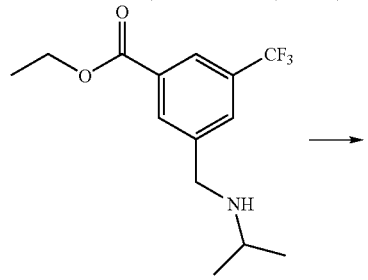

Ethyl 3-((isopropylamino)methyl)-5-(trifluoromethyl)benzoate (1.01 g, 3.49 mmol, 1 eq) is dissolved in THF/H$_2$O (1:1) 10 mL and LiOH 0.39 g (16.32 mmol, 4.6 eq) is added. The mixture is stirred at room temperature for 4 hours and then checked via LC/MS for a zero starting material peak. The organic solvent is removed and some more water is added to the reaction vessel. The reaction mixture is cooled and 1M HCl solution in ether is added drop-wise until the pH is between 4 and 5. The lithium chloride salts start to precipitate out of solution. Extra organic solvents are removed and the precipitate is transferred to small vials and freeze dried. MS: m/z [M+H+]) 262.20, $^1$H NMR: 8.45 (s, 1H), 8.27 (s, 1H), 8.15 (s, 1H), 4.26 (s, 2H), 3.25-3.38 (m, 2H), 1.33-1.34 (m, 2H).

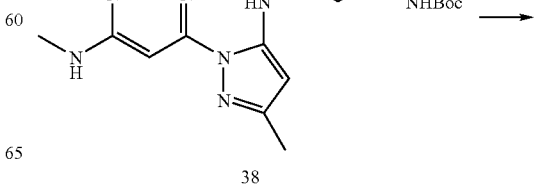

To a high pressure tube is added 6-(5-amino-3-methyl-1H-pyrazol-1-yl)-N-methylpyrimidin-4-amine 29 (2.0 g, 9.8 mmol), 3-bromo-4-methylphenyl carbamic acid tert-butyl ester 37 (2.4 g, 10.8 mmol), Pd(OAc)$_2$ (132 mg, 0.59 mmol), Cs$_2$CO$_3$ (3.5 g, 10.8 mmol), 4,5-bis(diphenylphosphino)-9,9-dimethylxanthene (340 mg, 0.59 mmol) and 1,4-dioxane (30 mL). The mixture is flushed with N$_2$ at 0° C. for a few minutes, then heated to 120° C. for 2 days. The mixture is poured into water and extracted with EtOAc. The organic layer is separated, dried with MgSO$_4$, then concentrated in vacuo. The residue is purified by flash chromatography [silica gel, hexane:EtOAc/5:5] to provide tert-butyl 4-methyl-3-(3-methyl-1-(6-(methylamino)-pyrimidin-4-yl)-1H-pyrazol-5-ylamino)phenylcarbamate 38.

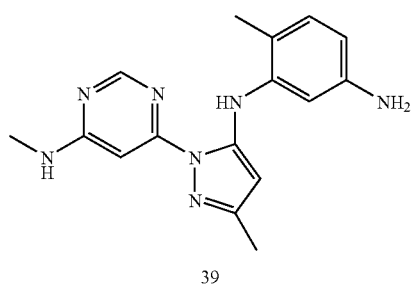

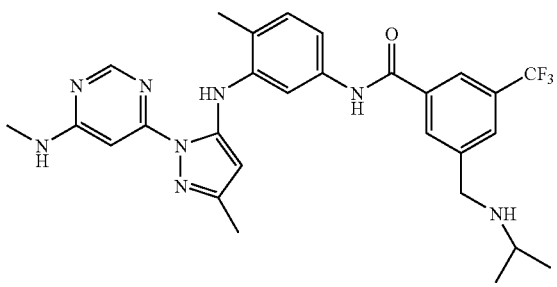

Tert-butyl 4-methyl-3-(3-methyl-1-(6-(methylamino)pyrimidin-4-yl)-1H-pyrazol-5-ylamino)phenylcarbamate 38 (2.0 g) is dissolved in a mixed solvent of TFA:DCM/1:1 (20 mL). The mixture is stirred at room temperature for 4 hours, then concentrated in vacuo. The residue is dissolved in EtOAc and washed with aqueous NaHCO₃. The organic layer is separated, dried with MgSO₄, then concentrated in vacuo to provide 6-methyl-N1-(3-methyl-1-(6-(methylamino)pyrimidin-4-yl)-1H-pyrazol-5-ylamino)benzene-1,3-diamine 39.

6-methyl-N1-(3-methyl-1-(6-(methylamino)pyrimidin-4-yl)-1H-pyrazol-5-yl)benzene-1,3-diamine 39 (360 mg, 1.16 mmol, 1 eq) is dissolved in dry DMF (10 mL), followed by 3-((isopropylamino)methyl)-5-(trifluoromethyl)benzoic acid (0.504 mg, 1.02 mmol, 0.9 eq), HATU (663 mg, 1.74 mmol, 1.5 eq), and DIEA (0.5 mL, 3.49 mmol, 3 eq). The reaction mixture is stirred at room temperature for about 4 hours until the reaction is complete as evidenced by the LC/MS product peak. The reaction mixture is then quenched by NaHCO₃ solution and extracted with ethyl acetate. The organic layers are combined and dried over magnesium sulfate. The solvents are removed under vacuo and the residue is purified by flash column chromatography to afford 3-((isopropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide. MS: m/z [M+H+]) 553.20, ¹H NMR: 11.07 (s, 1H), 10.61 (s, 1H), 9.17 (bs, 1H), 8.58 (s, 1H), 8.45 (s, 1H), 8.35 (s, 1H), 8.21 (s, 1H), 7.95 (s, 1H), 7.69 (s, 1H), 7.39 (m, 1H), 7.24 (m, 1H), 6.88 (s, 1H), 6.16 (s, 1H), 4.36 (m, 2H), 3.34-3.48 (m, 1H), 2.87 (m, 3H), 2.49 (m, 3H), 2.22 (m, 3H), 1.33-1.34 (m, 6H).

By repeating the procedures described in the above examples, using appropriate starting materials, the following compounds of Formula I, as identified in Table 1, are obtained.

TABLE 1

| Compound Number | Structure | Physical Data ¹H NMR 400 MHz or 600 MHz (DMSO-d₆) and/or MS (m/z) |
|---|---|---|
| 5 | 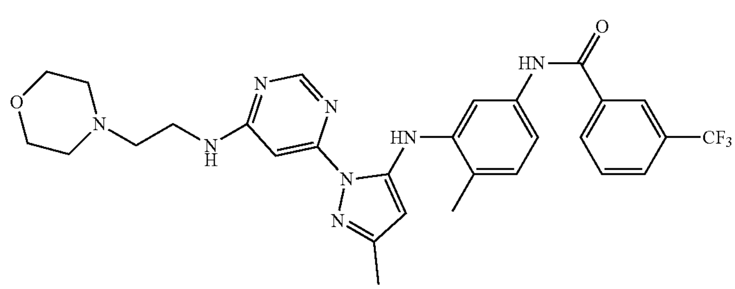 | MS m/z 581.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 6 | 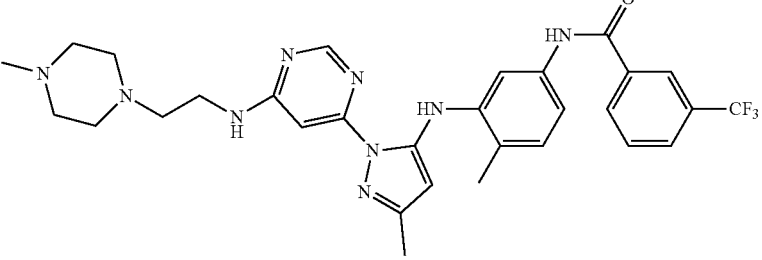 | MS m/z 594.3 (M + 1) |
| 7 | 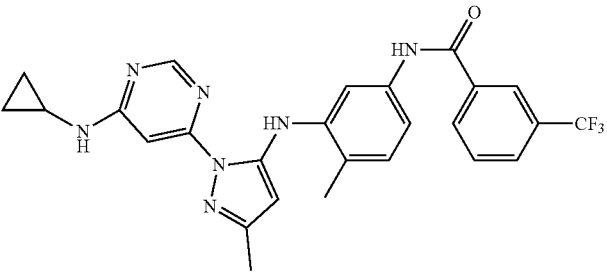 | MS m/z 508.2 (M + 1) |
| 8 | 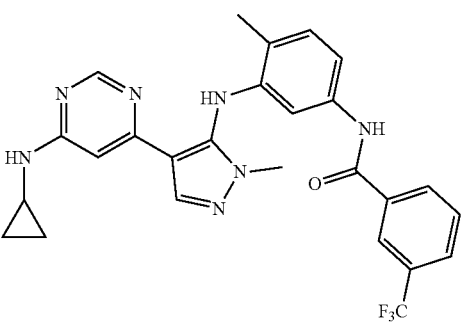 | MS m/z 508.2 (M + 1) |
| 9 | 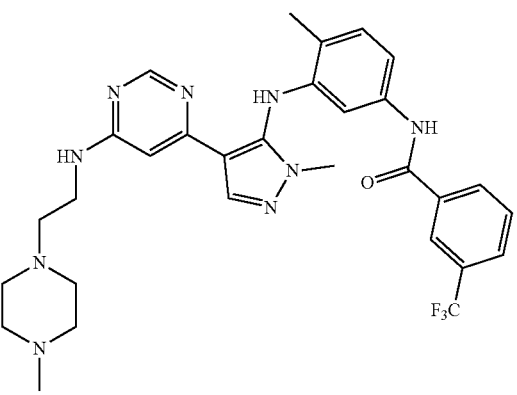 | MS m/z 594.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 10 | 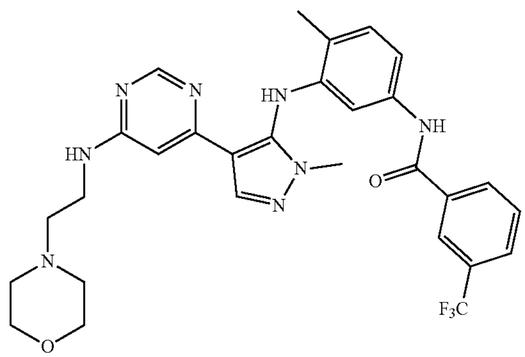 | MS m/z 581.3 (M + 1) |
| 11 | 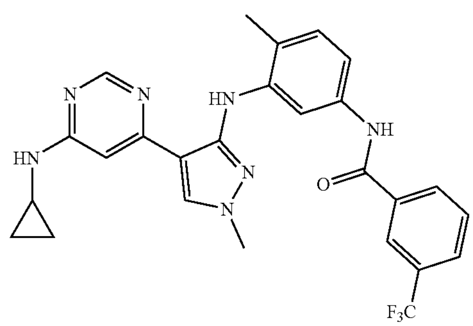 | MS m/z 508.2 (M + 1) |
| 12 | 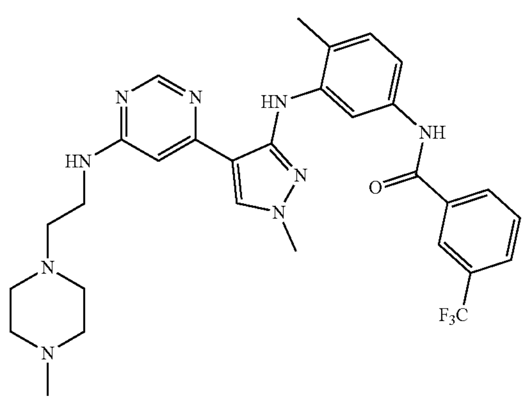 | MS m/z 594.3 (M + 1) |
| 13 | 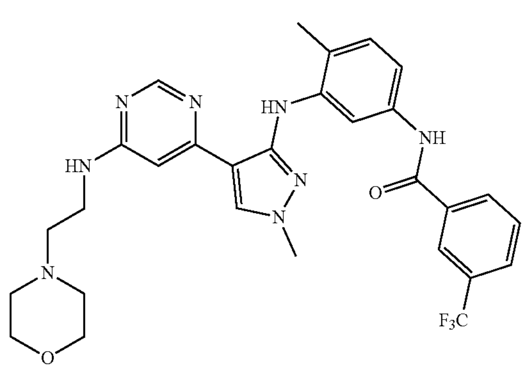 | MS m/z 581.3 (M + 1) |

TABLE 1-continued

| Compound Number | Structure | Physical Data ¹H NMR 400 MHz or 600 MHz (DMSO-d₆) and/or MS (m/z) |
|---|---|---|
| 14 | 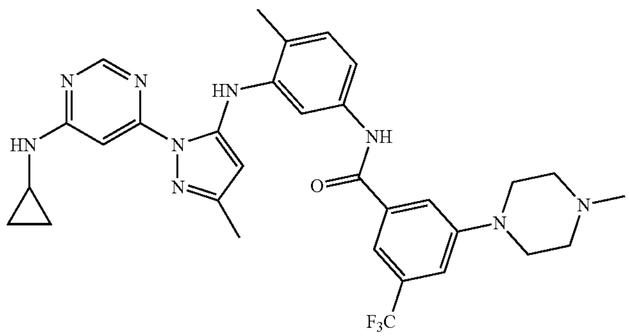 | MS m/z 606.3 (M + 1) |
| 15 | 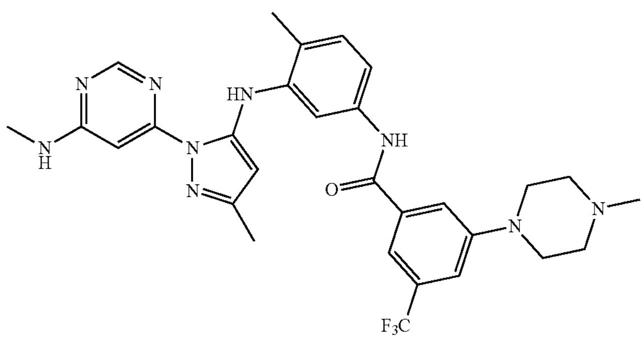 | MS m/z 580.3 (M + 1) |
| 16 | 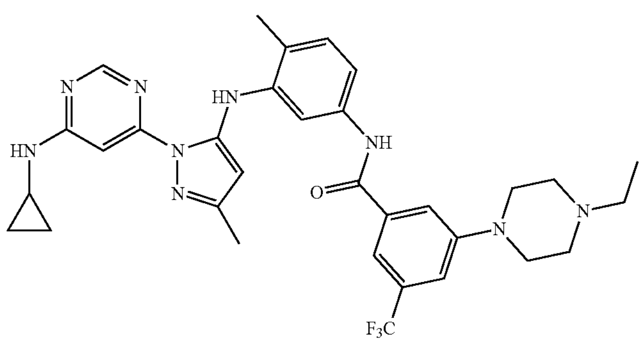 | MS m/z 620.3 (M + 1) |
| 17 | 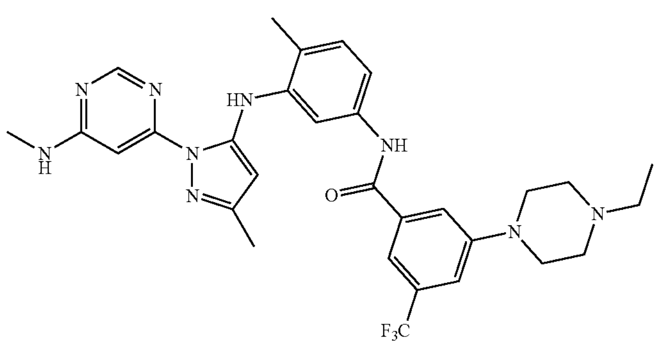 | MS m/z 594.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 18 | 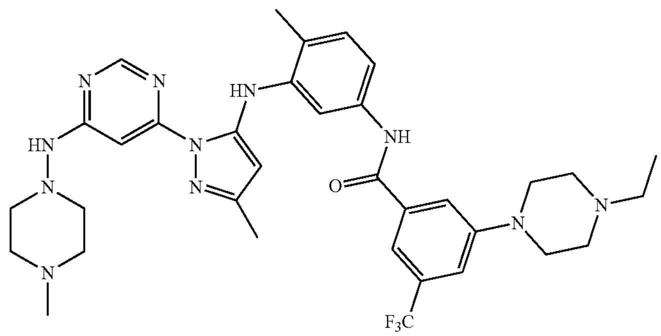 | MS m/z 678.4 (M + 1) |
| 19 | 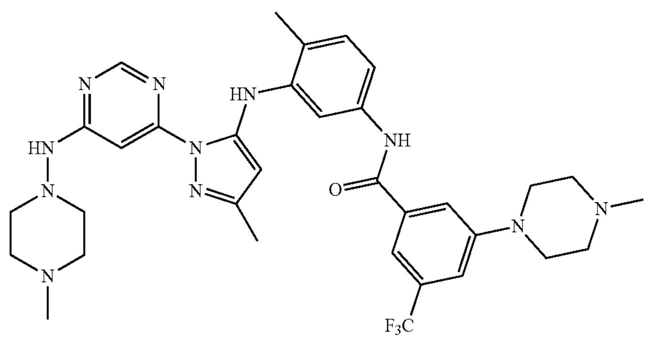 | MS m/z 664.3 (M + 1) |
| 20 | 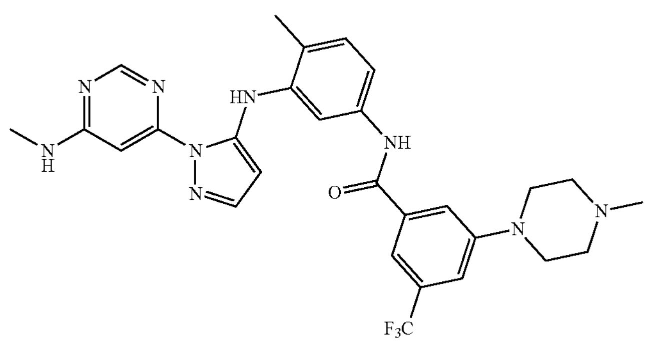 | MS m/z 566.3 (M + 1) |
| 21 | 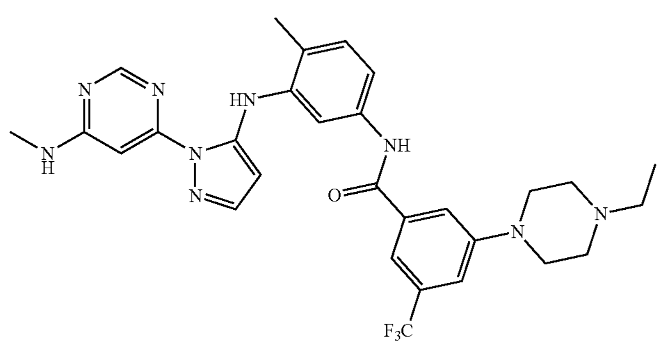 | MS m/z 580.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 22 | 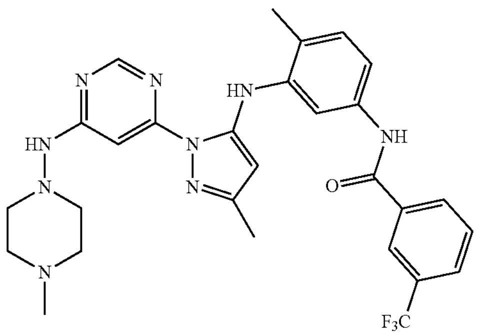 | MS m/z 566.3 (M + 1) |
| 23 | 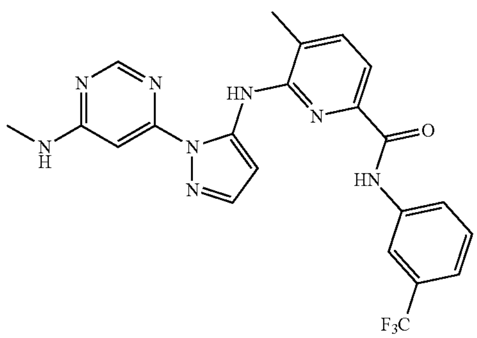 | MS m/z 469.2 (M + 1) |
| 24 | 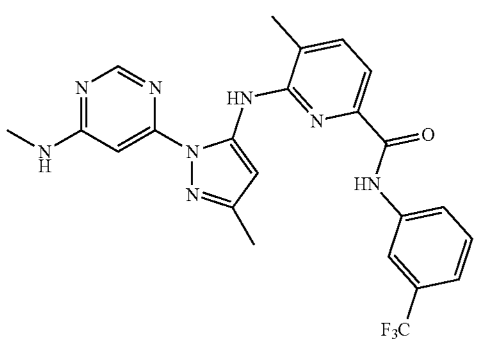 | MS m/z 483.2 (M + 1) |
| 25 | 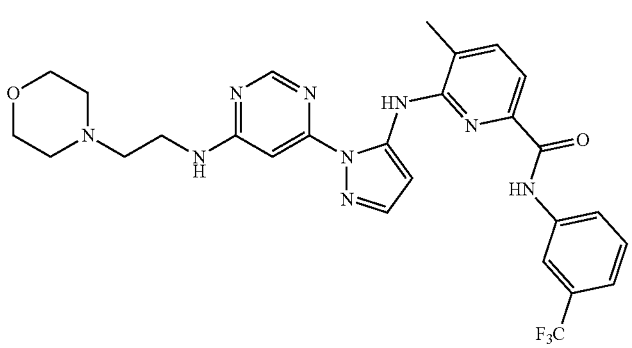 | MS m/z 568.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 26 | 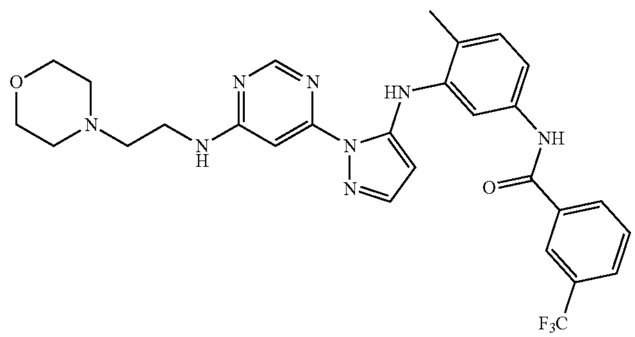 | MS m/z 567.2 (M + 1) |
| 27 | 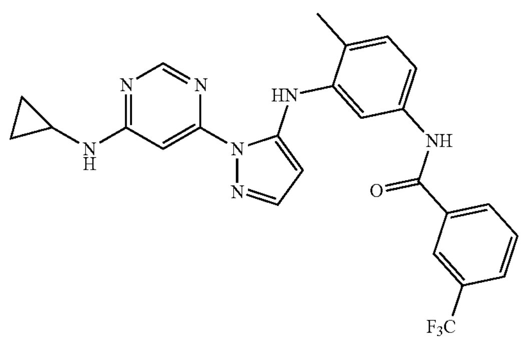 | MS m/z 494.2 (M + 1) |
| 28 | 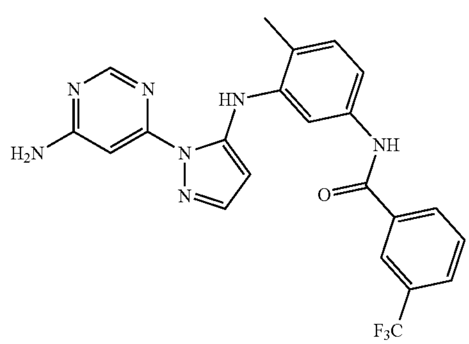 | MS m/z 454.2 (M + 1) |
| 29 | 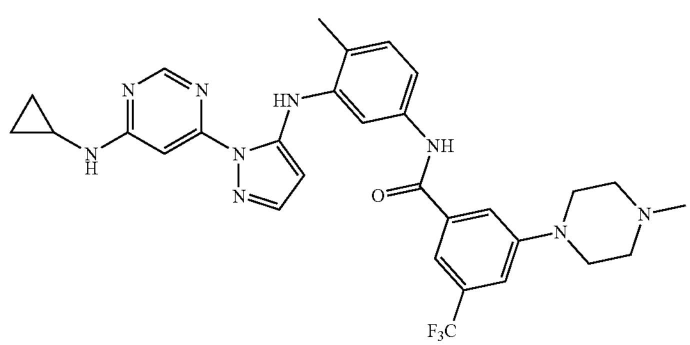 | MS m/z 592.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 30 | 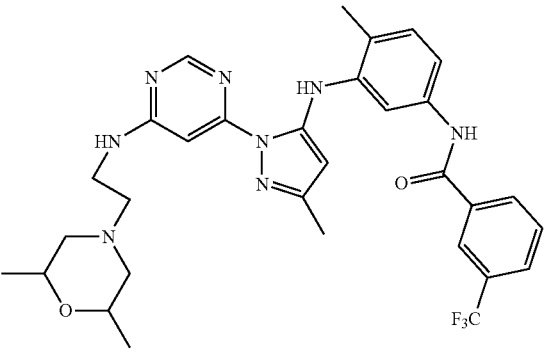 | MS m/z 609.3 (M + 1) |
| 31 | 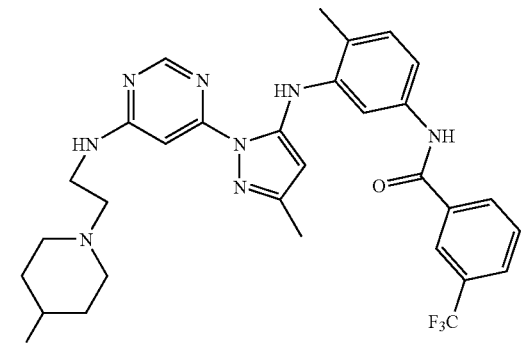 | MS m/z 595.3 (M + 1) |
| 32 | 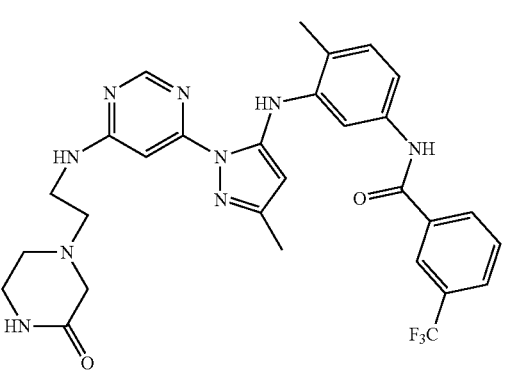 | MS m/z 594.3 (M + 1) |
| 33 | 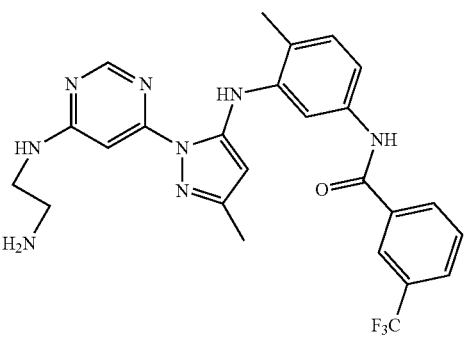 | MS m/z 511.2 (M + 1) |

TABLE 1-continued
| Compound Number | Structure | Physical Data $^1$H NMR 400 MHz or 600 MHz (DMSO-$d_6$) and/or MS (m/z) |
|---|---|---|
| 34 | 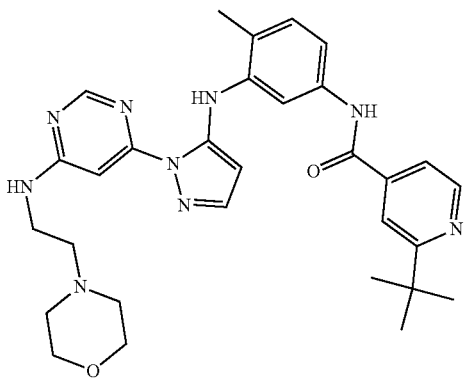 | MS m/z 511.2 (M + 1) |
| 35 | 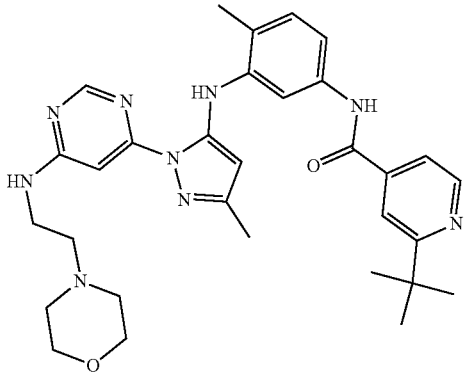 | MS m/z 570.3 (M + 1) |
| 36 | 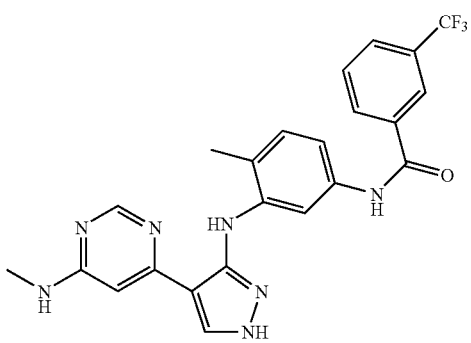 | MS m/z 468.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 37 | 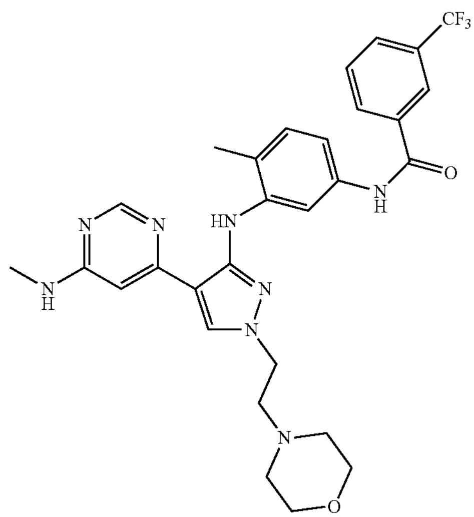 | MS m/z 581.3 (M + 1) |
| 38 | 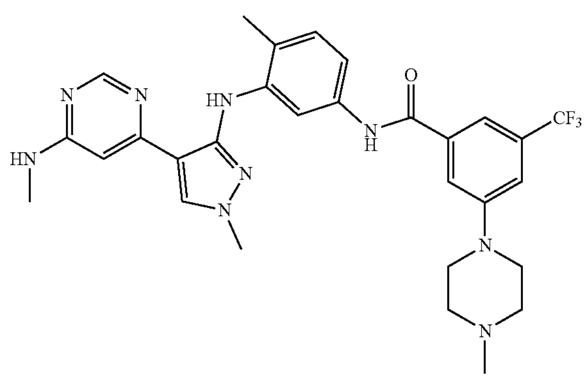 | MS m/z 580.3 (M + 1) |
| 39 | 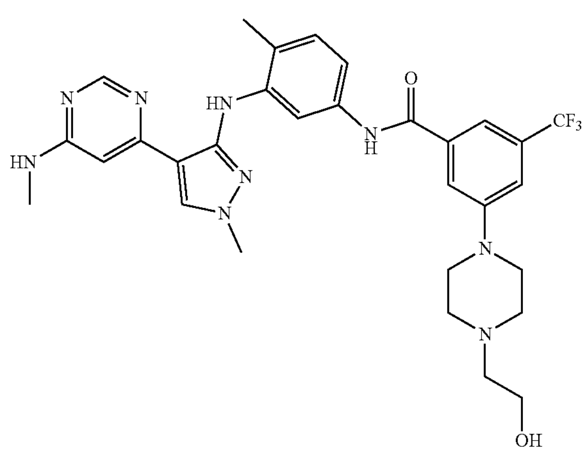 | MS m/z 610.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 40 | 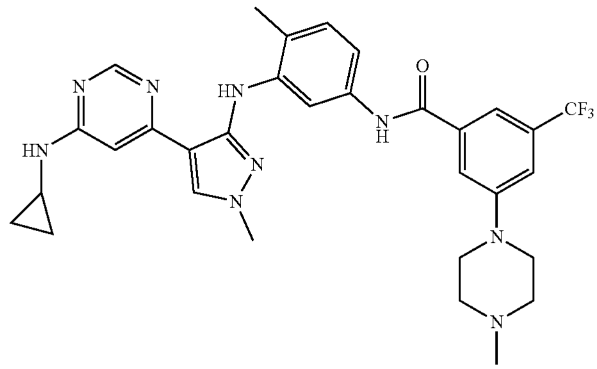 | MS m/z 606.3 (M + 1) |
| 41 | 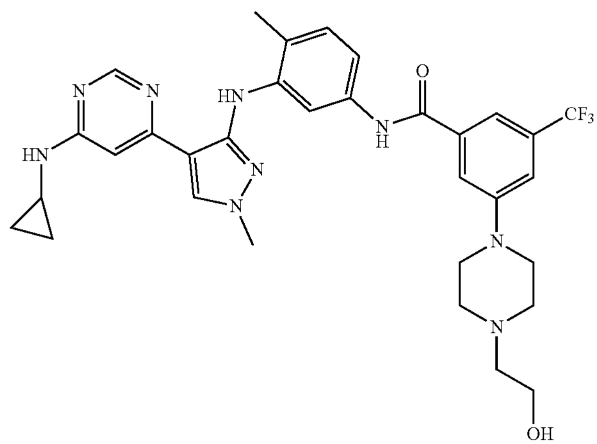 | MS m/z 636.3 (M + 1) |
| 42 | 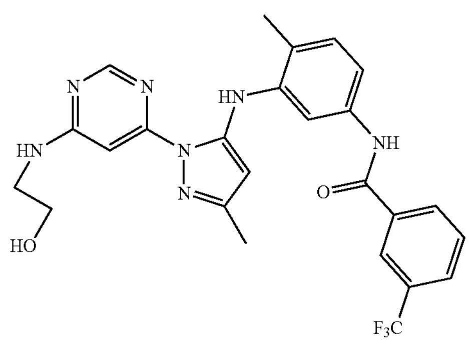 | MS m/z 512.2 (M + 1) |
| 43 | 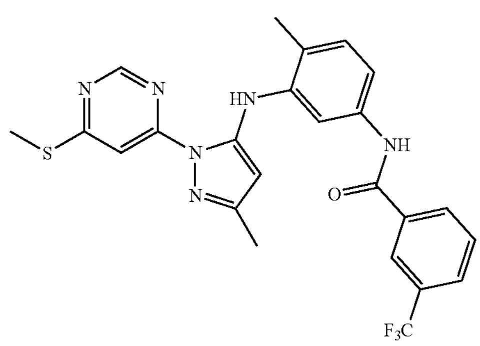 | MS m/z 499.1 (M + 1) |

TABLE 1-continued

| Compound Number | Structure | Physical Data ¹H NMR 400 MHz or 600 MHz (DMSO-d₆) and/or MS (m/z) |
|---|---|---|
| 44 | 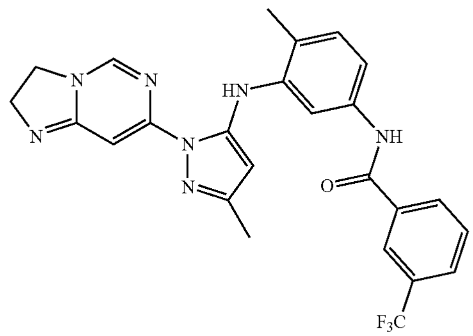 | MS m/z 494.2 (M + 1) |
| 45 | 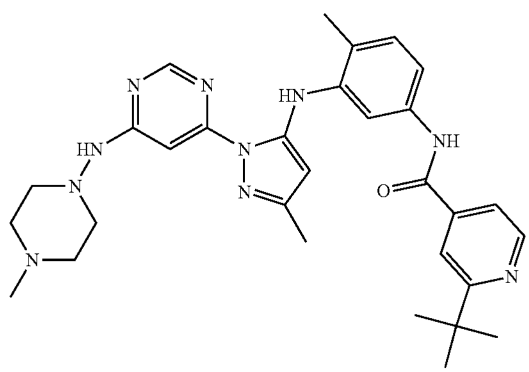 | MS m/z 555.3 (M + 1) |
| 46 | 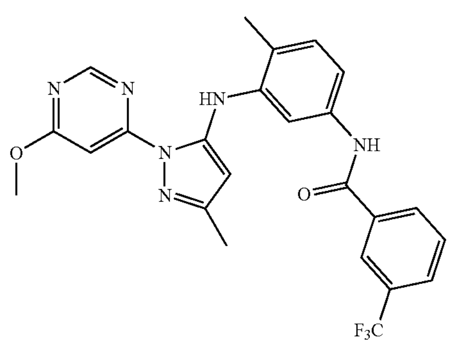 | MS m/z 483.2 (M + 1) |
| 47 | 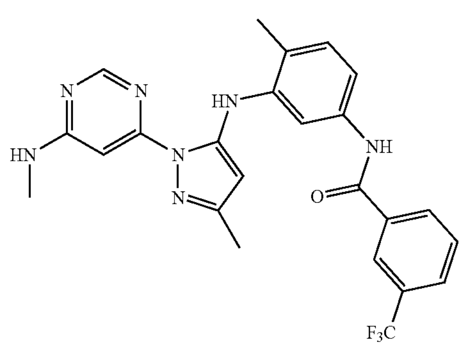 | MS m/z 482.2 (M + 1) |

TABLE 1-continued
| Compound Number | Structure | Physical Data ¹H NMR 400 MHz or 600 MHz (DMSO-$d_6$) and/or MS (m/z) |
|---|---|---|
| 48 | 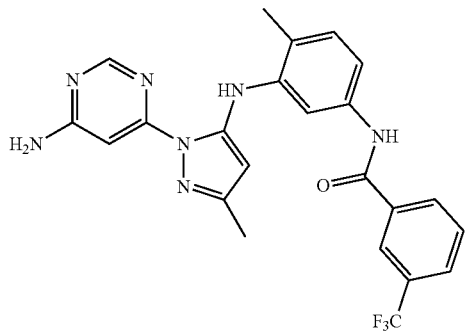 | MS m/z 468.2 (M + 1) |
| 49 | 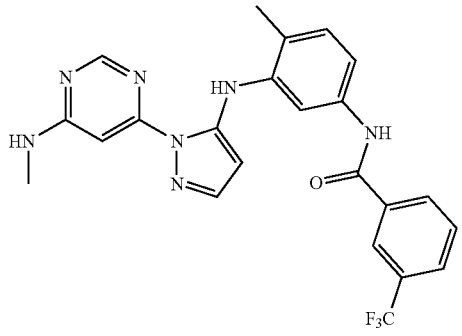 | MS m/z 468.2 (M + 1) |
| 50 | 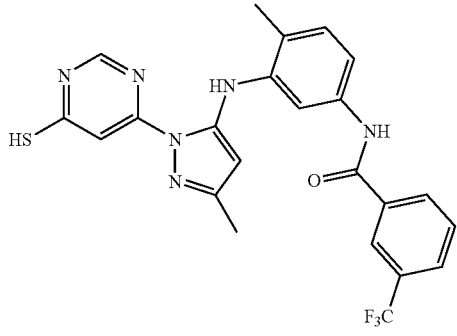 | MS m/z 484.1 (M + 1) |
| 51 | 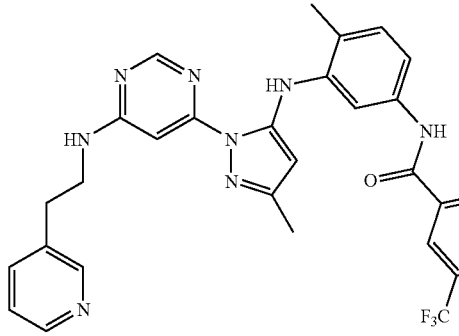 | MS m/z 573.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 52 | 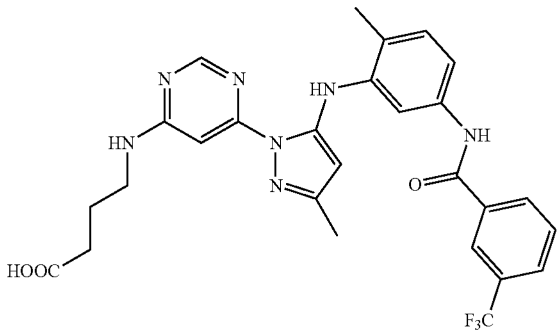 | MS m/z 554.2 (M + 1) |
| 53 | 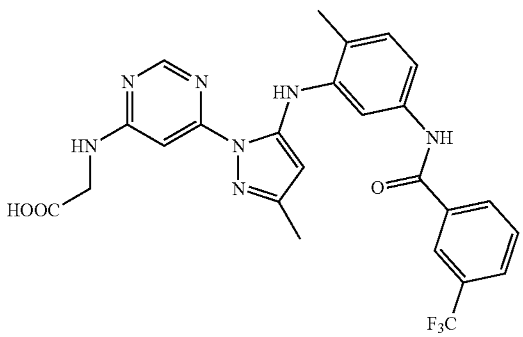 | MS m/z 556.2 (M + 1) |
| 54 | 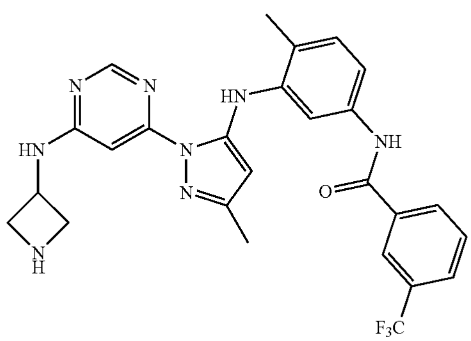 | MS m/z 523.2 (M + 1) |
| 55 | 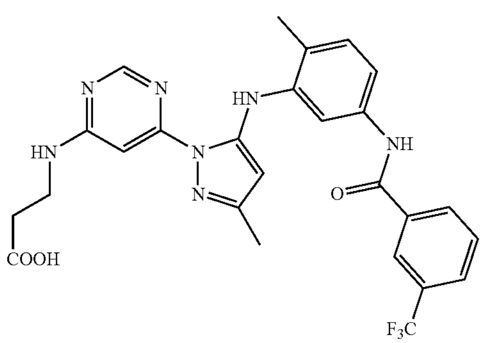 | MS m/z 540.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 56 | 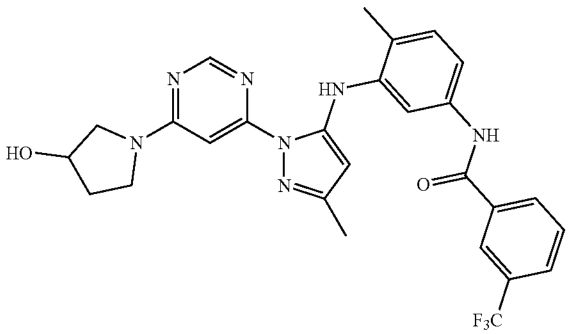 | MS m/z 538.2 (M + 1) |
| 57 | 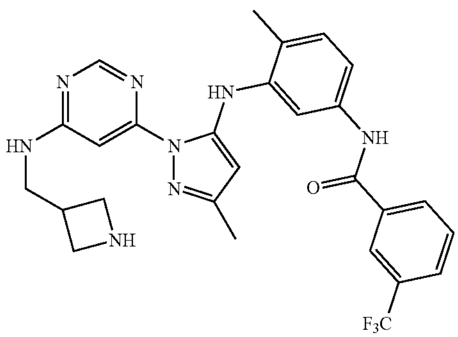 | MS m/z 537.2 (M + 1) |
| 58 | 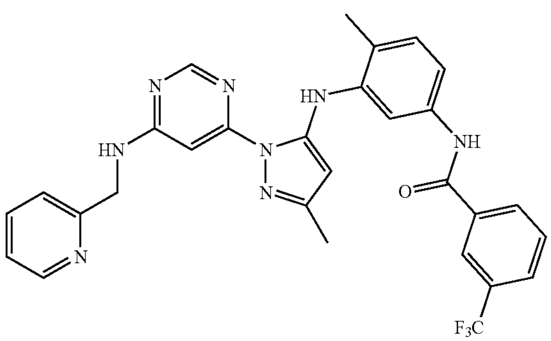 | MS m/z 559.2 (M + 1) |
| 59 | 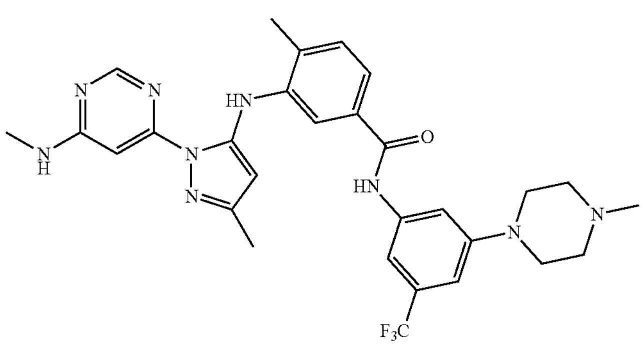 | MS m/z 580.3 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 60 | 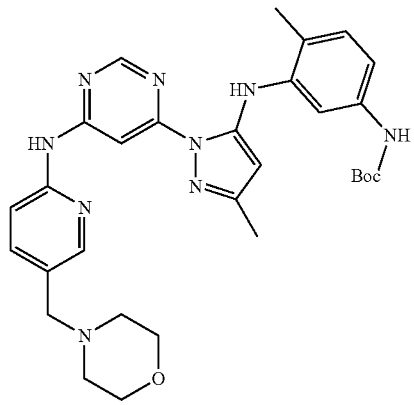 | MS m/z 572.3 (M + 1) |
| 61 | 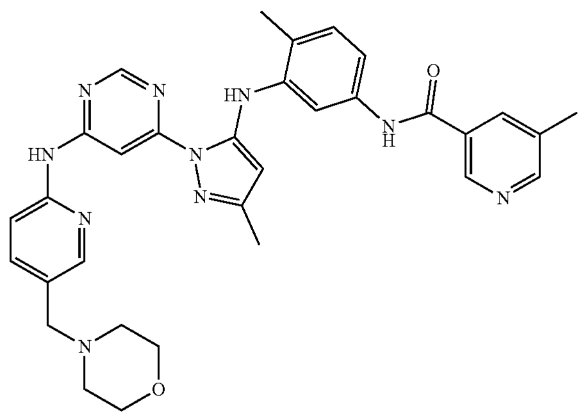 | MS m/z 591.3 (M + 1) |
| 62 | 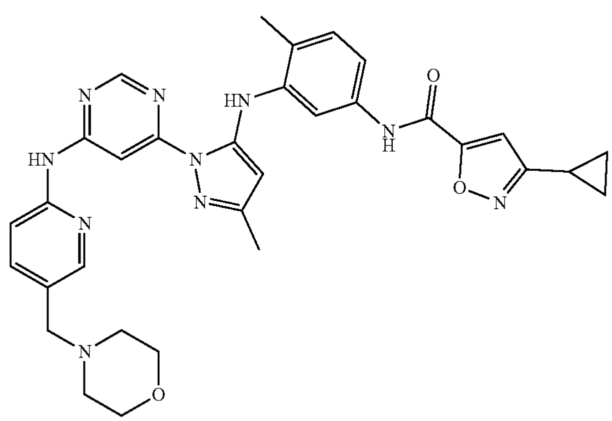 | MS m/z 607.3 (M + 1) |
| 63 | 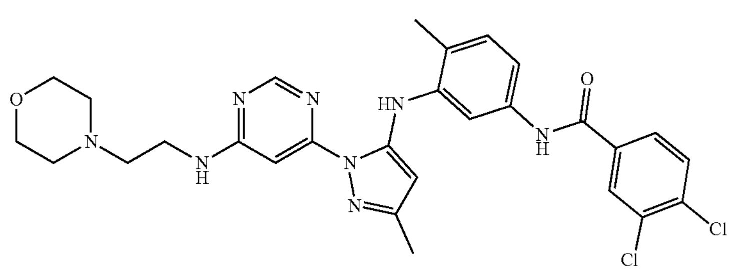 | MS m/z 581.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 64 | 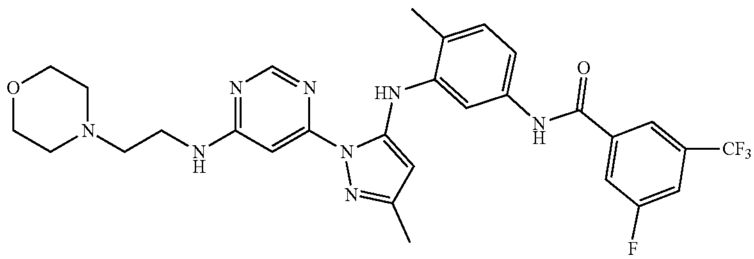 | MS m/z 599.2 (M + 1) |
| 65 | 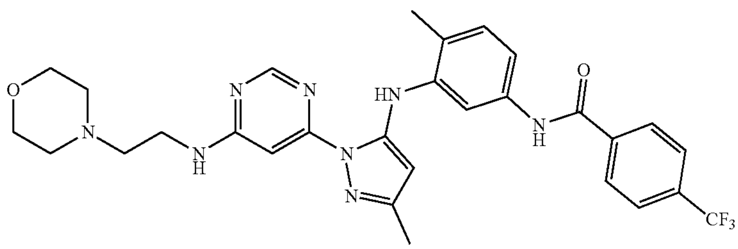 | MS m/z 581.3 (M + 1) |
| 66 | 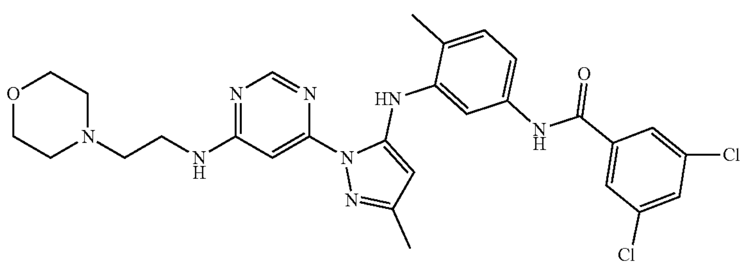 | MS m/z 581.2 (M + 1) |
| 67 | 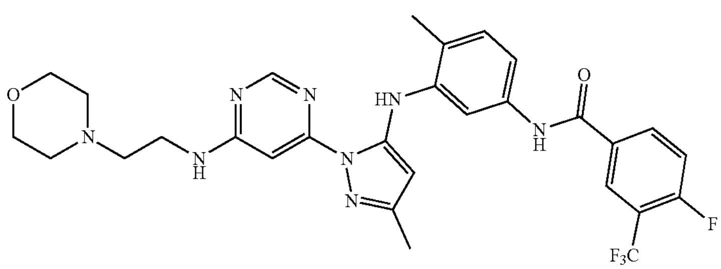 | MS m/z 599.2 (M + 1) |
| 68 | 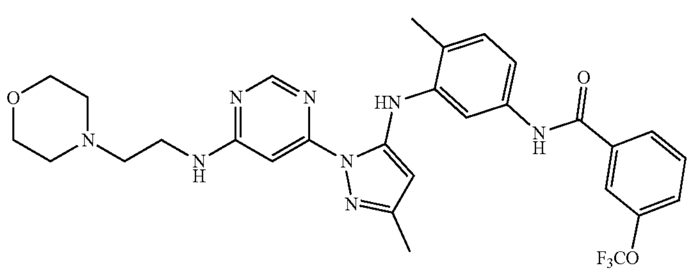 | MS m/z 597.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 69 | 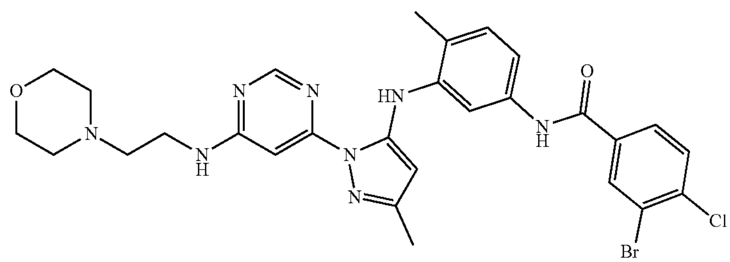 | MS m/z 625.1 (M + 1) |
| 70 | 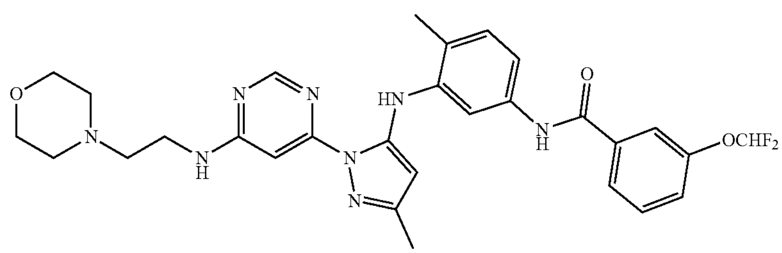 | MS m/z 579.3 (M + 1) |
| 71 | 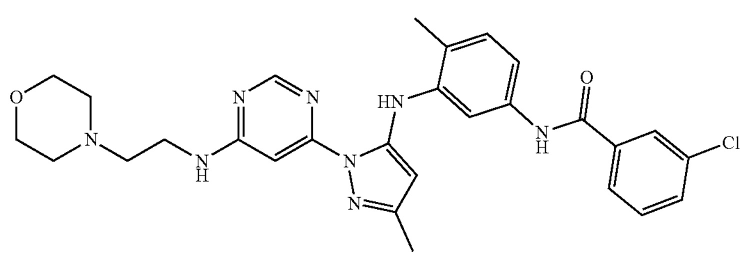 | MS m/z 547.2 (M + 1) |
| 72 | 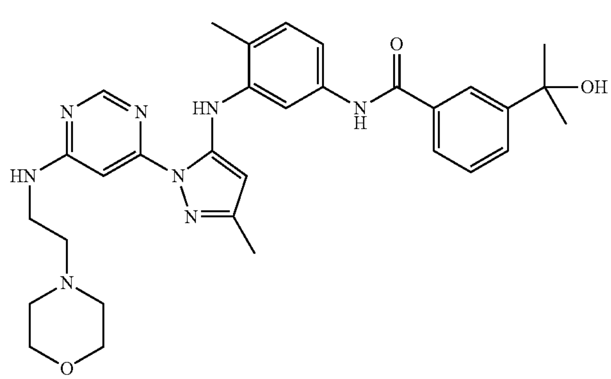 | MS m/z 571.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 73 | 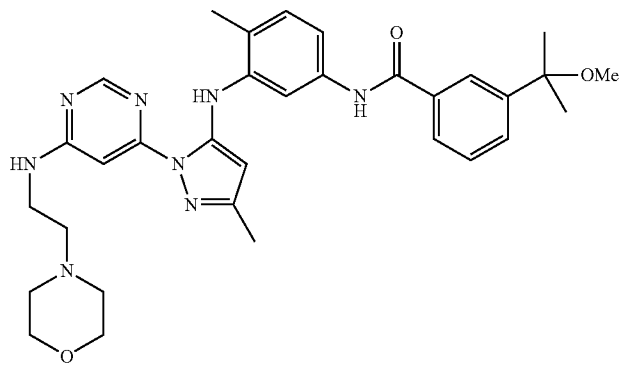 | MS m/z 585.3 (M + 1) |
| 74 | 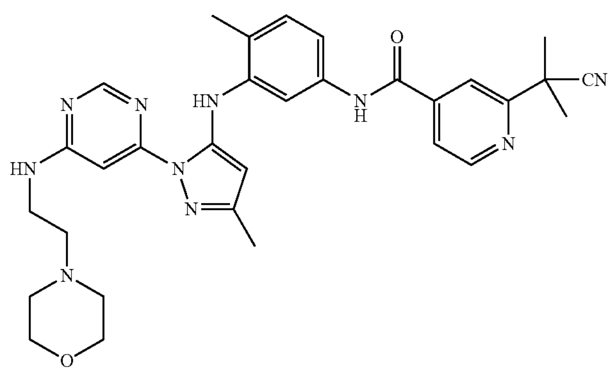 | MS m/z 581.3 (M + 1) |
| 75 | 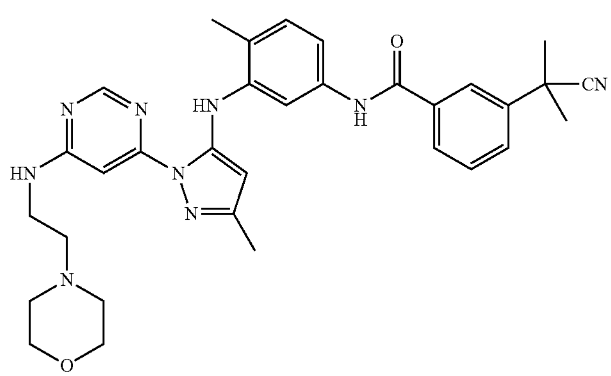 | MS m/z 580.3 (M + 1) |
| 76 | 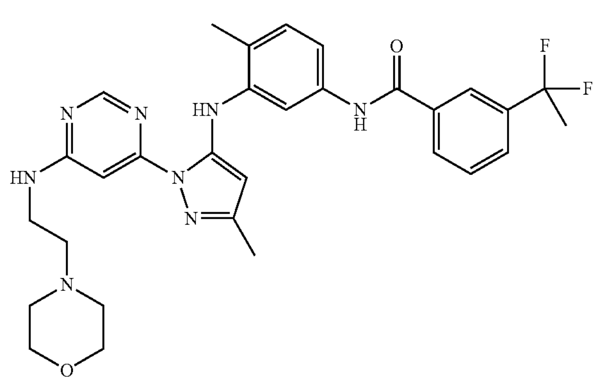 | MS m/z 577.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 77 | 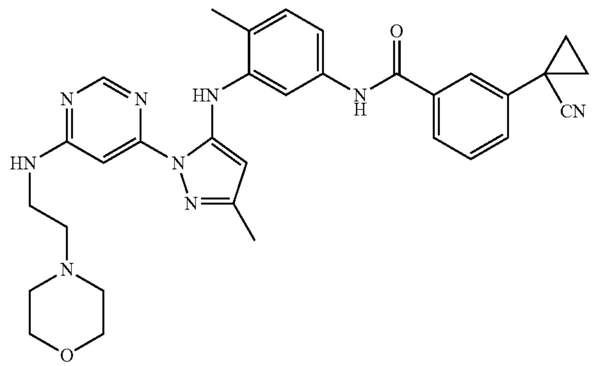 | MS m/z 578.3 (M + 1) |
| 78 | 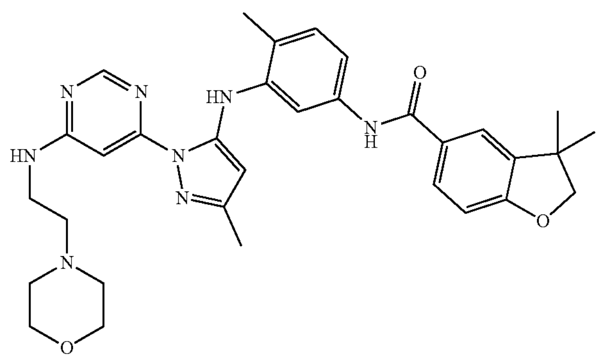 | MS m/z 583.3 (M + 1) |
| 79 | 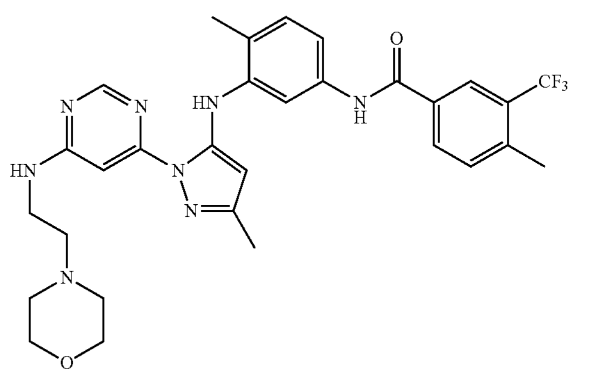 | MS m/z 595.3 (M + 1) |
| 80 | 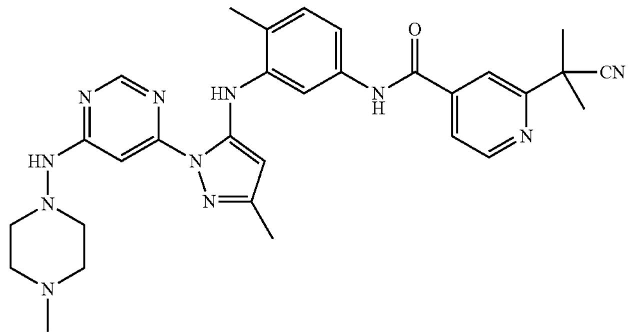 | MS m/z 566.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 81 | 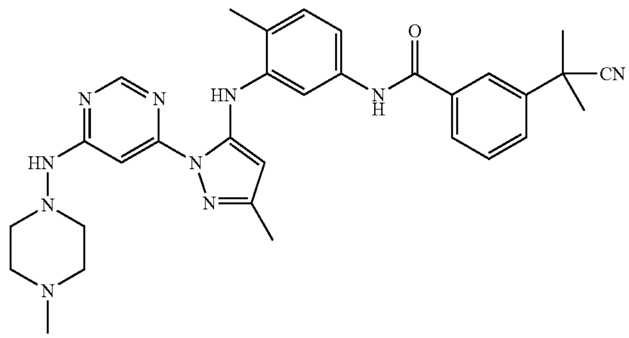 | MS m/z 565.3 (M + 1) |
| 82 | 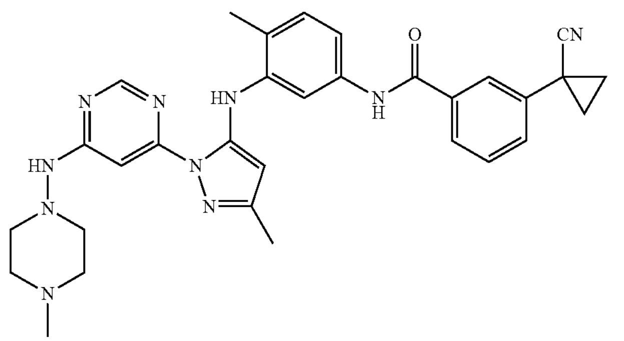 | MS m/z 563.3 (M + 1) |
| 83 | 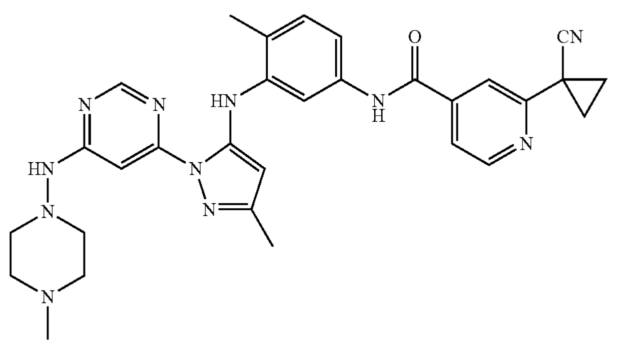 | MS m/z 564.3 (M + 1) |
| 84 | 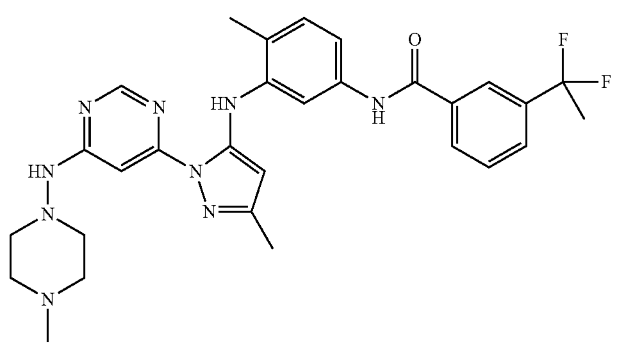 | MS m/z 562.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 85 | 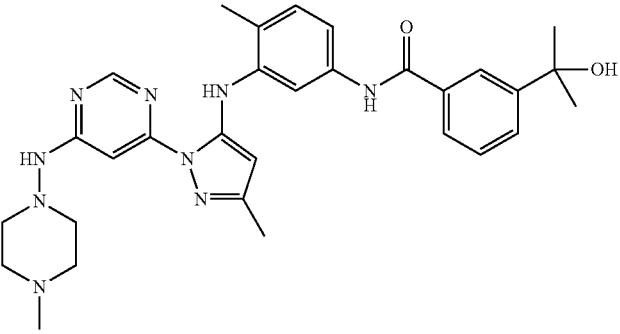 | MS m/z 556.3 (M + 1) |
| 86 | 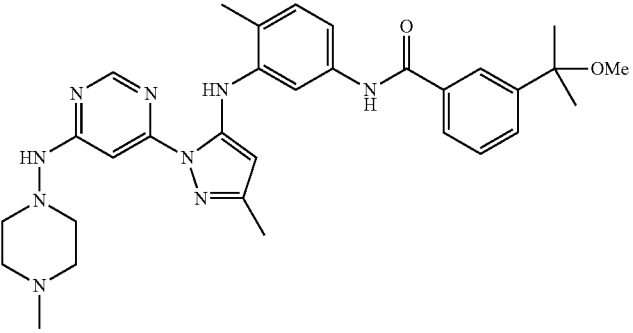 | MS m/z 570.3 (M + 1) |
| 87 | 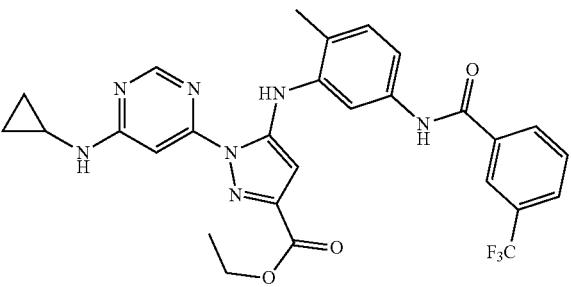 | MS m/z 566.2 (M + 1) |
| 88 | 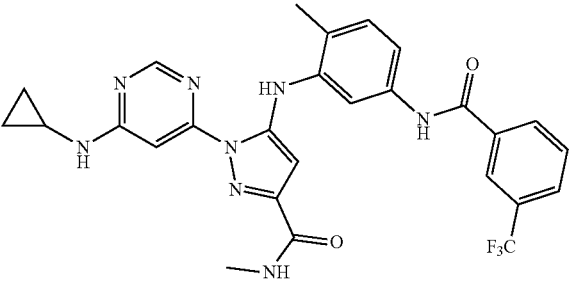 | MS m/z 551.2 (M + 1) |

TABLE 1-continued

| Compound Number | Structure | Physical Data ¹H NMR 400 MHz or 600 MHz (DMSO-d₆) and/or MS (m/z) |
|---|---|---|
| 89 | 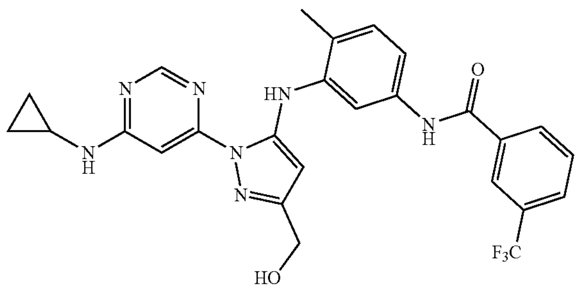 | MS m/z 524.2 (M + 1) |
| 90 | 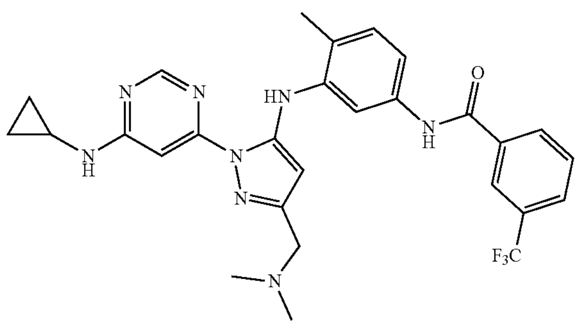 | MS m/z 551.2 (M + 1) |
| 91 | 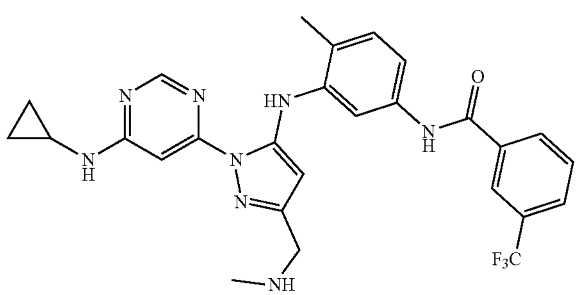 | MS m/z 537.2 (M + 1) |
| 92 | 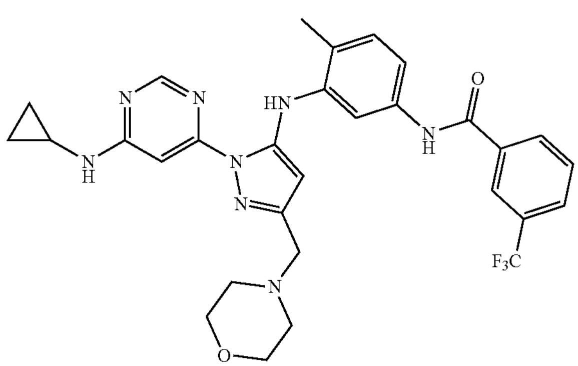 | MS m/z 593.3 (M + 1) |

TABLE 1-continued
| Compound Number | Structure | Physical Data 1H NMR 400 MHz or 600 MHz (DMSO-d6) and/or MS (m/z) |
|---|---|---|
| 93 | 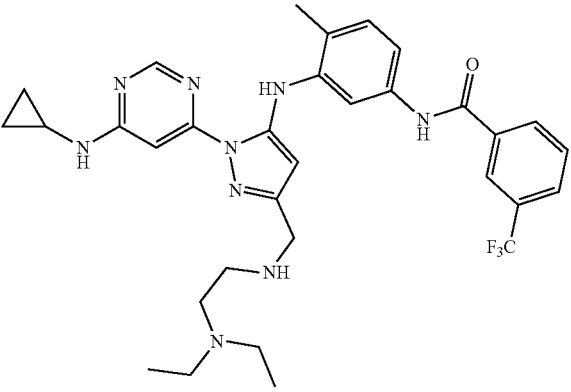 | MS m/z 622.3 (M + 1) |
| 94 | 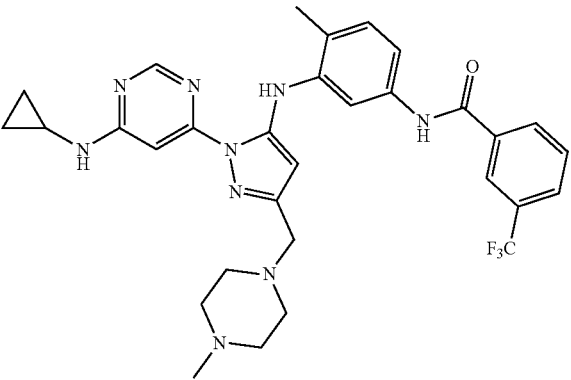 | MS m/z 606.3 (M + 1) |
| 95 | 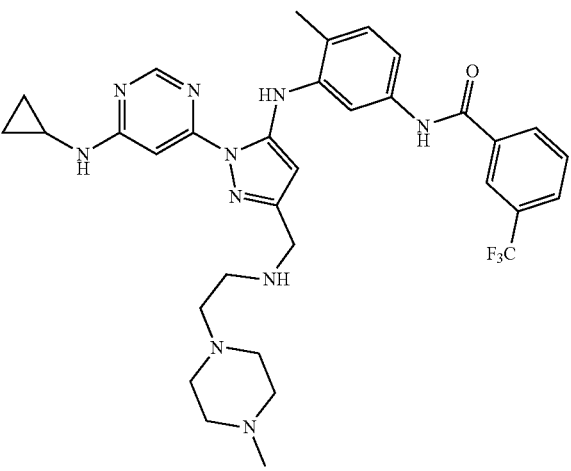 | MS m/z 649.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 96 | 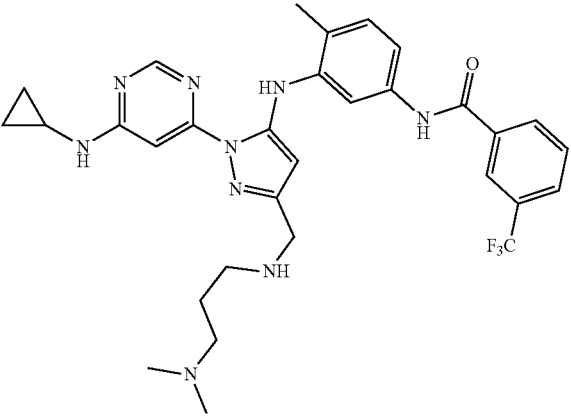 | MS m/z 608.3 (M + 1) |
| 97 | 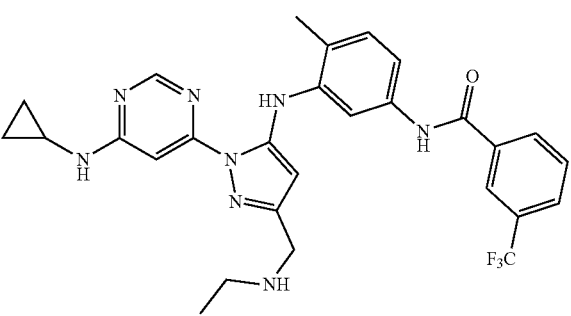 | MS m/z 551.2 (M + 1) |
| 98 | 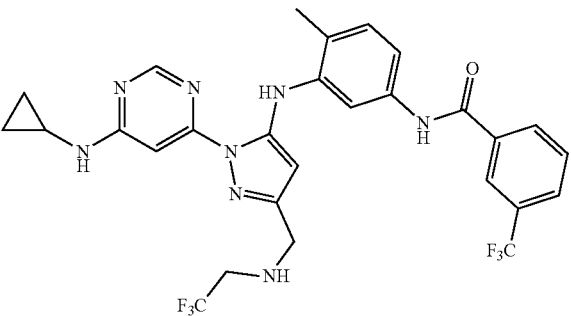 | MS m/z 605.2 (M + 1) |
| 99 | 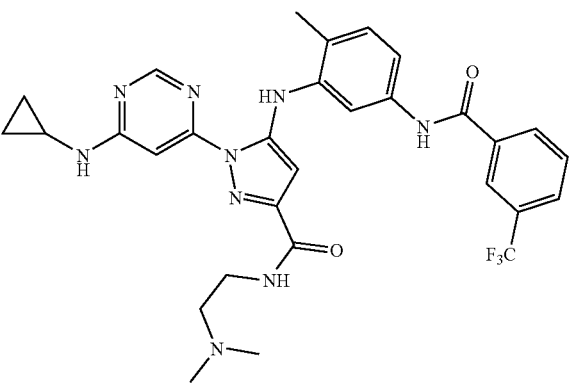 | MS m/z 608.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 100 | 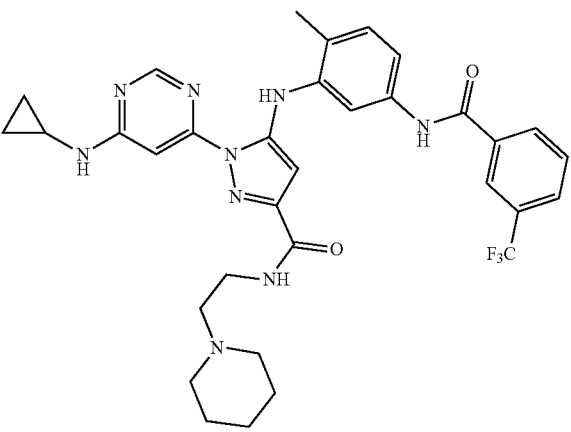 | MS m/z 648.3 (M + 1) |
| 101 | 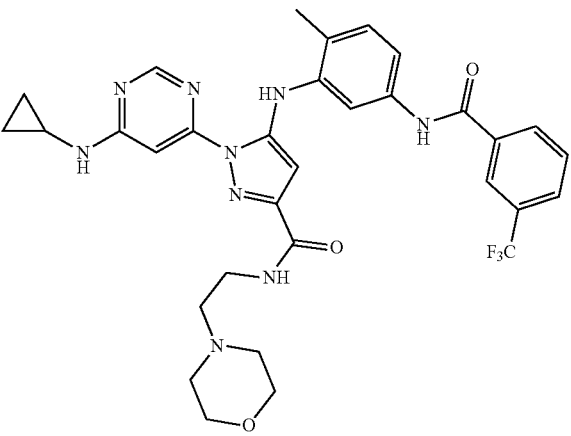 | MS m/z 650.3 (M + 1) |
| 102 | 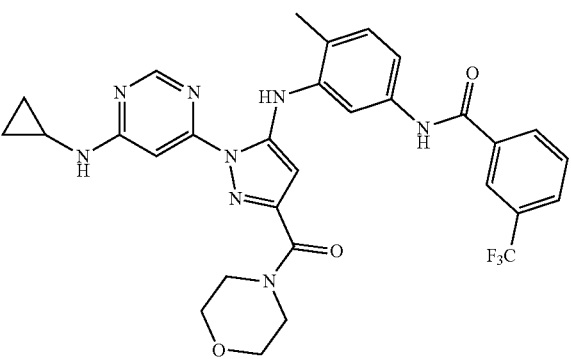 | MS m/z 607.2 (M + 1) |

TABLE 1-continued
| Compound Number | Structure | Physical Data ¹H NMR 400 MHz or 600 MHz (DMSO-$d_6$) and/or MS (m/z) |
|---|---|---|
| 103 | 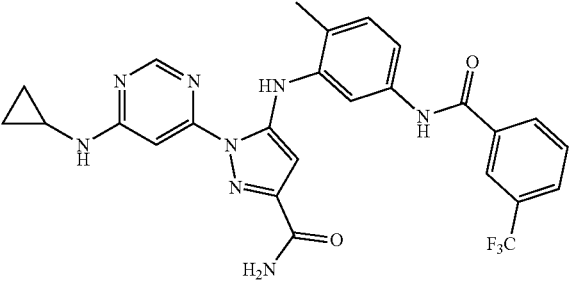 | MS m/z 537.2 (M + 1) |
| 104 | 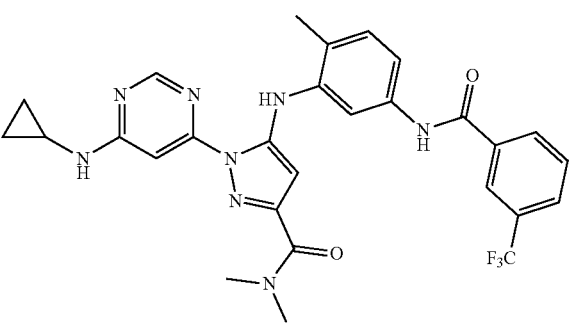 | MS m/z 562.2 (M + 1) |
| 105 | 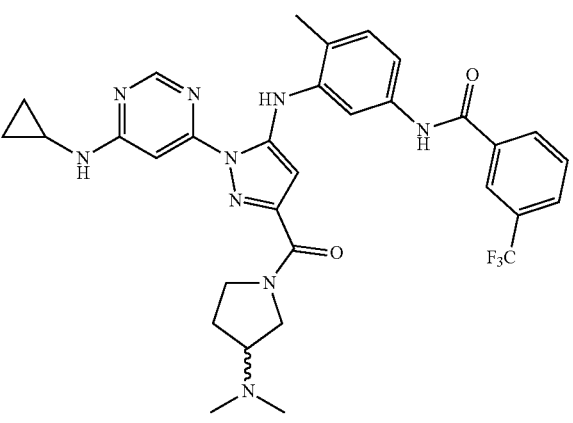 | MS m/z 634.3 (M + 1) |
| 106 | 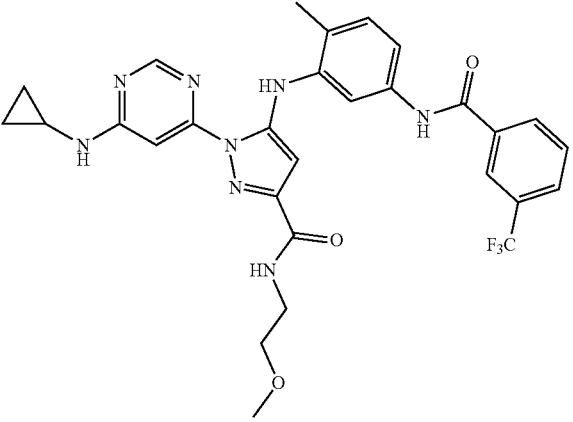 | MS m/z 595.3 (M + 1) |

TABLE 1-continued

| Compound Number | Structure | Physical Data ¹H NMR 400 MHz or 600 MHz (DMSO-d₆) and/or MS (m/z) |
|---|---|---|
| 107 | 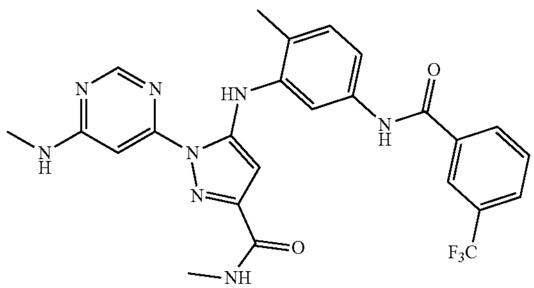 | MS m/z 525.3 (M + 1) |
| 108 | 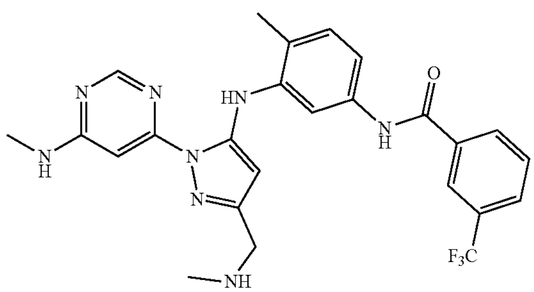 | MS m/z 511.2 (M + 1) |
| 109 | 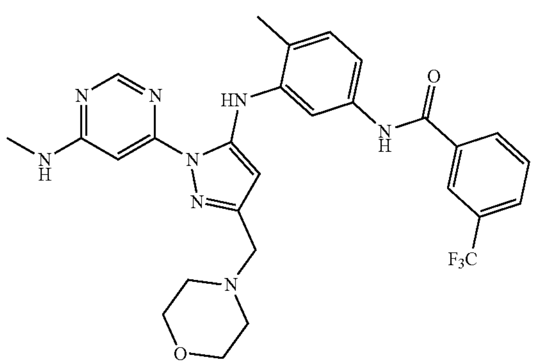 | MS m/z 567.2 (M + 1) |
| 110 | 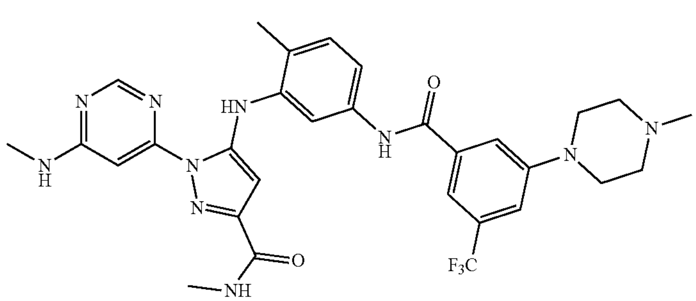 | MS m/z 623.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 111 | 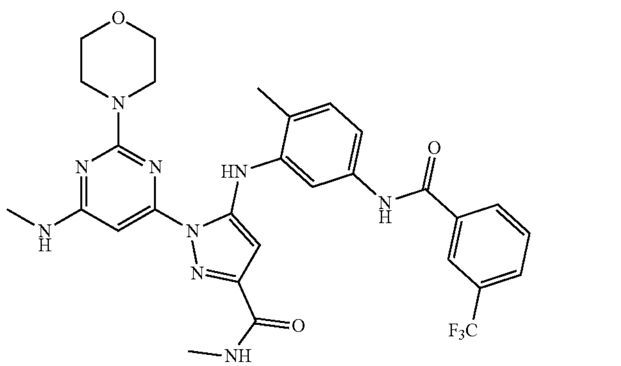 | MS m/z 610.2 (M + 1) |
| 112 | 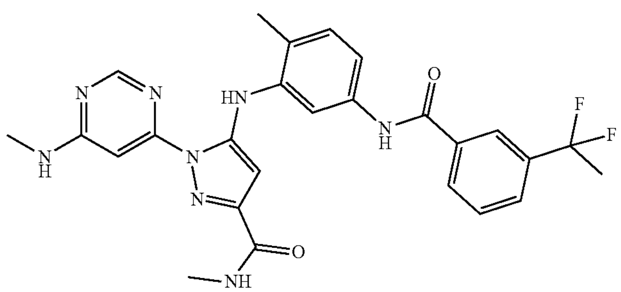 | MS m/z 521.2 (M + 1) |
| 113 | 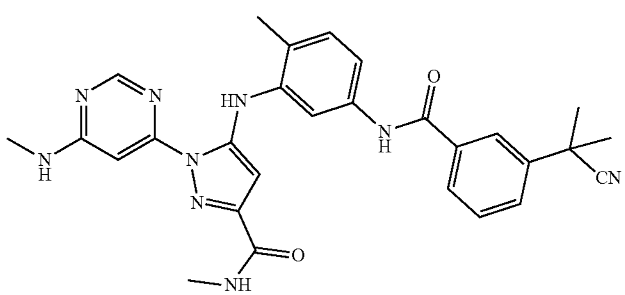 | MS m/z 524.2 (M + 1) |
| 114 | 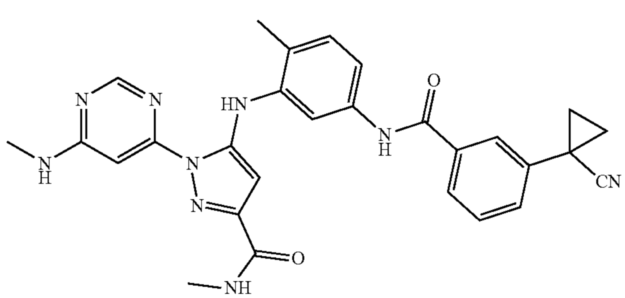 | MS m/z 507.2 (M + 1) |

TABLE 1-continued

| Compound Number | Structure | Physical Data ¹H NMR 400 MHz or 600 MHz (DMSO-d₆) and/or MS (m/z) |
|---|---|---|
| 115 | 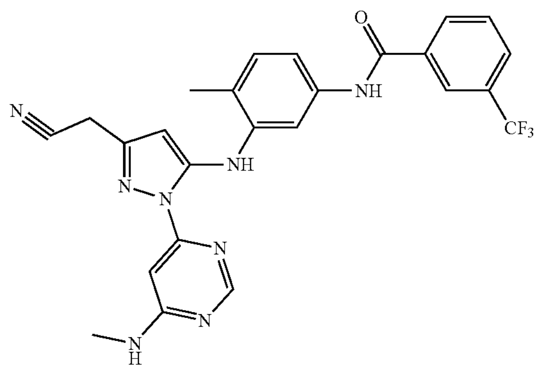 | MS m/z 522.2 (M + 1) |
| 116 | 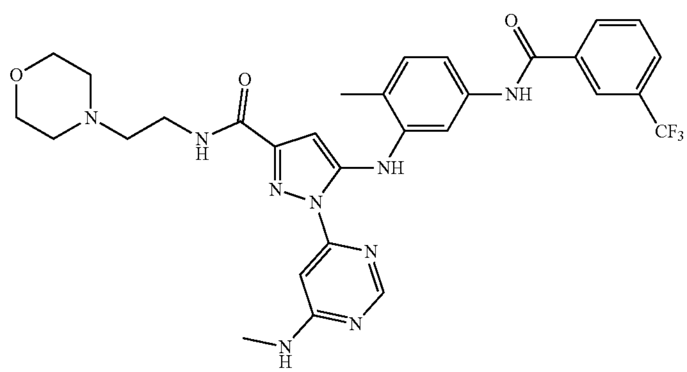 | MS m/z 624.3 (M + 1) |
| 117 | 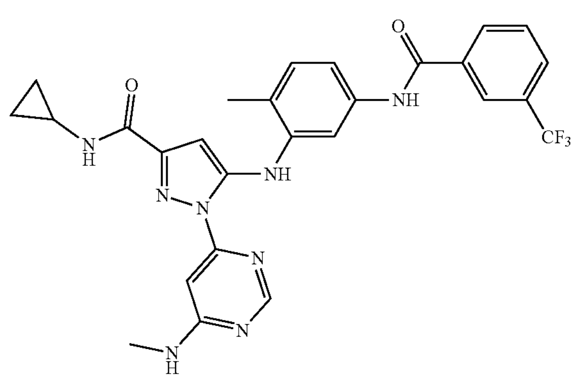 | MS m/z 551.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 118 | 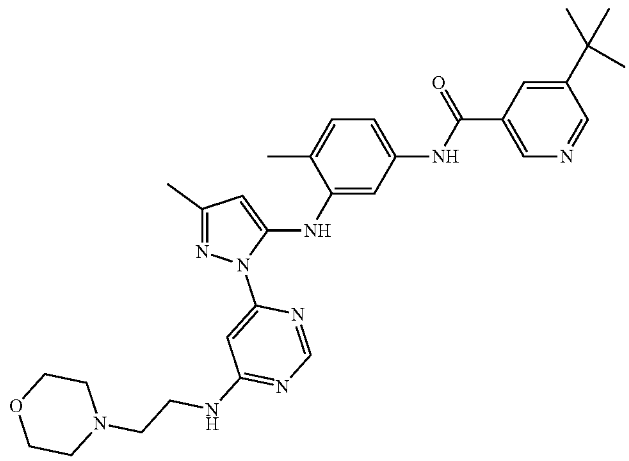 | MS m/z 570.3 (M + 1) |
| 119 | 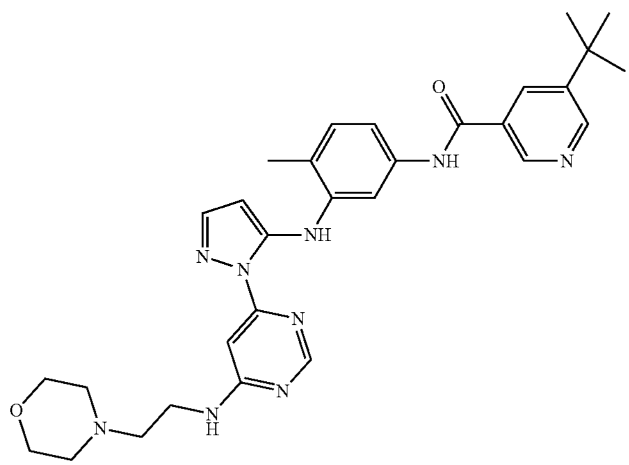 | MS m/z 556.3 (M + 1) |
| 120 | 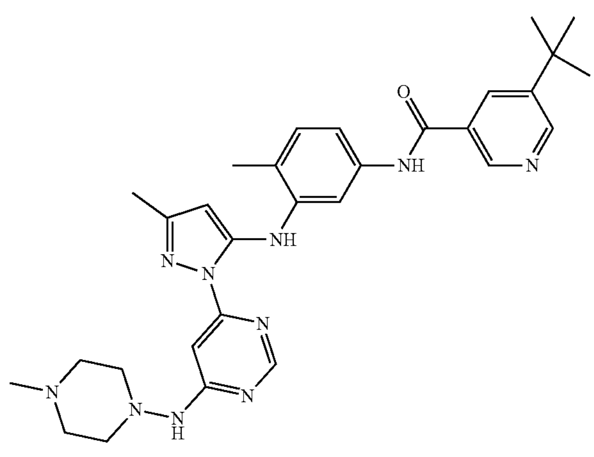 | MS m/z 555.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 121 | 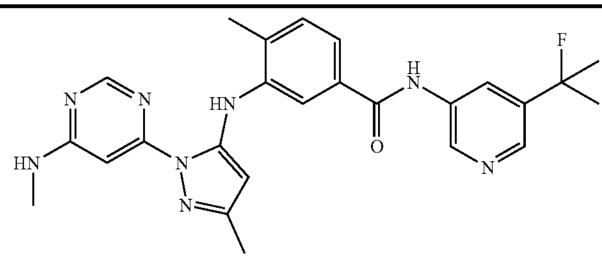 | MS m/z 475.2 (M + 1) |
| 122 | 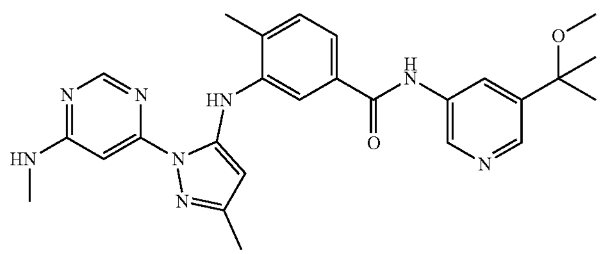 | MS m/z 487.3 (M + 1) |
| 123 | 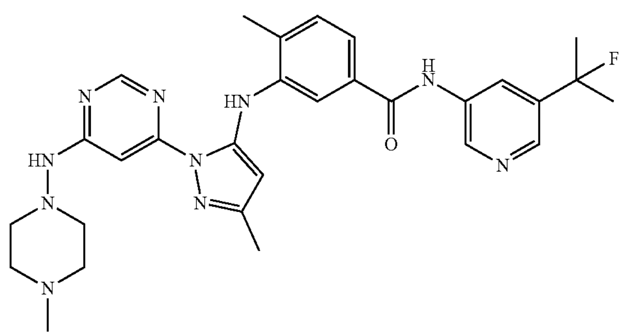 | MS m/z 559.3 (M + 1) |
| 124 | 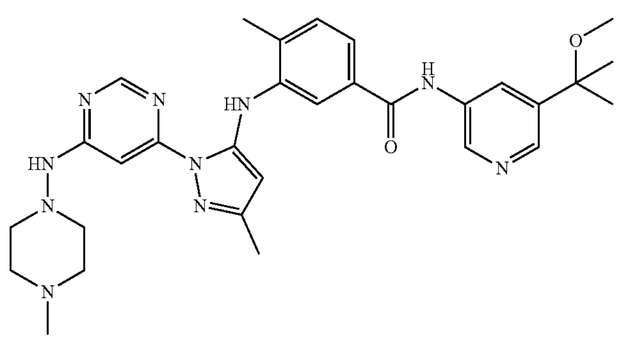 | MS m/z 571.3 (M + 1) |
| 125 | 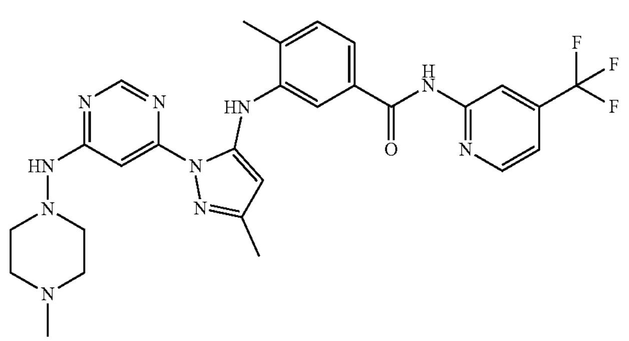 | MS m/z 567.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 126 | 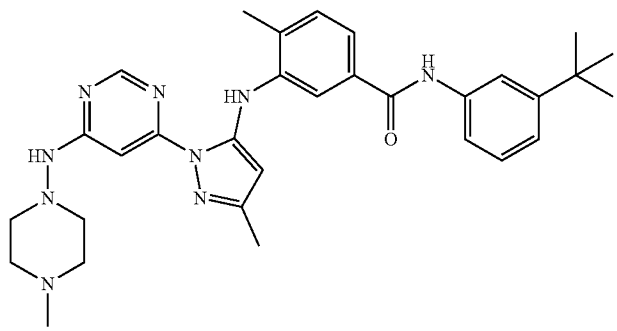 | MS m/z 554.3 (M + 1) |
| 127 | 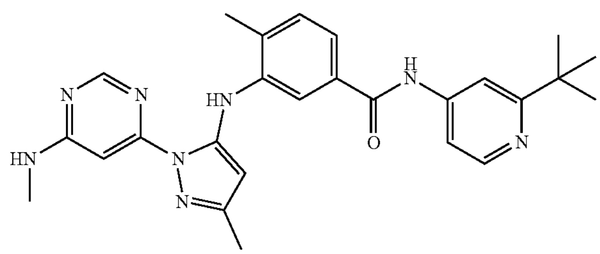 | MS m/z 471.3 (M + 1) |
| 128 | 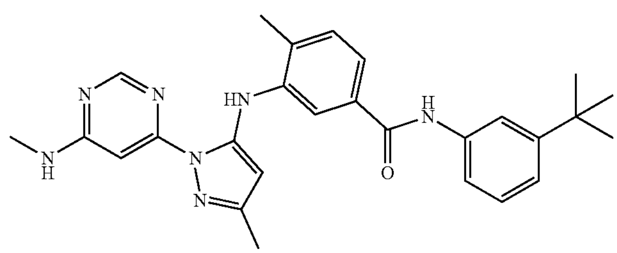 | MS m/z 470.3 (M + 1) |
| 129 | 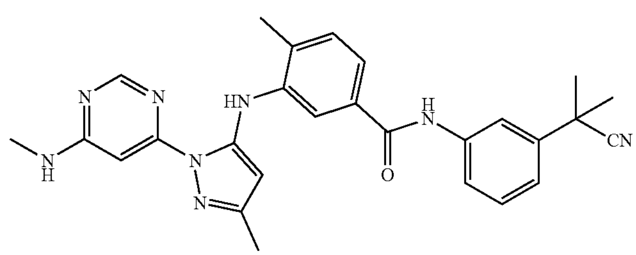 | MS m/z 481.3 (M + 1) |
| 130 | 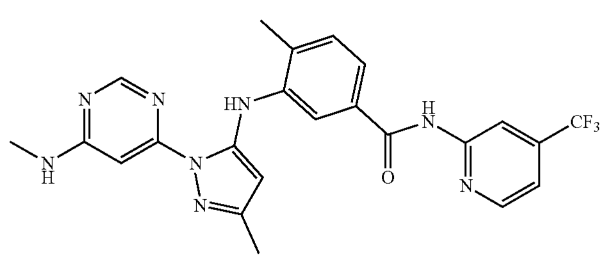 | MS m/z 483.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 131 | 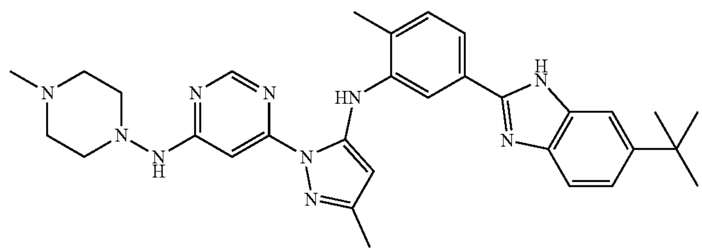 | MS m/z 551.3 (M + 1) |
| 132 | 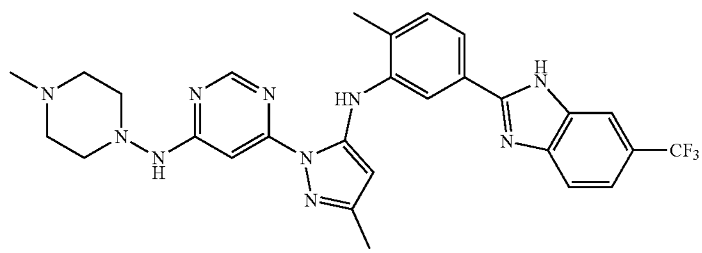 | MS m/z 563.3 (M + 1) |
| 133 | 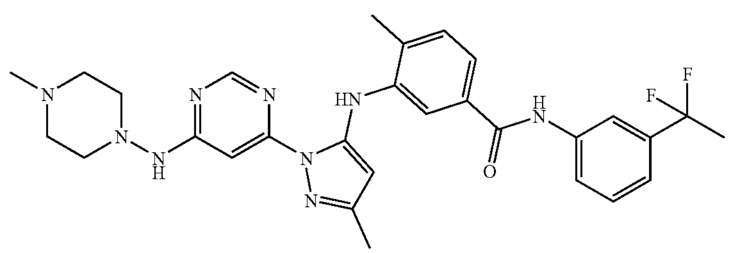 | MS m/z 562.3 (M + 1) |
| 134 | 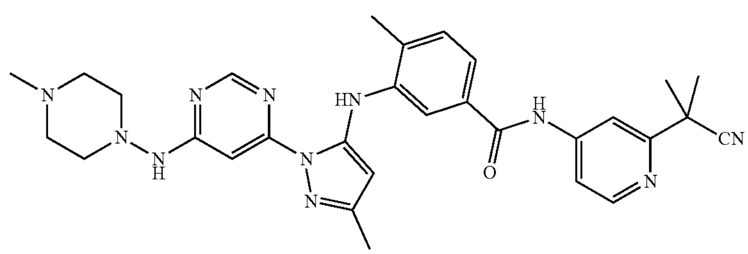 | MS m/z 566.3 (M + 1) |
| 135 | 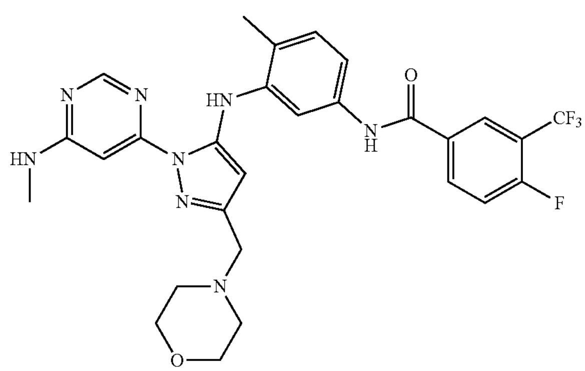 | MS m/z 585.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 136 | 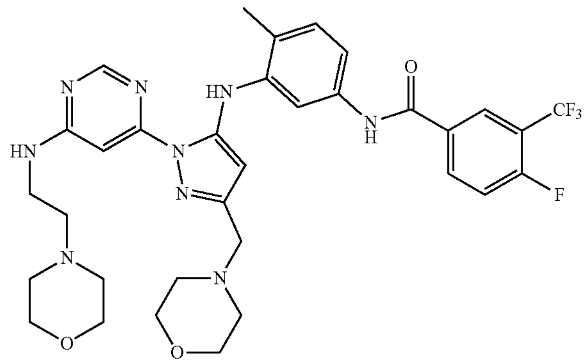 | MS m/z 684.3 (M + 1) |
| 137 | 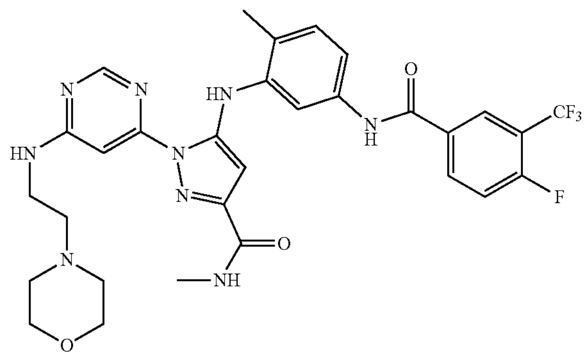 | MS m/z 642.3 (M + 1) |
| 138 | 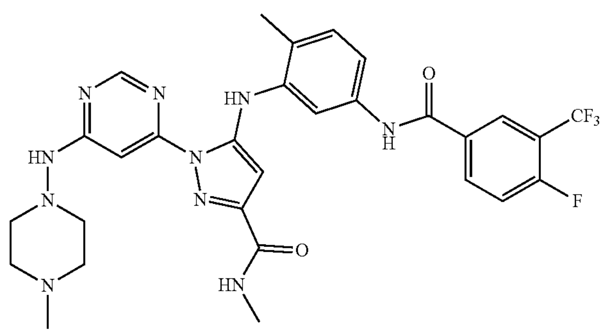 | MS m/z 627.3 (M + 1) |
| 139 | 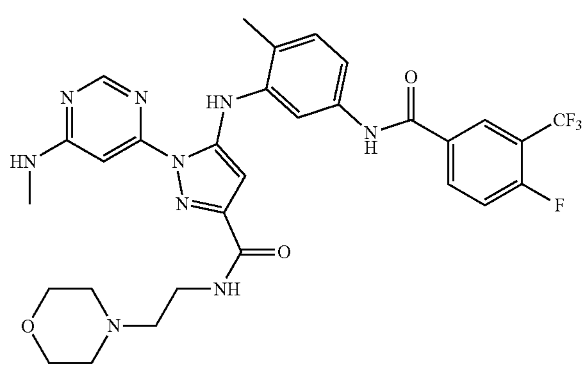 | MS m/z 642.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 140 | 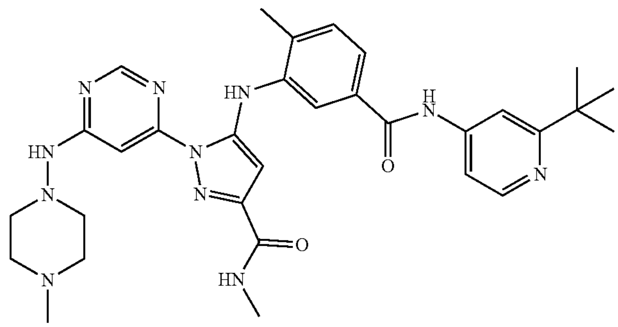 | MS m/z 598.3 (M + 1) |
| 141 | 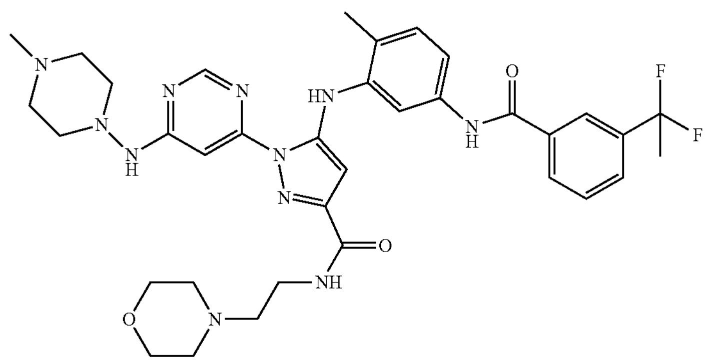 | MS m/z 704.3 (M + 1) |
| 142 | 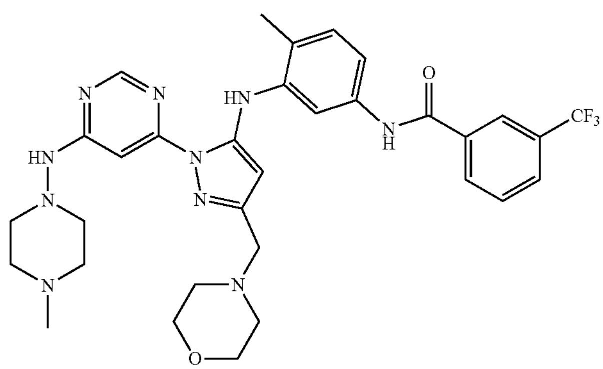 | MS m/z 651.3 (M + 1) |
| 143 | 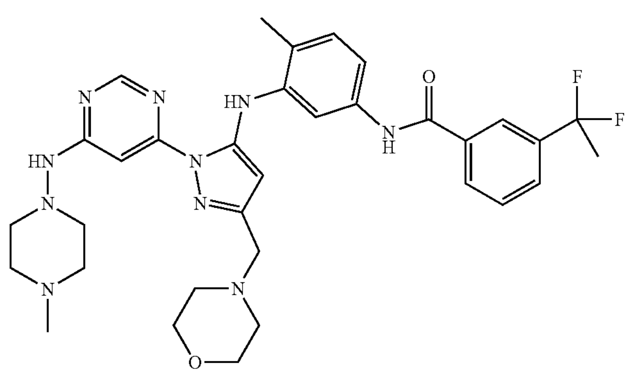 | MS m/z 647.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 144 | 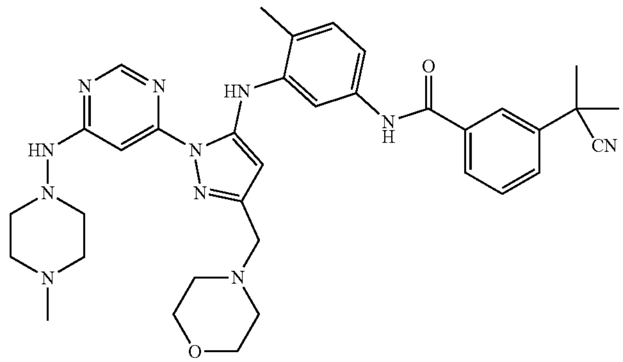 | MS m/z 650.3 (M + 1) |
| 145 | 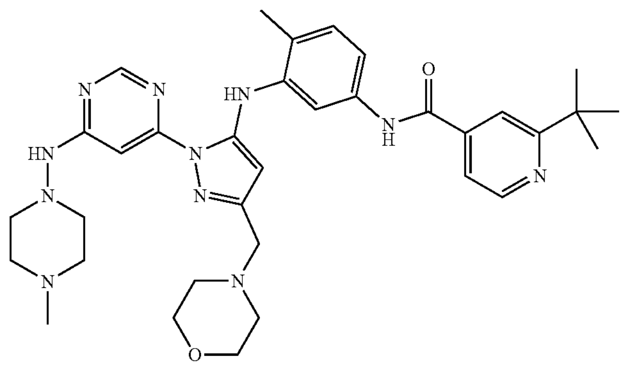 | MS m/z 640.3 (M + 1) |
| 146 | 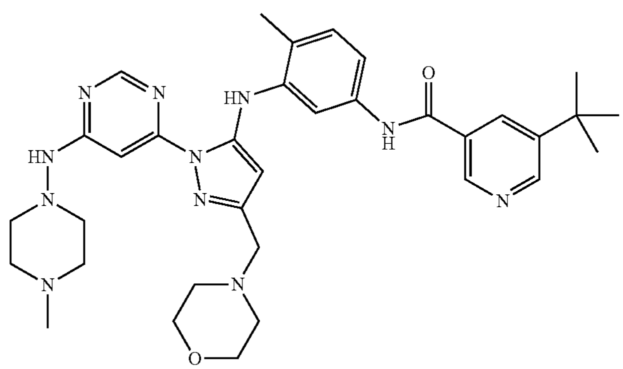 | MS m/z 640.3 (M + 1) |
| 147 | 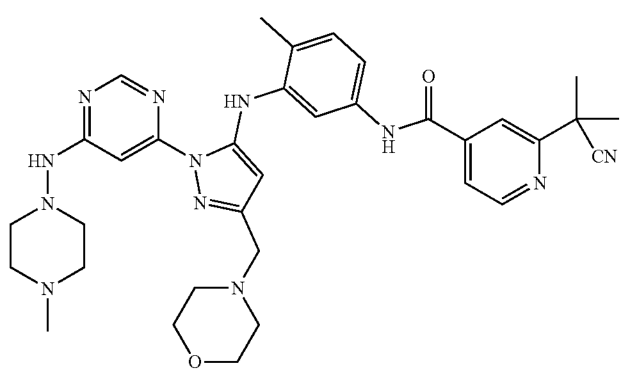 | MS m/z 651.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 148 | 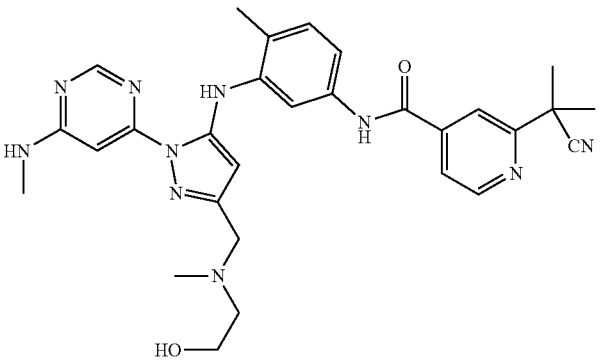 | MS m/z 555.3 (M + 1) |
| 149 | 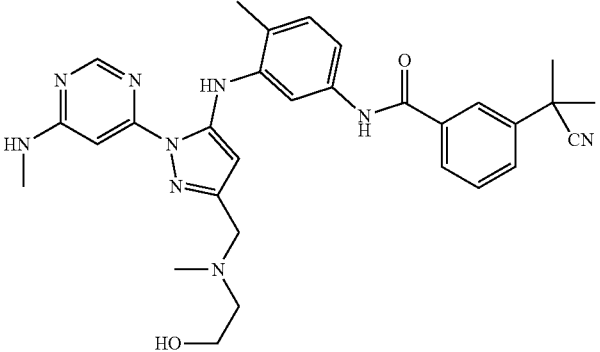 | MS m/z 554.3 (M + 1) |
| 150 | 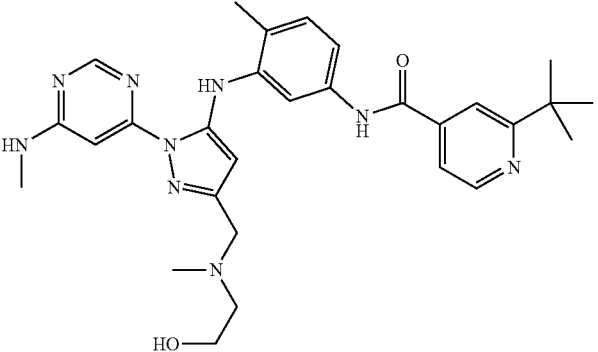 | MS m/z 544.3 (M + 1) |
| 151 | 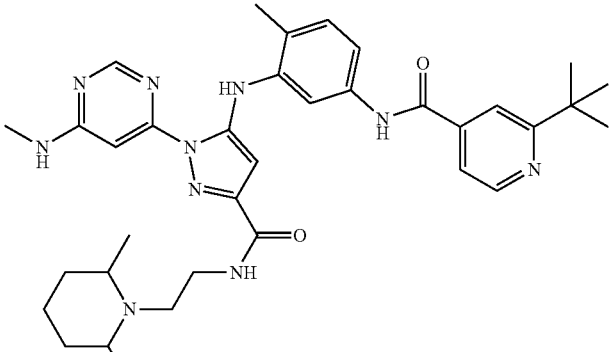 | MS m/z 639.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 152 | 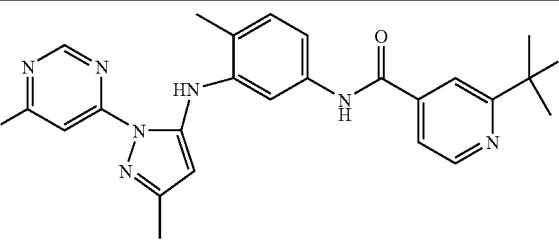 | MS m/z 482.2 (M + 1) |
| 153 | 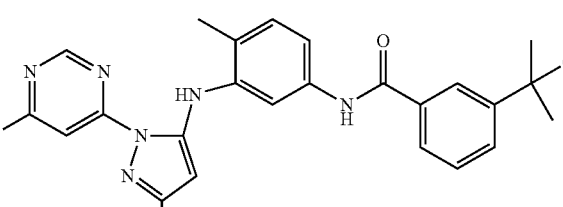 | MS m/z 481.2 (M + 1) |
| 154 | 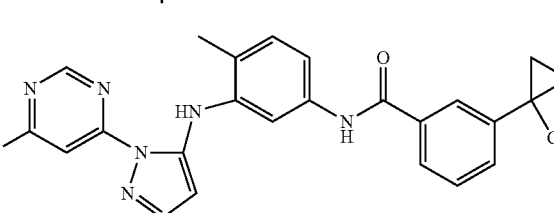 | MS m/z 479.2 (M + 1) |
| 155 | 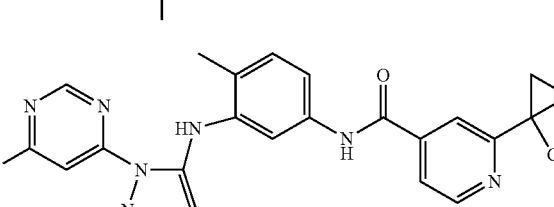 | MS m/z 480.2 (M + 1) |
| 156 | 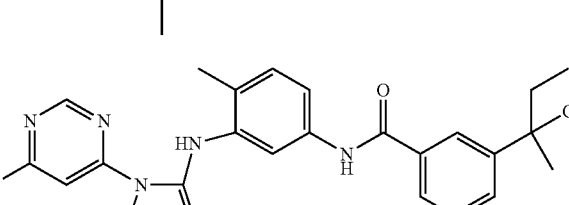 | MS m/z 495.3 (M + 1) |
| 157 | 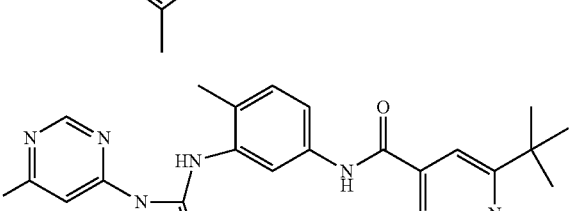 | MS m/z 471.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 158 | 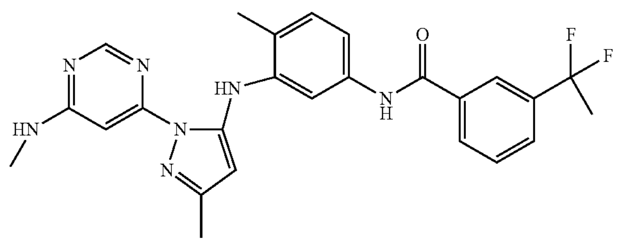 | MS m/z 478.2 (M + 1) |
| 159 | 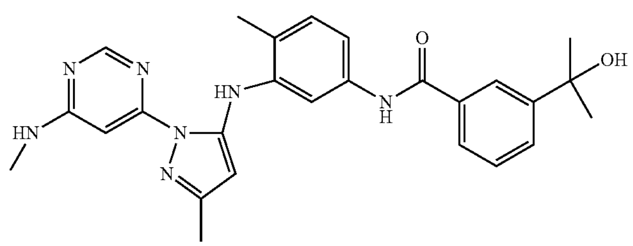 | MS m/z 472.2 (M + 1) |
| 160 | 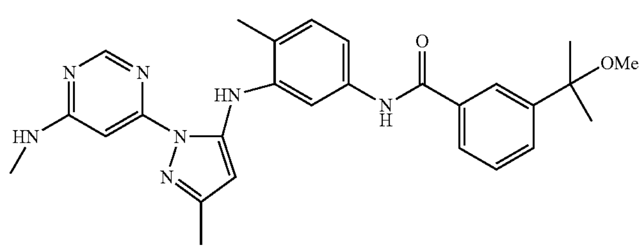 | MS m/z 486.3 (M + 1) |
| 161 | 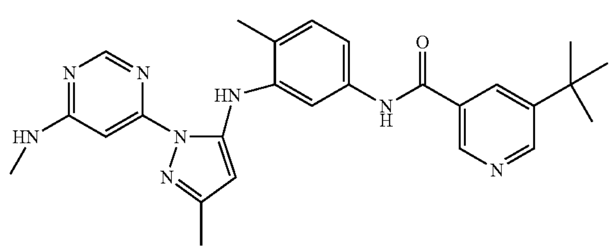 | MS m/z 471.3 (M + 1) |
| 162 | 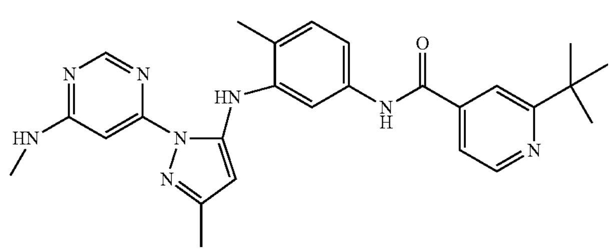 | MS m/z 471.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 163 | 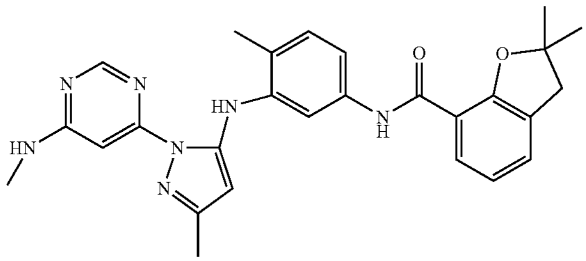 | MS m/z 484.2 (M + 1) |
| 164 | 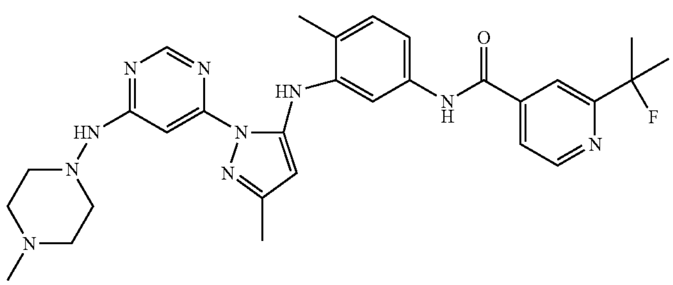 | MS m/z 559.3 (M + 1) |
| 165 | 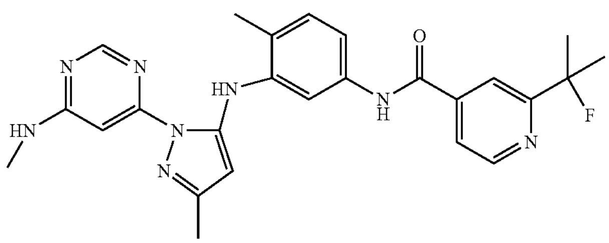 | MS m/z 475.2 (M + 1) |
| 166 | 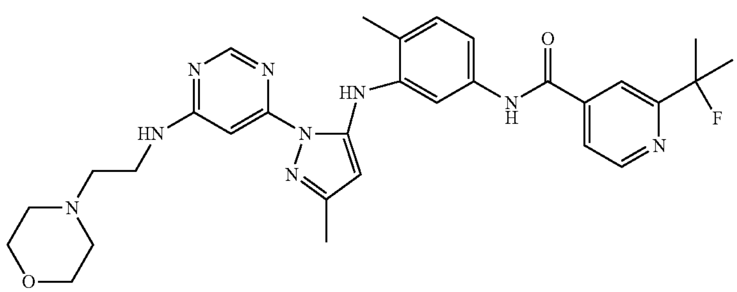 | MS m/z 574.3 (M + 1) |
| 167 | 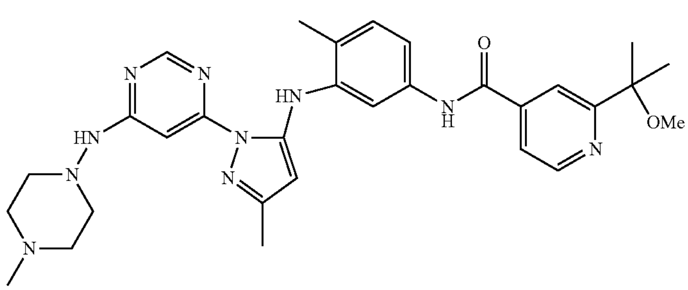 | MS m/z 571.3 (M + 1) |

TABLE 1-continued

| Compound Number | Structure | Physical Data ¹H NMR 400 MHz or 600 MHz (DMSO-d$_6$) and/or MS (m/z) |
|---|---|---|
| 168 | 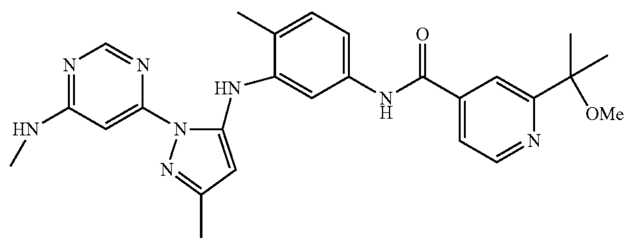 | MS m/z 487.3 (M + 1) |
| 169 | 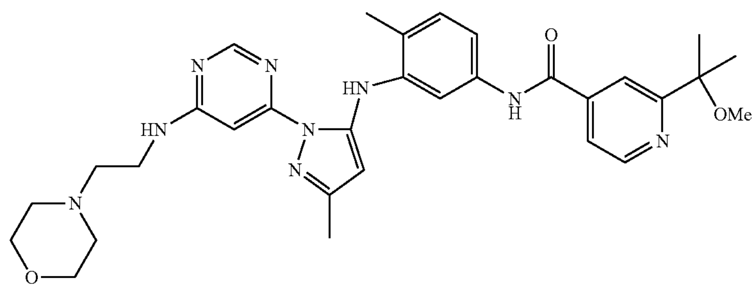 | MS m/z 586.3 (M + 1) |
| 170 | 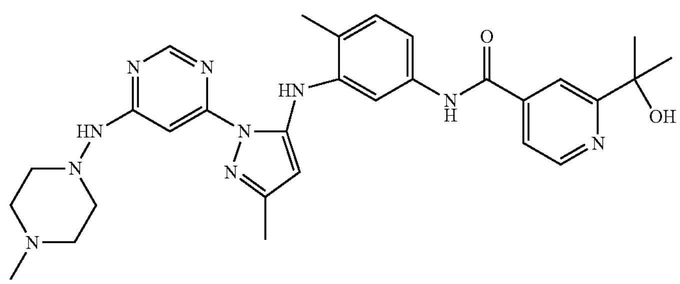 | MS m/z 557.3 (M + 1) |
| 171 | 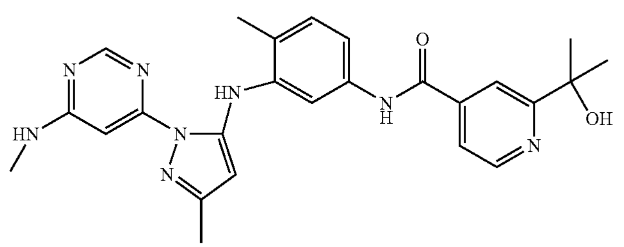 | MS m/z 473.2 (M + 1) |
| 172 | 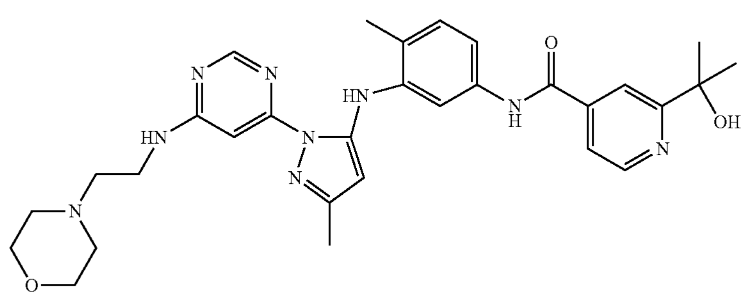 | MS m/z 572.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 173 | 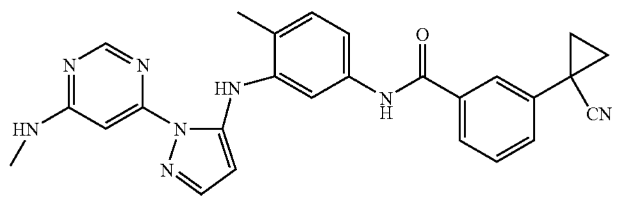 | MS m/z 465.2 (M + 1) |
| 174 | 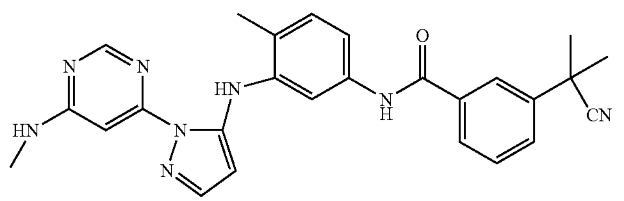 | MS m/z 467.2 (M + 1) |
| 175 | 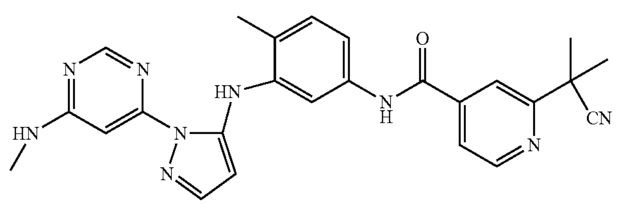 | MS m/z 468.2 (M + 1) |
| 176 | 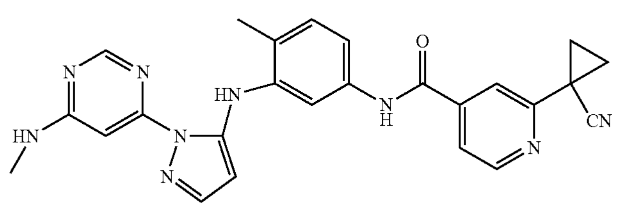 | MS m/z 466.2 (M + 1) |
| 177 | 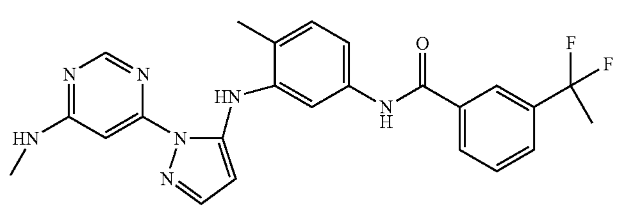 | MS m/z 464.2 (M + 1) |
| 178 | 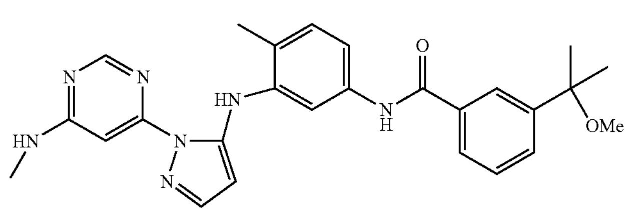 | MS m/z 472.2 (M + 1) |
| 179 | 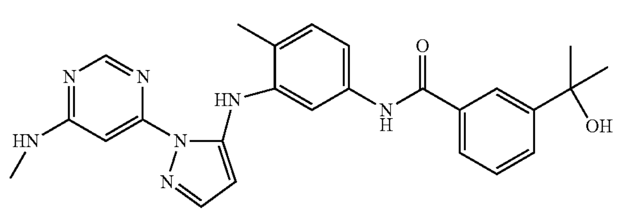 | MS m/z 458.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 180 | 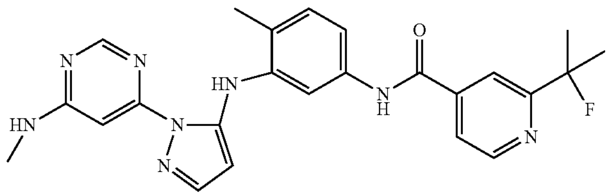 | MS m/z 461.2 (M + 1) |
| 181 | 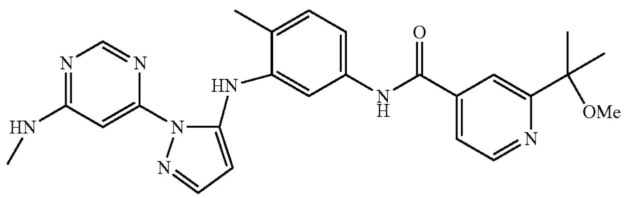 | MS m/z 473.2 (M + 1) |
| 182 | 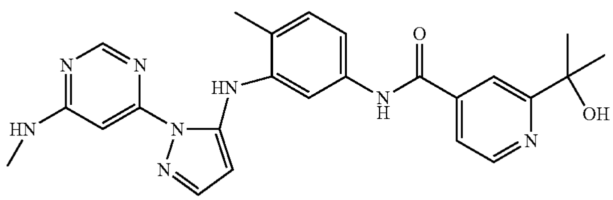 | MS m/z 459.2 (M + 1) |
| 183 | 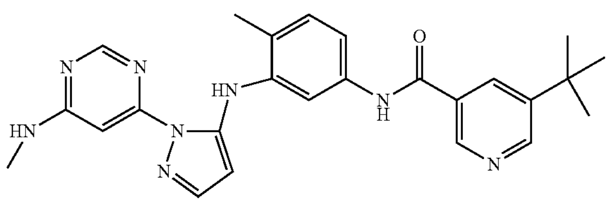 | MS m/z 457.2 (M + 1) |
| 184 | 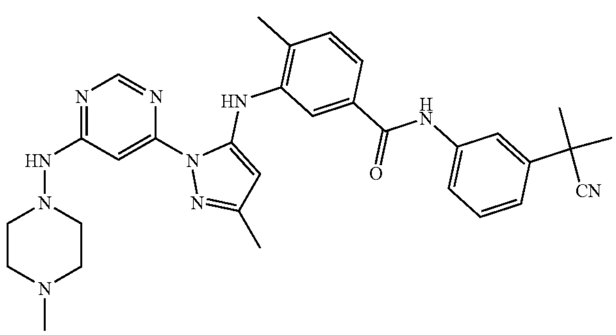 | MS m/z 565.3 (M + 1) |
| 185 | 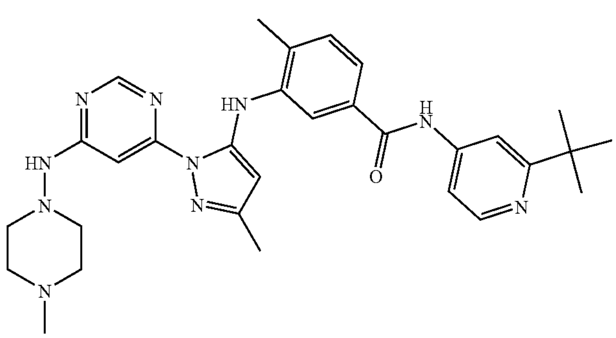 | MS m/z 555.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 186 | 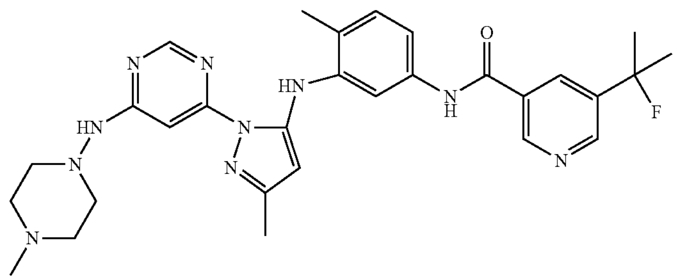 | MS m/z 559.3 (M + 1) |
| 187 | 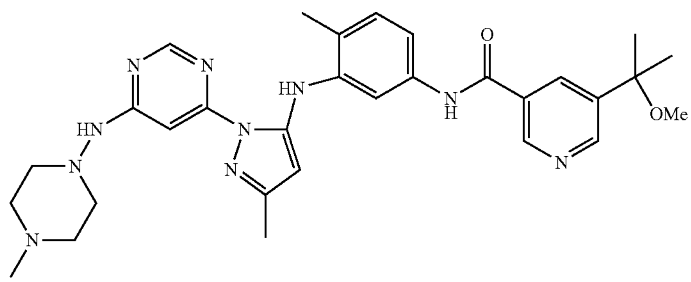 | MS m/z 571.3 (M + 1) |
| 188 | 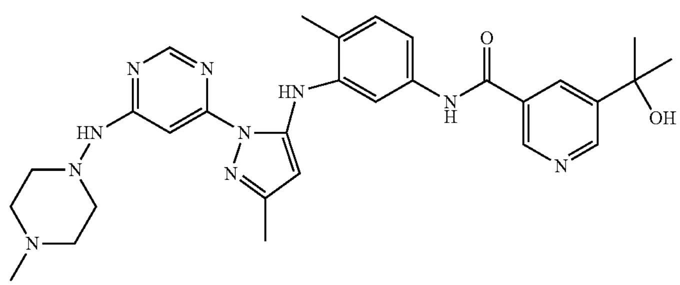 | MS m/z 557.3 (M + 1) |
| 189 | 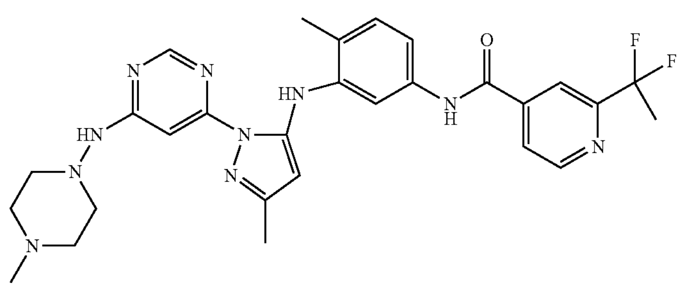 | MS m/z 563.3 (M + 1) |
| 190 | 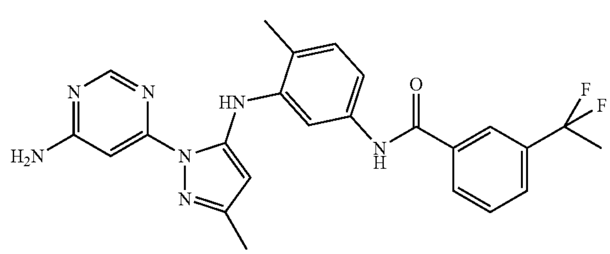 | MS m/z 464.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 191 | 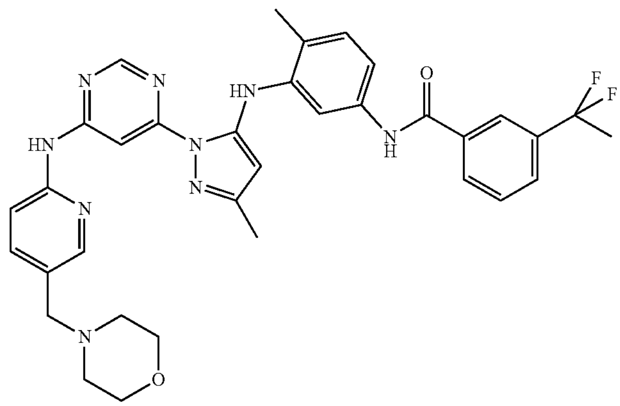 | MS m/z 640.3 (M + 1) |
| 192 | 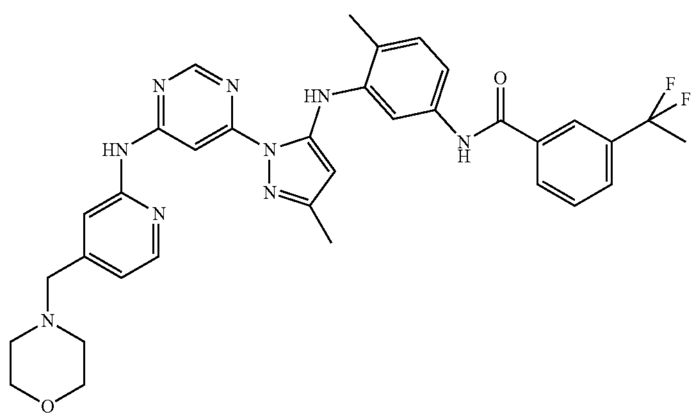 | MS m/z 640.3 (M + 1) |
| 193 | 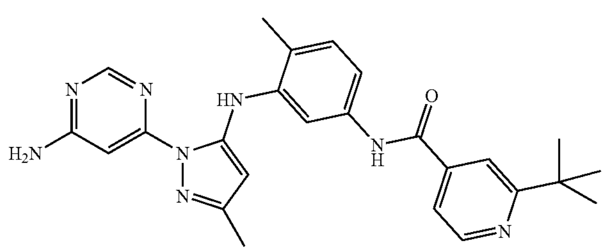 | MS m/z 457.2 (M + 1) |
| 194 | 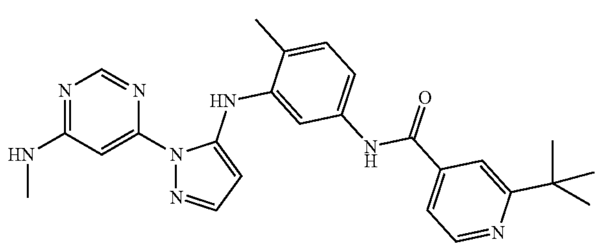 | MS m/z 457.2 (M + 1) |

TABLE 1-continued

| Compound Number | Structure | Physical Data ¹H NMR 400 MHz or 600 MHz (DMSO-d₆) and/or MS (m/z) |
|---|---|---|
| 195 | 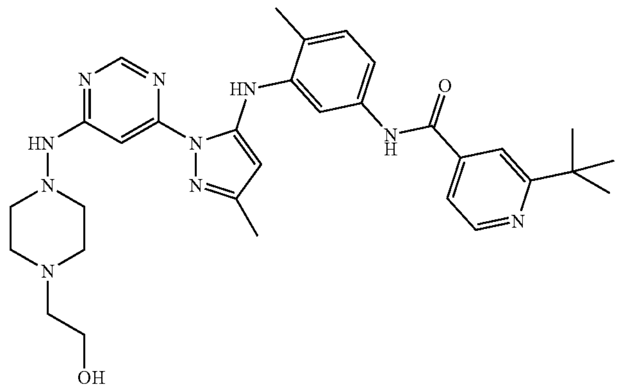 | MS m/z 585.3 (M + 1) |
| 196 | 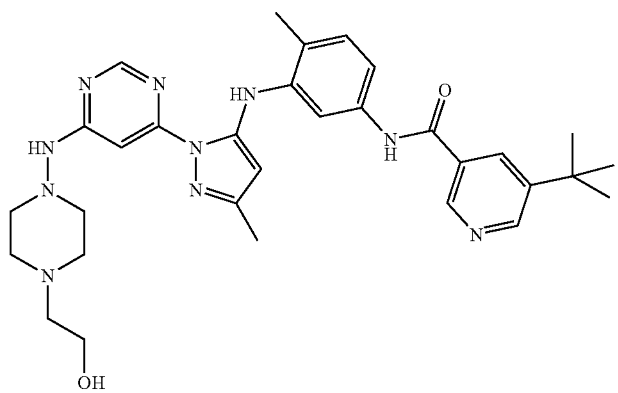 | MS m/z 585.3 (M + 1) |
| 197 | 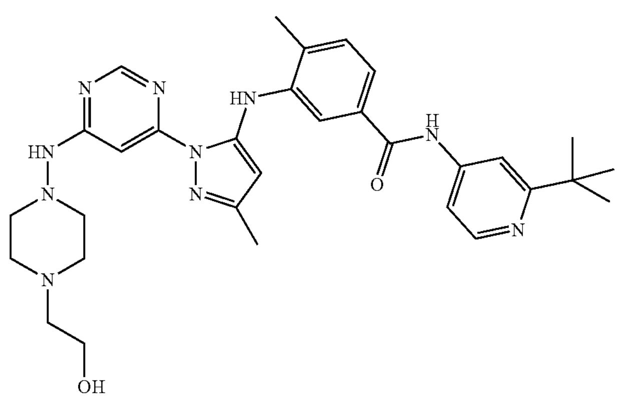 | MS m/z 585.3 (M + 1) |
| 198 | 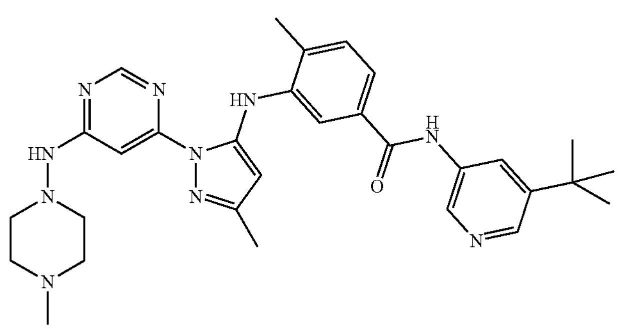 | MS m/z 555.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 199 | 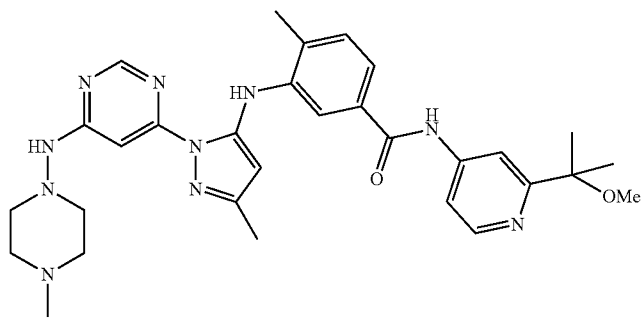 | MS m/z 571.3 (M + 1) |
| 200 | 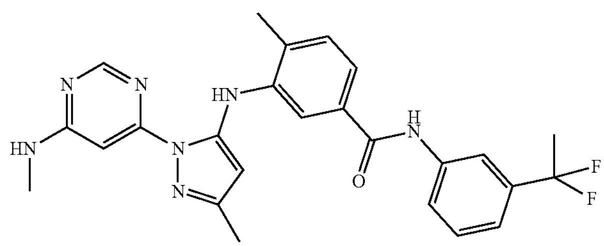 | MS m/z 478.2 (M + 1) |
| 201 | 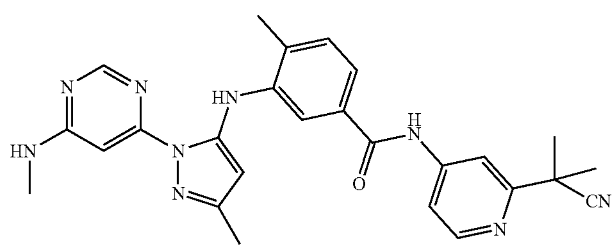 | MS m/z 482.2 (M + 1) |
| 202 | 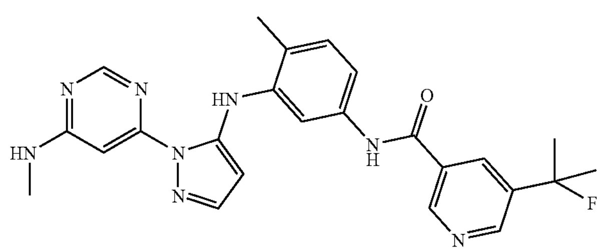 | MS m/z 461.2 (M + 1) |
| 203 | 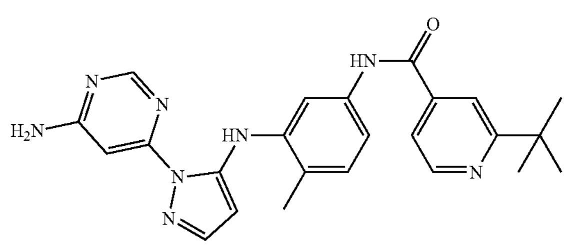 | MS 443.2 m/z (M + 1) |

TABLE 1-continued

| Compound Number | Structure | Physical Data ¹H NMR 400 MHz or 600 MHz (DMSO-d₆) and/or MS (m/z) |
|---|---|---|
| 204 | 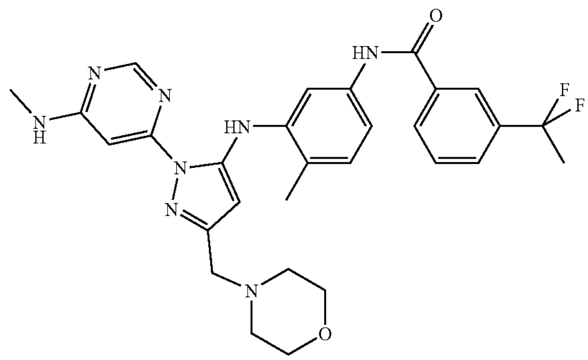 | MS 563.3 m/z (M + 1) |
| 205 | 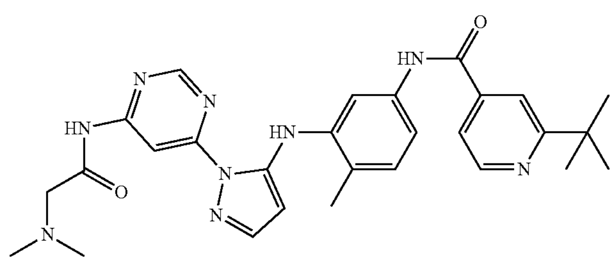 | Ms 528.3 m/z (M + 1) |
| 206 | N-[2-(1,1-Difluoro-ethyl)-pyridin-4-yl]-4-methyl-3-{5-methyl-2-[6-(2-morpholin-4-yl-ethylammino)-pyrimidin-4-yl]-2H-pyrazol-3-ylamino}-benzamide | Ms 577.3 m/z (M + 1) |

TABLE 1-continued

| Compound Number | Structure | Physical Data ¹H NMR 400 MHz or 600 MHz (DMSO-$d_6$) and/or MS (m/z) |
| --- | --- | --- |
| 207 | 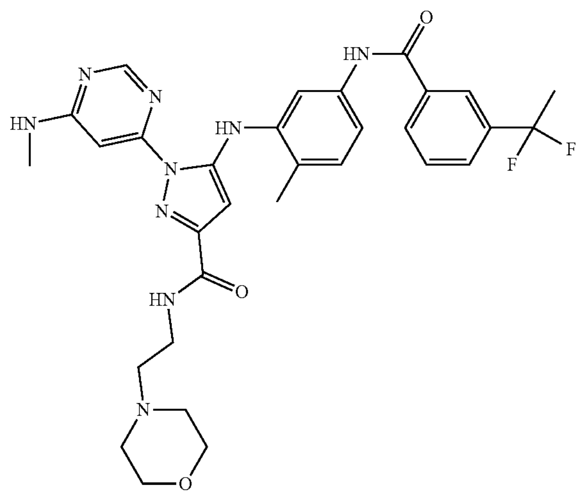 | Ms 620.3 m/z (M + 1) |
| 208 | 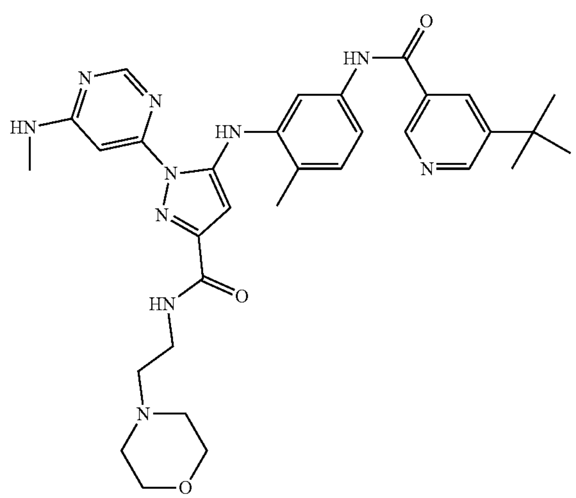 | Ms 613.3 m/z (M + 1) |
| 209 | 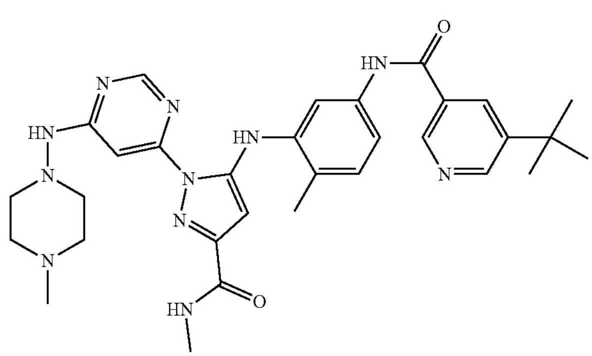 | Ms 598.3 m/z (M + 1) |

TABLE 1-continued
| Compound Number | Structure | Physical Data<br>¹H NMR 400 MHz or 600 MHz (DMSO-d₆) and/or MS (m/z) |
|---|---|---|
| 210 | 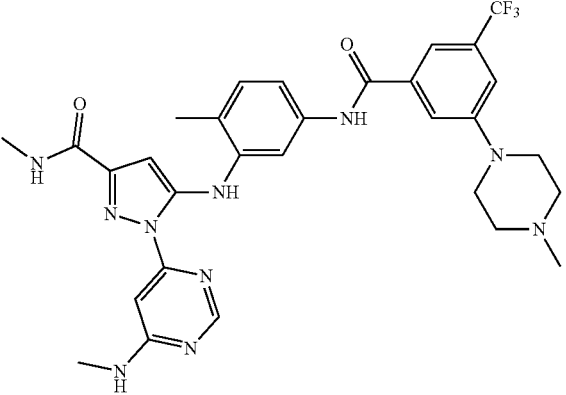 | MS m/z 623.3 (M + 1) |
| 211 | 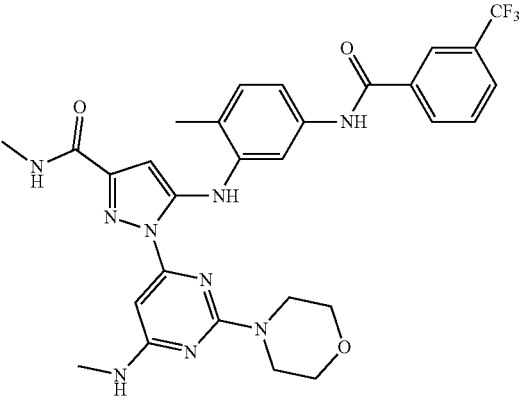 | MS m/z 610.3 (M + 1) |
| 212 | 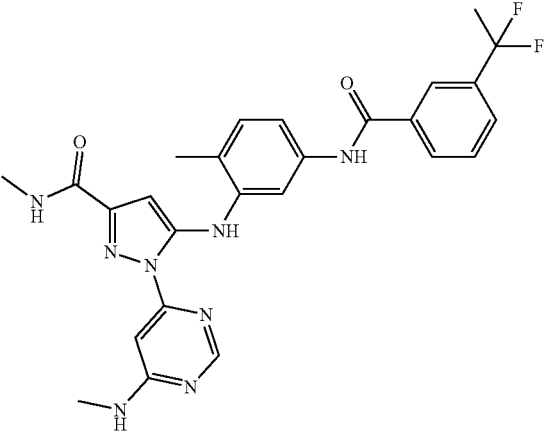 | MS m/z 521.3 (M + 1) |

TABLE 1-continued

| Compound Number | Structure | Physical Data ¹H NMR 400 MHz or 600 MHz (DMSO-d₆) and/or MS (m/z) |
|---|---|---|
| 213 | 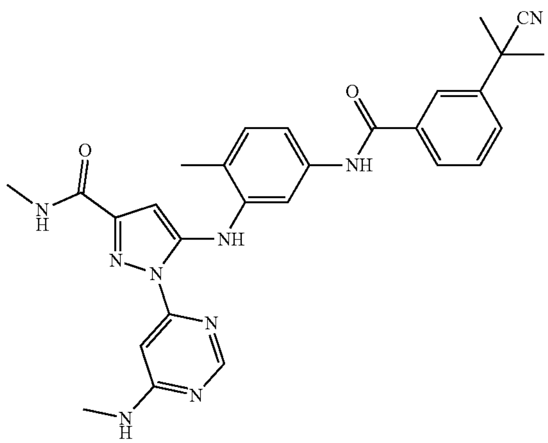 | MS m/z 524.3 (M + 1) |
| 214 | 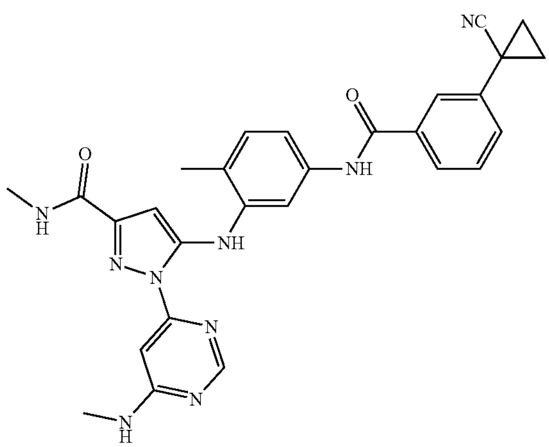 | MS m/z 522.3 (M + 1) |
| 215 | 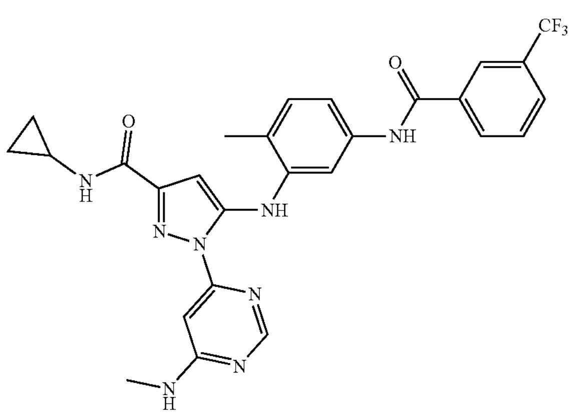 | MS m/z 551.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 216 | 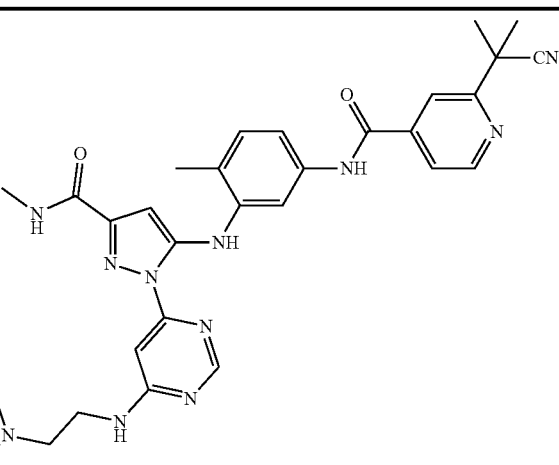 | MS m/z 624.3 (M + 1) |
| 217 | 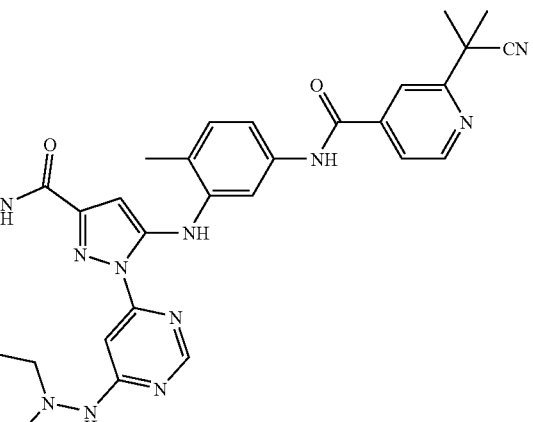 | MS m/z 609.3 (M + 1) |
| 218 | 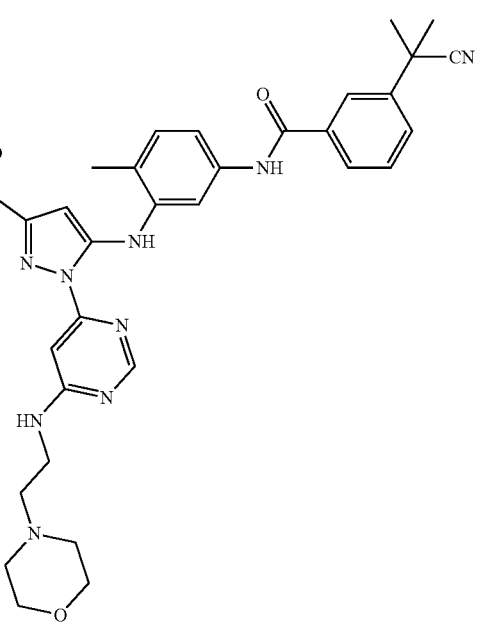 | MS m/z 623.3 (M + 1) |

TABLE 1-continued
| Compound Number | Structure | Physical Data ¹H NMR 400 MHz or 600 MHz (DMSO-d₆) and/or MS (m/z) |
|---|---|---|
| 219 | 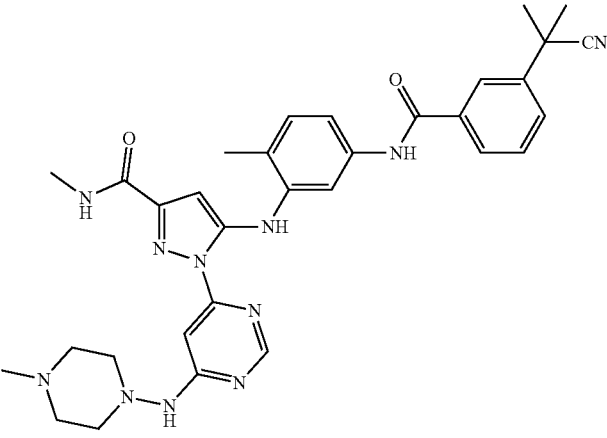 | MS m/z 608.3 (M + 1) |
| 220 | 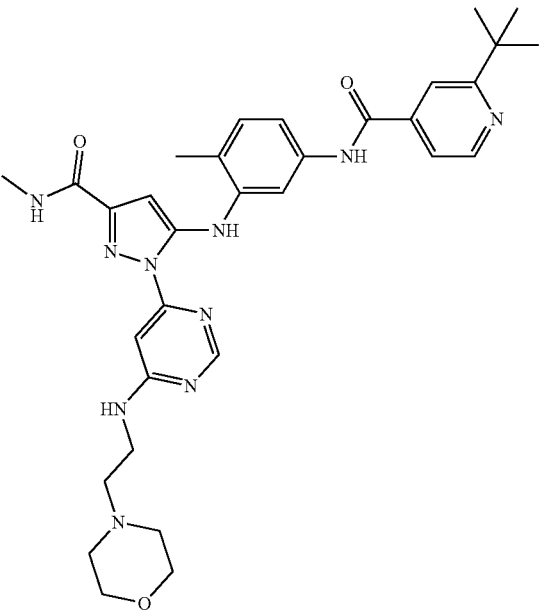 | MS m/z 613.3 (M + 1) |

TABLE 1-continued

| Compound Number | Structure | Physical Data ¹H NMR 400 MHz or 600 MHz (DMSO-d$_6$) and/or MS (m/z) |
|---|---|---|
| 221 | 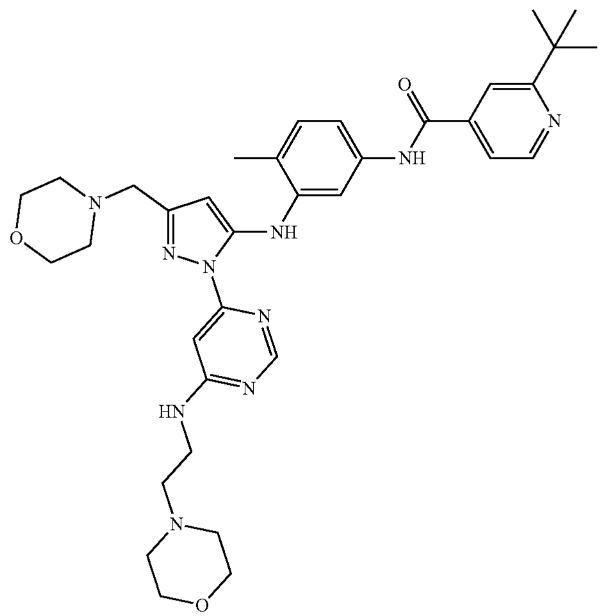 | MS m/z 655.4 (M + 1) |
| 222 | 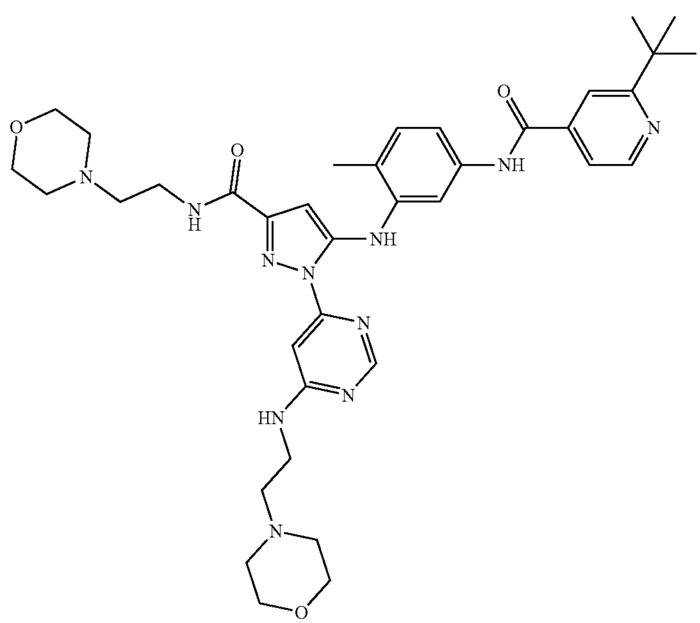 | MS m/z 712.4 (M + 1) |

TABLE 1-continued

| Compound Number | Structure | Physical Data ¹H NMR 400 MHz or 600 MHz (DMSO-$d_6$) and/or MS (m/z) |
|---|---|---|
| 223 | 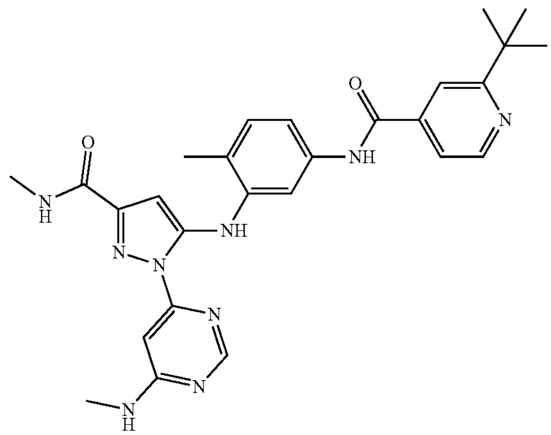 | MS m/z 514.3 (M + 1) |
| 224 | 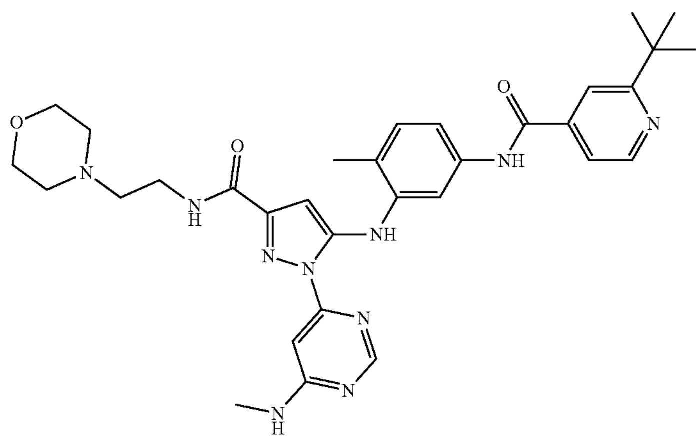 | MS m/z 613.3 (M + 1) |
| 225 | 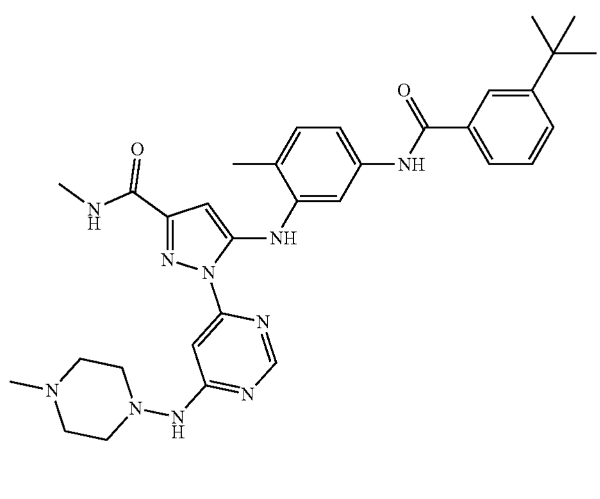 | MS m/z 597.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 226 | 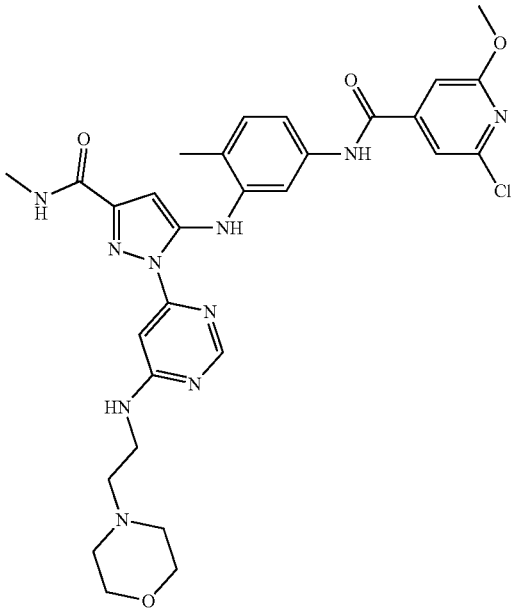<br>2-Chloro-6-methoxy-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide | MS m/z 620.3 (M + 1) |
| 227 | 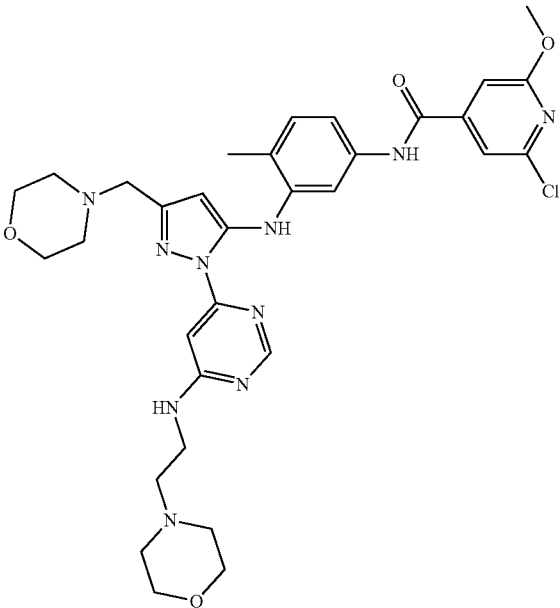 | MS m/z 663.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 228 | 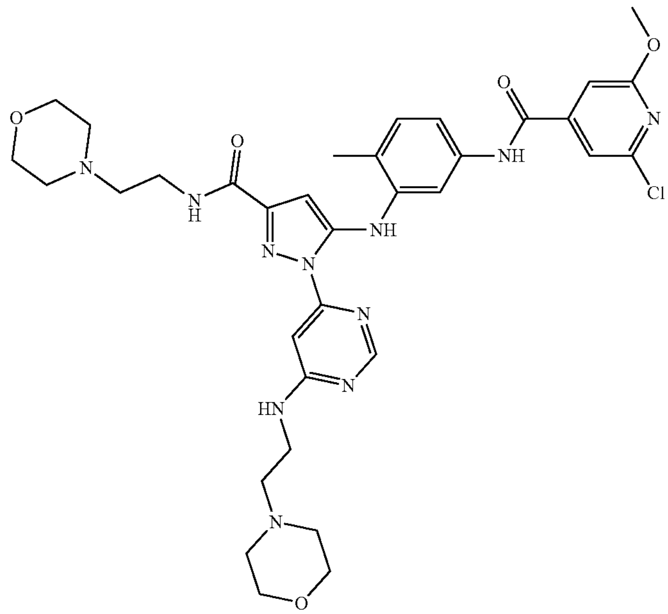 | MS m/z 720.3 (M + 1) |
| 229 | 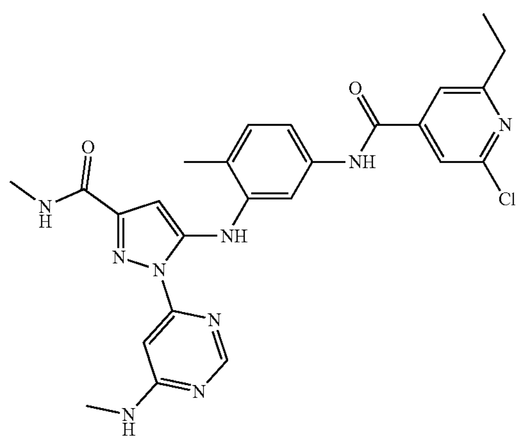 | MS m/z 520.2 (M + 1) |
| 230 | 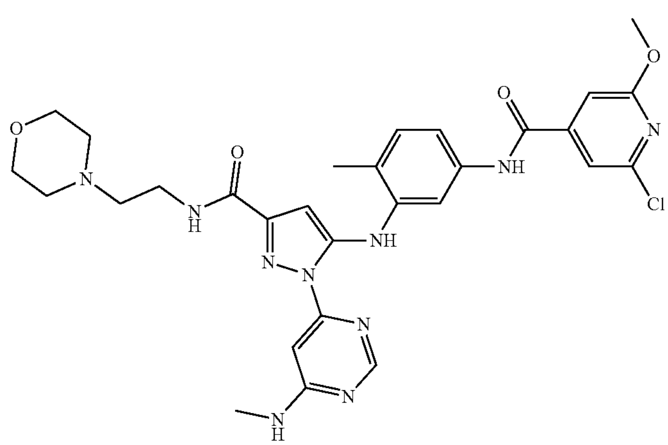 | MS m/z 620.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 231 | 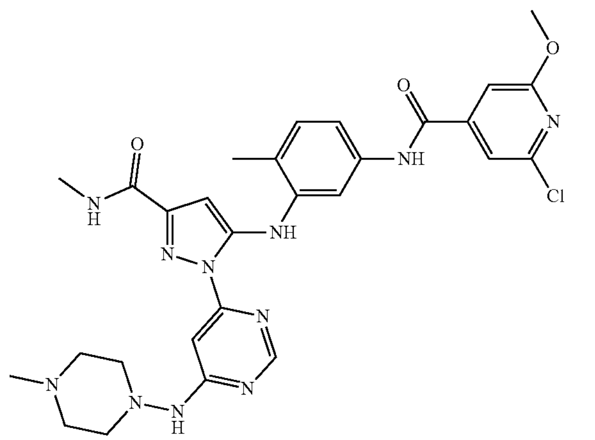 | MS m/z 606.2 (M + 1) |
| 232 | 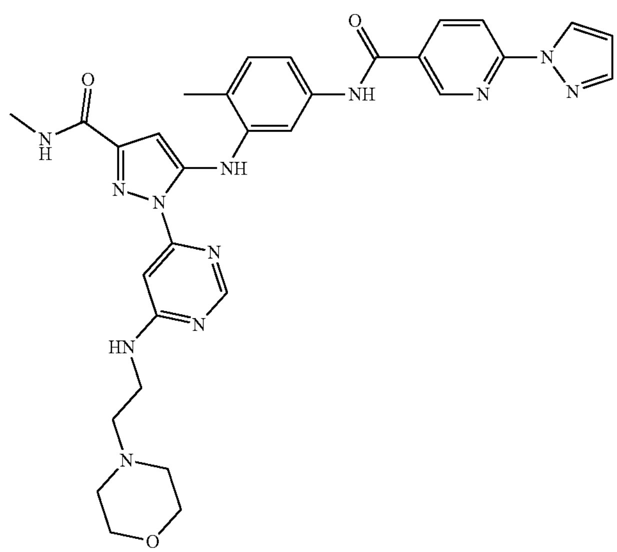 | MS m/z 623.3 (M + 1) |
| 233 | 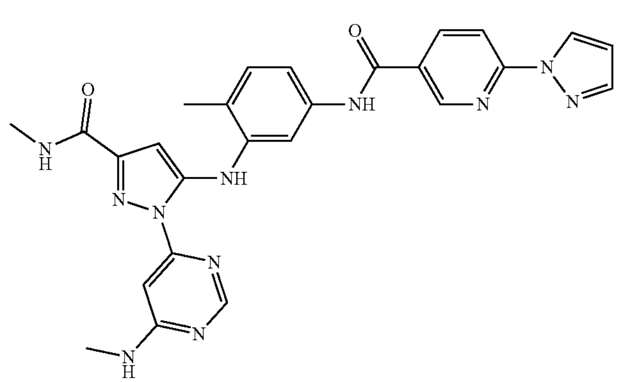 | MS m/z 524.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 234 | 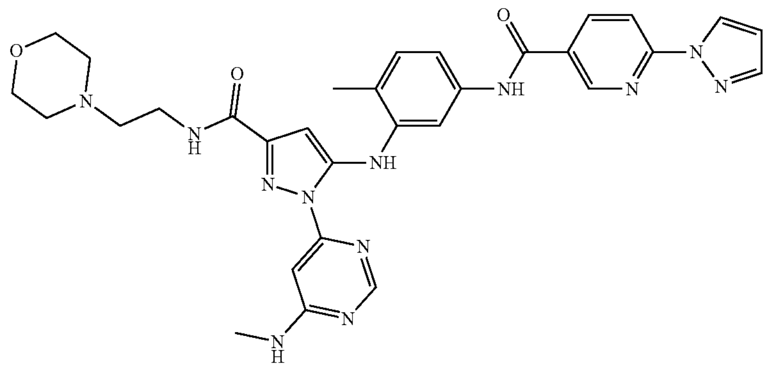 | MS m/z 623.3 (M + 1) |
| 235 | 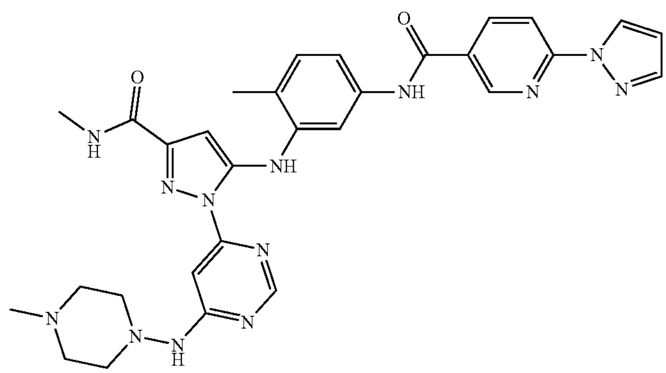 | MS m/z 608.3 (M + 1) |
| 236 | 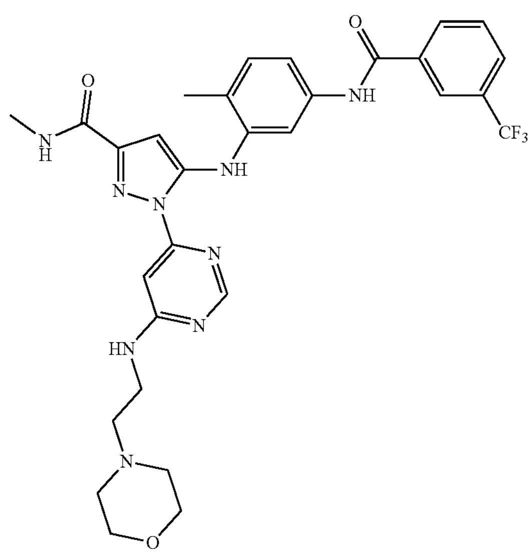 | MS m/z 624.3 (M + 1) |

TABLE 1-continued

| Compound Number | Structure | Physical Data ¹H NMR 400 MHz or 600 MHz (DMSO-d₆) and/or MS (m/z) |
|---|---|---|
| 237 | 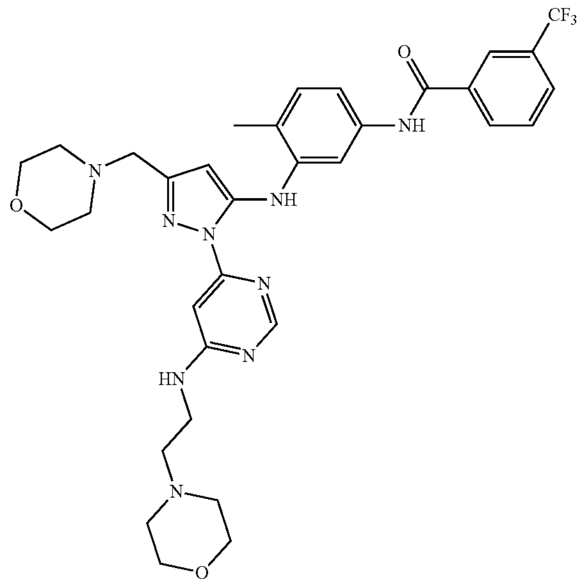 | MS m/z 666.3 (M + 1) |
| 238 | 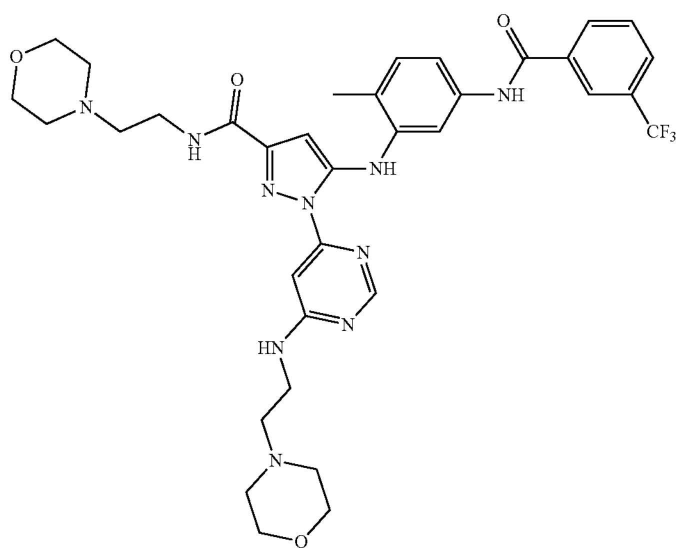 | MS m/z 723.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 239 | 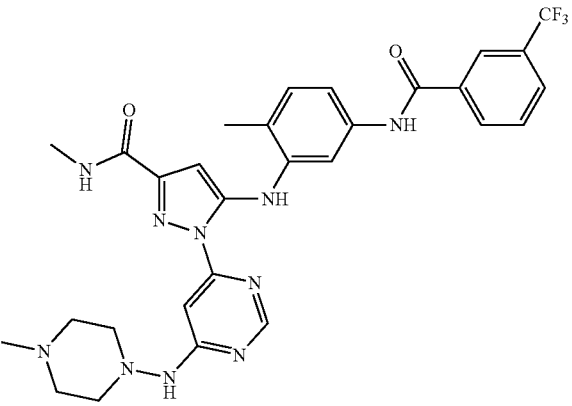 | MS m/z 609.3 (M + 1) |
| 240 | 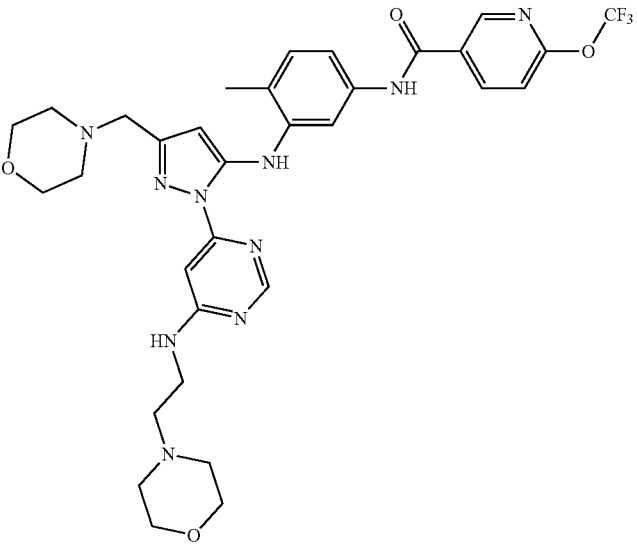 | MS m/z 683.3 (M + 1) |
| 241 | 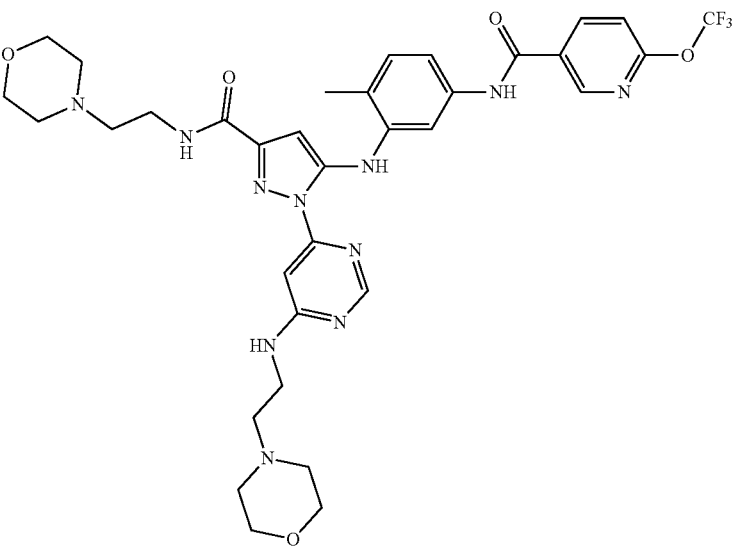 | MS m/z 740.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 242 | 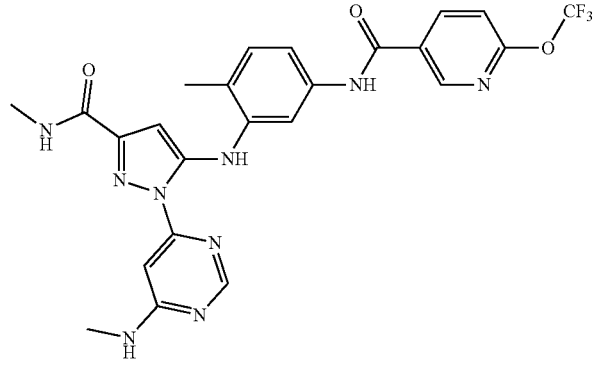 | MS m/z 542.2 (M + 1) |
| 243 | 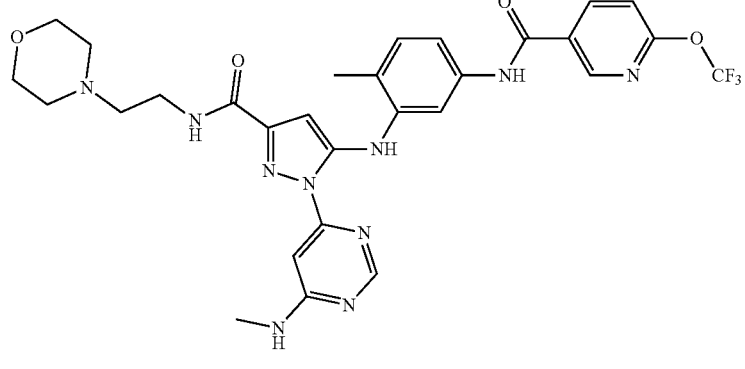 | MS m/z 640.3 (M + 1) |
| 244 | 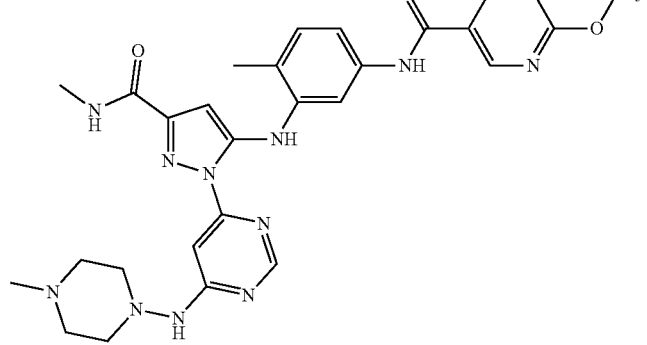 | MS m/z 626.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 245 | 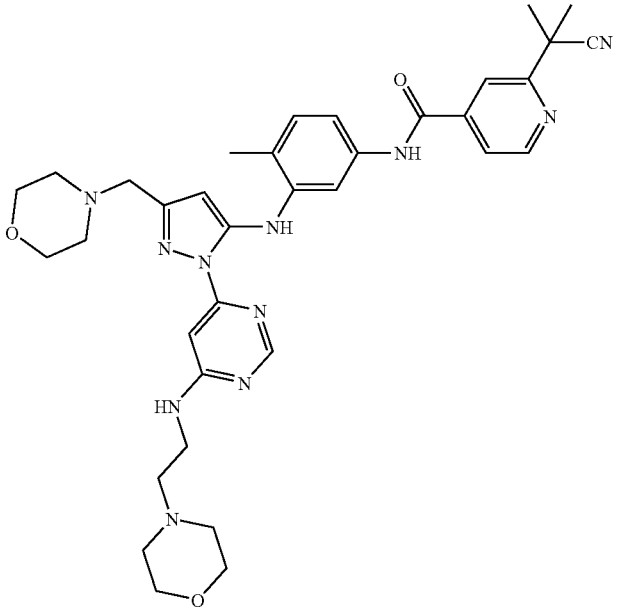 | MS m/z 666.4 (M + 1) |
| 246 | 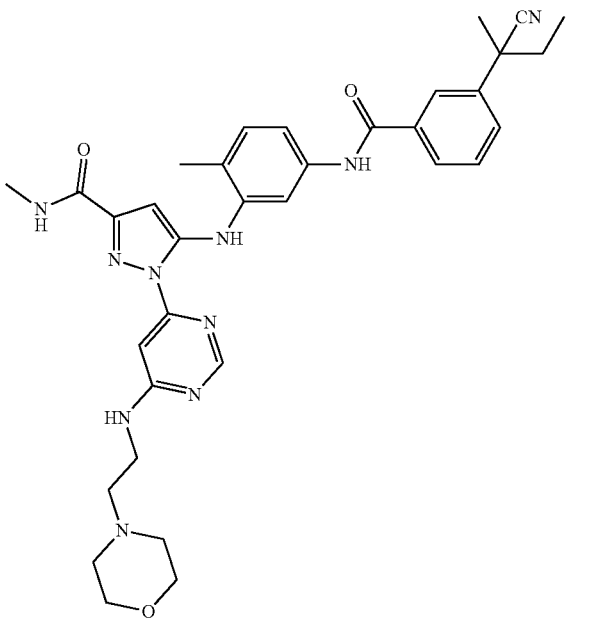 | MS m/z 637.3 (M + 1) |

TABLE 1-continued
| Compound Number | Structure | Physical Data $^1$H NMR 400 MHz or 600 MHz (DMSO-$d_6$) and/or MS (m/z) |
|---|---|---|
| 247 | 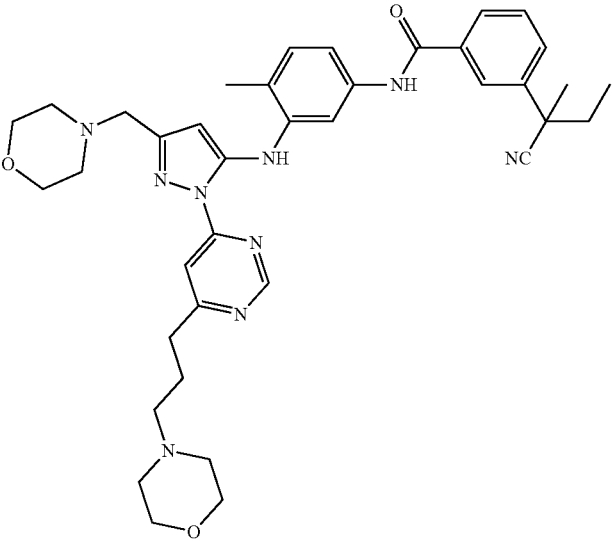 | MS m/z 679.4 (M + 1) |
| 248 | 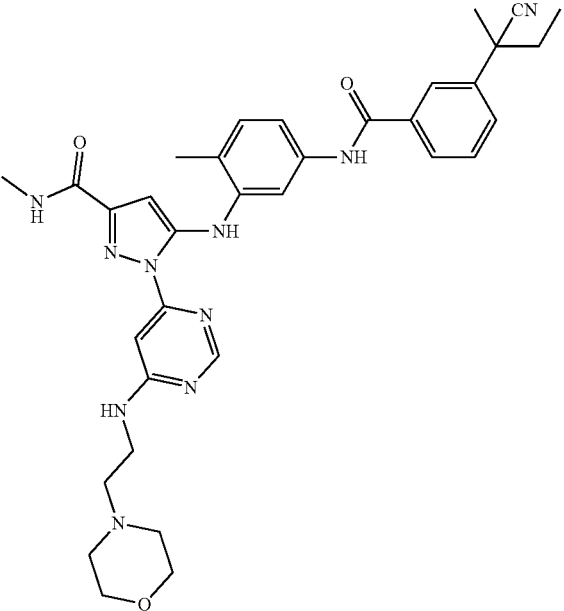 | MS m/z 637.3 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 249 | 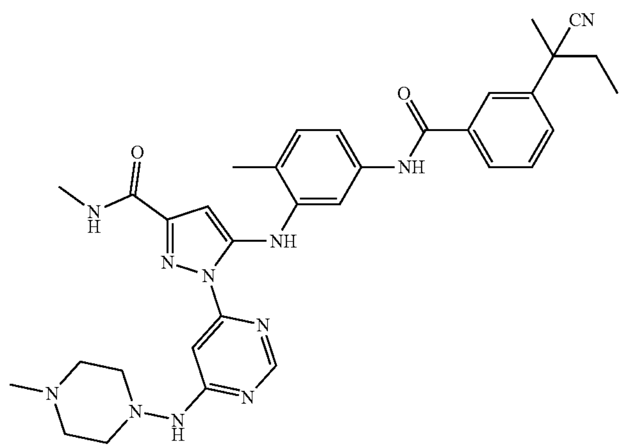 | MS m/z 622.3 (M + 1) |
| 250 | 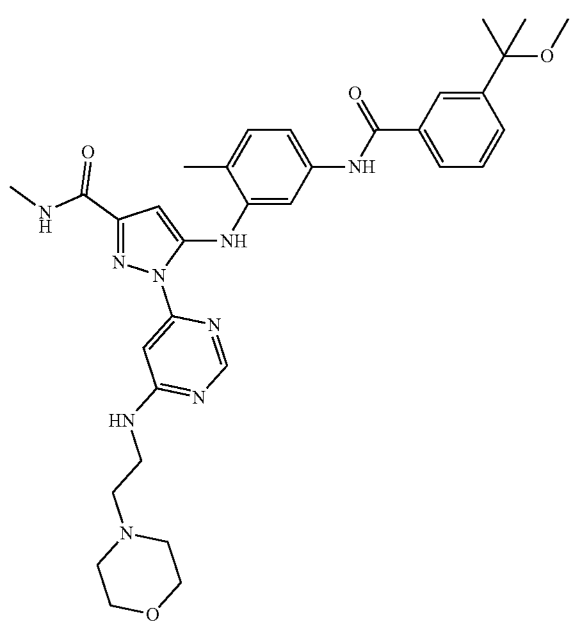 | MS m/z 628.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 251 | 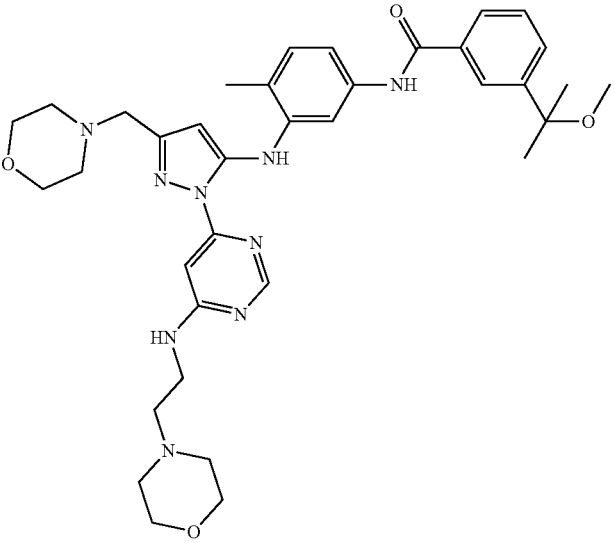 | MS m/z 670.4 (M + 1) |
| 252 | 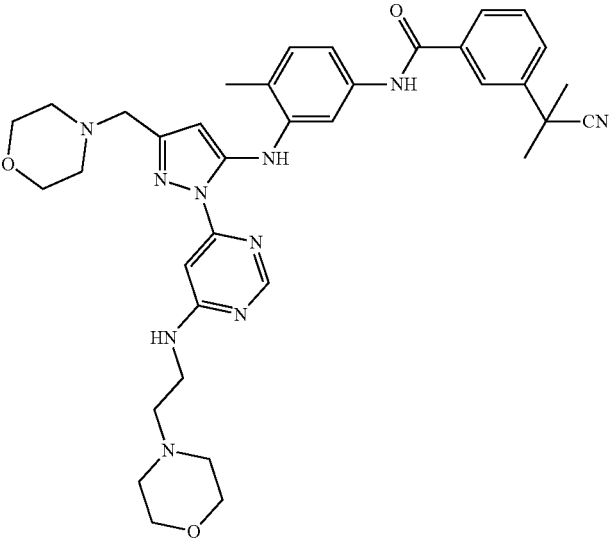 | MS m/z 665.4 (M + 1) |

TABLE 1-continued
| Compound Number | Structure | Physical Data ¹H NMR 400 MHz or 600 MHz (DMSO-$d_6$) and/or MS (m/z) |
|---|---|---|
| 253 | 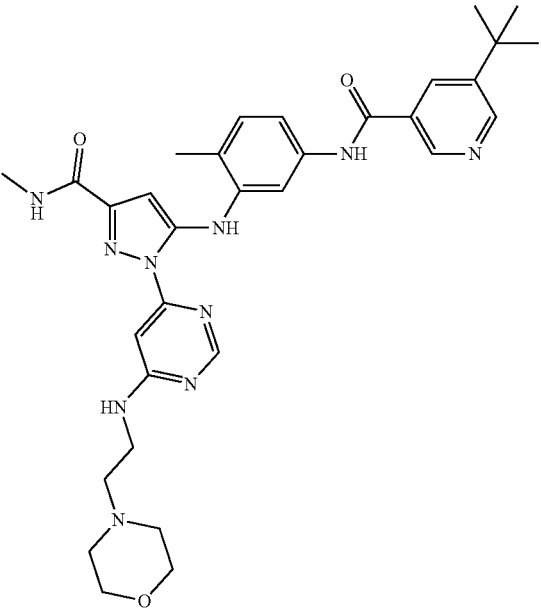 | MS m/z 613.3 (M + 1) |
| 254 | 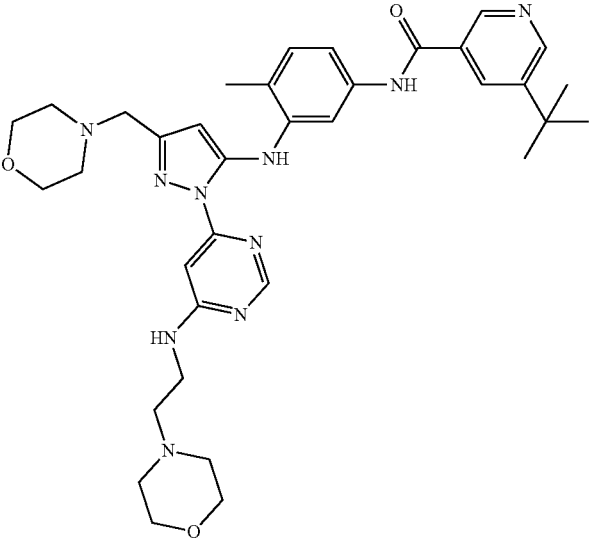 | MS m/z 655.4 (M + 1) |

TABLE 1-continued

| Compound Number | Structure | Physical Data ¹H NMR 400 MHz or 600 MHz (DMSO-$d_6$) and/or MS (m/z) |
|---|---|---|
| 255 | 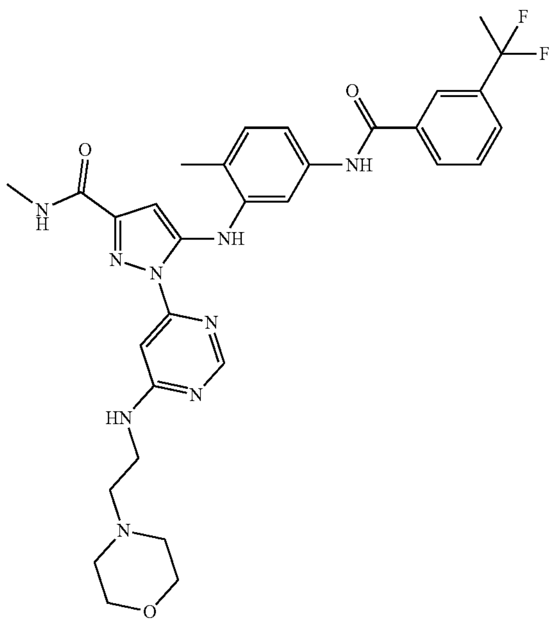 | MS m/z 620.3 (M + 1) |
| 256 | 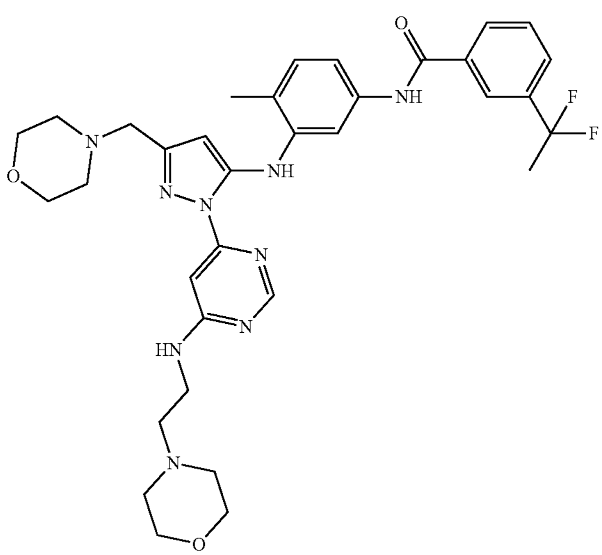 | MS m/z 662.3 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 257 | 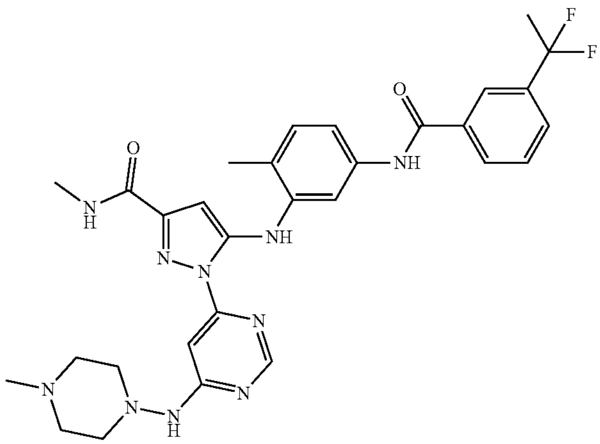 | MS m/z 605.3 (M + 1) |
| 258 | 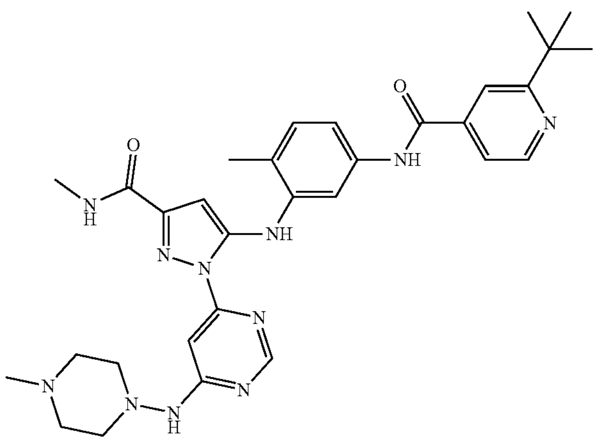 | MS m/z 598.3 (M + 1) |
| 259 | 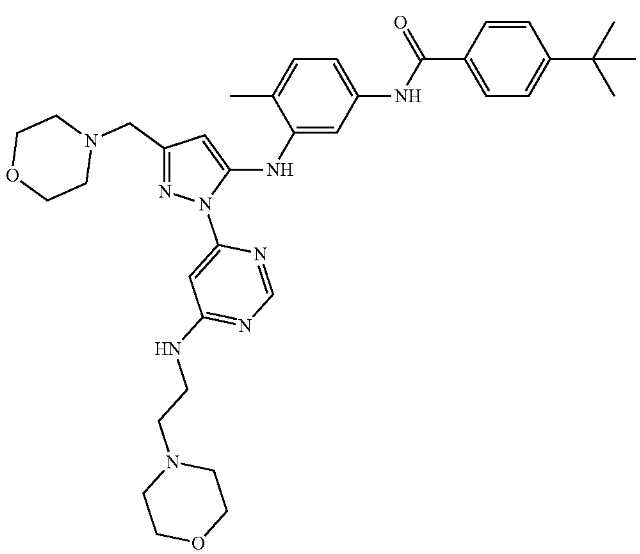 | MS m/z 654.4 (M + 1) |

TABLE 1-continued
| Compound Number | Structure | Physical Data ¹H NMR 400 MHz or 600 MHz (DMSO-$d_6$) and/or MS (m/z) |
|---|---|---|
| 260 | 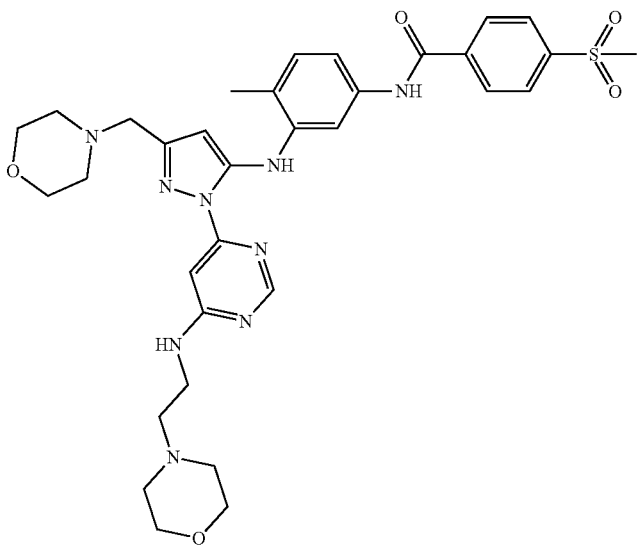 | MS m/z 676.3 (M + 1) |
| 261 | 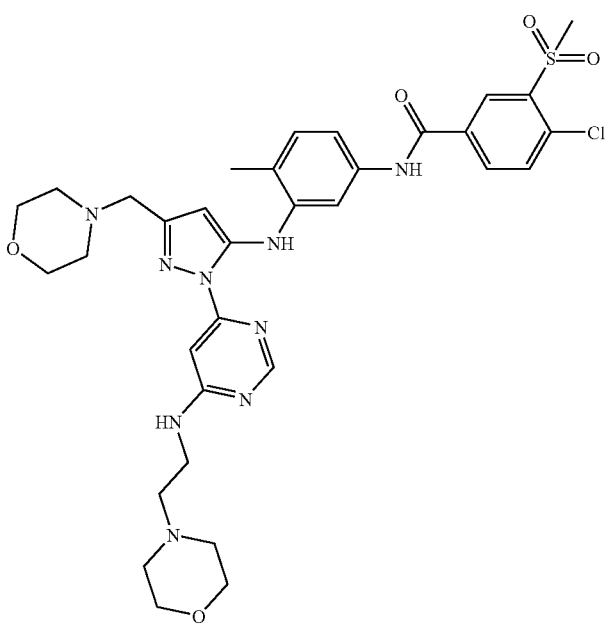 | MS m/z 710.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 262 | 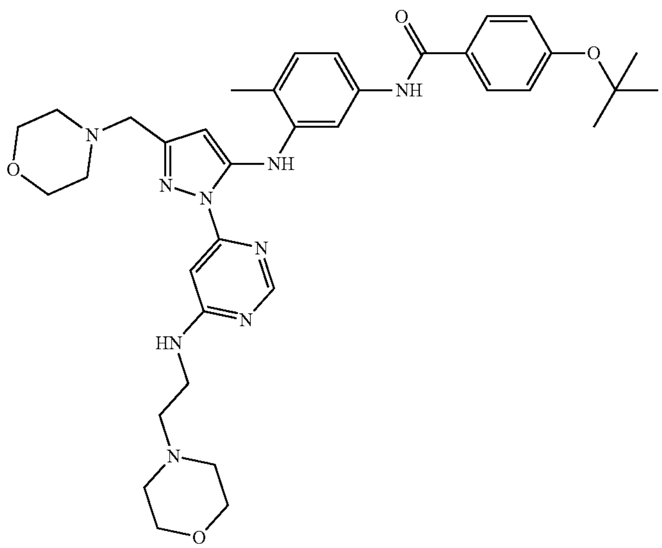 | MS m/z 670.4 (M + 1) |
| 263 | 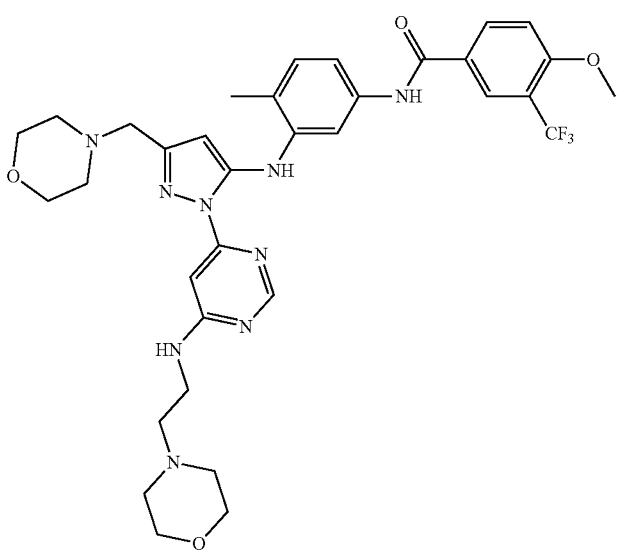 | MS m/z 696.3 (M + 1) |

TABLE 1-continued

| Compound Number | Structure | Physical Data $^1$H NMR 400 MHz or 600 MHz (DMSO-$d_6$) and/or MS (m/z) |
| --- | --- | --- |
| 264 | 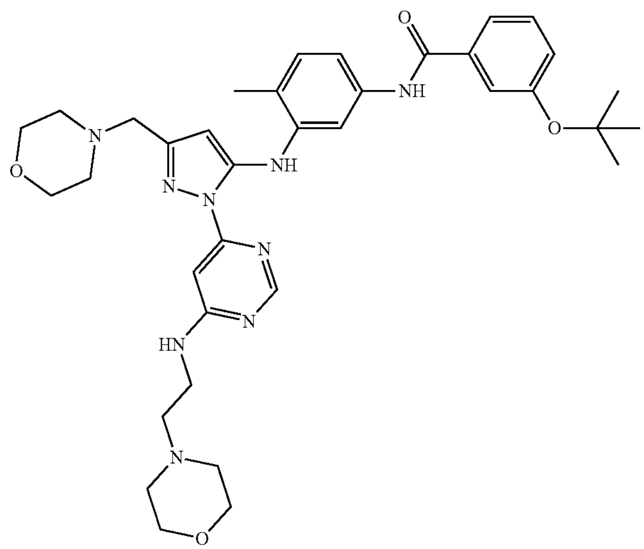 | MS m/z 670.4 (M + 1) |
| 265 | 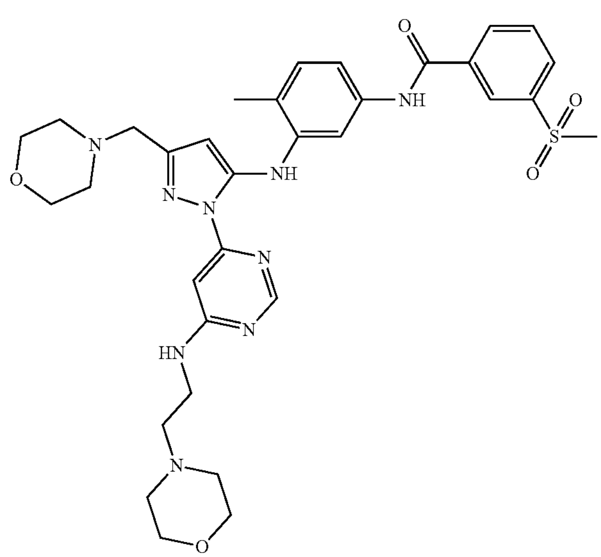 | MS m/z 676.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 266 | 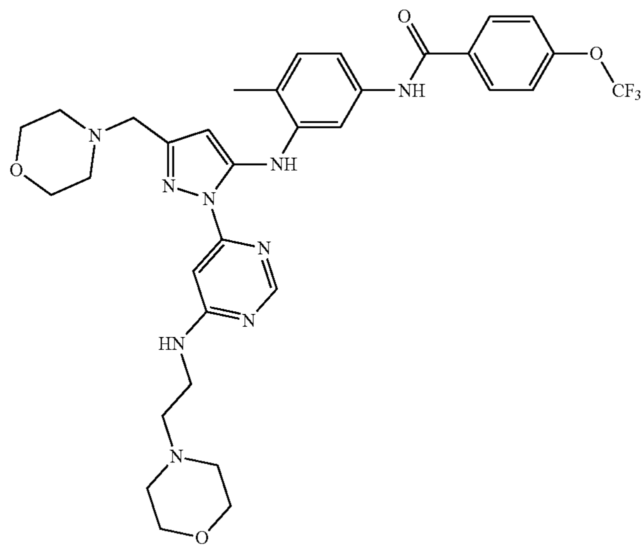 | MS m/z 682.3 (M + 1) |
| 267 | 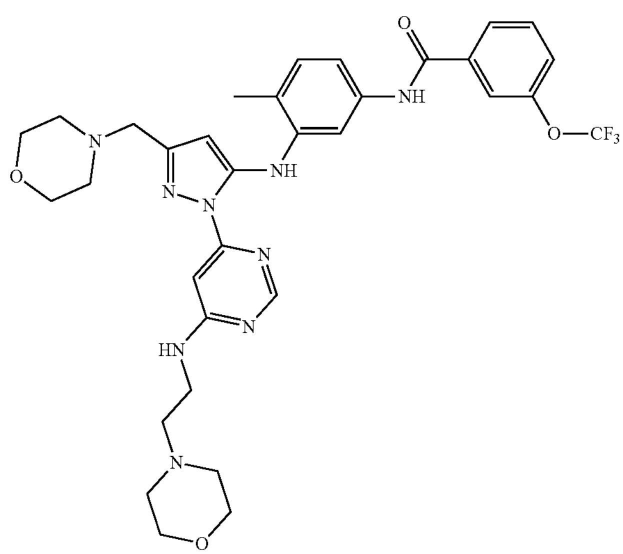 | MS m/z 682.3 (M + 1) |
| 268 | 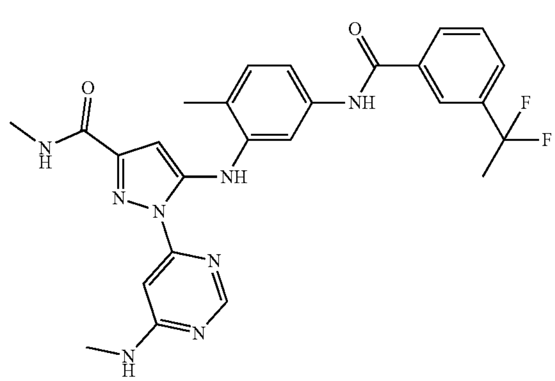 | MS m/z 521.2 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 269 | 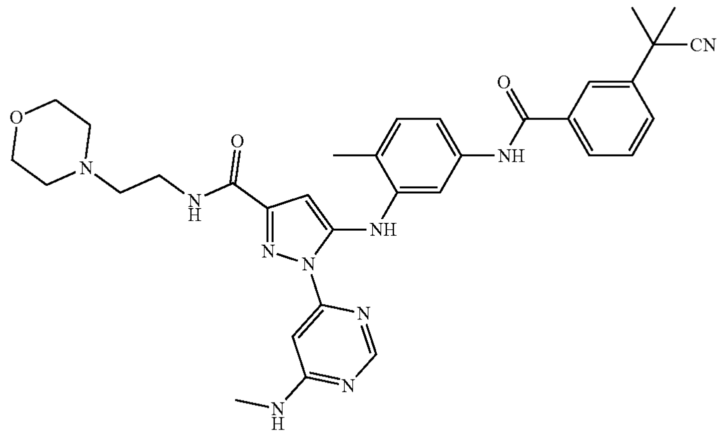 | MS m/z 623.3 (M + 1) |
| 270 | 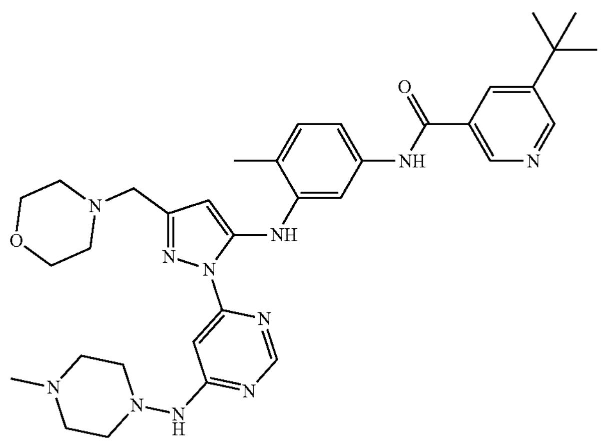 | MS m/z 640.4 (M + 1) |
| 271 | 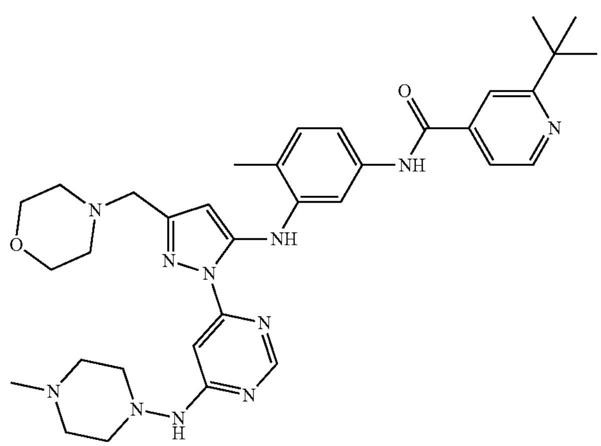 | MS m/z 682.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 272 | 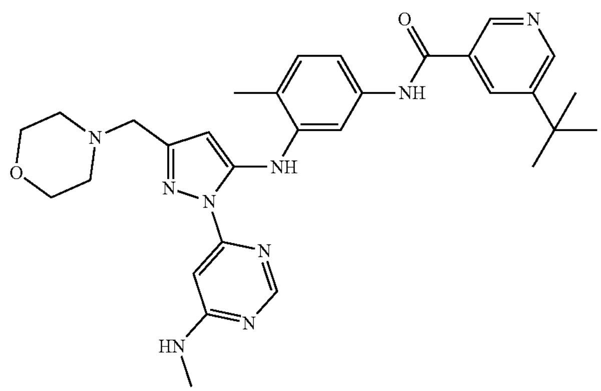 | MS m/z 556.3 (M + 1) |
| 273 | 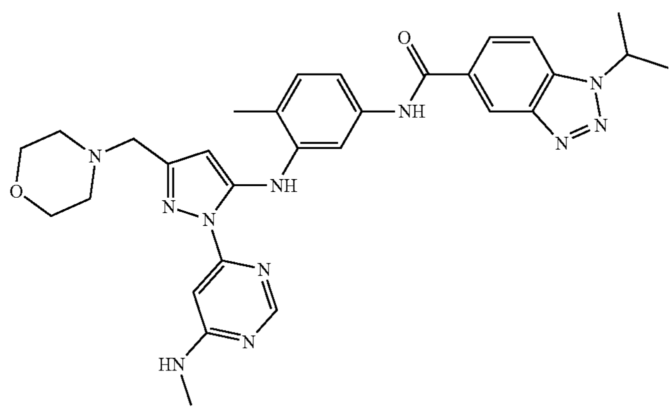 | MS m/z 582.3 (M + 1) |
| 274 | 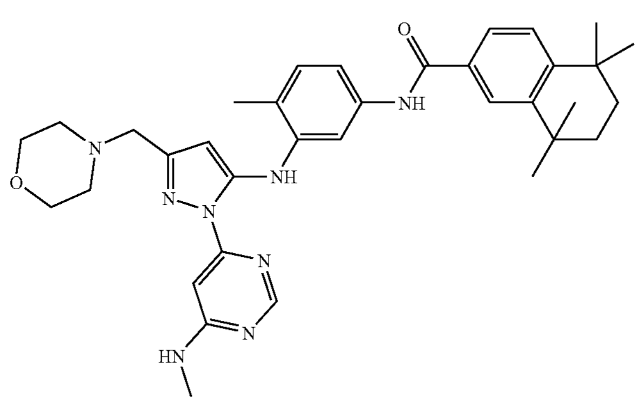 | MS m/z 609.4 (M + 1) |

TABLE 1-continued

| Compound Number | Structure | Physical Data<br>$^1$H NMR 400 MHz or 600 MHz (DMSO-$d_6$) and/or MS (m/z) |
|---|---|---|
| 275 | 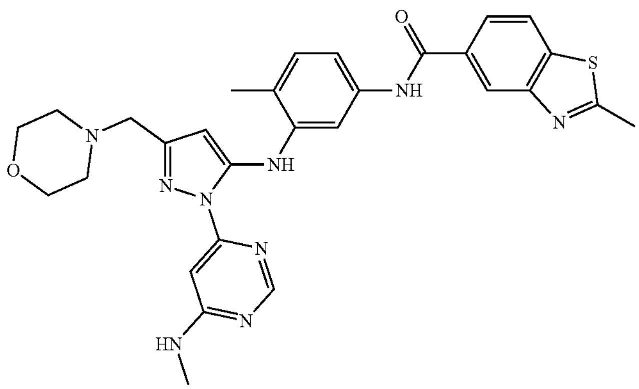 | MS m/z 570.2 (M + 1) |
| 276 | 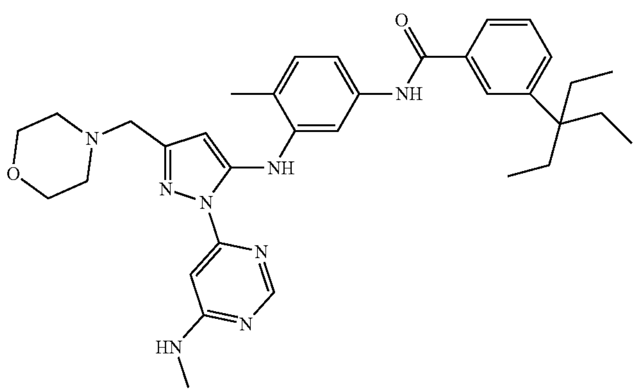 | MS m/z 597.4 (M + 1) |
| 277 | 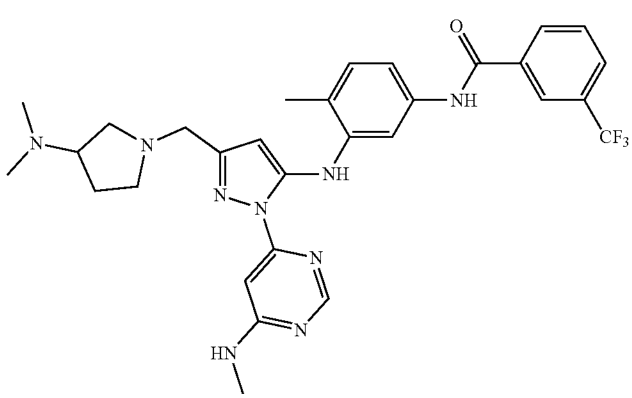 | MS m/z 594.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 278 | 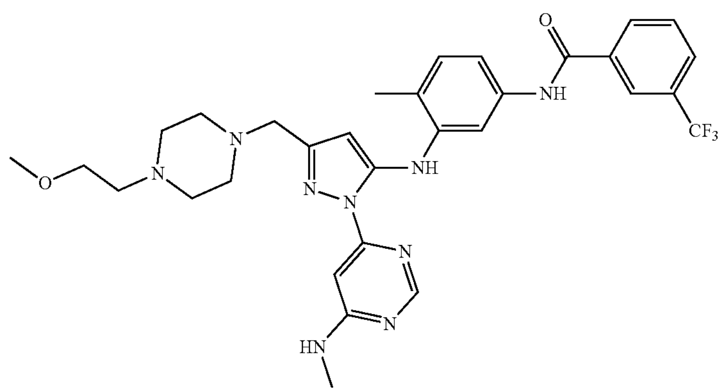 | MS m/z 624.3 (M + 1) |
| 279 | 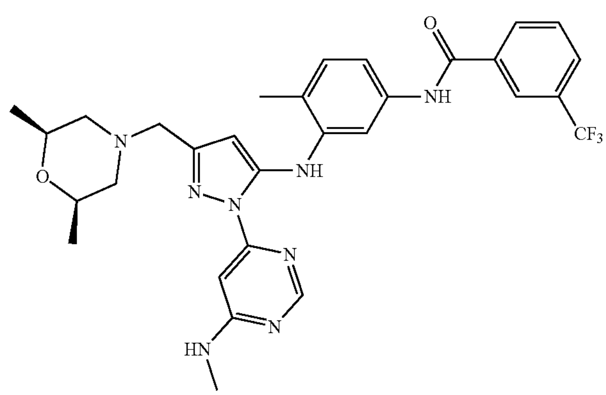 | MS m/z 595.3 (M + 1) |
| 280 | 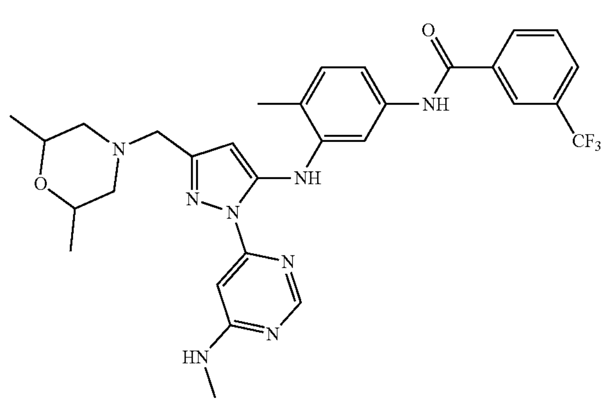 | MS m/z 595.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 281 | 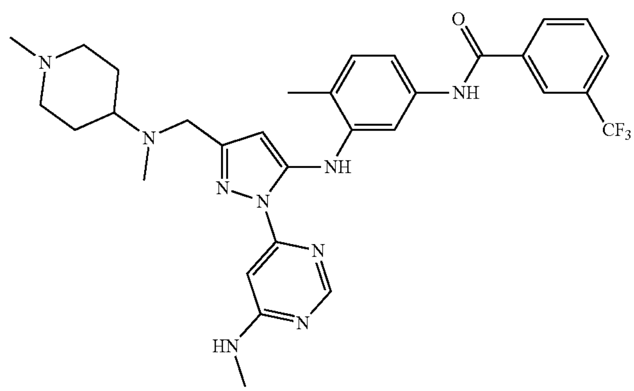 | MS m/z 608.3 (M + 1) |
| 282 | 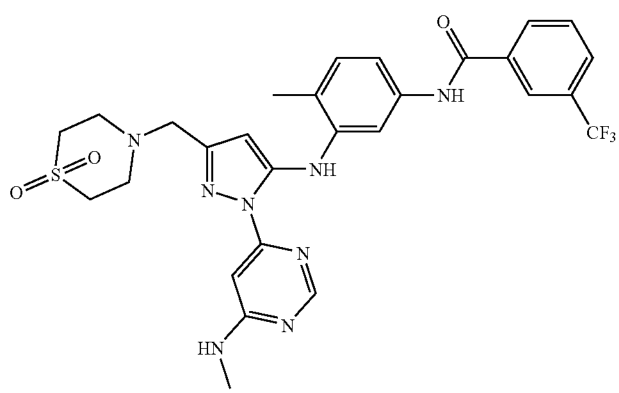 | MS m/z 615.2 (M + 1) |
| 283 | 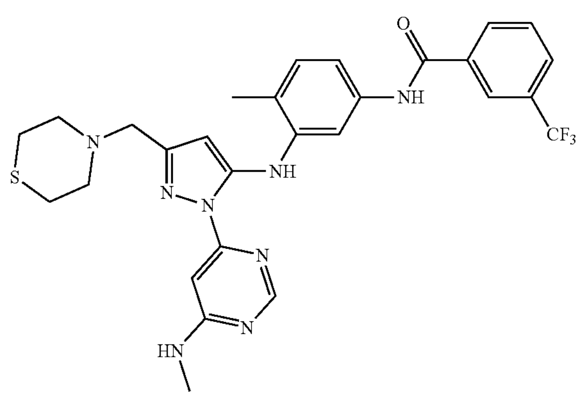 | MS m/z 583.2 (M + 1) |
| 284 | 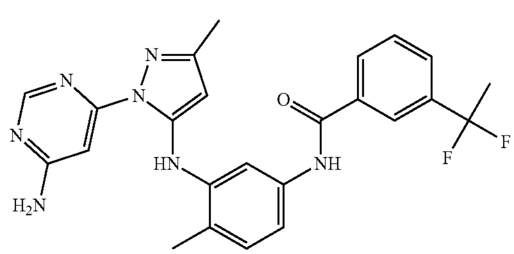 | MS m/z 464.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 285 | 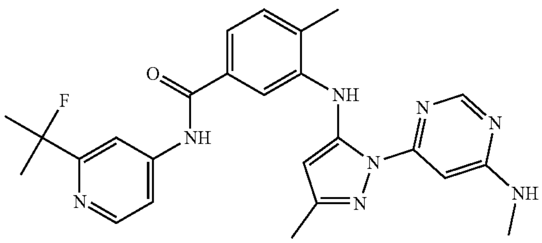 | MS 474.2 m/z (M + 1) |
| 286 | 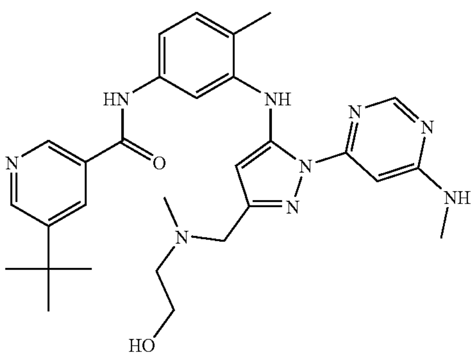 | MS m/z 544.3 (M + 1) |
| 287 | 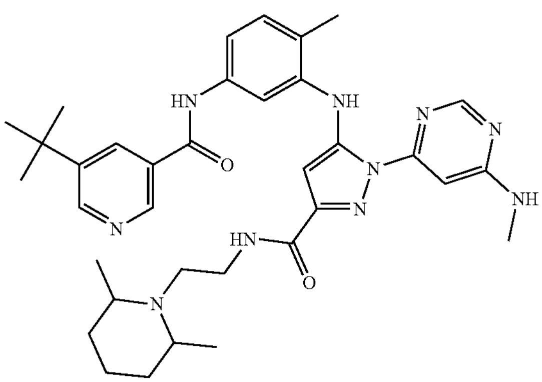 | MS m/z 639.4 (M + 1) |
| 288 | 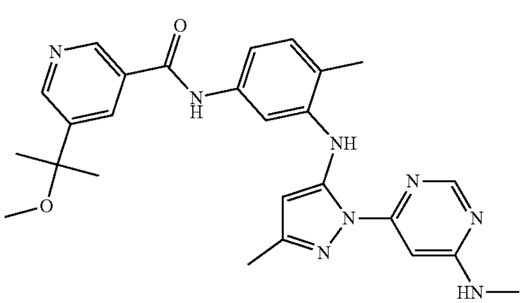 | MS m/z 487.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 289 | 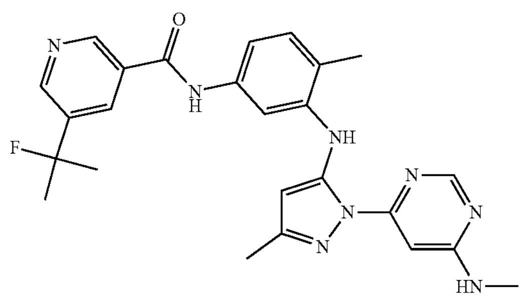 | MS m/z 475.2 (M + 1) |
| 290 | 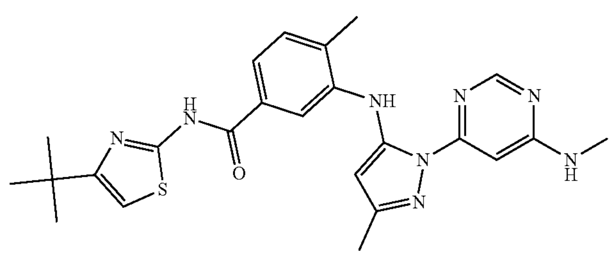 | MS m/z 477.2 (M + 1) |
| 291 | 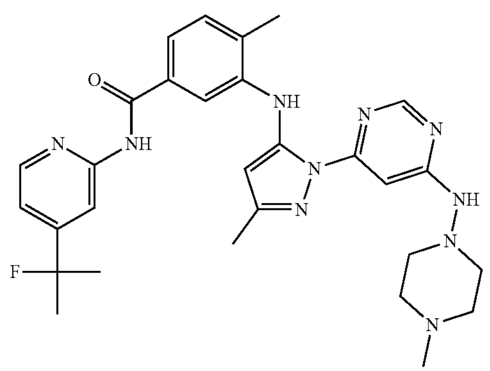 | MS m/z 559.3 (M + 1) |
| 292 | 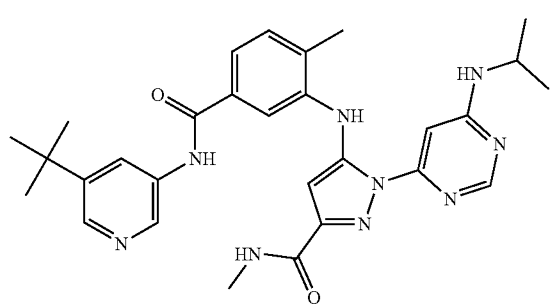 | MS m/z 542.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 293 | 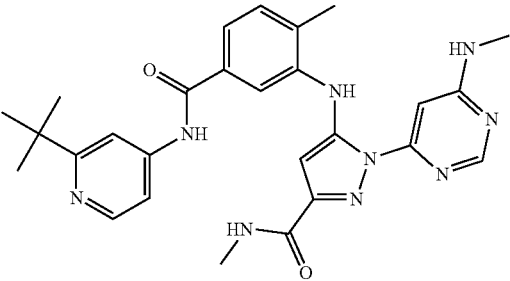 | MS m/z 514.3 (M + 1) |
| 294 | 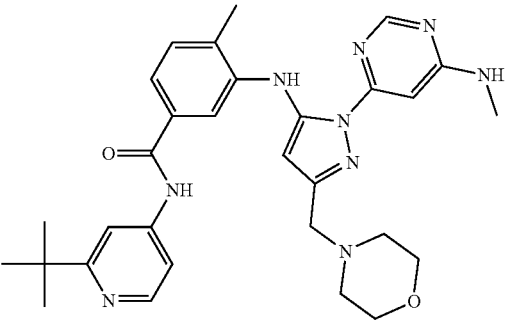 | MS m/z 556.3 (M + 1) |
| 295 | 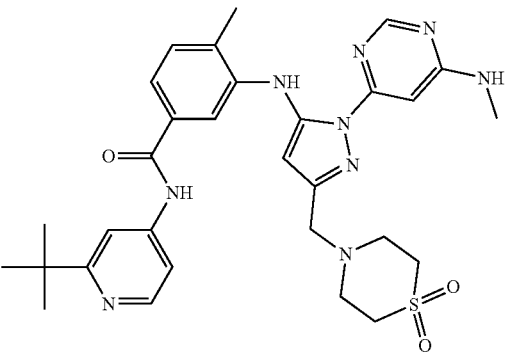 | MS m/z 604.3 (M + 1) |
| 296 | 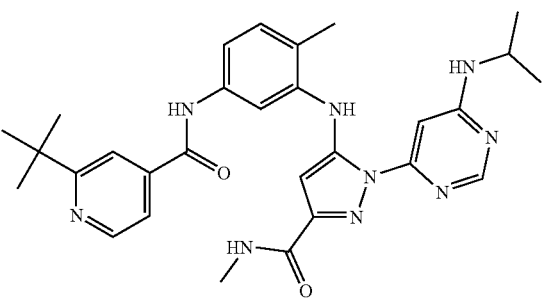 | MS m/z 542.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 297 | 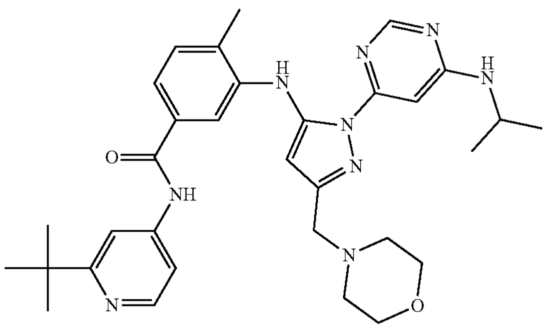 | MS m/z 584.3 (M + 1) |
| 298 | 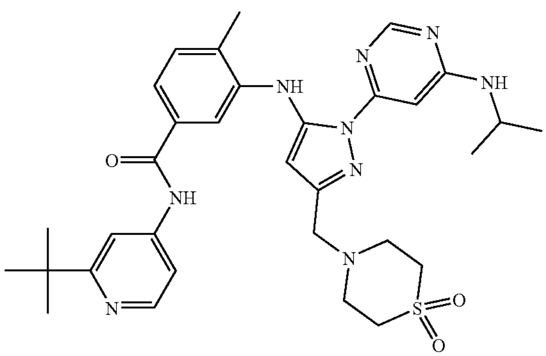 | MS m/z 632.3 (M + 1) |
| 299 | 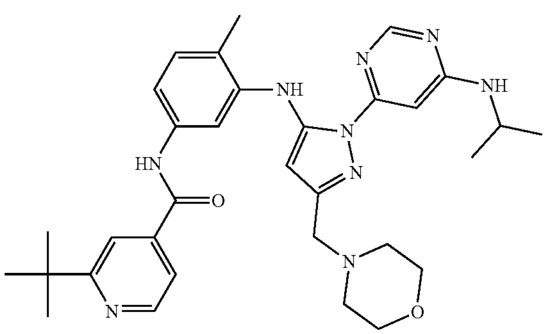 | MS m/z 584.3 (M + 1) |
| 300 | 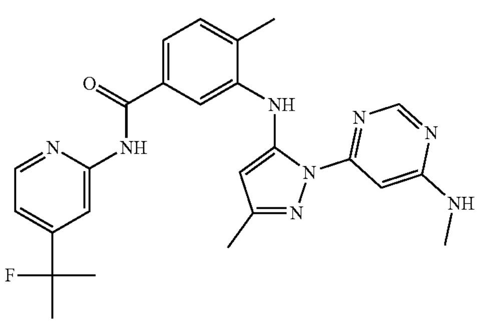 | MS m/z 475.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 301 | 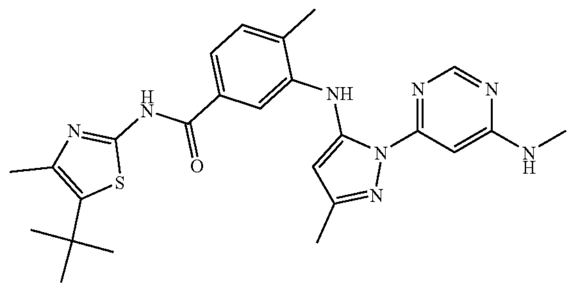 | MS m/z 491.2 (M + 1) |
| 302 | 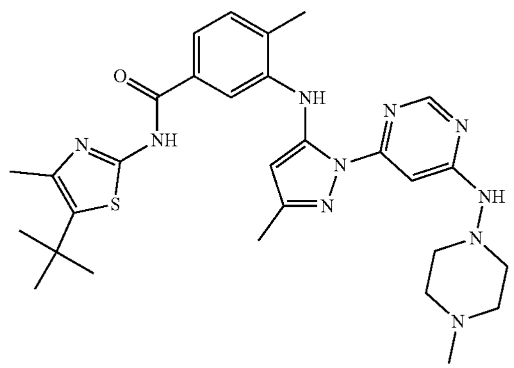 | MS m/z 575.3 (M + 1) |
| 303 | 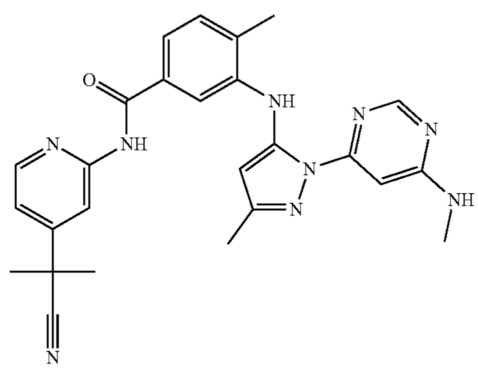 | MS m/z 482.2 (M + 1) |
| 304 | 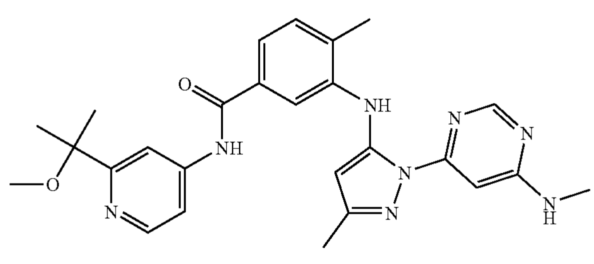 | MS m/z 487.3 (M + 1) |

TABLE 1-continued

| Compound Number | Structure | Physical Data ¹H NMR 400 MHz or 600 MHz (DMSO-$d_6$) and/or MS (m/z) |
| --- | --- | --- |
| 305 | 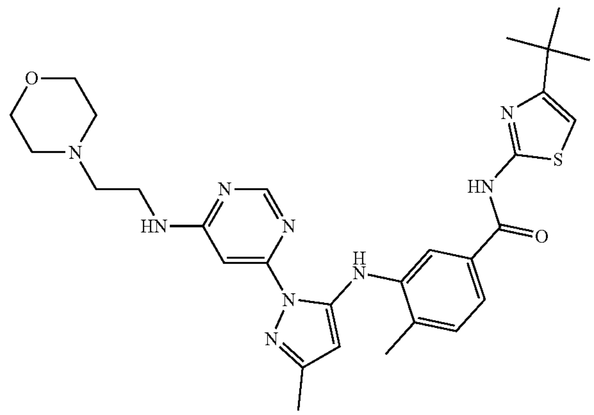 | MS m/z 576.3 (M + 1) |
| 306 | 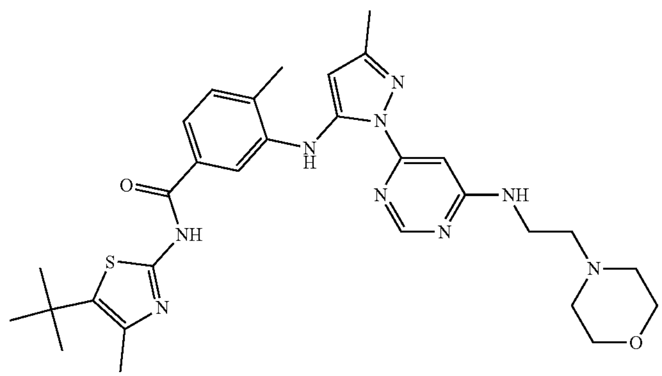 | MS m/z 590.3 (M + 1) |
| 307 | 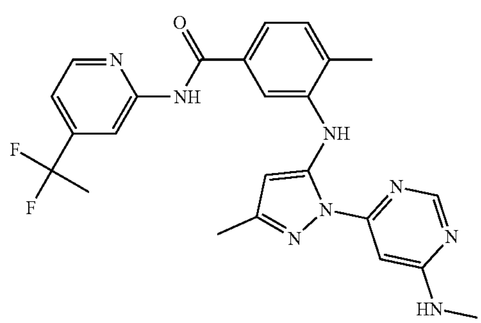 | MS m/z 479.2 (M + 1) |
| 308 | 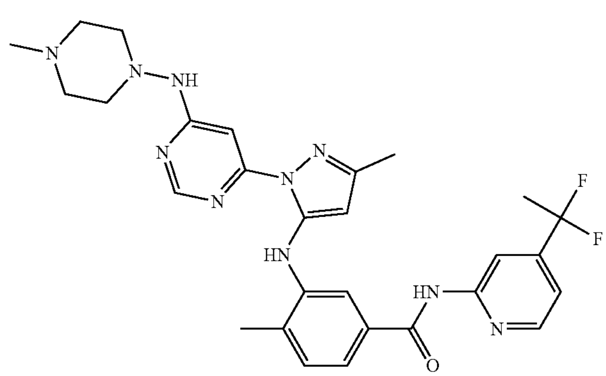 | MS m/z 563.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 309 | 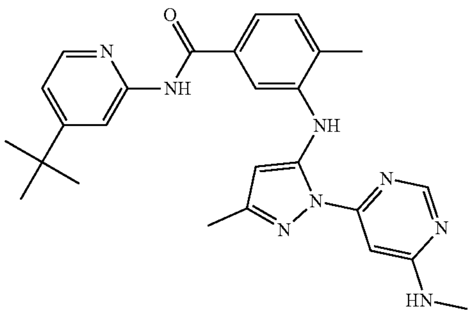 | MS m/z 471.3 (M + 1) |
| 310 | 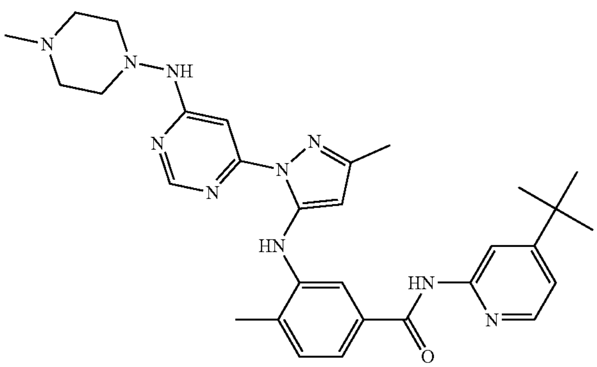 | MS m/z 555.3 (M + 1) |
| 311 | 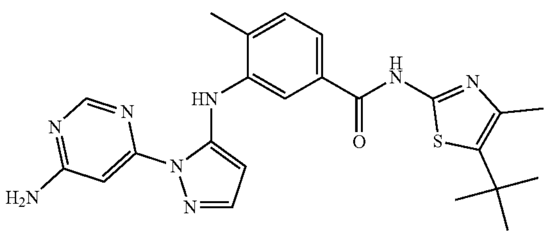 | MS m/z 463.2 (M + 1) |
| 312 | 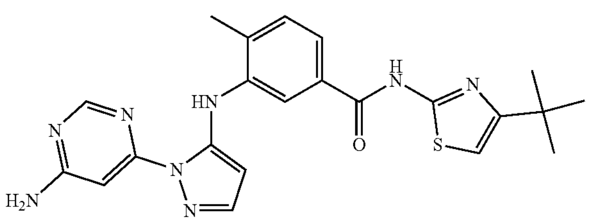 | MS m/z 449.2 (M + 1) |
| 313 | 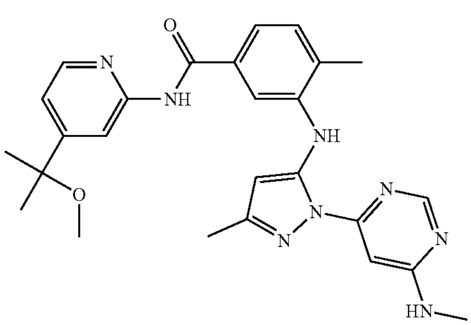 | MS m/z 487.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 314 | 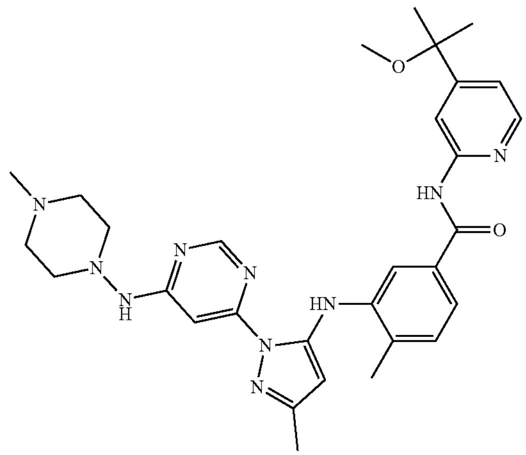 | MS m/z 571.3 (M + 1) |
| 315 | 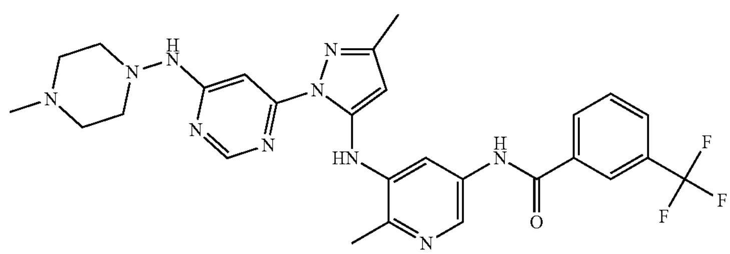 | MS m/z 567.3 (M + 1) |
| 316 | 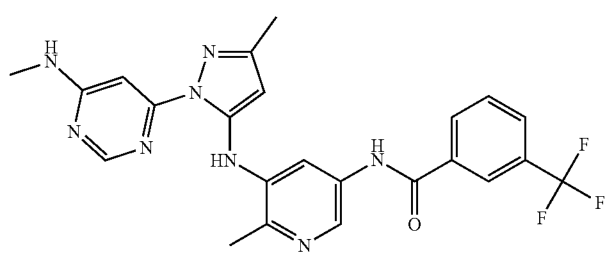 | MS m/z 483.2 (M + 1) |
| 317 | 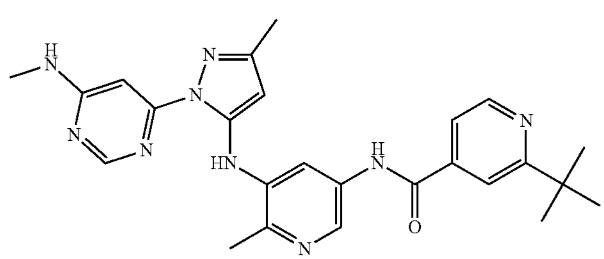 | MS m/z 472.3 (M + 1) |
| 318 | 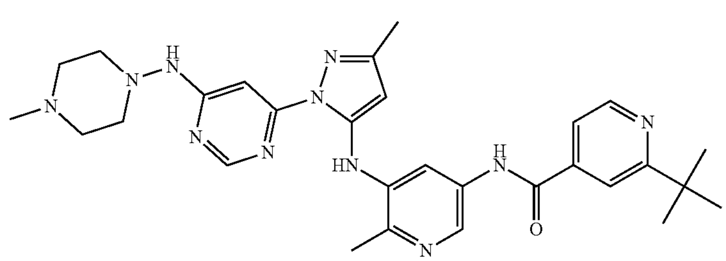 | MS m/z 556.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 319 | 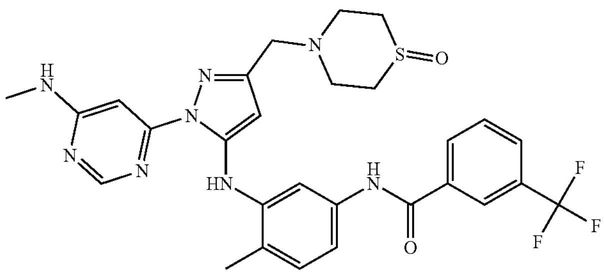 | MS m/z 599.6 (M + 1) |
| 320 | 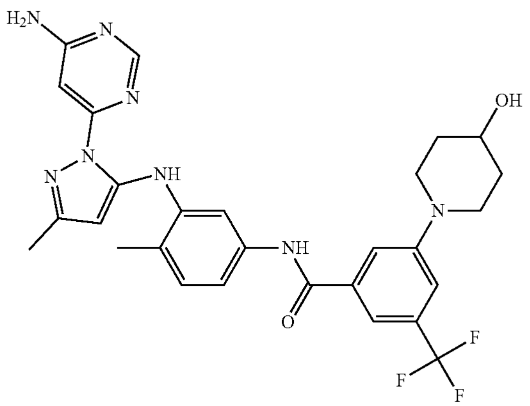 | MS m/z 567.2 (M + 1) |
| 321 | 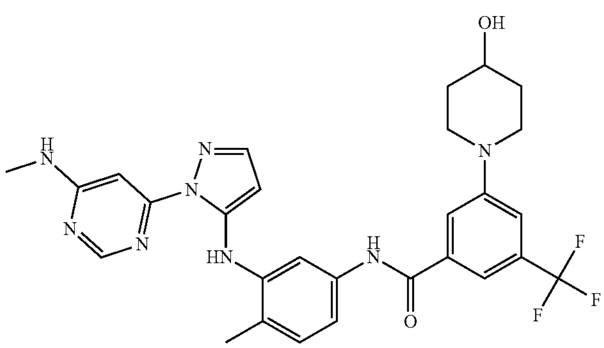 | MS m/z 567.2 (M + 1) |
| 322 | 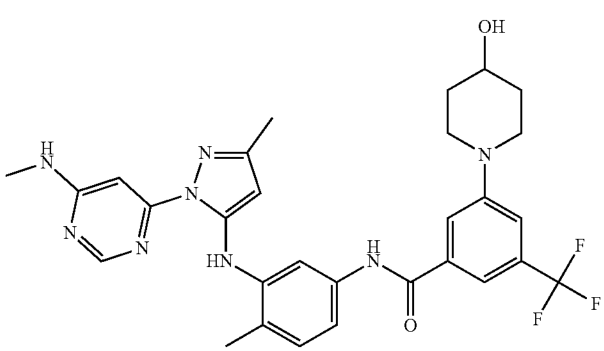 | MS m/z 581.3 (M + 1) |

TABLE 1-continued

| Compound Number | Structure | Physical Data ¹H NMR 400 MHz or 600 MHz (DMSO-d₆) and/or MS (m/z) |
|---|---|---|
| 323 | 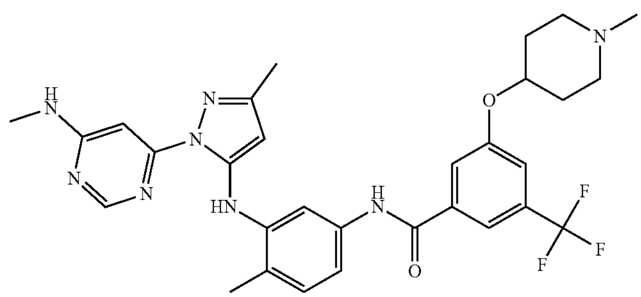 | MS m/z 595.3 (M + 1) |
| 324 | 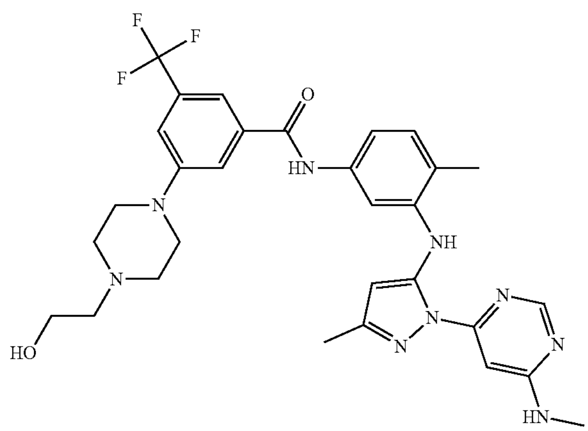 | MS m/z 610.3 (M + 1) |
| 325 | 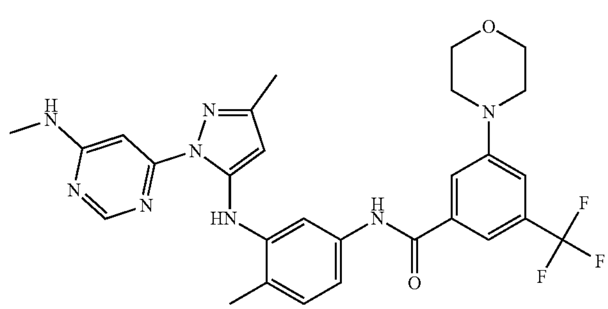 | MS m/z 567.2 (M + 1) |
| 326 | 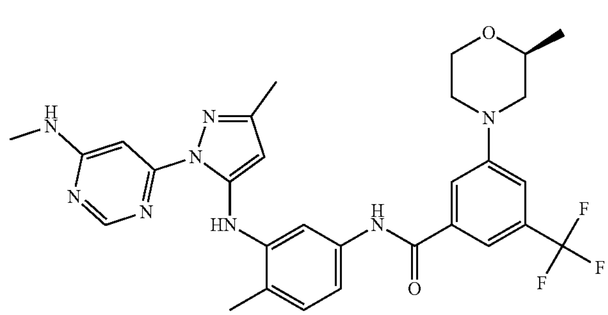 | MS m/z 581.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 327 | 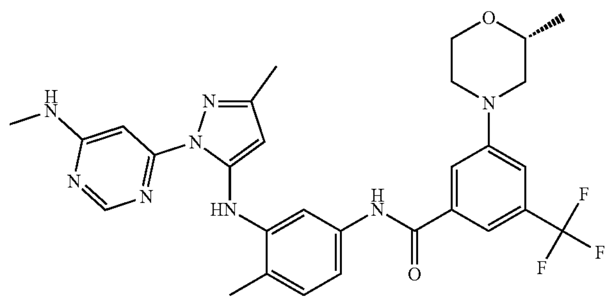 | MS m/z 581.3 (M + 1) |
| 328 | 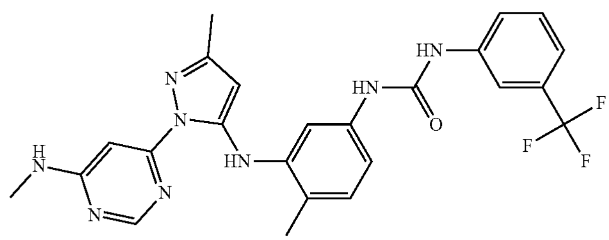 | MS m/z 497.2 (M + 1) |
| 329 | 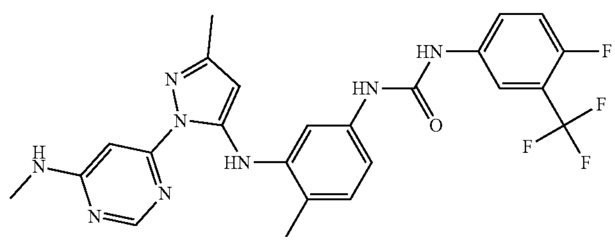 | MS m/z 515.2 (M + 1) |
| 330 | 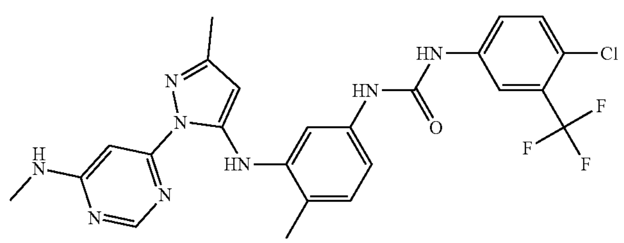 | MS m/z 531.2 (M + 1) |
| 331 | 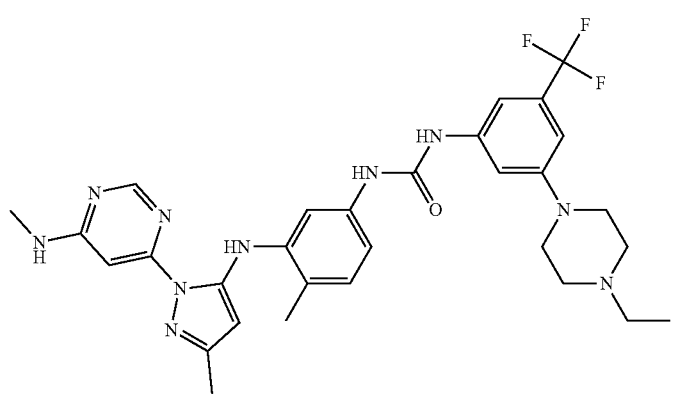 | MS m/z 609.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 332 | 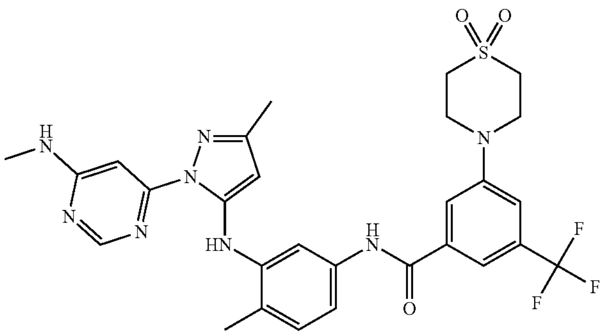 | MS m/z 615.2 (M + 1) |
| 333 | 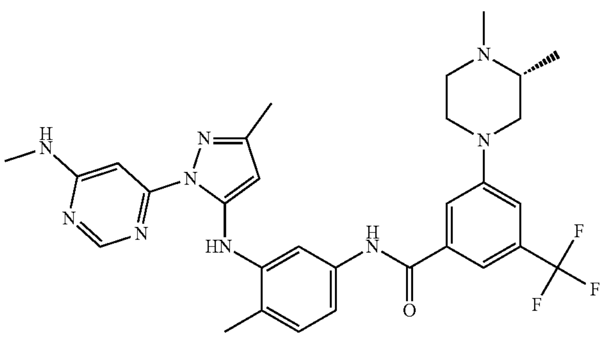 | MS m/z 594.3 (M + 1) |
| 334 | 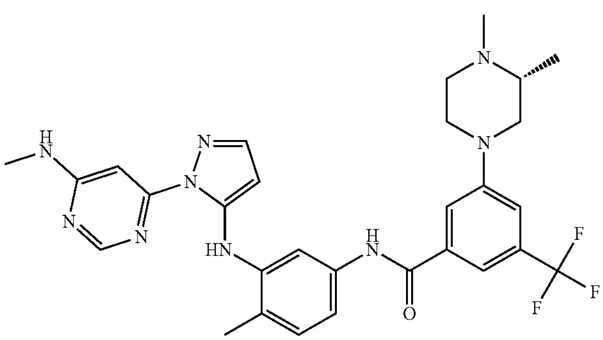 | MS m/z 580.3 (M + 1) |
| 335 | 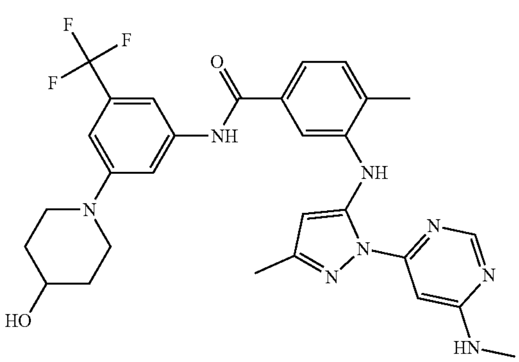 | MS m/z 581.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 336 | 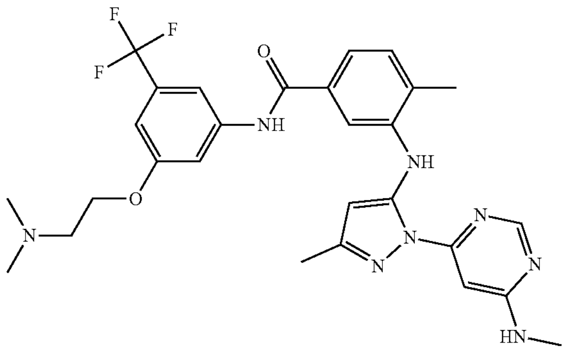 | MS m/z 569.3 (M + 1) |
| 337 | 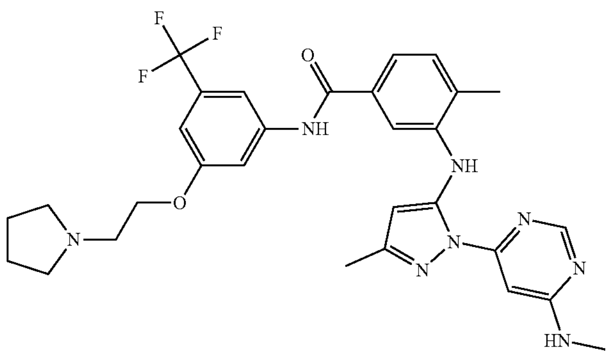 | MS m/z 595.3 (M + 1) |
| 338 | 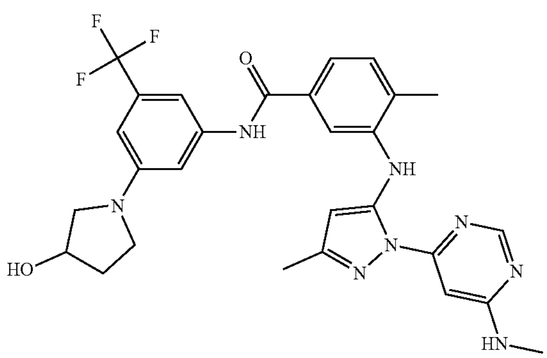 | MS m/z 567.2 (M + 1) |
| 339 | 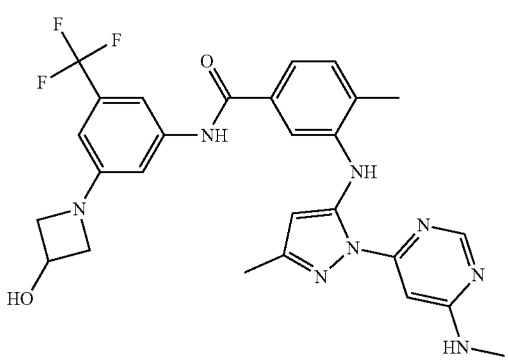 | MS m/z 553.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 340 | 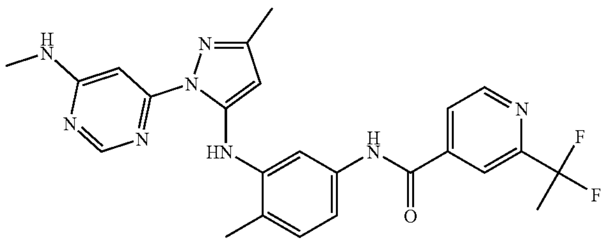 | MS m/z 479.2 (M + 1) |
| 341 | 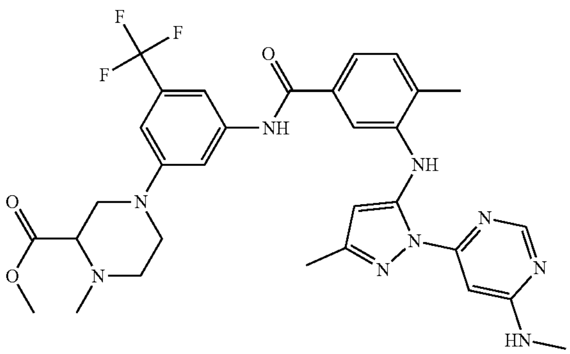 | MS m/z 638.3 (M + 1) |
| 342 | 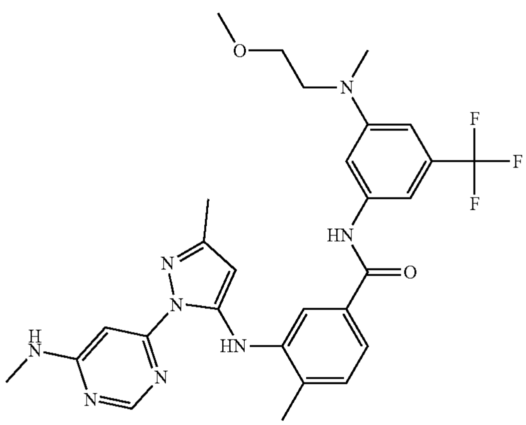 | MS m/z 569.3 (M + 1) |
| 343 | 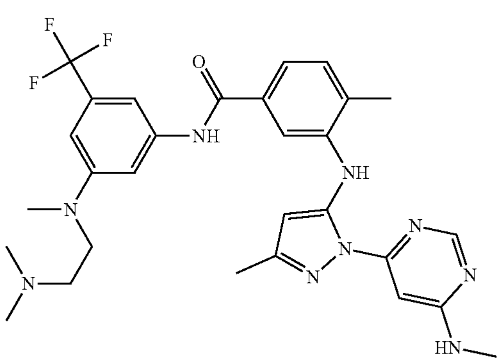 | MS m/z 582.3 (M + 1) |

TABLE 1-continued

| Compound Number | Structure | Physical Data ¹H NMR 400 MHz or 600 MHz (DMSO-d₆) and/or MS (m/z) |
|---|---|---|
| 344 | 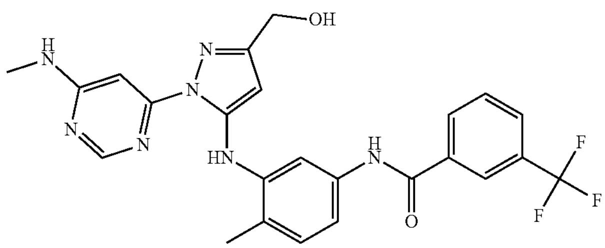 | MS m/z 494.2 (M + 1) |
| 345 | 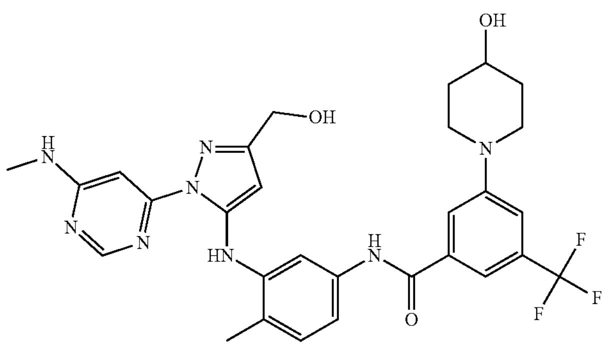 | MS m/z 597.3 (M + 1) |
| 346 | 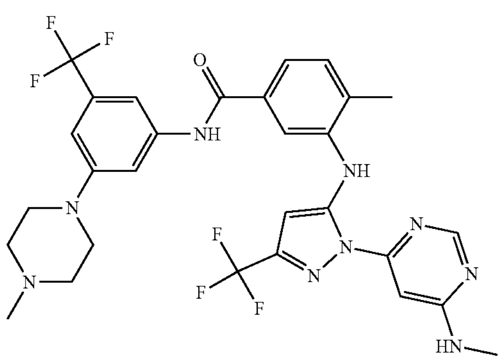 | MS m/z 634.2 (M + 1) |
| 347 | 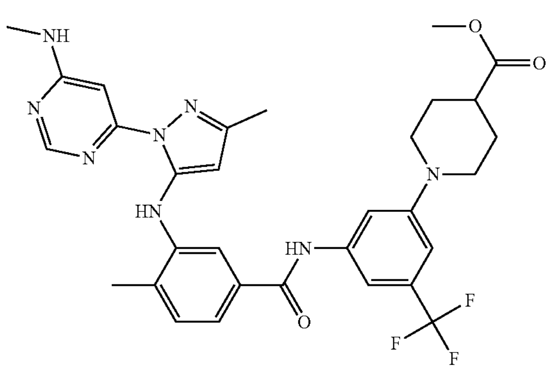 | MS m/z 623.3 (M + 1) |

TABLE 1-continued
| Compound Number | Structure | Physical Data ¹H NMR 400 MHz or 600 MHz (DMSO-$d_6$) and/or MS (m/z) |
|---|---|---|
| 348 | 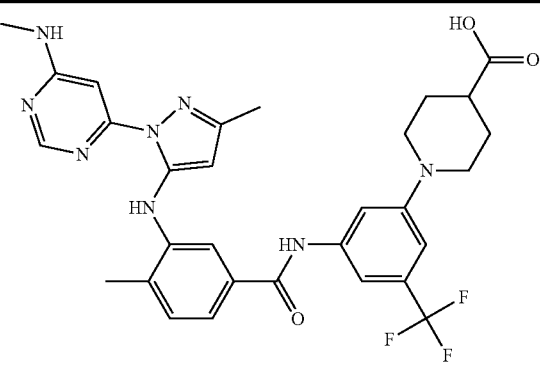 | MS m/z 609.3 (M + 1) |
| 349 | 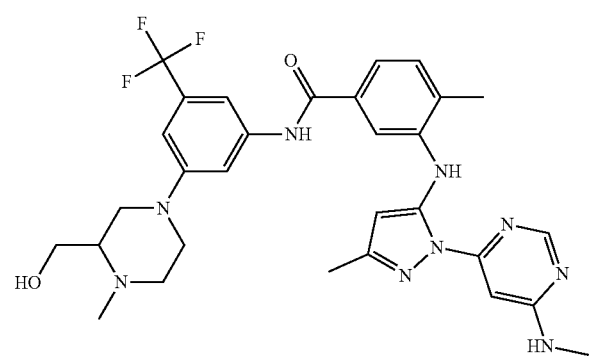 | MS m/z 610.3 (M + 1) |
| 350 | 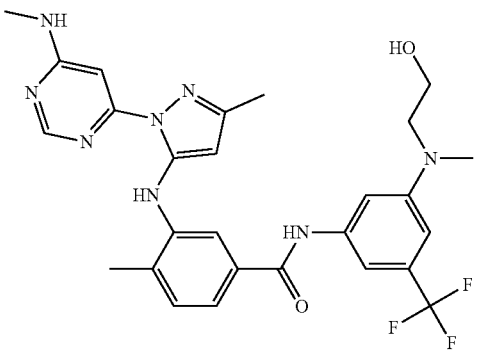 | MS m/z 555.2 (M + 1) |
| 351 | 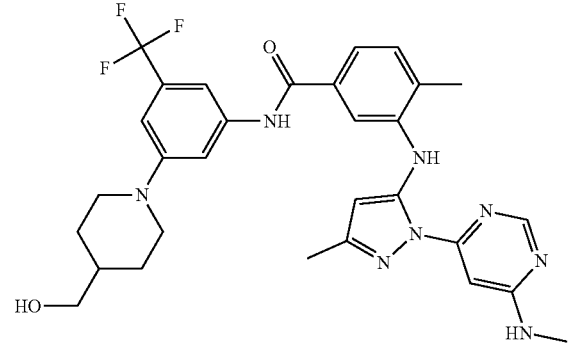 | MS m/z 595.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 352 | 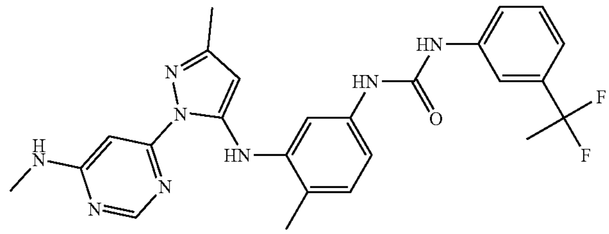 | MS m/z 493.2 (M + 1) |
| 353 | 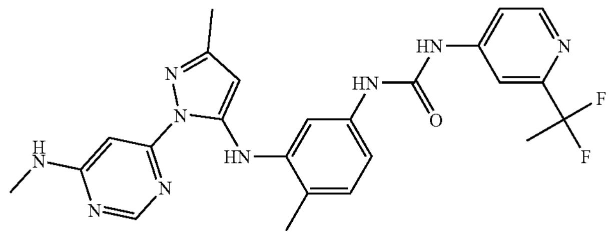 | MS m/z 494.2 (M + 1) |
| 354 | 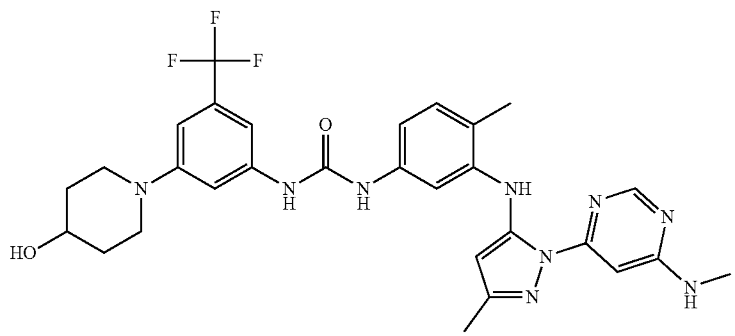 | MS m/z 596.3 (M + 1) |
| 355 | 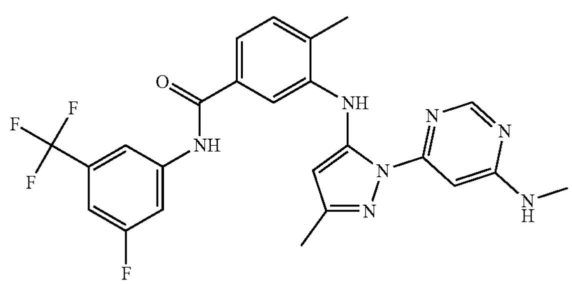 | MS m/z 500.2 (M + 1) |
| 356 | 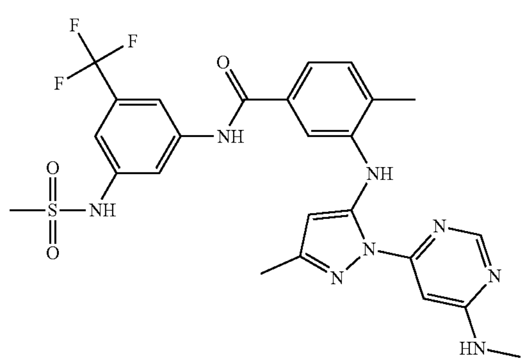 | MS m/z 575.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 357 | 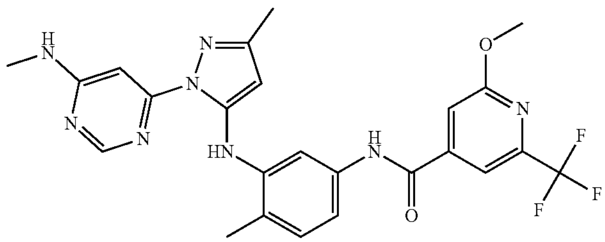 | MS m/z 513.2 (M + 1) |
| 358 | 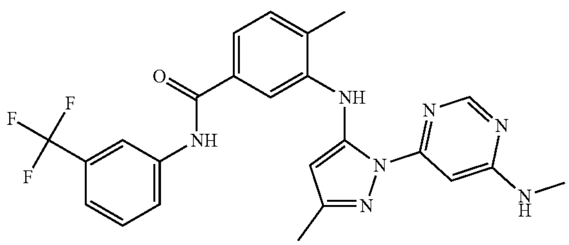 | MS m/z 482.2 (M + 1) |
| 359 | 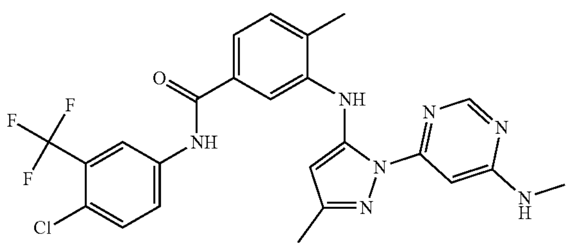 | MS m/z 516.1 (M + 1) |
| 360 | 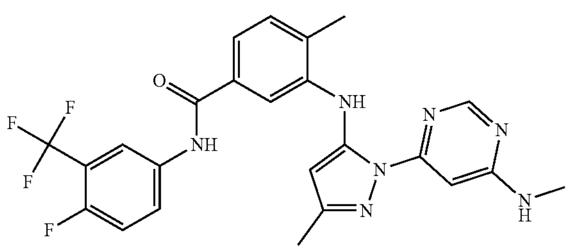 | MS m/z 500.2 (M + 1) |
| 361 | 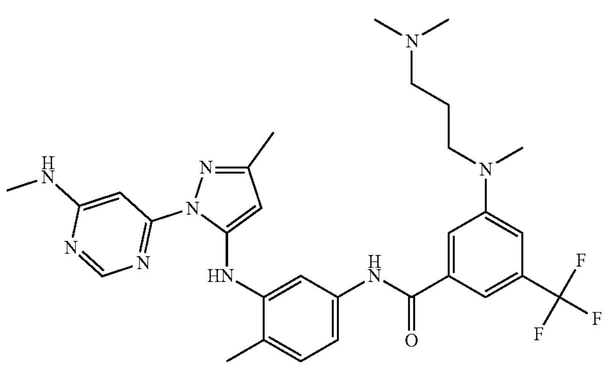 | MS m/z 596.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 362 | 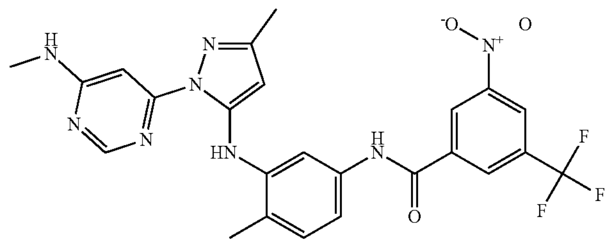 | MS m/z 527.2 (M + 1) |
| 363 | 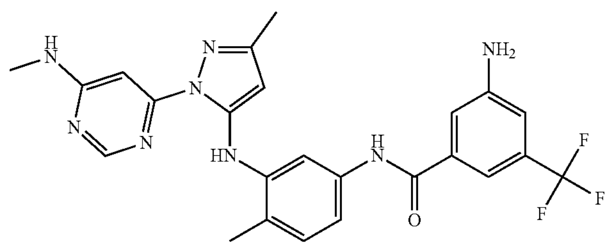 | MS m/z 497.2 (M + 1) |
| 364 | 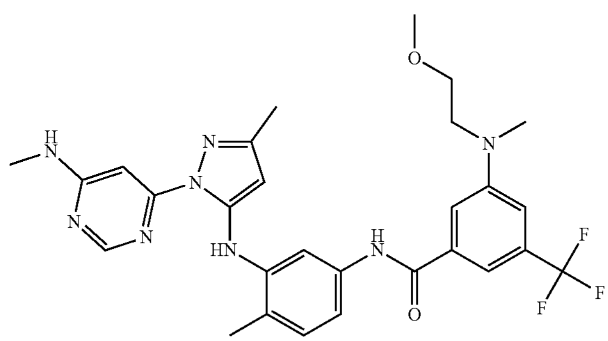 | MS m/z 569.3 (M + 1) |
| 365 | 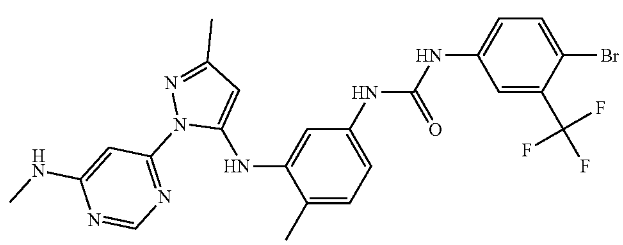 | MS m/z 575.1 (M + 1) |
| 366 | 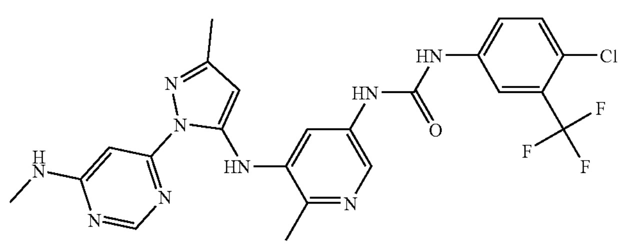 | MS m/z 532.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 367 | 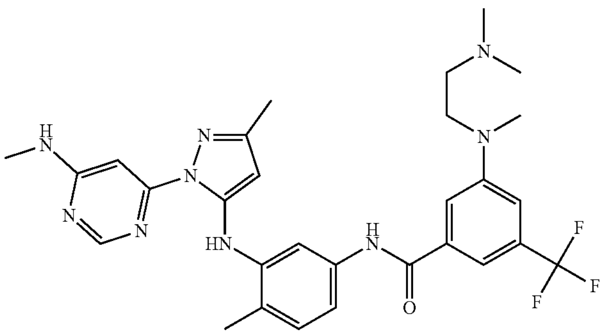 | MS m/z 582.3 (M + 1) |
| 368 | 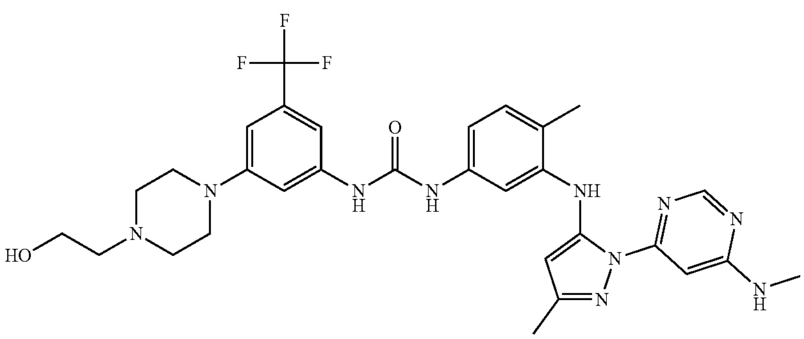 | MS m/z 625.3 (M + 1) |
| 369 | 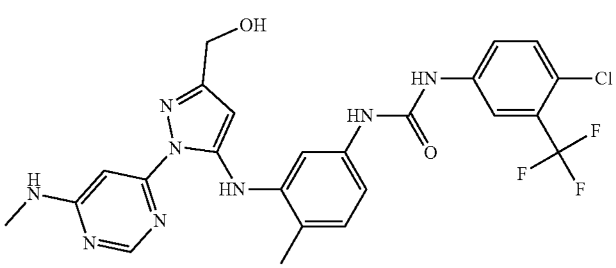 | MS m/z 547.2 (M + 1) |
| 370 | 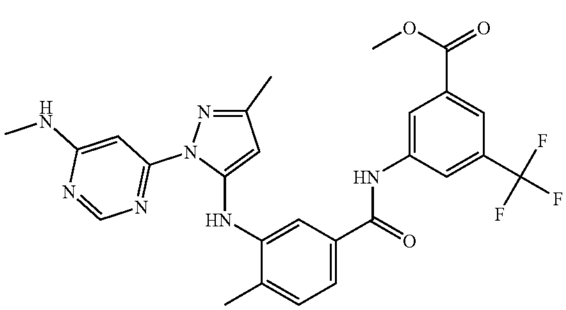 | MS m/z 540.2 (M + 1) |

TABLE 1-continued
| Compound Number | Structure | Physical Data ¹H NMR 400 MHz or 600 MHz (DMSO-$d_6$) and/or MS (m/z) |
|---|---|---|
| 371 | 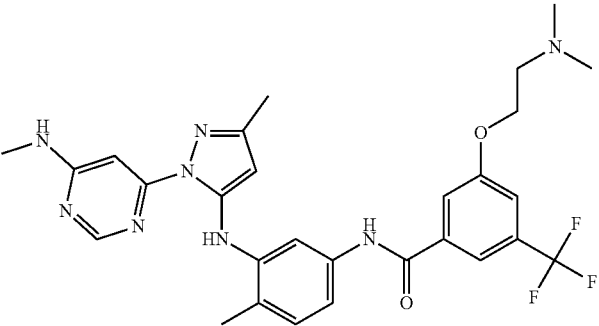 | MS m/z 569.3 (M + 1) |
| 372 | 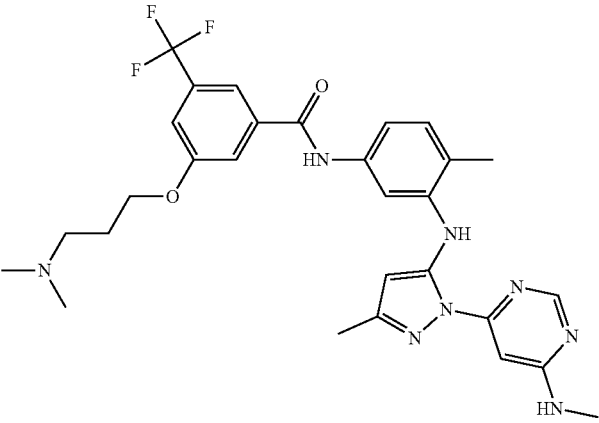 | MS m/z 583.3 (M + 1) |
| 373 | 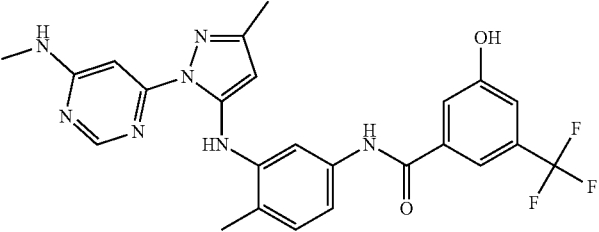 | MS m/z 498.2 (M + 1) |
| 374 | 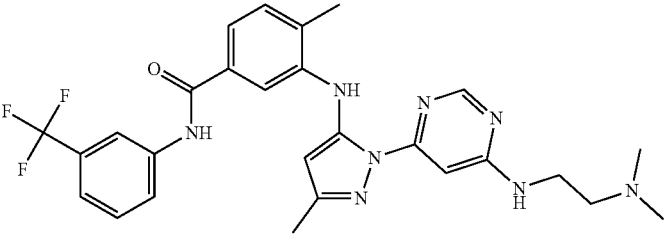 | MS m/z 539.2 (M + 1) |

TABLE 1-continued
| Compound Number | Structure | Physical Data ¹H NMR 400 MHz or 600 MHz (DMSO-$d_6$) and/or MS (m/z) |
|---|---|---|
| 375 | 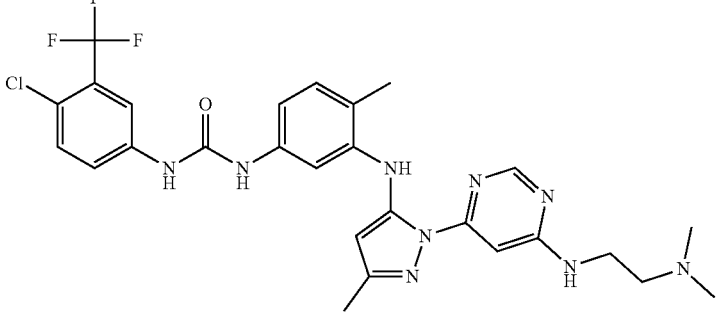 | MS m/z 588.2 (M + 1) |
| 376 | 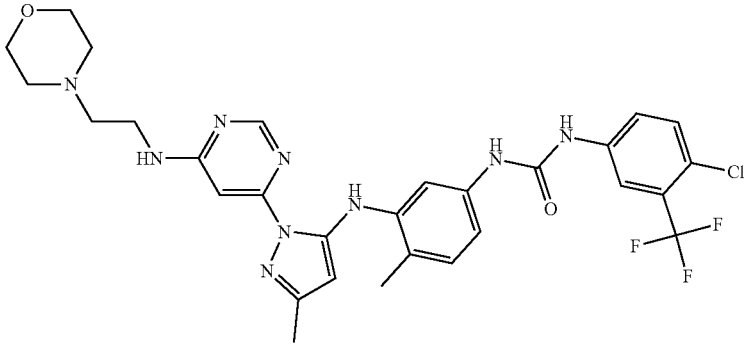 | MS m/z 630.22 (M + 1) |
| 377 | 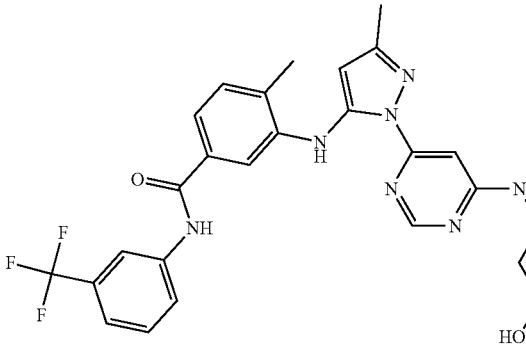 | MS m/z 526.2 (M + 1) |
| 378 | 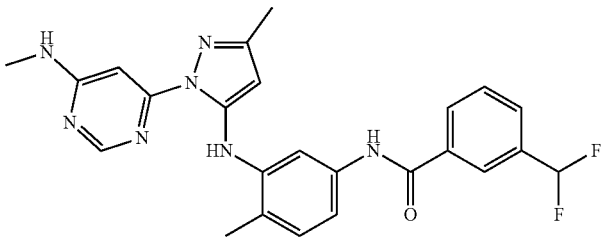 | MS m/z 464.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 379 | 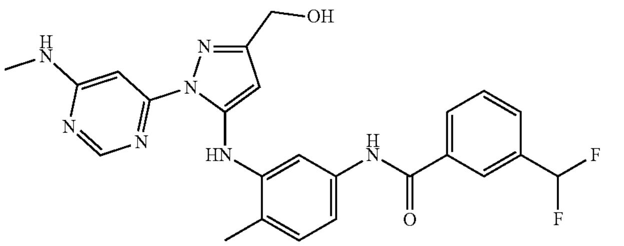 | MS m/z 480.2 (M + 1) |
| 380 | 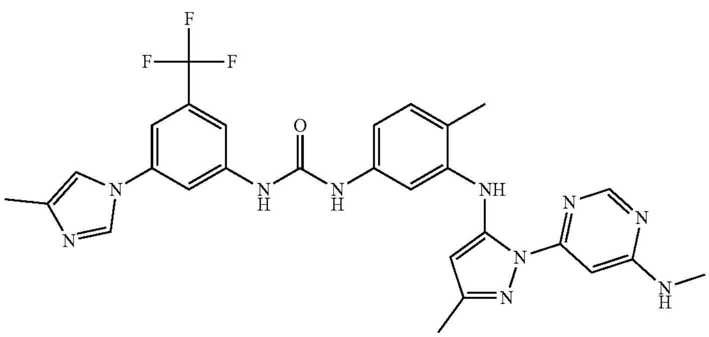 | MS m/z 577.2 (M + 1) |
| 381 | 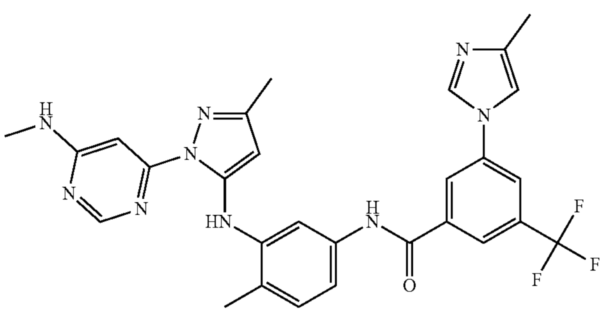 | MS m/z 562.2 (M + 1) |
| 382 | 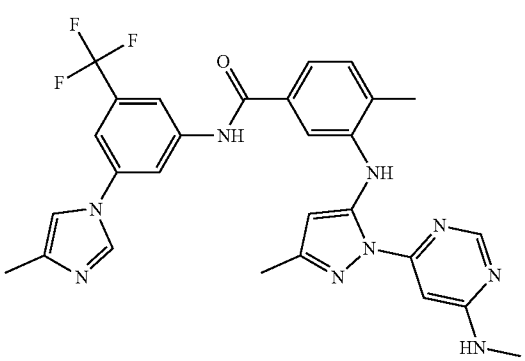 | MS m/z 562.2 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 383 | 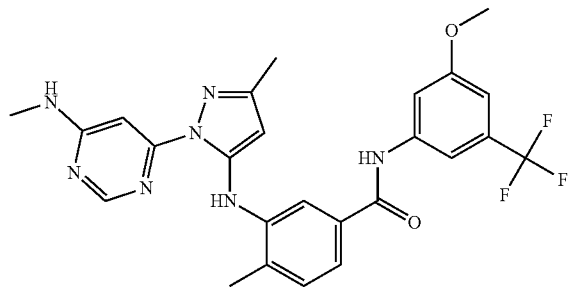 | MS m/z 512.2 (M + 1) |
| 384 | 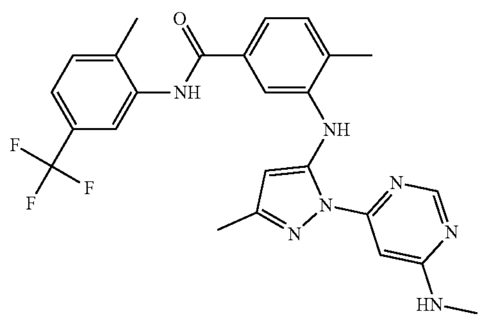 | MS m/z 496.2 (M + 1) |
| 385 | 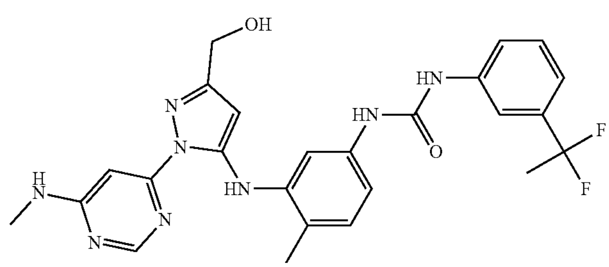 | MS m/z 509.2 (M + 1) |
| 386 | 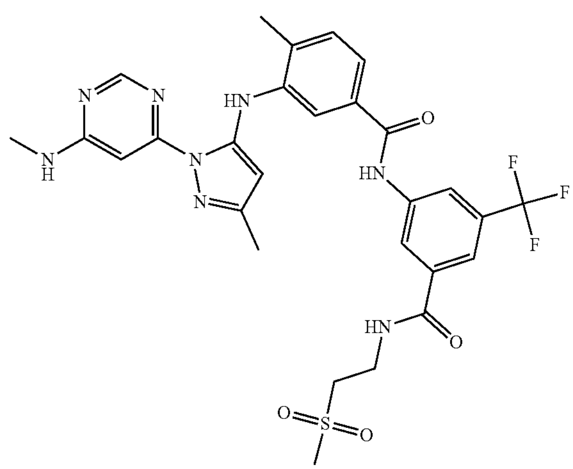 | MS m/z 631.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 387 | 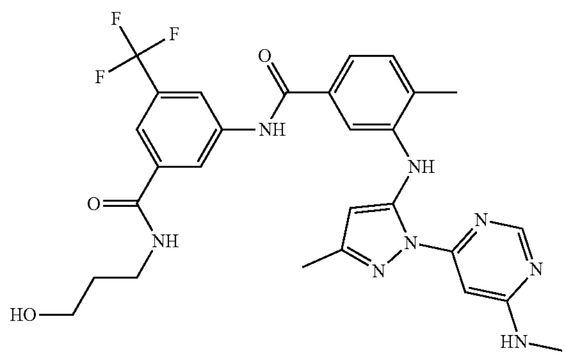 | MS m/z 583.2 (M + 1) |
| 388 | 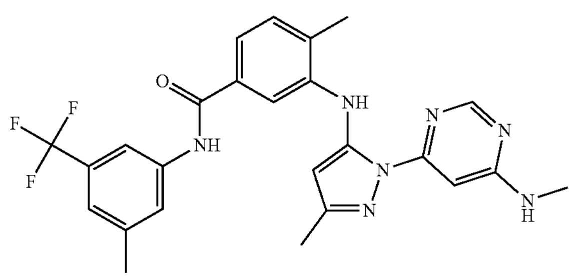 | MS m/z 496.2 (M + 1) |
| 389 | 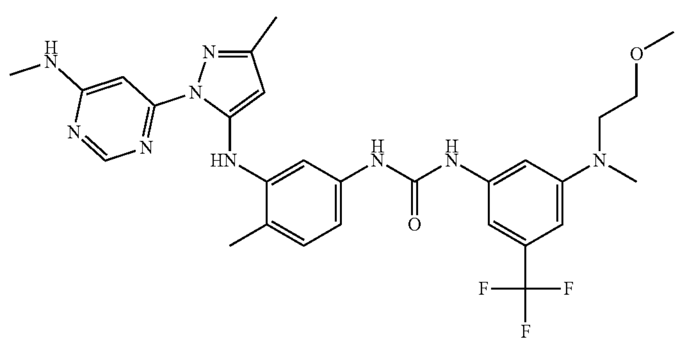 | MS m/z 584.3 (M + 1) |
| 390 | 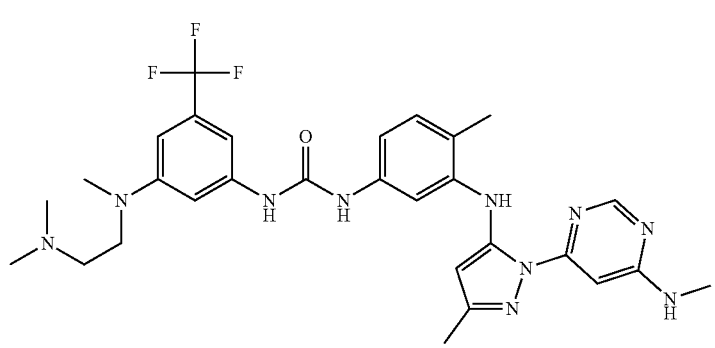 | MS m/z 597.3 (M + 1) |

TABLE 1-continued

| Compound Number | Structure | Physical Data ¹H NMR 400 MHz or 600 MHz (DMSO-d₆) and/or MS (m/z) |
|---|---|---|
| 391 | 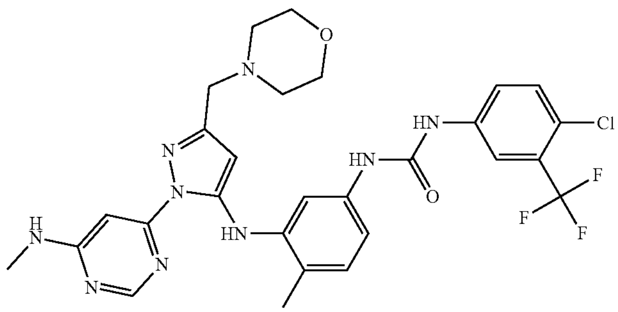 | MS m/z 616.2 (M + 1) |
| 392 | 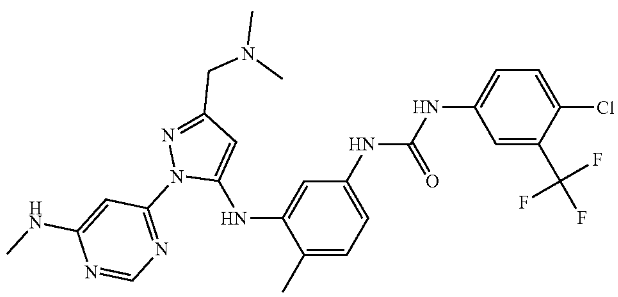 | MS m/z 574.2 (M + 1) |
| 393 | 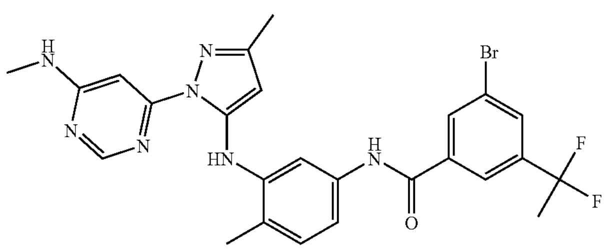 | MS m/z 556.1 (M + 1) |
| 394 | 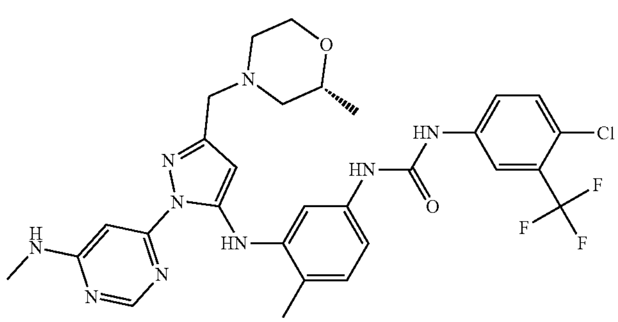 | MS m/z 630.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 395 | 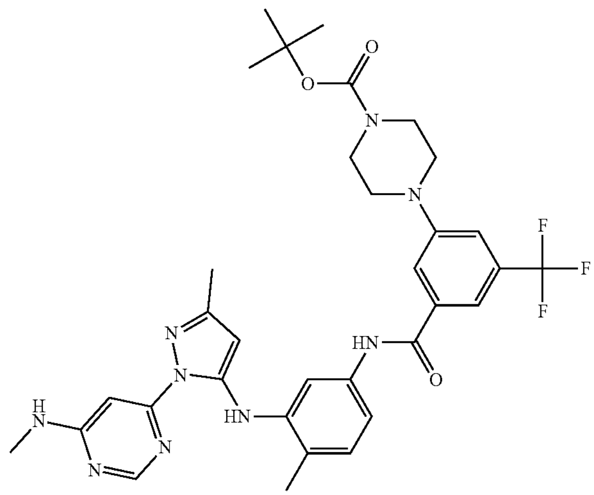 | MS m/z 666.3 (M + 1) |
| 396 | 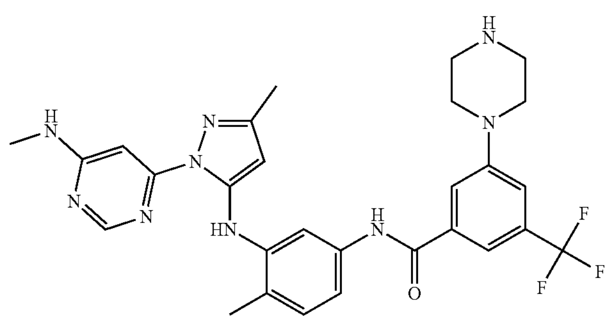 | MS m/z 566.3 (M + 1) |
| 397 | 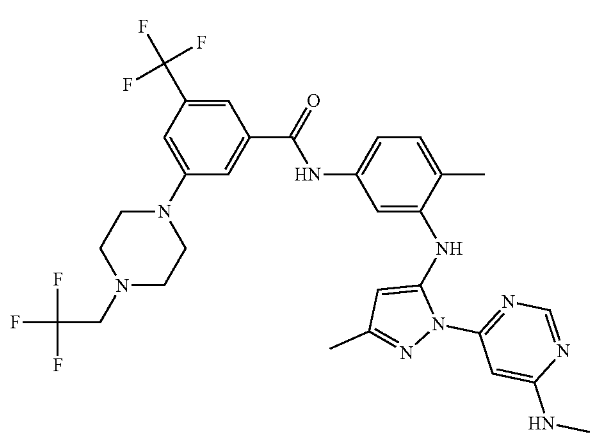 | MS m/z 648.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 398 | 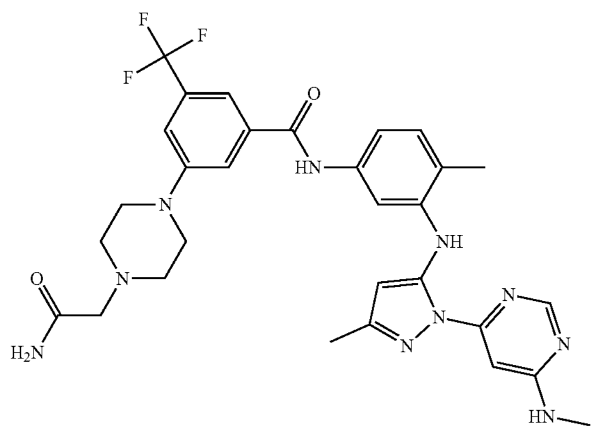 | MS m/z 623.3 (M + 1) |
| 399 | 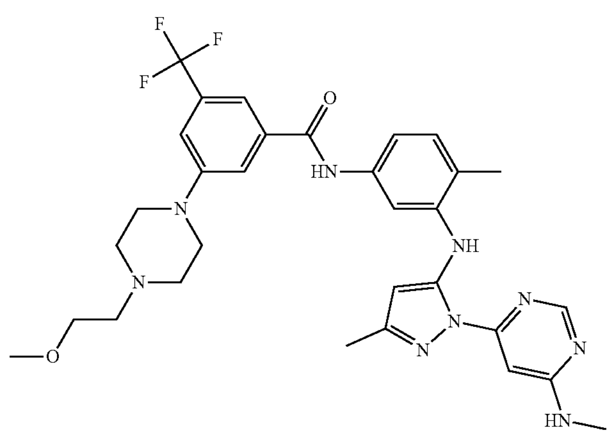 | MS m/z 624.3 (M + 1) |
| 400 | 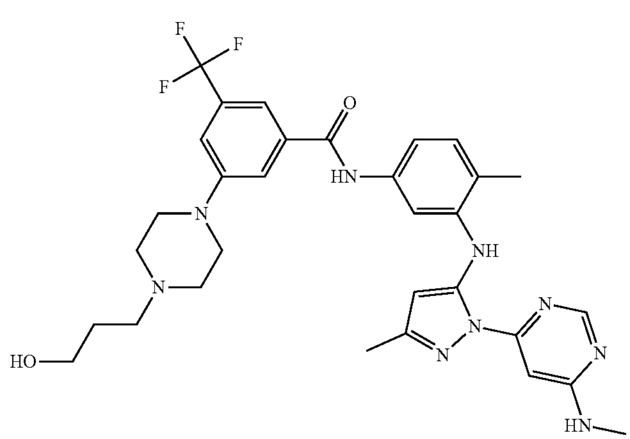 | MS m/z 624.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 401 | 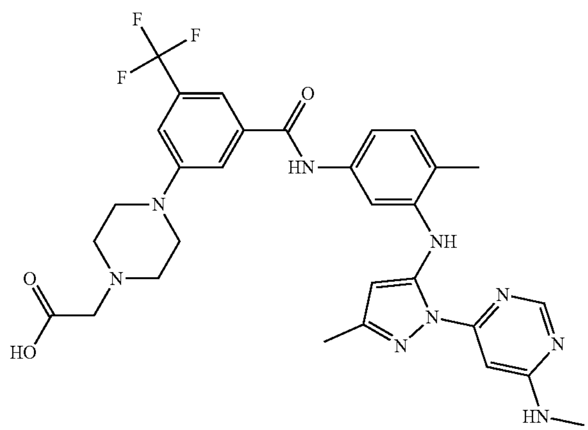 | MS m/z 624.3 (M + 1) |
| 402 | 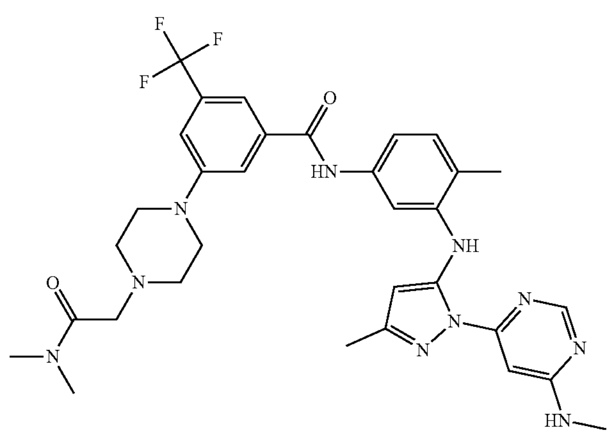 | MS m/z 651.3 (M + 1) |
| 403 | 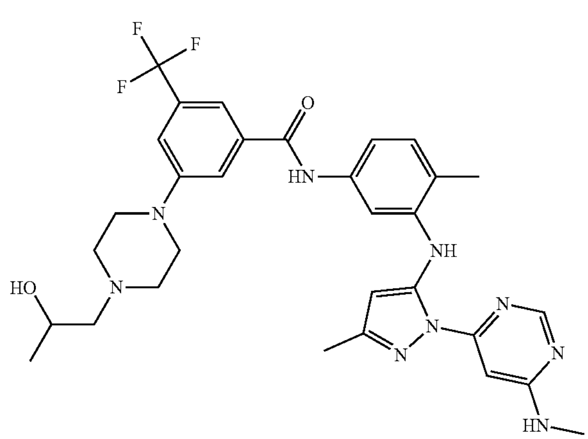 | MS m/z 624.3 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 404 | 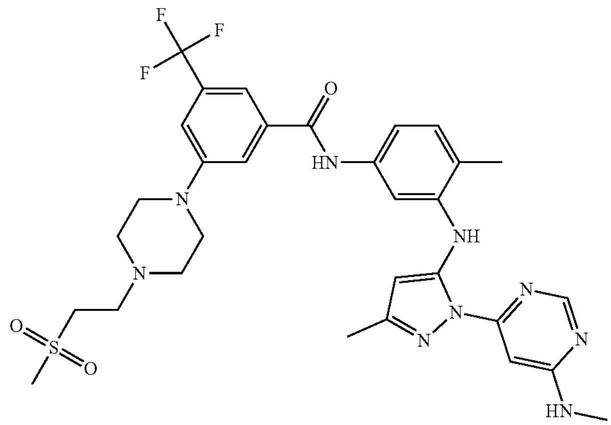 | MS m/z 672.3 (M + 1) |
| 405 | 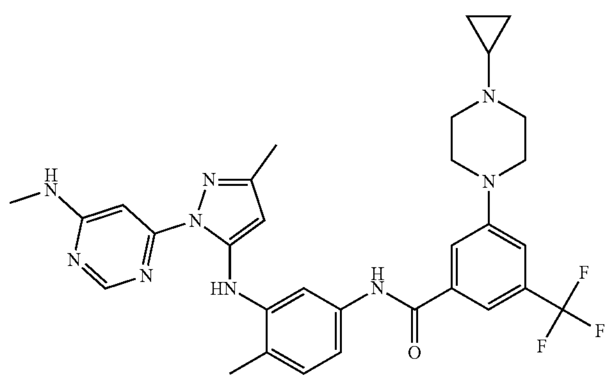 | MS m/z 606.3 (M + 1) |
| 406 | 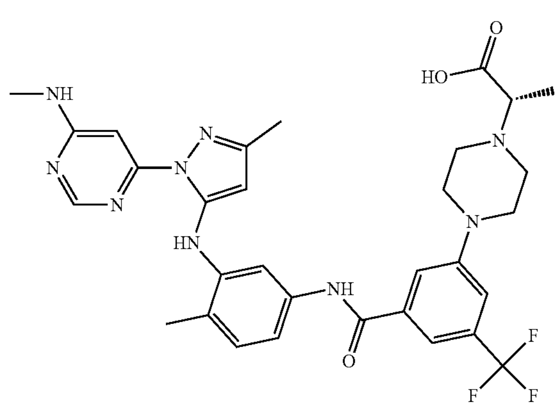 | MS m/z 638.3 (M + 1) |

TABLE 1-continued

| Compound Number | Structure | Physical Data <br> ¹H NMR 400 MHz or 600 MHz (DMSO-d₆) and/or MS (m/z) |
|---|---|---|
| 407 | 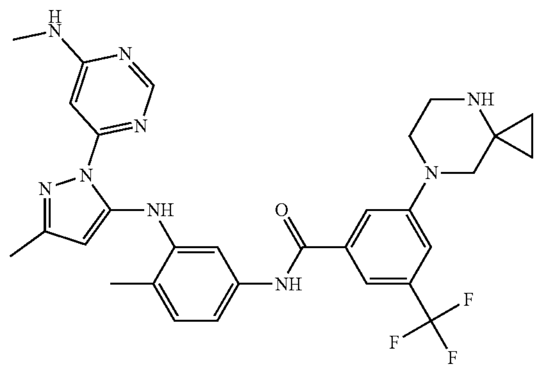 | MS m/z 592.3 (M + 1) |
| 408 | 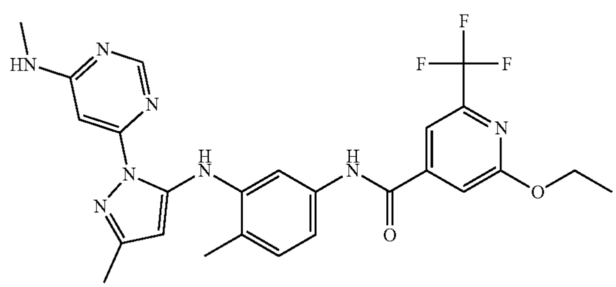 | MS m/z 527.2 (M + 1) |
| 409 | 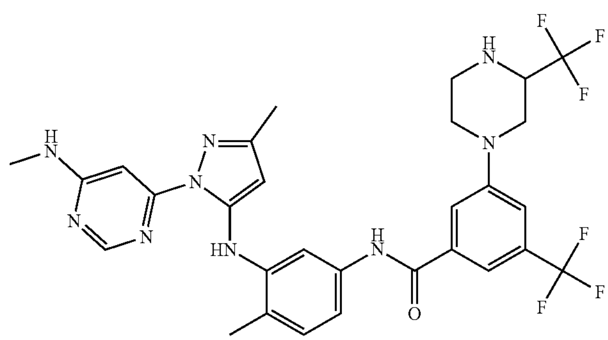 | MS m/z 634.2 (M + 1) |
| 410 | 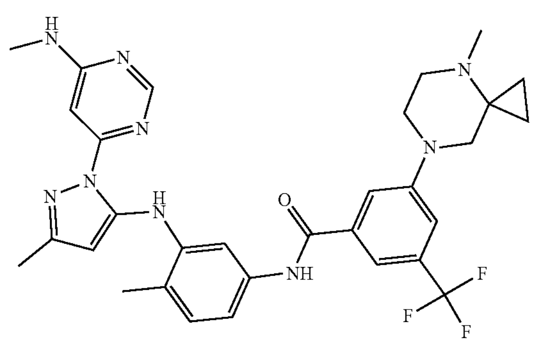 | MS m/z 606.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 411 | 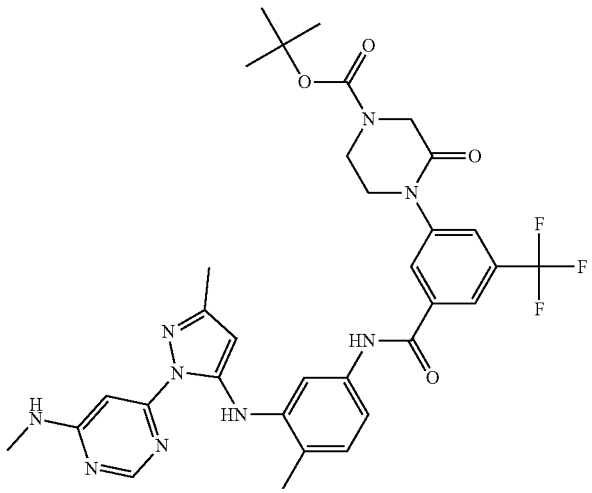 | MS m/z 680.3 (M + 1) |
| 412 | 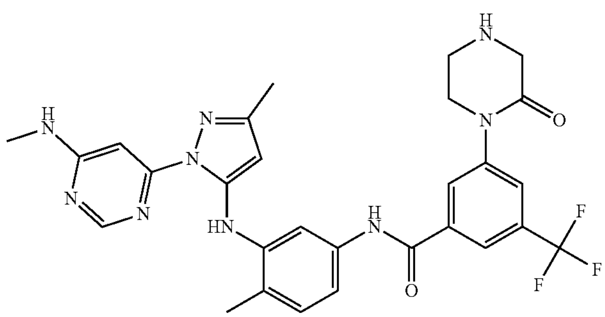 | MS m/z 580.2 (M + 1) |
| 413 | 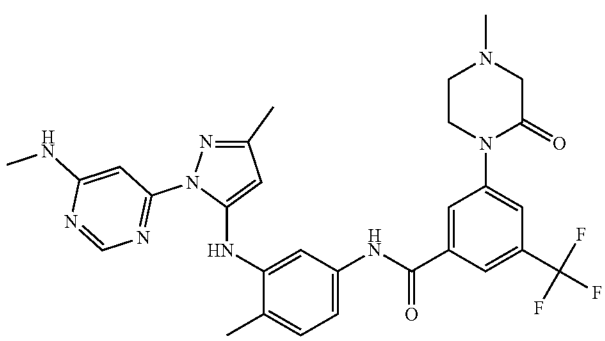 | MS m/z 594.3 (M + 1) |
| 414 | 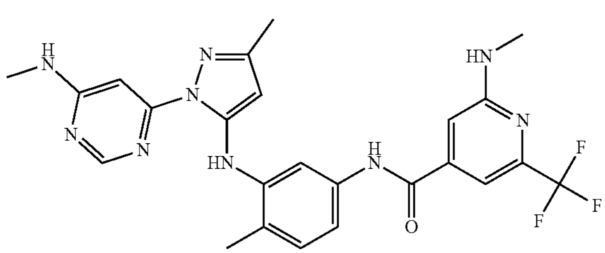 | MS m/z 512.2 (M + 1) |

TABLE 1-continued

| Compound Number | Structure | Physical Data ¹H NMR 400 MHz or 600 MHz (DMSO-d₆) and/or MS (m/z) |
|---|---|---|
| 415 | 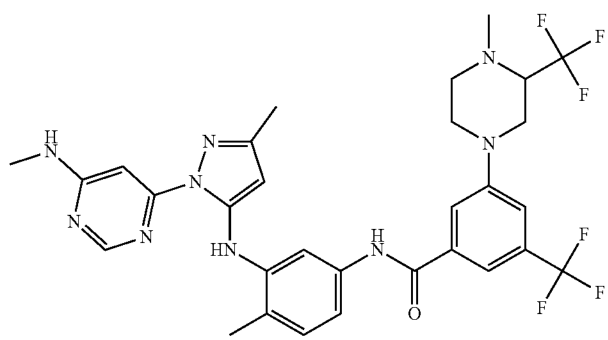 | MS m/z 648.3 (M + 1) |
| 416 | 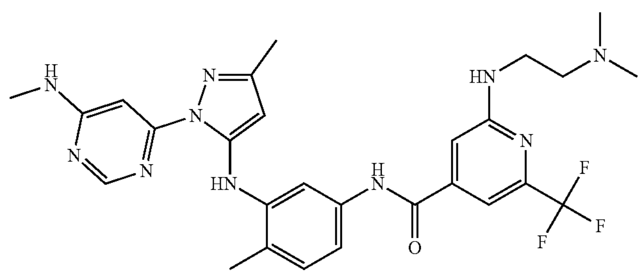 | MS m/z 569.3 (M + 1) |
| 417 | 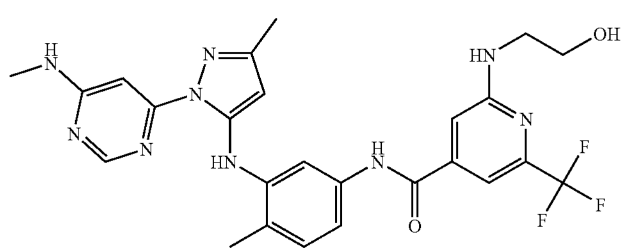 | MS m/z 542.2 (M + 1) |
| 418 | 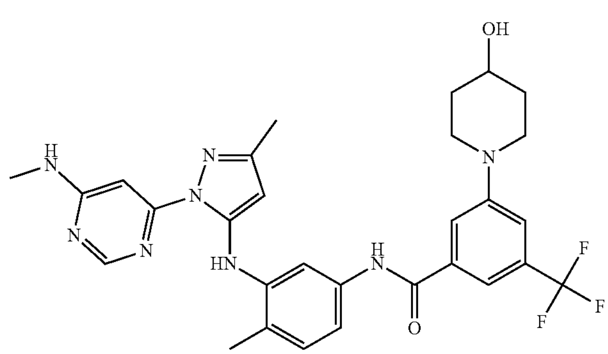 | MS m/z 581.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 419 | 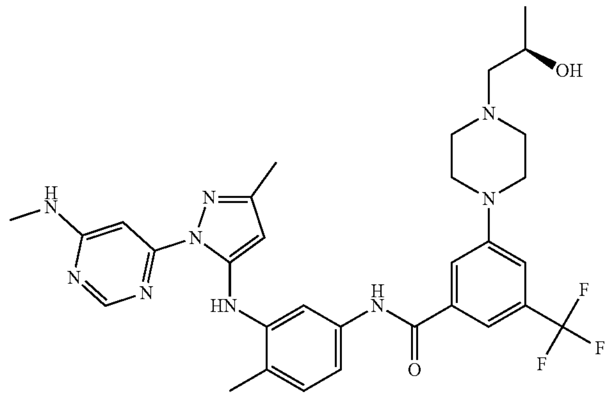 | MS m/z 624.3 (M + 1) |
| 420 | 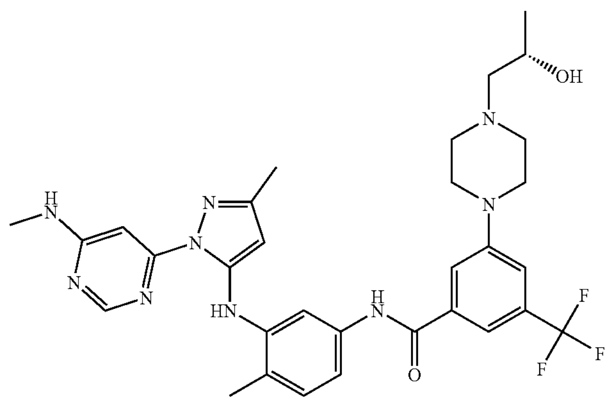 | MS m/z 624.3 (M + 1) |
| 421 | 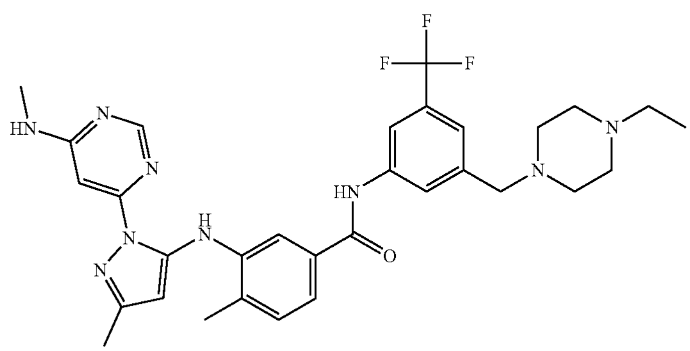 | MS m/z 608.3 (M + 1) |
| 422 | 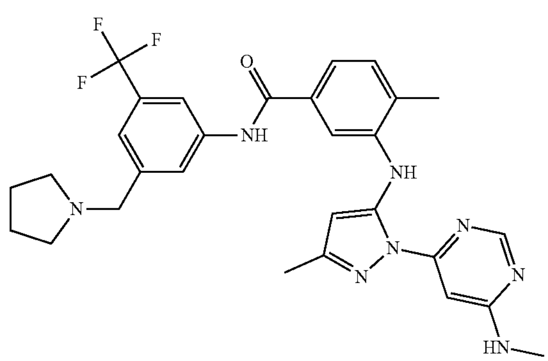 | MS m/z 565.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 423 | 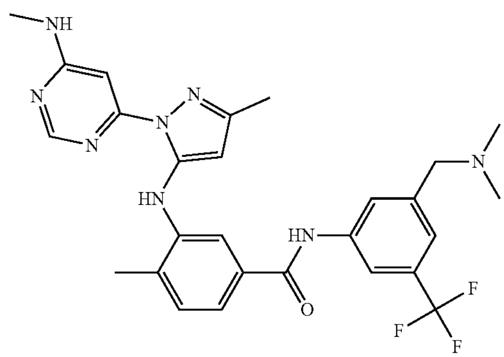 | MS m/z 539.2 (M + 1) |
| 424 | 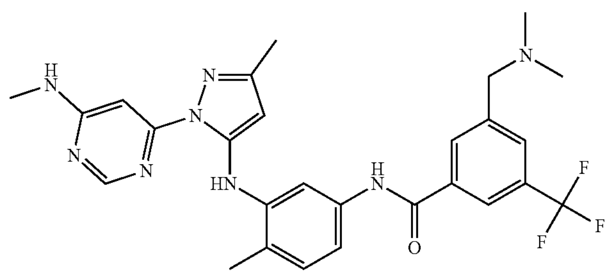 | MS m/z 539.2 (M + 1) |
| 425 | 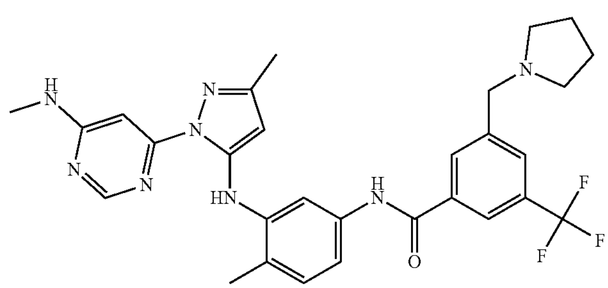 | MS m/z 565.3 (M + 1) |
| 426 | 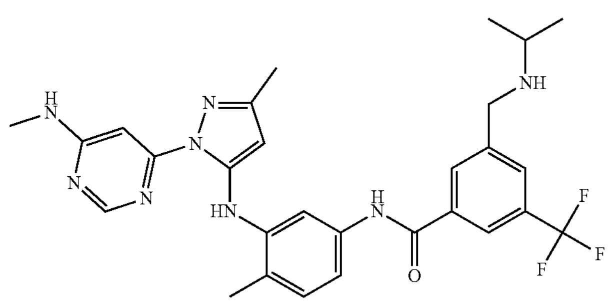 | MS m/z 553.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 427 | 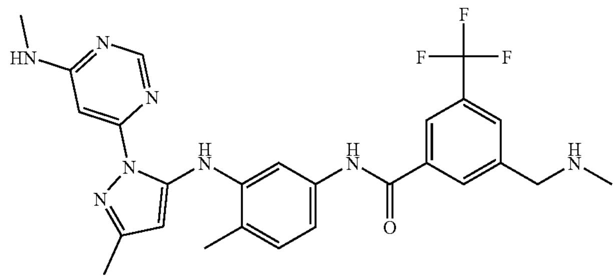 | MS m/z 525.2 (M + 1) |
| 428 | 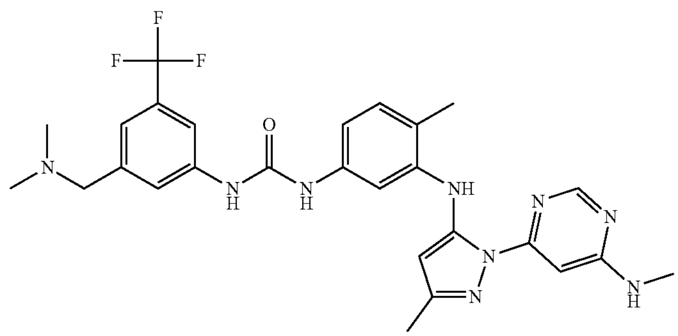 | MS m/z 554.3 (M + 1) |
| 429 | 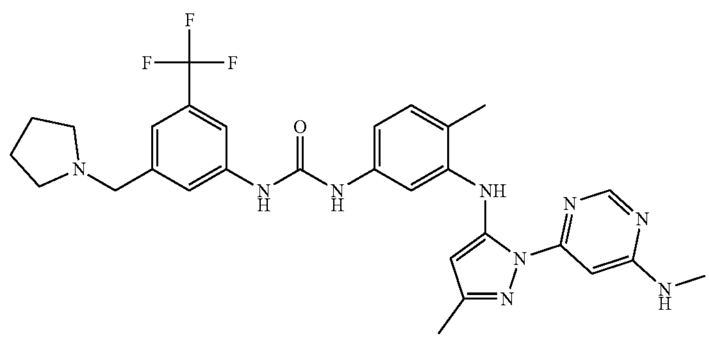 | MS m/z 580.3 (M + 1) |
| 430 | 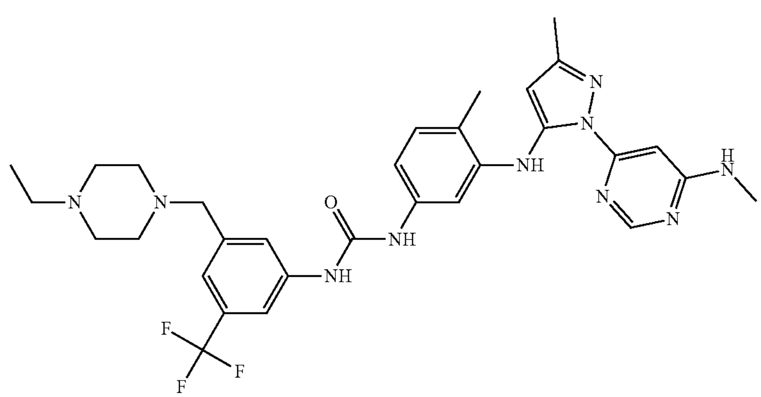 | MS m/z 623.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 431 | 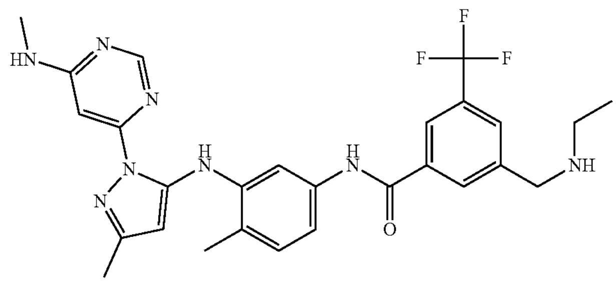 | MS m/z 539.2 (M + 1) |
| 432 | 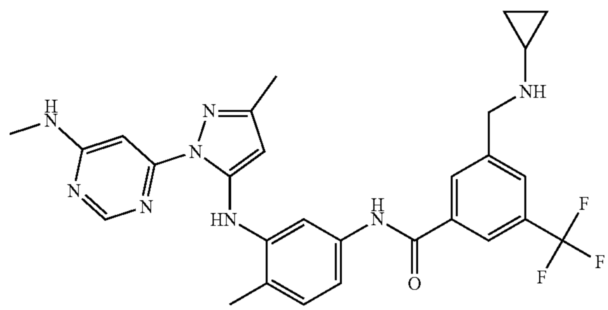 | MS m/z 551.2 (M + 1) |
| 433 | 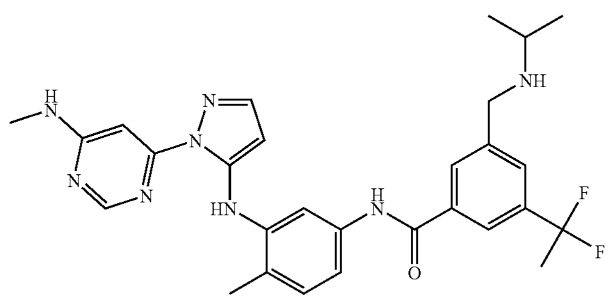 | MS m/z 535.3 (M + 1) |
| 434 | 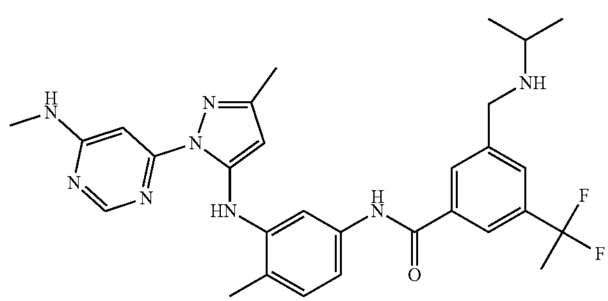 | MS m/z 549.3 (M + 1) |
| 435 | 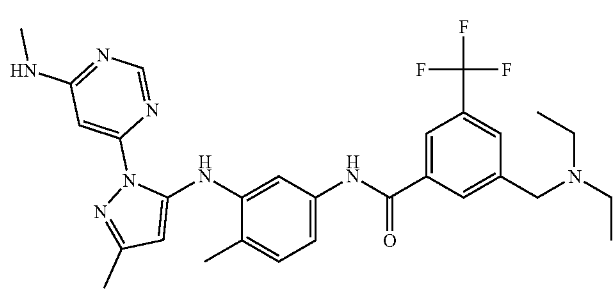 | MS m/z 567.3 (M + 1) |

TABLE 1-continued

| Compound Number | Structure | Physical Data ¹H NMR 400 MHz or 600 MHz (DMSO-d₆) and/or MS (m/z) |
|---|---|---|
| 436 | 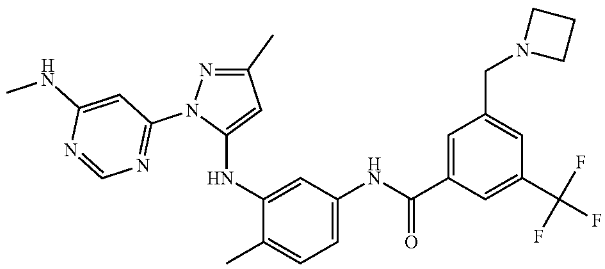 | MS m/z 551.2 (M + 1) |
| 437 | 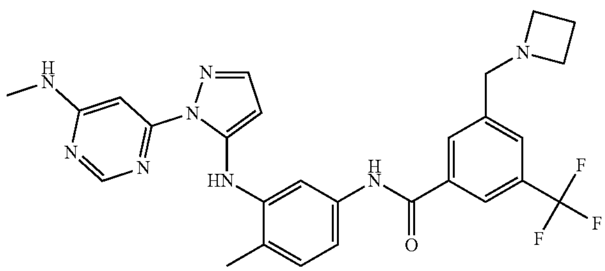 | MS m/z 537.2 (M + 1) |
| 438 | 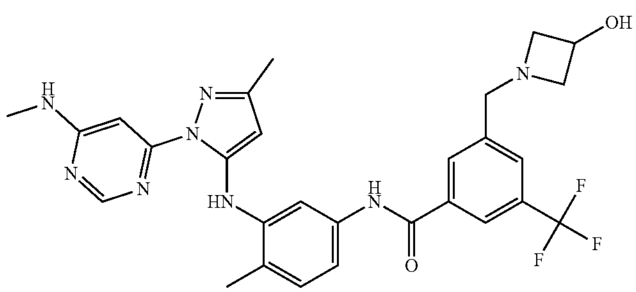 | MS m/z 567.2 (M + 1) |
| 439 | 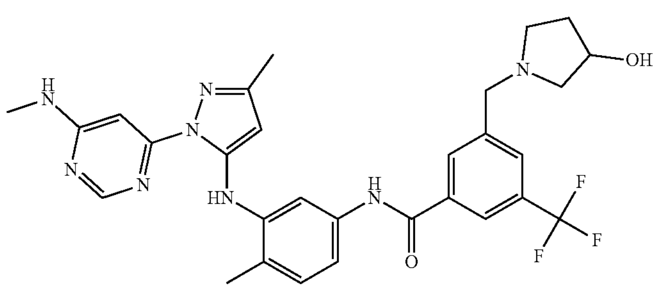 | MS m/z 581.3 (M + 1) |
| 440 | 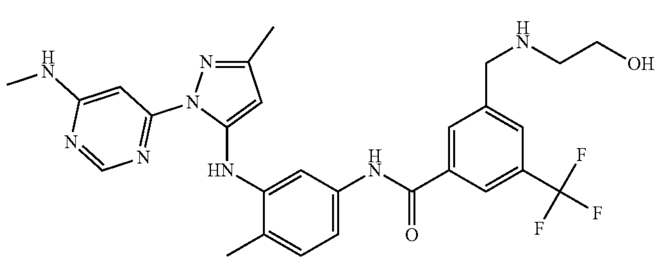 | MS m/z 555.2 (M + 1) |

TABLE 1-continued

| Compound Number | Structure | Physical Data ¹H NMR 400 MHz or 600 MHz (DMSO-d₆) and/or MS (m/z) |
|---|---|---|
| 441 | 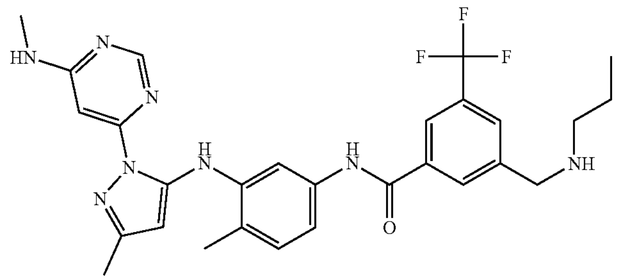 | MS m/z 553.3 (M + 1) |
| 442 | 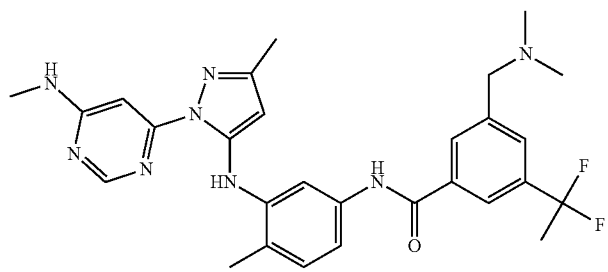 | MS m/z 535.3 (M + 1) |
| 443 | 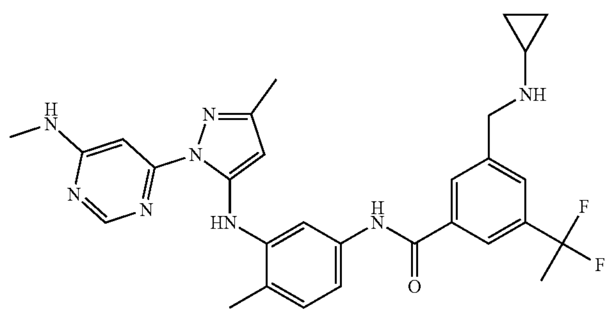 | MS m/z 547.3 (M + 1) |
| 444 | 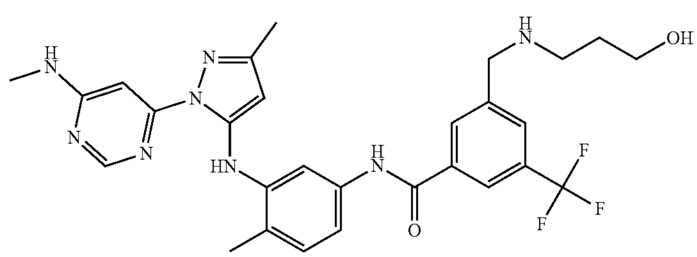 | MS m/z 569.3 (M + 1) |
| 445 | 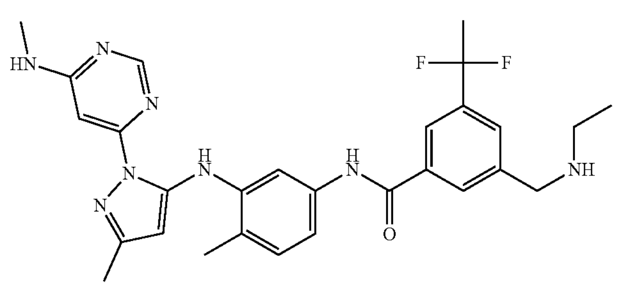 | MS m/z 535.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 446 | 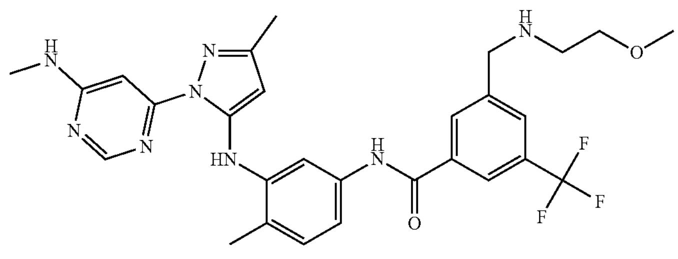 | MS m/z 569.3 (M + 1) |
| 447 | 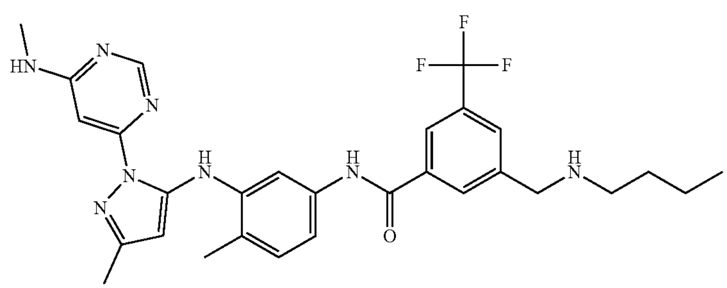 | MS m/z 567.3 (M + 1) |
| 448 | 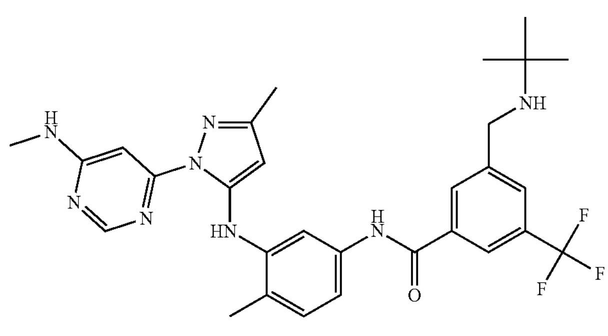 | MS m/z 567.3 (M + 1) |
| 449 | 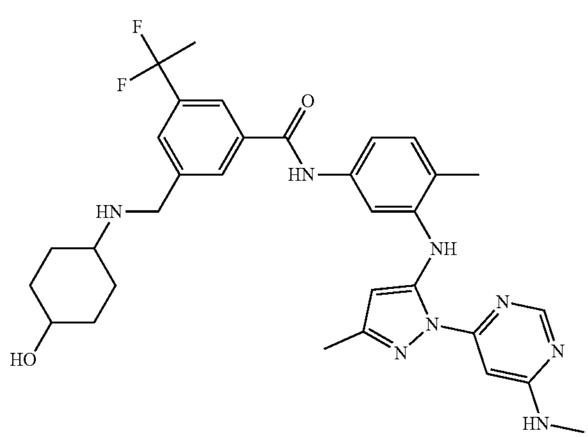 | MS m/z 605.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 450 | 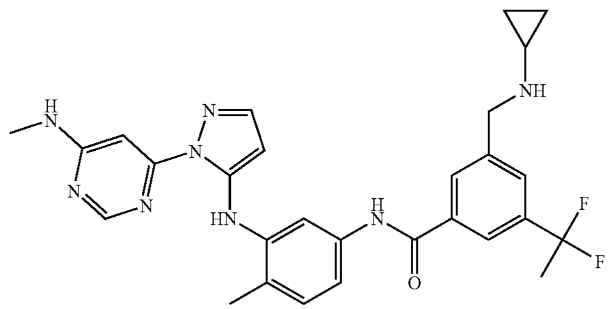 | MS m/z 533.3 (M + 1) |
| 451 | 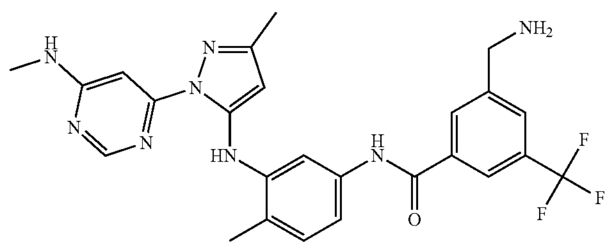 | MS m/z 511.2 (M + 1) |
| 452 | 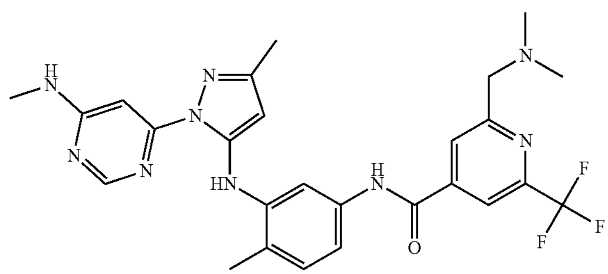 | MS m/z 540.2 (M + 1) |
| 453 | 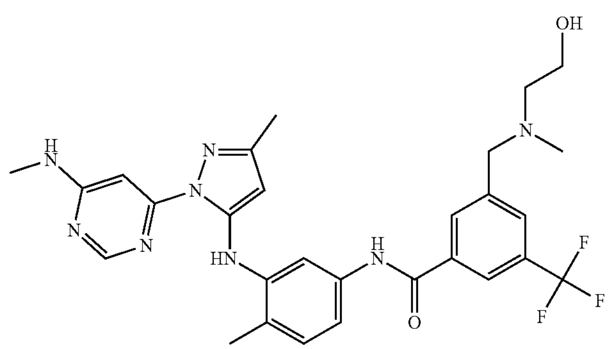 | MS m/z 569.3 (M + 1) |
| 454 | 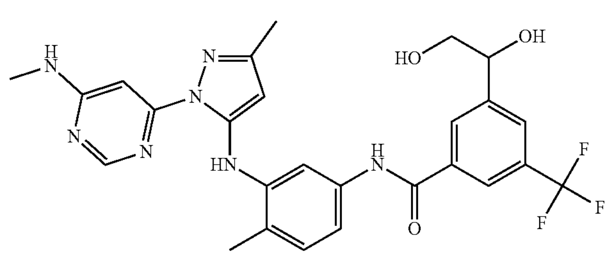 | MS m/z 542.2 (M + 1) |

TABLE 1-continued

| Compound Number | Structure | Physical Data ¹H NMR 400 MHz or 600 MHz (DMSO-d₆) and/or MS (m/z) |
|---|---|---|
| 455 | 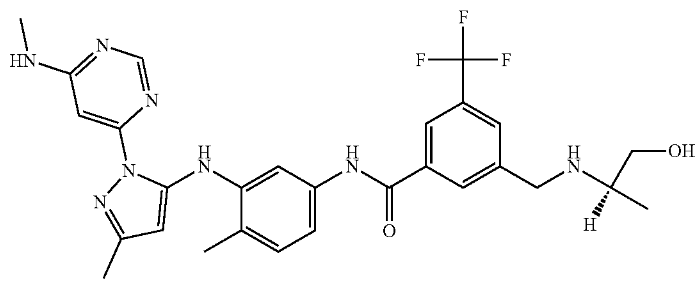 | MS m/z 569.3 (M + 1) |
| 456 | 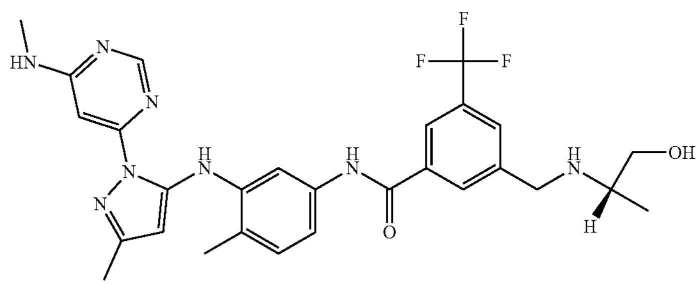 | MS m/z 569.3 (M + 1) |
| 457 | 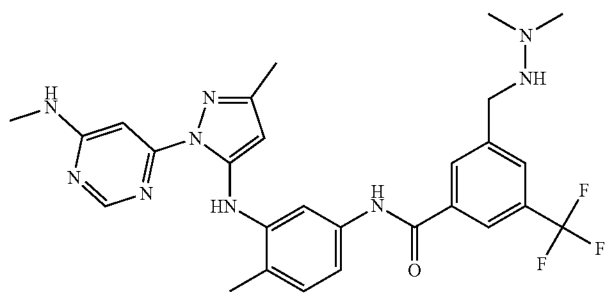 | MS m/z 554.3 (M + 1) |
| 458 | 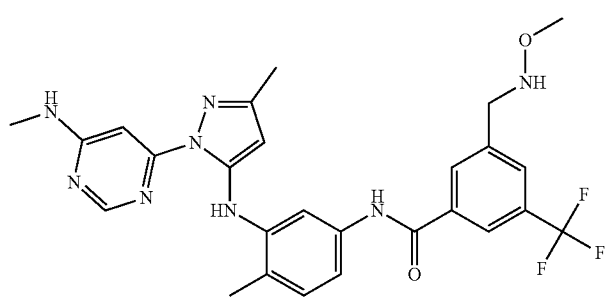 | MS m/z 541.2 (M + 1) |
| 459 | 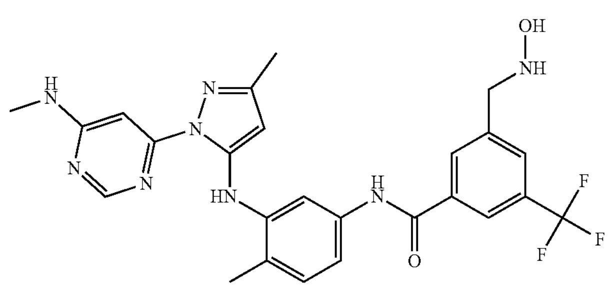 | MS m/z 527.2 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 460 | 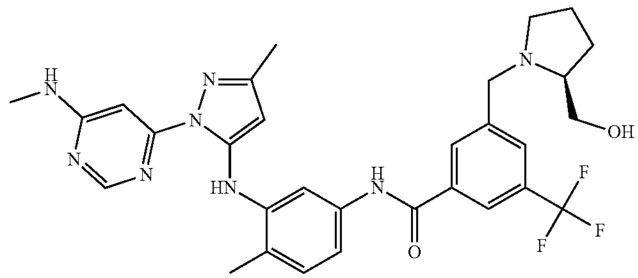 | MS m/z 595.3 (M + 1) |
| 461 | 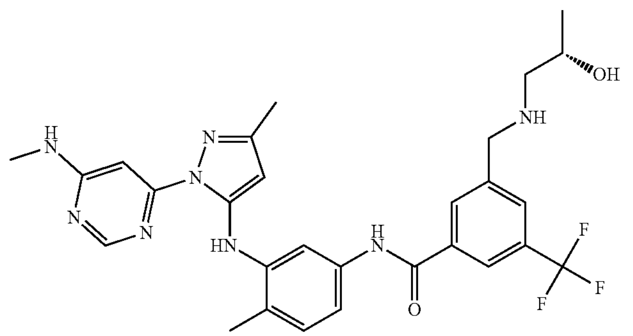 | MS m/z 569.3 (M + 1) |
| 462 | 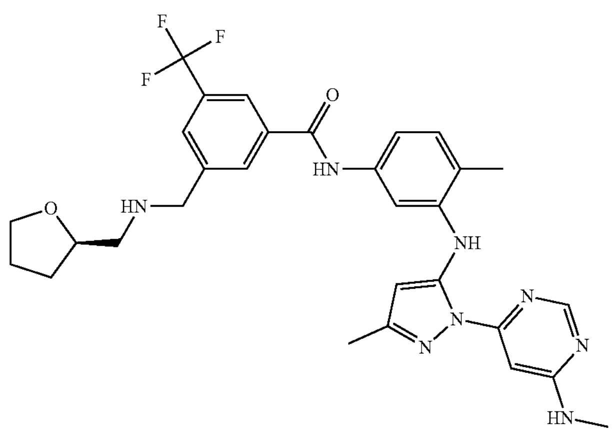 | MS m/z 595.3 (M + 1) |
| 463 | 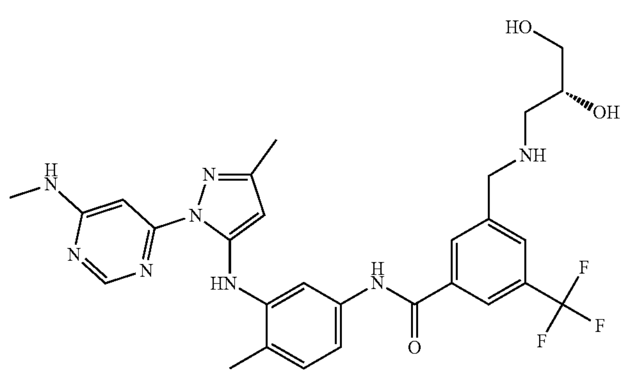 | MS m/z 585.3 (M + 1) |

TABLE 1-continued
| Compound Number | Structure | Physical Data ¹H NMR 400 MHz or 600 MHz (DMSO-d₆) and/or MS (m/z) |
|---|---|---|
| 464 | 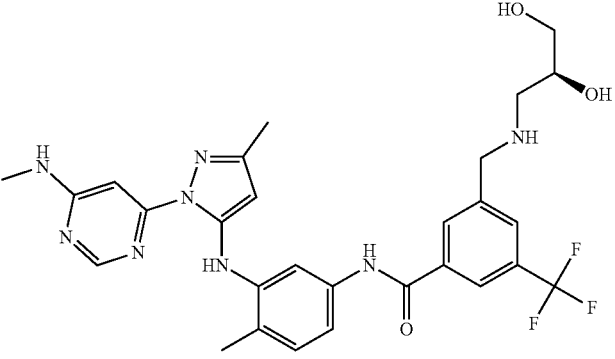 | MS m/z 585.3 (M + 1) |
| 465 | 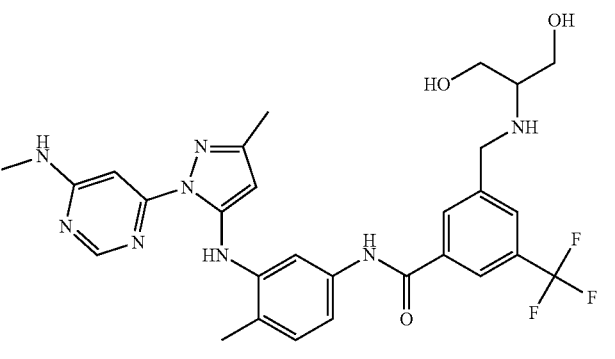 | MS m/z 585.3 (M + 1) |
| 466 | 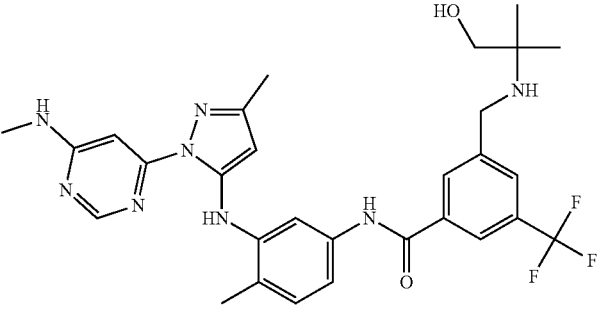 | MS m/z 583.3 (M + 1) |
| 467 | 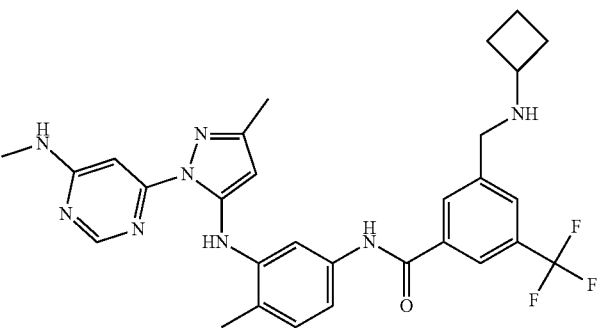 | MS m/z 565.3 (M + 1) |

TABLE 1-continued

| Compound Number | Structure | Physical Data ¹H NMR 400 MHz or 600 MHz (DMSO-$d_6$) and/or MS (m/z) |
| --- | --- | --- |
| 468 | 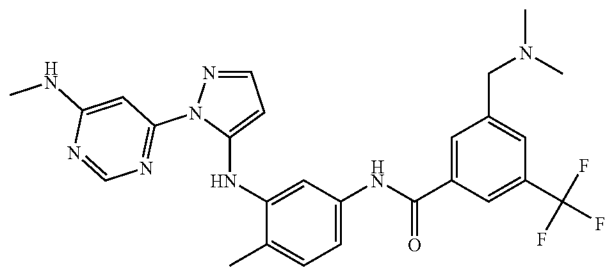 | MS m/z 525.2 (M + 1) |
| 469 | 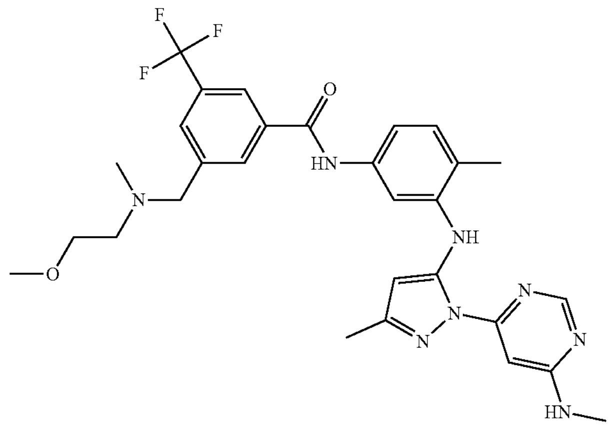 | MS m/z 583.3 (M + 1) |
| 470 | 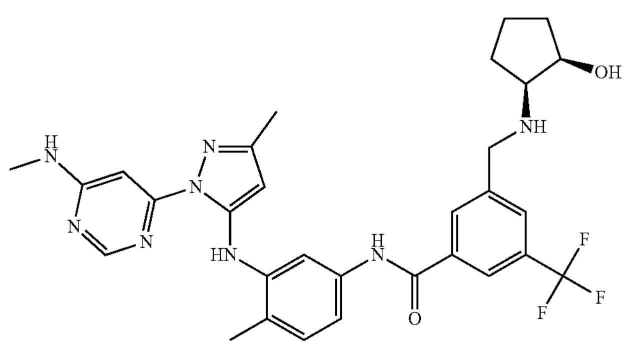 | MS m/z 595.3 (M + 1) |
| 471 | 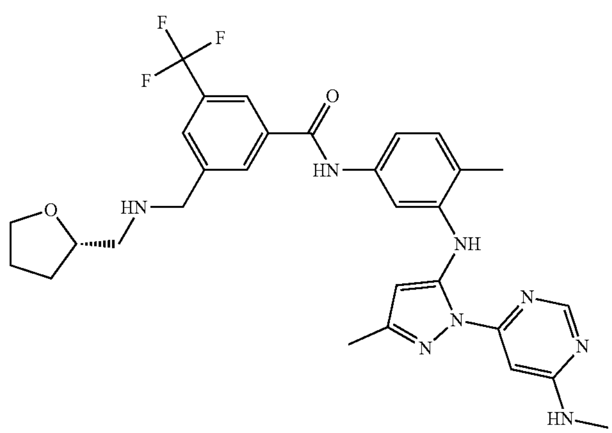 | MS m/z 595.3 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 472 | 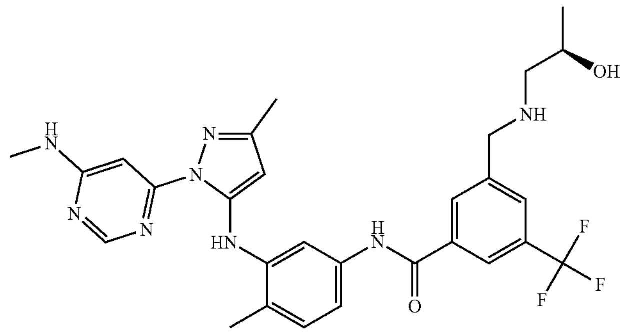 | MS m/z 569.3 (M + 1) |
| 473 | 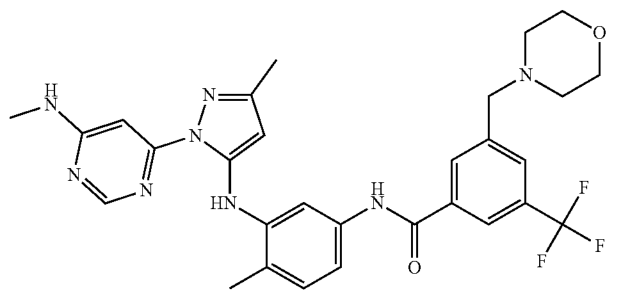 | MS m/z 581.3 (M + 1) |
| 474 | 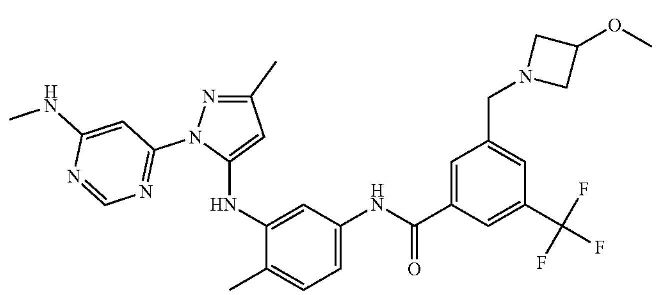 | MS m/z 581.3 (M + 1) |
| 475 | 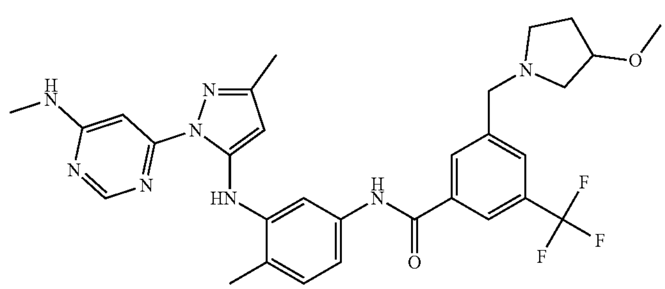 | MS m/z 595.3 (M + 1) |
| 476 | 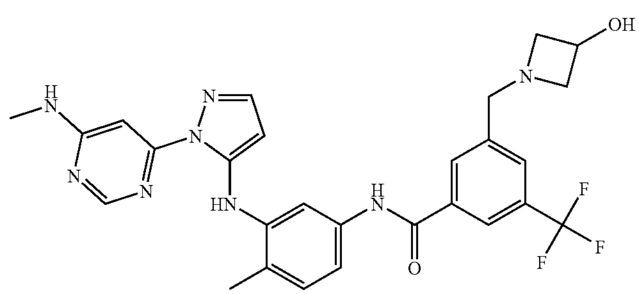 | MS m/z 553.3 (M + 1) |

US 8,202,876 B2

TABLE 1-continued

| Compound Number | Structure | Physical Data ¹H NMR 400 MHz or 600 MHz (DMSO-$d_6$) and/or MS (m/z) |
|---|---|---|
| 477 | 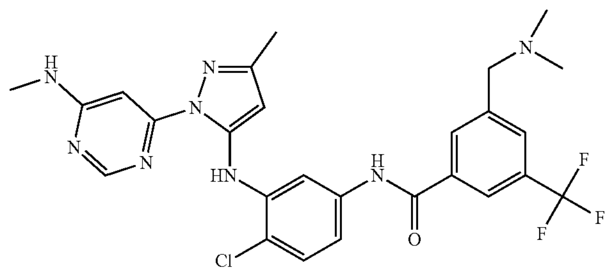 | MS m/z 559.2 (M + 1) |
| 478 | 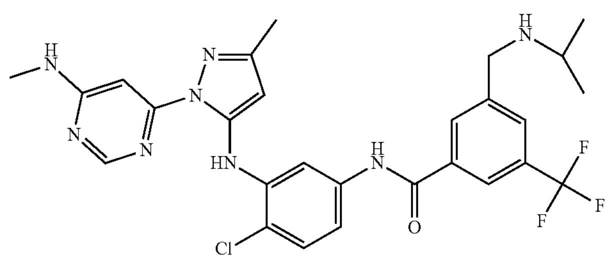 | MS m/z 573.2 (M + 1) |
| 479 | 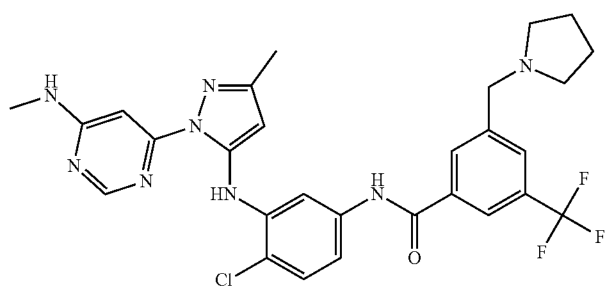 | MS m/z 585.2 (M + 1) |
| 480 | 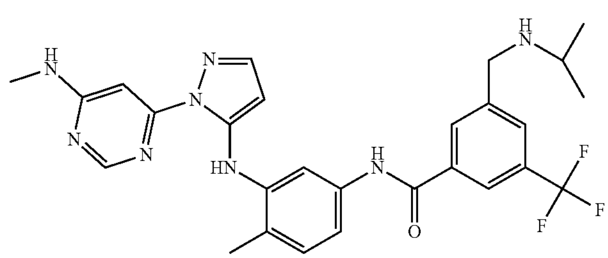 | MS m/z 539.2 (M + 1) |
| 481 | 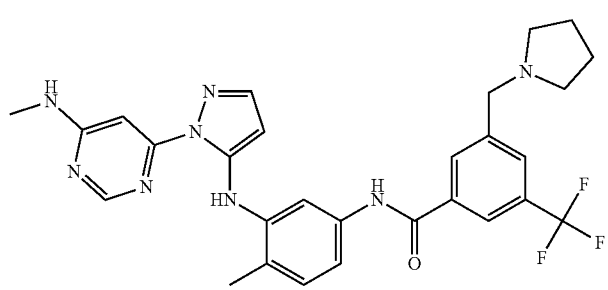 | MS m/z 551.2 (M + 1) |

TABLE 1-continued

| Compound Number | Structure | Physical Data $^1$H NMR 400 MHz or 600 MHz (DMSO-$d_6$) and/or MS (m/z) |
|---|---|---|
| 482 | 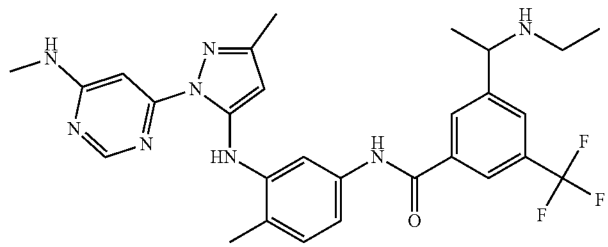 | MS m/z 553.3 (M + 1) |
| 483 | 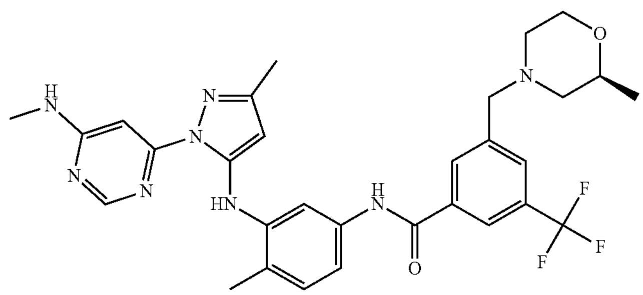 | MS m/z 595.3 (M + 1) |
| 484 | 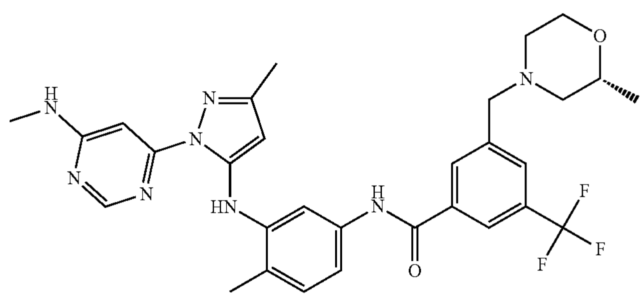 | MS m/z 595.3 (M + 1) |
| 485 | 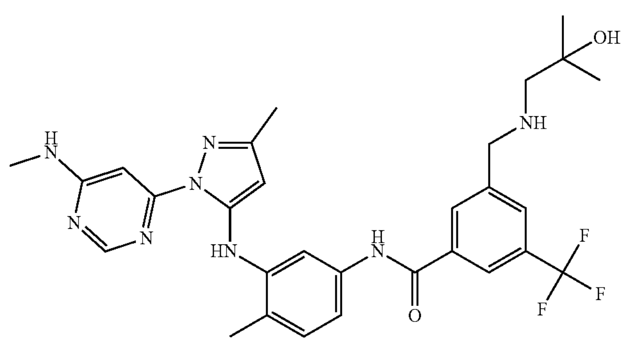 | MS m/z 583.3 (M + 1) |
| 486 | 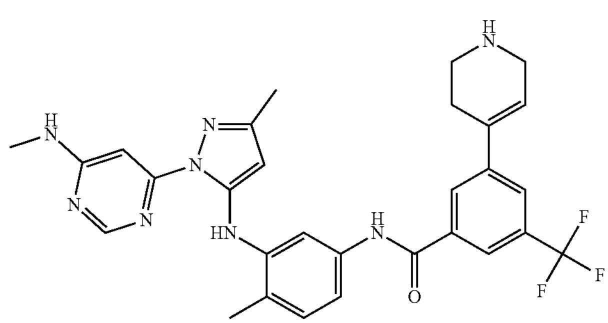 | MS m/z 563.2 (M + 1) |

TABLE 1-continued

| Compound Number | Structure | Physical Data ¹H NMR 400 MHz or 600 MHz (DMSO-$d_6$) and/or MS (m/z) |
|---|---|---|
| 487 | 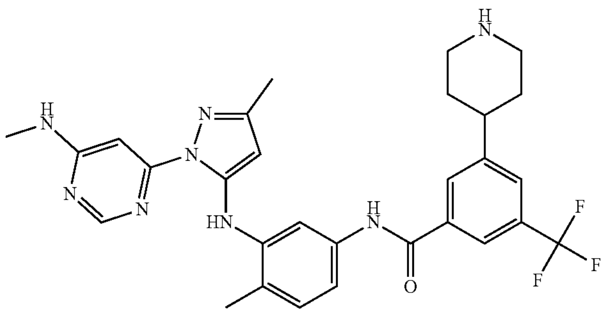 | MS m/z 565.3 (M + 1) |
| 488 | 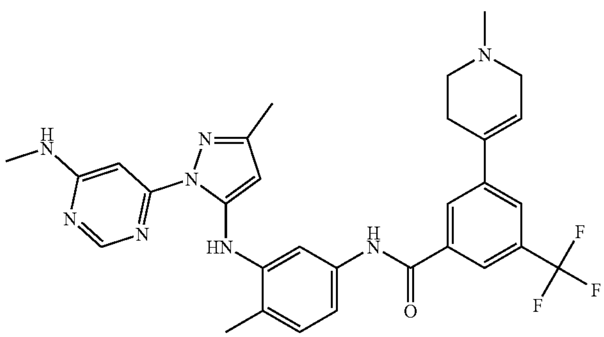 | MS m/z 577.3 (M + 1) |
| 489 | 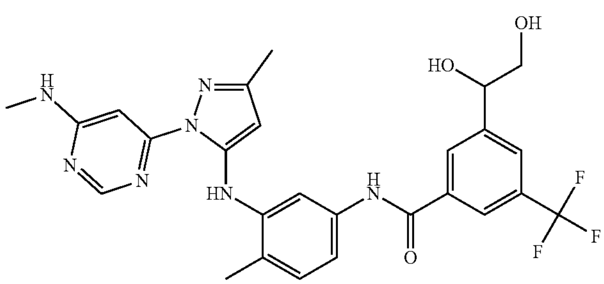 | MS m/z 542.2 (M + 1) |
| 490 | 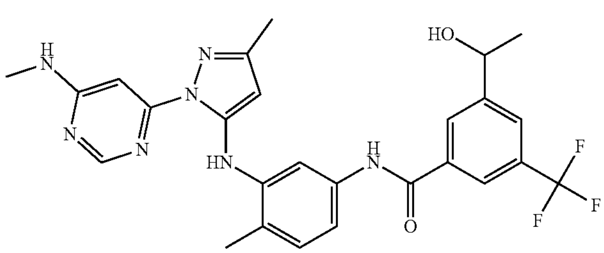 | MS m/z 526.2 (M + 1) |

TABLE 1-continued
| Compound Number | Structure | Physical Data ¹H NMR 400 MHz or 600 MHz (DMSO-d₆) and/or MS (m/z) |
|---|---|---|
| 491 | 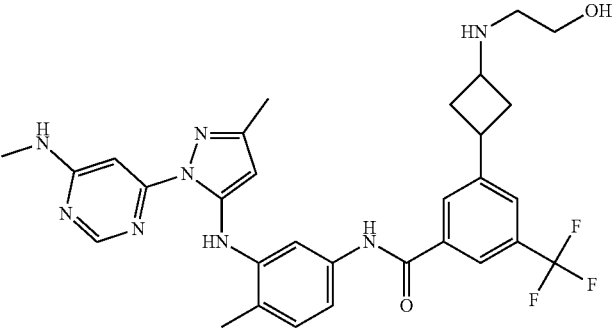 | |
| 492 | 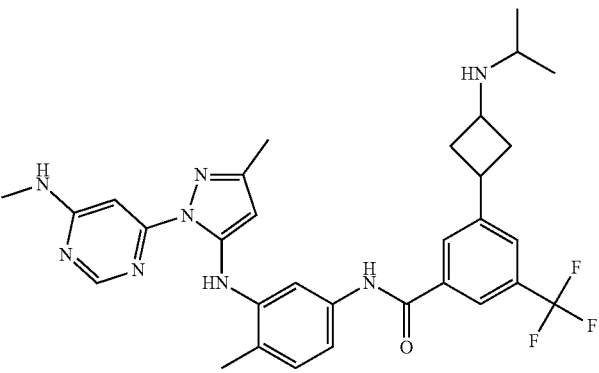 | |
| 493 | 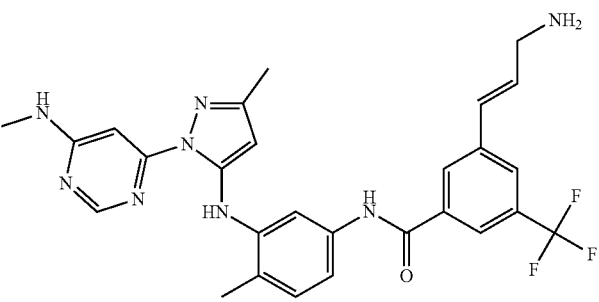 | |
| 494 | 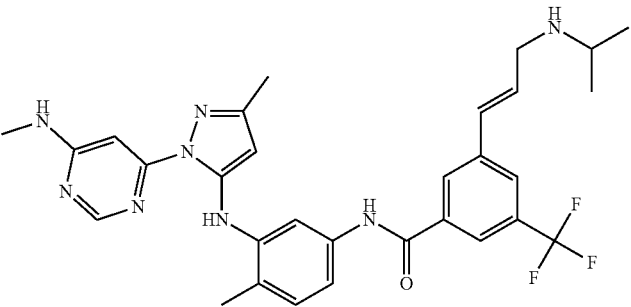 | |

TABLE 1-continued

| Compound Number | Structure | Physical Data <br> ¹H NMR 400 MHz or 600 MHz (DMSO-d₆) and/or MS (m/z) |
| --- | --- | --- |
| 495 | 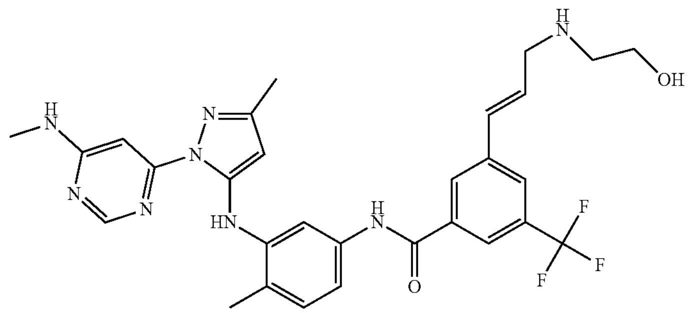 | |
| 496 | 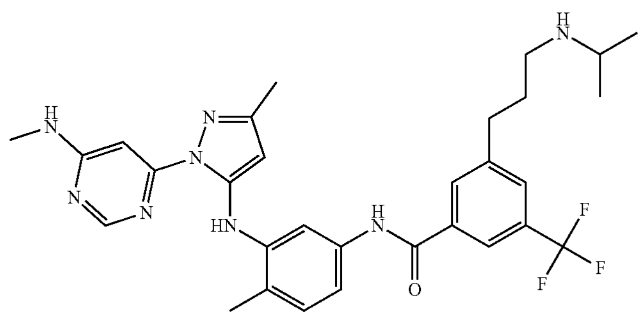 | |
| 497 | 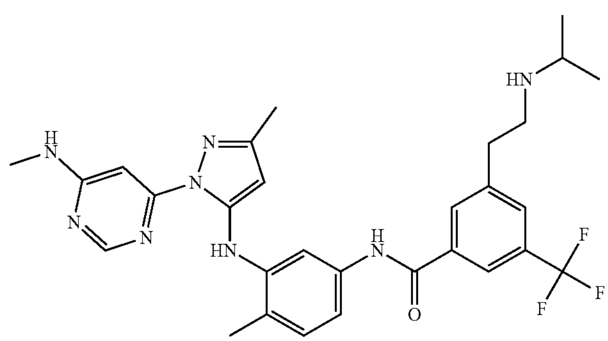 | |
| 498 | 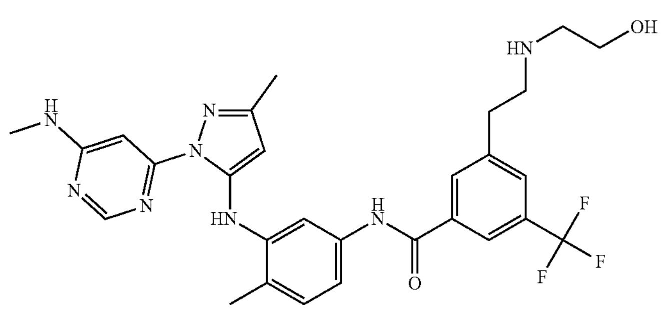 | |

| Compound Number | Structure | Physical Data ¹H NMR 400 MHz or 600 MHz (DMSO-$d_6$) and/or MS (m/z) |
|---|---|---|
| 499 | 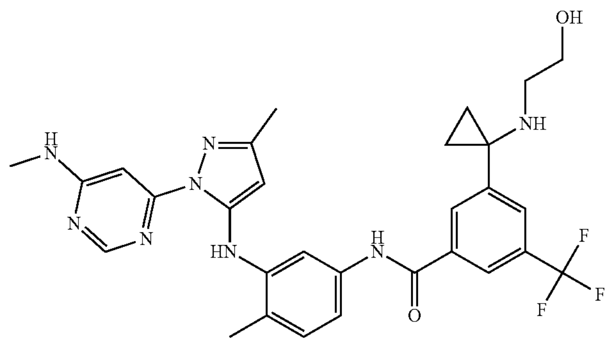 | |
| 500 | 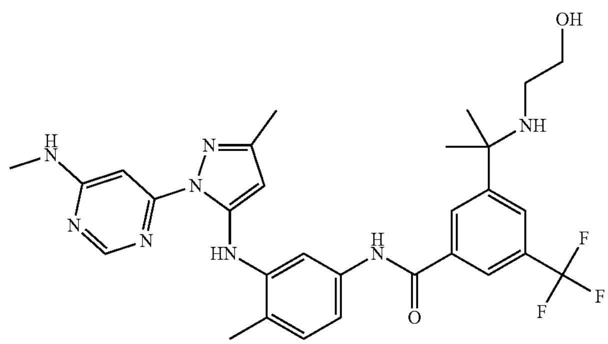 | |
| 501 | 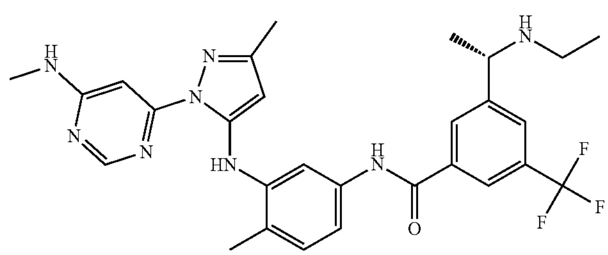 | |
| 502 | 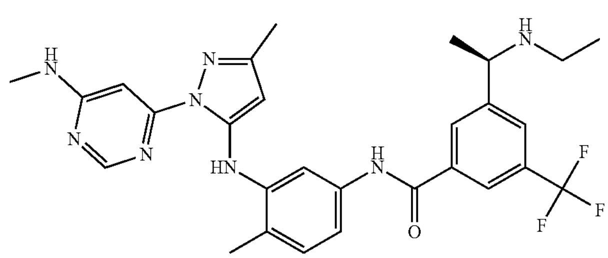 | |
| 503 | 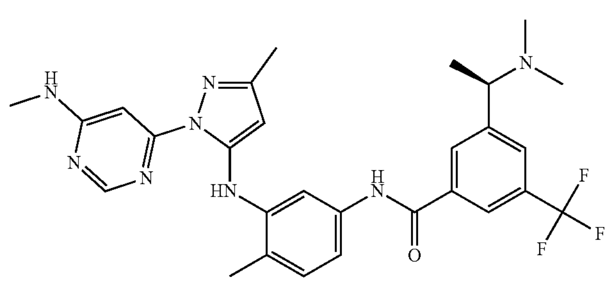 | |

TABLE 1-continued

| Compound Number | Structure | Physical Data ¹H NMR 400 MHz or 600 MHz (DMSO-d₆) and/or MS (m/z) |
|---|---|---|
| 504 | 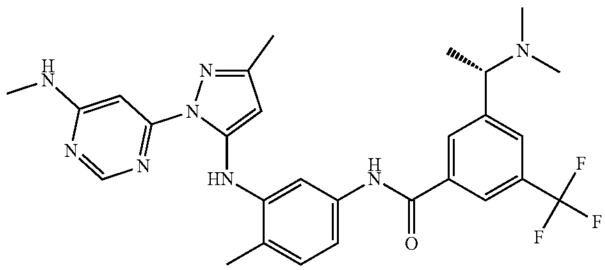 | |
| 505 | 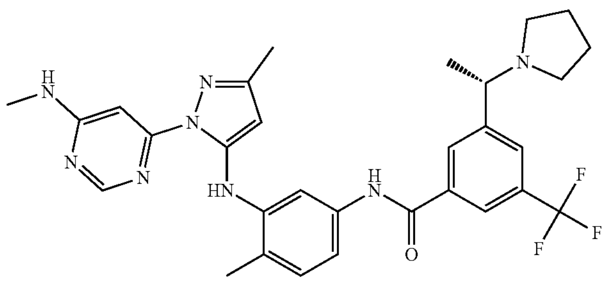 | |
| 506 | 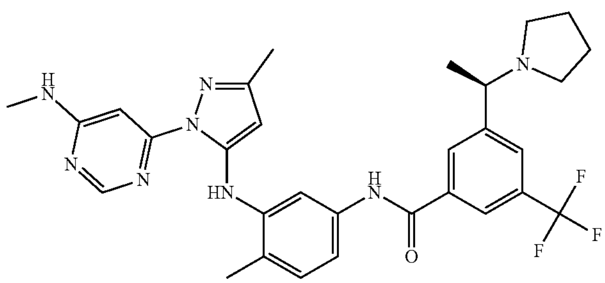 | |
| 507 | 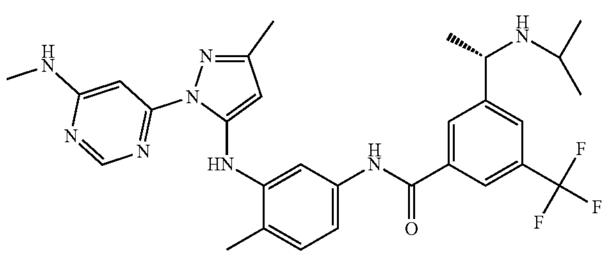 | |
| 508 | 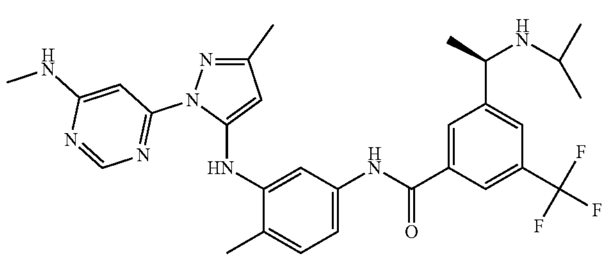 | |

TABLE 1-continued

| Compound Number | Structure | Physical Data ¹H NMR 400 MHz or 600 MHz (DMSO-d₆) and/or MS (m/z) |
|---|---|---|
| 509 | 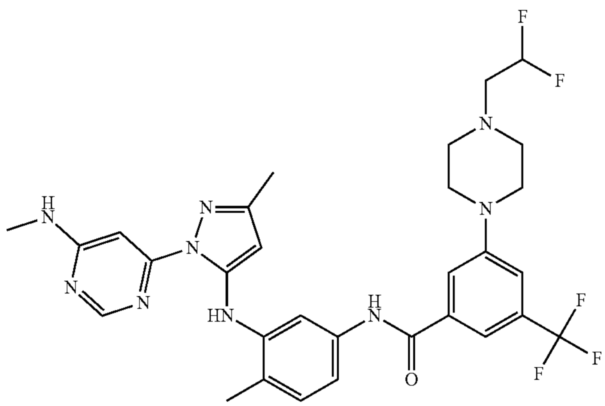 | MS m/z 630.3 (M + 1) |
| 510 | 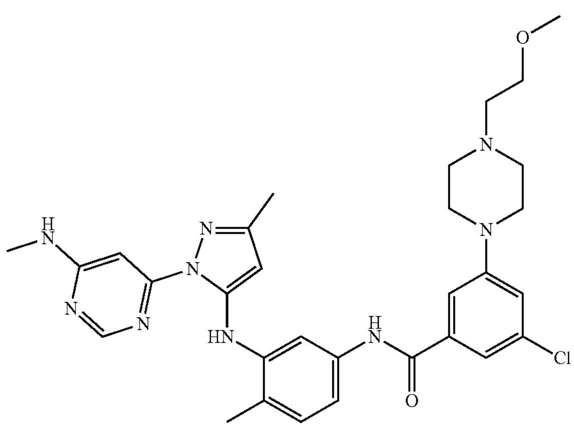 | MS m/z 590.3 (M + 1) |
| 511 | 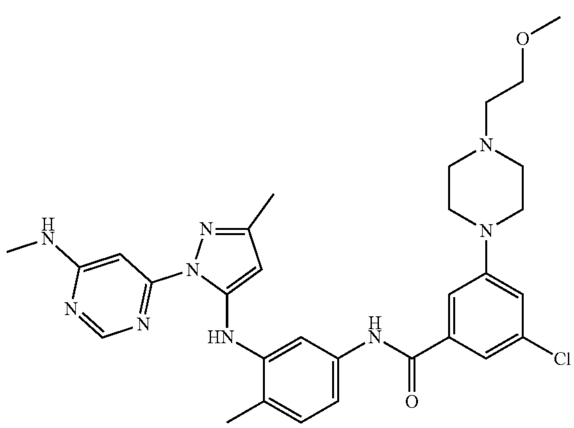 | MS m/z 604.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 512 | 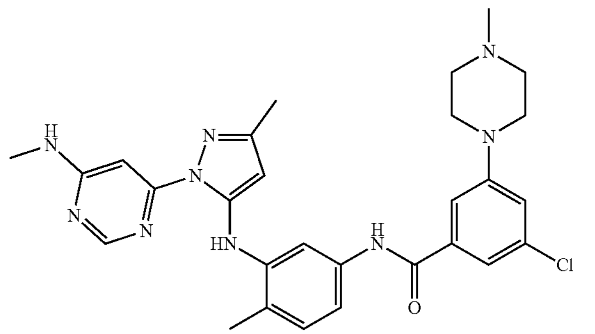 | MS m/z 546.3 (M + 1) |
| 513 | 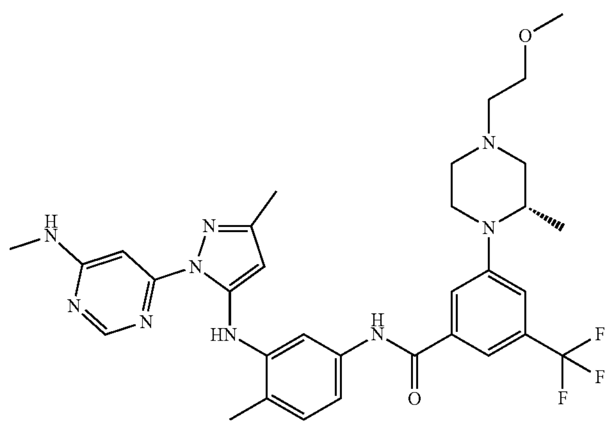 | MS m/z 638.3 (M + 1) |
| 514 | 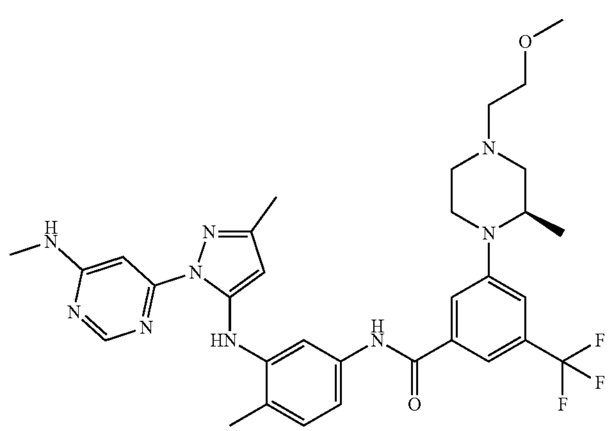 | MS m/z 638.3 (M + 1) |

TABLE 1-continued

| Compound Number | Structure | Physical Data ¹H NMR 400 MHz or 600 MHz (DMSO-$d_6$) and/or MS (m/z) |
|---|---|---|
| 515 | 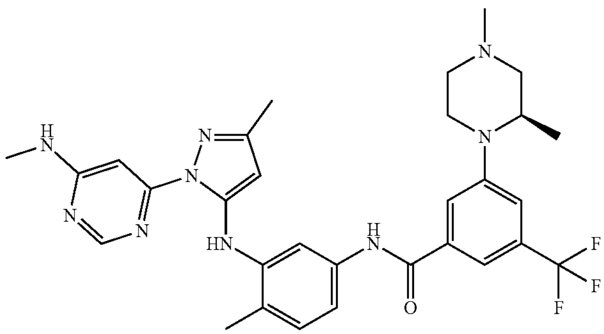 | MS m/z 594.3 (M + 1) |
| 516 | 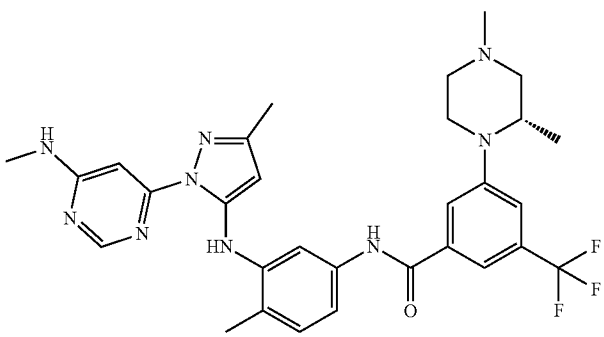 | MS m/z 594.3 (M + 1) |
| 517 | 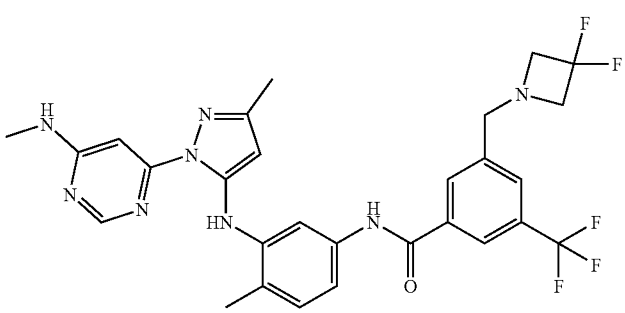 | |
| 518 | 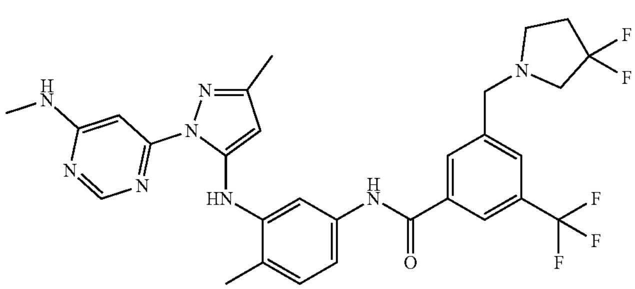 | |

TABLE 1-continued

| Compound Number | Structure | Physical Data $^1$H NMR 400 MHz or 600 MHz (DMSO-$d_6$) and/or MS (m/z) |
|---|---|---|
| 519 | 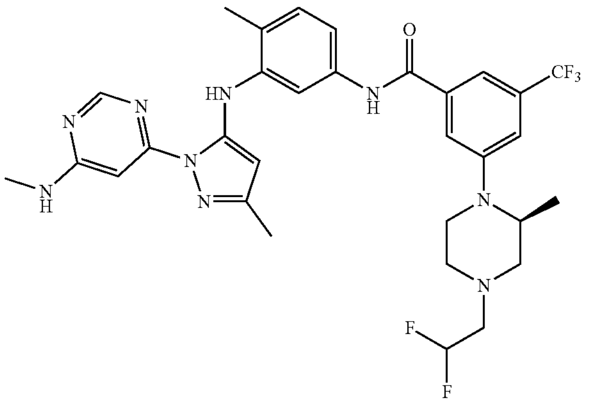 | |
| 520 | 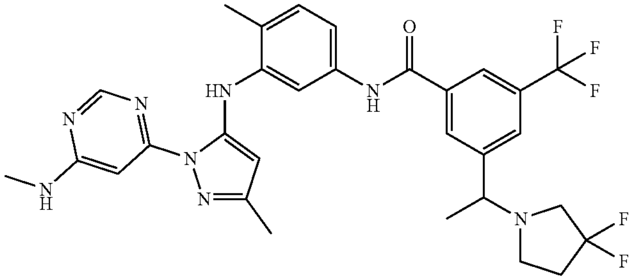 | |
| 521 | 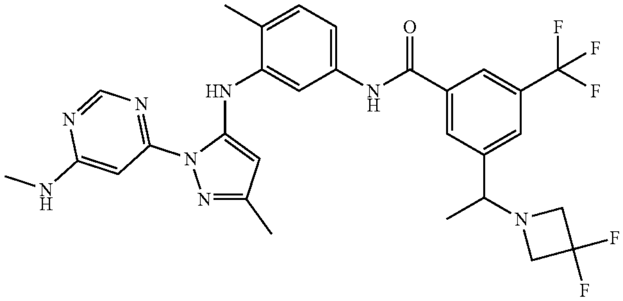 | |
| 522 | 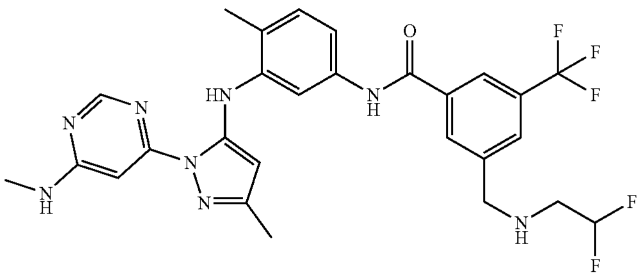 | |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit Abl, ARG, BCR-Abl, BRK, EphB, Fms, Fyn, KDR, c-Kit, LCK, PDGF-R, b-Raf, c-Raf, SAPK2, Src, Tie2 and TrkB kinases.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 µg/mL, streptomycin 50 µg/mL and L-glutamine 200 mM. Untransformed 32D cells are similarly maintained with the addition of 15% of WEHI conditioned medium as a source of IL3.

50 µl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% $CO_2$. 10 µl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 µL of two fold serial dilutions of the test compound ($C_{max}$ is 40 µM) are added to each well (STI571 is included as a positive control). After incubating the cells for 48 hours at 37° C., 5% $CO_2$, 15 µL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 ml of medium and test compound at 1 or 10 µM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2 \times 10^5$ cells per well in 50 µL of medium. 50 µL of two fold serial dilutions of test compounds ($C_{max}$ is 10 µM) are added to each well (STI571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96 well optiplates previously coated with anti-abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 µM as described above (in media lacking IL3). The $IC_{50}$ values of the compounds lacking toxicity on the untransformed cells were determined from the dose response curves obtained as describe above.

FGFR3 (Enzymatic Assay)

Kinase activity assay with purified FGFR3 (Upstate) is carried out in a final volume of 10 µL containing 0.25 µg/mL of enzyme in kinase buffer (30 mM Tris-HCl pH7.5, 15 mM $MgCl_2$, 4.5 mM $MnCl_2$, 15 µM $Na_3VO_4$ and 50 µg/mL BSA), and substrates (5 µg/mL biotin-poly-EY (Glu, Tyr) (CIS-US, Inc.) and 3 µM ATP). Two solutions are made: the first solution of 5 µl contains the FGFR3 enzyme in kinase buffer was first dispensed into 384-format ProxiPlate® (Perkin-Elmer) followed by adding 50 nL of compounds dissolved in DMSO, then 5 µl of second solution contains the substrate (poly-EY) and ATP in kinase buffer was added to each wells. The reactions are incubated at room temperature for one hour, stopped by adding 10 µL of HTRF detection mixture, which contains 30 mM Tris-HCl pH7.5, 0.5 M KF, 50 mM ETDA, 0.2 mg/mL BSA, 15 µg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 µM to 0.28 nM). In this assay, compounds of the invention have an $IC_{50}$ in the range of 10 nM to 2 µM.

FGFR3 (Cellular Assay)

Compounds of the invention are tested for their ability to inhibit transformed Ba/F3-TEL-FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsufoxide (DMSO). Twelve points 1:3 serial dilutions are made into DMSO to create concentrations gradient ranging typically from 10 mM to 0.05 µM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

FLT3 and PDGFRβ (Cellular Assay)

The effects of compounds of the invention on the cellular activity of FLT3 and PDGFRβ are conducted using identical methods as described above for FGFR3 cellular activity, except that instead of using Ba/F3-TEL-FGFR3, Ba/F3-FLT3-ITD and Ba/F3-Tel-PDGFRβ are used, respectively.

b-Raf—Enzymatic Assay

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of fluorescent Attophos AP substrate (Promega) is added to each well and plates are incubated at room temperature for 15 minutes. Plates are read on Acquest or Analyst GT using a Fluorescence Intensity Program (Excitation 455 nm, Emission 580 nm).

b-Raf—Cellular Assay

Compounds of the invention are tested in A375 cells for their ability to inhibit phosphorylation of MEK. A375 cell line (ATCC) is derived from a human melanoma patient and it has a V599E mutation on the B-Raf gene. The levels of phosphorylated MEK are elevated due to the mutation of B-Raf. Sub-confluent to confluent A375 cells are incubated with compounds for 2 hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to western blotting with anti-phospho-MEK antibody (ser217/221) (Cell Signaling). The amount of phosphorylated MEK is monitored by the density of phospho-MEK bands on the nitrocellulose membranes.

Upstate KinaseProfiler™—Radio-enzymatic Filter Binding Assay

Compounds of the invention are assessed for their ability to inhibit individual members of the kinase panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing $MnCl_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Antimalarial Assay Using SYBR Green I

Compounds of the present invention can be assayed to measure their capacity to inhibit the proliferation of parasitemia in infected red blood cells. The proliferation is quantified by addition of SYBR Green I (Invitrogen)® dye which has a high affinity for double stranded DNA.

For drug screening, 20 μl of screening media, containing no human serum, is dispensed into 3 assay plates. 50 nl of each of the compounds of the invention, including antimalarial controls (chloroquine and artimesinin), are then transferred into the assay plates. 50 nl of DMSO is transferred into the baseline and background control plates. Then 30 μl of a suspension of *P. falciparum* infected human red blood cells in screening media is dispensed into the assay plates and the baseline control plate such that the final hematocrit is 2.5% with a final parasitemia of 3%. Non-infected red blood cells are dispensed into the background control plate such that the final hematocrit is 2.5%. The plates are placed in a 37° C. incubator for 72 hours with a 93% $N_2$, 4% $CO_2$, and 3% $O_2$ gas mixture. 10 μl of a 10× solution of SYBR Green I® is dispensed into the plates. The plates are sealed and placed in a −80° C. freezer overnight for the lysis of the red blood cells. The plates are thawed and left at room temperature overnight for optimal staining. The fluorescence intensity is measured (excitation 497 nm, emission 520 nm) using the Acquest system (Molecular Devices). The percentage inhibition is calculated for each compound.

Compounds of Formula I, in free form or in pharmaceutically acceptable salt form, exhibit valuable pharmacological properties, for example, as indicated by the in vitro tests described in this application.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

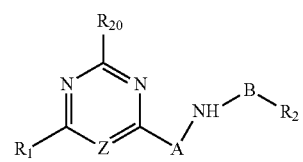

in which:
A is a pyrazole optionally substituted with one or two $R_3$ radicals; wherein $R_3$ is selected from hydrogen, substituted or unsubstituted-$C_{1-6}$alkyl, substituted or unsubstituted $C_{2-6}$alkenyl, substituted or unsubstituted $C_{2-6}$alkynyl, —$XOR_{4a}$, —$XCN$, —$XC(O)OR_{4a}$, —$XC(O)R_{4b}$, —$XNR_{4a}R_{4a}$, —$XNR_{4a}XNR_{4a}R_{4a}$, —$XC(O)NR_{4a}XNR_{4a}R_{4a}$, —$XC(O)NR_{4a}XR_{4b}$, —$XC(O)NR_{4a}XNR_{4a}R_{4b}$, —$XC(O)NR_{4a}XOR_{4a}$, —$XNR_{4a}XNR_{4a}R_{4b}$, —$XNR_{4a}XOR_{4a}$, —$XNR_{4a}XCF_3$, —$XC(O)NR_{4a}R_{4a}$, and —$XR_{4b}$; wherein each X is independently selected from a bond and $C_{1-4}$alkylene;

$R_{4a}$ is selected from hydrogen and substituted or unsubstituted $C_{1-6}$alkyl, and two $R_{4a}$ on the same or adjacent atoms can optionally be joined to form a 5-6 membered ring containing up to two heteroatoms selected from N, O and S as ring members;

and $R_{4b}$ is selected from $C_{6-10}$aryl, $C_{1-10}$heteroaryl, $C_{3-10}$cycloalkyl and $C_{3-10}$heterocycloalkyl; wherein any cycloalkyl, heterocycloalkyl, aryl or heteroaryl of $R_{4b}$ is optionally substituted with 1 to 3 radicals independently selected from $C_{1-6}$alkyl and —$NR_{4c}R_{4d}$;

wherein each $R_{4c}$ and $R_{4d}$ is independently selected from hydrogen and substituted or unsubstituted $C_{1-6}$alkyl, and $R_{4c}$ and $R_{4d}$ can optionally be joined together to form a 5-6 membered ring containing N and optionally containing an additional heteroatom selected from N, O and S;

B is phenyl or pyridinyl optionally substituted with 1 to 3 radicals independently selected from $C_{1-6}$alkyl, halo-substituted-$C_{1-6}$alkyl and halo;

Z is selected from CH;

$R_1$ is selected from —$XNR_5R_6$, —$XNR_5XNR_5R_6$, —$XNR_5XR_5$, —$XNR_5XOR_6$, —$XNR_6XC(O)OR_5$, —$XNR_6XC(O)NR_6R_6$, —$XOR_5$, —$XC(O)R_5$, and —$XS(O)_{0-2}R_5$; wherein X is selected from a bond and $C_{1-4}$alkylene optionally substituted by 1 to 2 $C_{1-6}$alkyl radicals;

$R_5$ is selected from hydrogen, substituted or unsubstituted $C_{1-6}$alkyl, $C_{6-10}$aryl-$C_{0-4}$alkyl, $C_{1-10}$heteroaryl-$C_{0-4}$alkyl, $C_{3-10}$cycloalkyl-$C_{0-4}$alkyl, piperazinyl-one and $C_{3-10}$heterocycloalkyl-$C_{0-4}$alkyl; and each $R_6$ is independently selected from hydrogen and substituted or unsubstituted $C_{1-6}$alkyl;

or $R_5$ and $R_6$ together with the nitrogen to which $R_5$ and $R_6$ are both attached form heteroaryl or heterocycloalkyl that can contain an additional heteroatom selected from N, O and S as a ring member;

or $R_1$ together with the N1 of the pyrimidine ring to which $R_1$ is attached forms 2,3-dihydroimidazo[1,2-f]pyrimidine;

wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —$XNR_7R_8$, —$XOR_7$, —$XNR_7S(O)_2R_8$, —$XNR_7S(O)R_8$, —$XNR_7SR_8$, —$XC(O)NR_7R_8$, —$XC(O)NR_7XNR_7R_8$, —$XNR_7XNR_7R_8$, —$XNR_7XOR_7$, —$XNR_7C(=NR_7)NR_7R_8$, —$XS(O)_2R_9$, —$XNR_7C(O)R_8$, —$XNR_7C(O)R_9$, —$XR_9$, —$XC(O)OR_8$, —$XS(O)_2NR_7R_8$, —$XS(O)NR_7R_8$ and —$XSNR_7R_8$; wherein X is a bond or $C_{1-4}$alkylene;

$R_7$ and $R_8$ are independently selected from the group consisting of hydrogen and substituted or unsubstituted $C_{1-4}$alkyl, and wherein $R_7$ and $R_8$ on one nitrogen can optionally cyclize to form a 5-6 membered ring that can contain an additional heteroatom selected from N, O and S as a ring member; and $R_9$ is selected from $C_{3-10}$heterocycloalkyl and $C_{1-10}$heteroaryl; wherein said heterocycloalkyl or heteroaryl of $R_9$ is optionally substituted with a radical selected from the group consisting of $C_{1-4}$alkyl, —$XNR_7XNR_7R_7$, $XNR_7XOR_7$ and —$XOR_7$;

$R_2$ is selected from —$R_{11}$, —$CONR_{10}R_{11}$, $SO_2NR_{10}R_{11}$, —$NR_{10}R_{11}$, —$NR_{10}C(O)R_{11}$, —$NR_{10}S(O)_{0-2}R_{11}$ and —$NR_{10}C(O)NR_{10}R_{11}$; wherein $R_{10}$ is selected from hydrogen and substituted or unsubstituted $C_{1-6}$alkyl;

$R_{11}$ is selected from $C_{6-10}$aryl, $C_{1-10}$heteroaryl, $C_{3-10}$cycloalkyl and $C_{3-10}$heterocycloalkyl; wherein $R_{10}$ and $R_{11}$ on the same nitrogen can optionally cyclize to form a 5-6 membered ring that can contain an additional heteroatom selected from N, O and S as a ring member, and any aryl, heteroaryl, cycloalkyl or heterocycloalkyl of $R_{11}$ is optionally substituted by 1 to 3 radicals selected from halo, nitro, cyano, hydroxy, substituted or unsubstituted $C_{1-6}$alkyl, $C_{1-6}$alkoxy, halo-substituted-$C_{1-6}$alkyl, cyano-substituted-$C_{1-6}$alkyl, hydroxy-substituted-$C_{1-6}$alkyl, halo-substituted-$C_{1-6}$alkoxy, —$X_2R_{13}$, —$X_2NR_{12}C(O)R_{13}$, —$X_2NR_{12}C(O)NR_{12}R_{13}$, —$X_2NR_{12}R_{12}$, —$X_2NR_{12}R_{13}$, —$X_2NR_{12}X_2R_{13}$, —$X_2NR_{12}NR_{12}R_{12}$, —$X_2NR_{12}X_2OR_{12}$, —$X_2C(O)NR_{12}R_{13}$, —$X_2NR_{12}S(O)_{0-2}R_{13}$ and —$X_2S(O)_{0-2}NR_{12}R_{13}$; wherein $X_2$ is selected from a bond, $C_{1-4}$alkylene and $C_{2-4}$alkenylene;

$R_{12}$ is selected from hydrogen, $C_{1-6}$alkyl and hydroxy-substituted-$C_{1-6}$alkyl;

$R_{13}$ is selected from substituted or unsubstituted $C_{1-6}$alkyl, $C_{6-10}$aryl, $C_{1-10}$heteroaryl, $C_{3-10}$cycloalkyl and $C_{3-10}$heterocycloalkyl; wherein two $R_{12}$ groups or $R_{12}$ and $R_{13}$ on the same nitrogen can optionally cyclize to form a 5-6 membered ring that can contain an additional heteroatom selected from N, O and S as a ring member, any aryl, heteroaryl, cycloalkyl or heterocycloalkyl of $R_{13}$ is optionally substituted with 1 to 3 radicals independently selected from halo, cyano, hydroxy, nitro, amino, $C_{1-6}$alkyl, halo-substituted-$C_{1-6}$alkyl, hydroxy-substituted-$C_{1-6}$alkyl, cyano-substituted-$C_{1-6}$alkyl, hydroxy-substituted-$C_{1-6}$alkyl, $C_{1-6}$alkoxy, halo-substituted-$C_{1-6}$alkoxy, —$X_3NR_7R_8$, —$X_3NR_7X_3OR_7$, $C_{6-10}$aryl-$C_{0-4}$alkyl, $C_{1-10}$heteroaryl-$C_{0-4}$alkyl, $C_{3-10}$cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein $X_3$ is selected from a bond and $C_{1-4}$alkylene; $R_7$ and $R_8$ are as described above and wherein any aryl, heteroaryl, cycloalkyl or heterocycloalkyl substituents of $R_{13}$ is further optionally substituted by 1 to 3 radicals independently selected from halo, hydroxy, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy;

$R_{20}$ is selected from hydrogen, substituted or unsubstituted $C_{1-6}$alkyl, and $N(R_{21})_2$, wherein each $R_{21}$ is independently H or substituted or unsubstituted $C_{1-6}$ alkyl, and wherein two $R_{21}$ on the same nitrogen can cyclize to form a 5-6 membered ring that can contain an additional heteroatom selected from N, O and S;

and the pharmaceutically acceptable salts thereof.

2. The compound of claim 1 of Formla Ia:

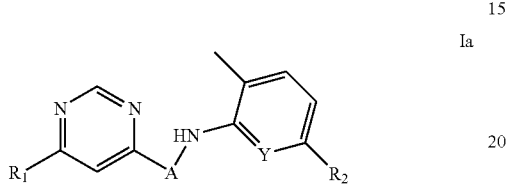

Ia in which:

A is a pyrazole optionally substituted with an $R_3$ radical; wherein $R_3$ is selected from hydrogen, halo-substituted-$C_{1-6}$ alkyl, $C_{1-6}$alkyl, —$XOR_{4a}$, —XCN, —XC(O)OR$_{4a}$, —XC(O)R$_{4b}$, —XNR$_{4a}$R$_{4a}$, —XNR$_{4a}$XNR$_{4a}$R$_{4a}$, —XC(O)NR$_{4a}$XNR$_{4a}$R$_{4a}$, —XC(O)NR$_{4a}$XR$_{4b}$, —XC(O)NR$_{4a}$XNR$_{4a}$R$_{4b}$, —XC(O)NR$_{4a}$XOR$_{4a}$, —XNR$_{4a}$XNR$_{4a}$R$_{4b}$, —XNR$_{4a}$XOR$_{4a}$, —XNR$_{4a}$XCF$_3$, —XC(O)NR$_{4a}$R$_{4a}$, and —XR$_{4b}$; wherein X is selected from a bond and $C_{1-4}$alkylene;

$R_{4a}$ is selected from hydrogen and $C_{1-6}$alkyl; and $R_{4b}$ is selected from $C_{6-10}$aryl, $C_{1-10}$heteroaryl, $C_{3-10}$cycloalkyl and $C_{3-10}$heterocycloalkyl; wherein any cycloalkyl, heterocycloalkyl, aryl or heteroaryl of $R_{4b}$ is optionally substituted with 1 to 3 radicals independently selected from $C_{1-6}$alkyl and —NR$_{4c}$R$_{4d}$; wherein each $R_{4c}$ and $R_{4d}$ is independently selected from hydrogen and $C_{1-6}$alkyl;

$R_1$ is selected from —XNR$_5$R$_6$, —XNR$_5$XNR$_5$R$_6$, —XNR$_5$XR$_5$, —XNR$_5$XOR$_6$, —XNR$_6$XC(O)OR$_5$, —XNR$_6$XC(O)NR$_6$R$_6$, —XOR$_5$, —XC(O)R$_5$, and —XS(O)$_{0-2}$R$_5$; wherein X is selected from a bond and $C_{1-4}$alkylene optionally substituted by 1 to 2 $C_{1-6}$alkyl radicals;

$R_5$ is selected from hydrogen, $C_{1-6}$alkyl, $C_{6-10}$aryl-$C_{0-4}$alkyl, $C_{1-10}$heteroaryl-$C_{0-4}$alkyl, $C_{3-10}$cycloalkyl-$C_{0-4}$alkyl, piperazinyl-one and $C_{3-10}$heterocycloalkyl-$C_{0-4}$alkyl; and each $R_6$ is independently selected from hydrogen and $C_{1-6}$alkyl;

or $R_5$ and $R_6$ together with the nitrogen to which $R_5$ and $R_6$ are both attached form heteroaryl or heterocycloalkyl;

or $R_1$ together with the N1 of the pyrimidine ring to which $R_1$ is attached forms 2,3-dihydroimidazo[1,2-f]pyrimidine;

wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —XNR$_7$R$_8$, —XOR$_7$, —XNR$_7$S(O)$_2$R$_8$, —XNR$_7$S(O)R$_8$, —XNR$_7$SR$_8$, —XC(O)NR$_7$R$_8$, —XC(O)NR$_7$XNR$_7$R$_8$, —XNR$_7$C(O)NR$_7$R$_8$, —XNR$_7$XNR$_7$R$_8$, —XNR$_7$XOR$_7$, —XNR$_7$C(=NR$_7$)NR$_7$R$_8$, —XS(O)$_2$R$_9$, —XNR$_7$C(O)R$_8$, —XNR$_7$C(O)R$_9$, —XR$_9$, —XC(O)OR$_8$, —XS(O)$_2$NR$_7$R$_8$, —XS(O)NR$_7$R$_8$ and —XSNR$_7$R$_8$; wherein X is a bond or $C_{1-4}$alkylene; $R_7$ and $R_8$ are independently selected from the group consisting of hydrogen and $C_{1-4}$alkyl; and $R_9$ is selected from $C_{3-10}$heterocycloalkyl and $C_{1-10}$heteroaryl; wherein said heterocycloalkyl or heteroaryl of $R_9$ is optionally substituted with a radical selected from the group consisting of $C_{1-4}$alkyl, —XNR$_7$XNR$_7$R$_7$, XNR$_7$XOR$_7$ and —XOR$_7$;

$R_2$ is selected from —$R_{11}$, —CONR$_{10}$R$_{11}$, —SO$_2$NR$_{10}$R$_{11}$, —NR$_{10}$R$_{11}$, —NR$_{10}$C(O)R$_{11}$, —NR$_{10}$S(O)$_{0-2}$R$_{11}$ and —NR$_{10}$C(O)NR$_{10}$R$_{11}$;

$R_{10}$ is selected from hydrogen and $C_{1-6}$alkyl;

$R_{11}$ is selected from $C_{6-10}$aryl, $C_{1-10}$heteroaryl, $C_{3-10}$cycloalkyl and $C_{3-10}$heterocycloalkyl; wherein any aryl, heteroaryl, cycloalkyl or heterocycloalkyl of $R_{11}$ is optionally substituted by 1 to 3 radicals selected from halo, nitro, cyano, hydroxy, $C_{1-6}$alkyl, $C_{1-6}$alkoxy, halo-substituted-$C_{1-6}$alkyl, cyano-substituted-$C_{1-6}$alkyl, hydroxy-substituted-$C_{1-6}$alkyl, halo-substituted-$C_{1-6}$alkoxy, —$X_2R_{13}$, —$X_2$NR$_{12}$C(O)R$_{13}$, —$X_2$NR$_{12}$C(O)NR$_{12}$R$_{13}$, —$X_2$NR$_{12}$R$_{12}$, —$X_2$NR$_{12}$R$_{13}$, —$X_2$NR$_{12}$X$_2$R$_{13}$, —$X_2$NR$_{12}$NR$_{12}$R$_{12}$, —$X_2$NR$_{12}$X$_2$OR$_{12}$, —$X_2$C(O)NR$_{12}$R$_{13}$, —$X_2$NR$_{12}$S(O)$_{0-2}$R$_{13}$ and —$X_2$S(O)$_{0-2}$NR$_{12}$R$_{13}$; wherein $R_{12}$ is selected from hydrogen, $C_{1-6}$alkyl and hydroxy-substituted-$C_{1-6}$alkyl; wherein $X_2$ is selected from a bond, $C_{1-4}$alkylene and $C_{2-4}$alkenylene;

$R_{13}$ is selected from $C_{6-10}$aryl, $C_{1-10}$heteroaryl, $C_{3-10}$cycloalkyl and $C_{3-10}$heterocycloalkyl; wherein any aryl, heteroaryl, cycloalkyl or heterocycloalkyl of $R_{13}$ is optionally substituted with 1 to 3 radicals independently selected from halo, cyano, hydroxy, nitro, amino, $C_{1-6}$alkyl, halo-substituted-$C_{1-6}$alkyl, hydroxy-substituted-$C_{1-6}$alkyl, cyano-substituted-$C_{1-6}$alkyl, hydroxy-substituted-$C_{1-6}$alkyl, $C_{1-6}$alkoxy, halo-substituted-$C_{1-6}$alkoxy, —$X_3$NR$_7$R$_8$, —$X_3$NR$_7$X$_3$OR$_7$, $C_{6-10}$aryl-$C_{0-4}$alkyl, $C_{1-10}$heteroaryl-$C_{0-4}$alkyl, $C_{3-10}$cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein $X_3$ is selected from a bond and $C_{1-4}$alkyelene; $R_7$ and $R_8$ are as described above and wherein any aryl, heteroaryl, cycloalkyl or heterocycloalkyl substituents of $R_{13}$ is further optionally substituted by 1 to 3 radicals independently selected from halo, hydroxy, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy; and Y is selected from C and N.

3. The compound of claim 2 selected from Formula Ib, Ic and Id:

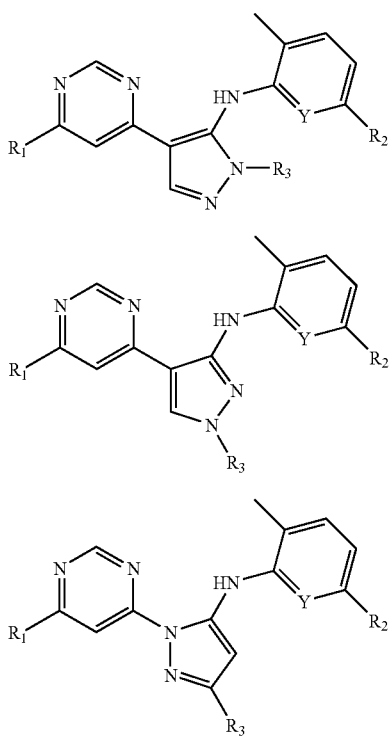

in which:
R$_1$ is selected from —XNR$_5$R$_6$, —XNR$_5$XNR$_5$R$_6$, —XNR$_5$XR$_5$, —XNR$_5$XOR$_6$, —XNR$_6$XC(O)OR$_5$, —XNR$_6$XC(O)NR$_6$R$_6$, —OR$_5$, —XC(O)R$_5$, and —XS(O)$_{0-2}$R$_5$; wherein
  X is selected from a bond and C$_{1-4}$alkylene optionally substituted by 1 to 2 C$_{1-6}$alkyl radicals;
  R$_5$ is selected from hydrogen, C$_{1-6}$alkyl, C$_{6-10}$aryl-C$_{0-4}$alkyl, C$_{1-10}$heteroaryl-C$_{0-4}$alkyl, C$_{3-10}$cycloalkyl-C$_{0-4}$ alkyl, piperazinyl-one and C$_{3-10}$heterocycloalkyl-C$_{0-4}$alkyl; and each R$_6$ is independently selected from hydrogen and C$_{1-6}$alkyl;
  or R$_5$ and R$_6$ together with the nitrogen to which R$_5$ and R$_6$ are both attached form heteroaryl or heterocycloalkyl;
  or R$_1$ together with the N1 of the pyrimidine ring to which R$_1$ is attached forms 2,3—dihydroimidazol[1,2-f]pyrimidine;
  wherein any aryl, heteroaryl, cycloalkyl and heterocycloalkyl of R$_5$ or the combination of R$_5$ and R$_6$ can be optionally substituted with 1 to 3 radicals independently selected from halo, nitro, cyano, hydroxy, C$_{1-6}$alkyl, C$_{1-6}$alkoxy, halo-substituted-alkyl, halo-substituted-alkoxy, —XNR$_7$R$_8$, —XOR$_7$, —XNR$_7$S(O)$_2$R$_8$, —XNR$_7$S(O)R$_8$, —XNR$_7$SR$_8$, —XC(O)NR$_7$R$_8$, —XC(O)NR$_7$XNR$_7$R$_8$, —XNR$_7$C(O)NR$_7$R$_8$, —XNR$_7$NR$_7$R$_8$, —XNR$_7$XOR$_7$, —XNR$_7$C(=NR$_7$)NR$_7$R$_8$, —XS(O)$_2$R$_9$, —XNR$_7$C(O)R$_8$, —XNR$_7$C(O)R$_9$, —XR$_9$, —XC(O)OR$_8$, —XS(O)$_2$NR$_7$R$_8$, —XS(O)NR$_7$R$_8$ and —XSNR$_7$R$_8$; wherein X is a bond or C$_{1-4}$alkylene; each R$_7$ and R$_8$ are independently selected from the group consisting of hydrogen and C$_{1-4}$alkyl, or R$_7$ and R$_8$ together with the nitrogen to which R$_7$ and R$_8$ are both attached form heteroaryl or heterocycloalkyl; and R$_9$ is selected from C$_{3-10}$heterocycloalkyl and C$_{1-10}$heteroaryl; wherein said heterocycloalkyl or heteroaryl of R$_9$ is optionally substituted with a radical selected from the group consisting of C$_{1-4}$alkyl, —XNR$_7$XNR$_7$R$_7$, XNR$_7$XOR$_7$ and —XOR$_7$;

R$_2$ is selected from —R$_{11}$, —CONR$_{10}$R$_{11}$, SO$_2$NR$_{10}$R$_{11}$, —NR$_{10}$R$_{11}$, —NR$_{10}$C(O)R$_{11}$, —NR$_{10}$S(O)$_{0-2}$R$_{11}$ and —NR$_{10}$C(O)NR$_{10}$R$_{11}$; wherein R$_{10}$ is selected from hydrogen and C$_{1-6}$alkyl; R$_{11}$ is selected from C$_{6-10}$aryl, C$_{1-10}$heteroaryl, C$_{3-10}$cycloalkyl and C$_{3-10}$heterocycloalkyl; and any aryl, heteroaryl, cycloalkyl or heterocycloalkyl of R$_{11}$ is optionally substituted by 1 to 3 radicals selected from halo, nitro, cyano, hydroxy, C$_{1-6}$alkyl, C$_{1-6}$alkoxy, halo-substituted-C$_{1-6}$alkyl, cyano-substituted-C$_{1-6}$alkyl, hydroxy-substituted-C$_{1-6}$ alkyl, halo-substituted-C$_{1-6}$alkoxy, —X$_2$R$_{13}$, —X$_2$NR$_{12}$C(O)R$_{13}$, —X$_2$NR$_{12}$C(O)NR$_{12}$R$_{13}$, —X$_2$NR$_{12}$R$_{12}$, —X$_2$NR$_{12}$R$_{13}$, —X$_2$NR$_{12}$X$_2$R$_{13}$, —X$_2$NR$_{12}$NR$_{12}$R$_{12}$, —X$_2$NR$_{12}$X$_2$OR$_{12}$, —X$_2$C(O)NR$_{12}$R$_{13}$, —X$_2$S(O)$_{0-2}$R$_{12}$, —X$_2$NR$_{12}$S(O)$_{0-2}$R$_{13}$ and —X$_2$S(O)$_{0-2}$NR$_{12}$R$_{13}$; wherein X$_2$ is selected from a bond, C$_{1-4}$alkylene and C$_{2-4}$alkenylene; R$_{12}$ is selected from hydrogen, C$_{1-6}$alkyl and hydroxy-substituted-C$_{1-6}$alkyl; R$_{13}$ is selected from C$_{6-10}$aryl, C$_{1-10}$heteroaryl, C$_{3-10}$cycloalkyl and C$_{3-10}$heterocycloalkyl; wherein two R$_{12}$ of NR$_{12}$R$_{12}$ or R$_{12}$ and R$_{13}$ of NR$_{12}$R$_{13}$ together with the nitrogen to which both are attached optionally form heteroaryl or heterocycloalkyl, and any aryl, heteroaryl, cycloalkyl or heterocycloalkyl of R$_{13}$ is optionally substituted with 1 to 3 radicals independently selected from halo, cyano, hydroxy, nitro, amino, C$_{1-6}$alkyl, halo-substituted-C$_{1-6}$alkyl, hydroxy-substituted-C$_{1-6}$alkyl, cyano-substituted-C$_{1-6}$alkyl, hydroxy-substituted-C$_{1-6}$ alkyl, C$_{1-6}$alkoxy, halo-substituted-C$_{1-6}$alkoxy, —X$_3$NR$_7$R$_8$, —X$_3$NR$_7$X$_3$OR$_7$, C$_{6-10}$aryl-C$_{0-4}$alkyl, C$_{1-10}$heteroaryl-C$_{0-4}$alkyl, C$_{3-10}$cycloalkyl-C$_{0-4}$alkyl, C$_{3-10}$heterocycloalkyl-C$_{0-4}$alkoxy and C$_{3-10}$heterocycloalkyl-C$_{0-4}$alkyl; wherein X$_3$ is selected from a bond and C$_{1-4}$alkyelene; R$_7$ and R$_8$ are as described above and wherein any aryl, heteroaryl, cycloalkyl or heterocycloalkyl substituents of R$_{13}$ is further optionally substituted by 1 to 3 radicals independently selected from halo, hydroxy, C$_{1-6}$alkyl, halo-substituted-C$_{1-6}$alkyl, hydroxy-substituted-C$_{1-6}$alkyl, C$_{1-6}$alkoxy, C$_{3-10}$heterocycloalkyl and halo-substituted-C$_{1-6}$alkoxy;

R$_3$ is selected from hydrogen, halo-substituted-C$_{1-6}$alkyl, C$_{1-6}$alkyl, —XOR$_{4a}$, —XCN, —XC(O)OR$_{4a}$, —XC(O)R$_{4b}$, —XNR$_{4a}$R$_{4a}$, —XNR$_{4a}$XNR$_{4a}$R$_{4a}$, —XC(O)NR$_{4a}$XNR$_{4a}$R$_{4a}$, —XC(O)NR$_{4a}$XR$_{4b}$, —XC(O)NR$_{4a}$XNR$_{4a}$R$_{4b}$, —XC(O)NR$_{4a}$XOR$_{4a}$, —XNR$_{4a}$XNR$_{4a}$R$_{4b}$, —XNR$_{4a}$XOR$_{4a}$, —XNR$_{4a}$XCF$_3$, —XC(O)NR$_{4a}$R$_{4a}$, and —XR$_{4b}$;
wherein
X is selected from a bond and C$_{1-4}$alkylene;
R$_{4a}$ is selected from hydrogen and C$_{1-6}$alkyl; and R$_{4b}$ is selected from C$_{6-10}$aryl, C$_{1-10}$heteroaryl, C$_{3-10}$cycloalkyl and C$_{3-10}$heterocycloalkyl; wherein two R$_{4a}$ of NR$_{4a}$R$_{4a}$ together with the nitrogen to which both are attached optionally form heteroaryl or heterocycloalkyl, and any cycloalkyl, heterocycloalkyl, aryl or heteroaryl of R$_{4b}$ is optionally substituted with 1 to 3 radicals independently selected from C$_{1-6}$alkyl and —NR$_{4c}$R$_{4d}$; wherein each R$_{4c}$ and R$_{4d}$ is independently selected from hydrogen and C$_{1-6}$alkyl, and R$_{4c}$ and R$_{4d}$ of NR$_{4c}$R$_{4d}$ together with the nitrogen to which $R_{4c}$ and $R_{4d}$ are attached optionally form a heteroaryl or heterocycloalkyl; and Y is selected from CH and N.

4. The compound of claim 3 in which $R_3$ is selected from hydrogen, methyl, morpholino-ethyl, ethoxy-carbonyl, chloro, trifluoromethyl, (methyl-piperidinyl)(methyl)amino-methyl, methyl-amino-carbonyl, hydroxy-methyl, dimethyl-amino-methyl, methyl-amino-methyl, morpholino-methyl, diethyl-amino-ethyl-amino-methyl, methyl-piperazinyl-methyl, methyl-piperazinyl-ethyl-amino-methyl, dimethyl-amino-propyl-amino-methyl, ((2-hydroxyethyl)(methyl) amino)methyl, ethyl-amino-methyl, trifluoromethyl-amino-methyl, dimethyl-amino-ethyl-amino-carbonyl, piperidinyl-ethyl-amino-carbonyl, morpholino-ethyl-amino-carbonyl, morpholino-carbonyl, amino-carbonyl, dimethyl-amino-carbonyl, dimethyl-amino-pyrrolidinyl-methyl, dimethyl-amino-pyrrolidinyl-carbonyl, thiomorpholino-methyl, methoxy-ethyl-piperazinyl-methyl, methoxy-ethyl-amino-carbonyl, cyano-methyl, (2,6-dimethylmorpholino)methyl, (2,6-dimethyl-piperidinyl)ethyl-amino-carbonyl and cyclopropyl-amino-carbonyl.

5. The compound of claim 4 in which $R_1$ is selected from morpholino-ethyl-amino, methyl-amino, methyl-piperazinyl-ethyl-amino, cyclopropyl-amino, hydroxy-ethyl-piperazinyl-amino, isopropyl-amino, dimethyl-amino-ethyl-amino, methyl-piperazinyl-amino, amino, 2,6-dimethyl-morpholino-ethyl-amino, hydroxy-pyridinyl-ethyl-amino, amino-ethyl-amino, 3-oxopiperazin-1-yl-ethyl-amino, hydroxy-ethyl-amino, hydroxy-propyl-amino, methyl-sulfanyl, methoxy, sulfanyl, pyridinyl-ethyl-amino, pyridinyl-methyl-amino, morpholino-methyl-pyridinyl-amino, carboxy-propyl-amino, carboxy-methyl-amino, azetidin-3-yl-amino, azetidin-3-yl-methyl-amino, carboxy-ethyl-amino and hydroxy-pyrrolidinyl.

6. The compound of claim 5 in which $R_2$ is selected from —$R_{11}$, —CONHR$_{11}$, SO$_2$NHR$_{11}$, —NHR$_{11}$, —NHC(O)R$_{11}$, —NHS(O)$_{0-2}$R$_{11}$ and —NHC(O)NHR$_{11}$; wherein $R_{11}$ is selected from phenyl, pyridinyl, thiazolyl, benzimidazolyl, isoxazolyl, 1,2,3,4-tetrahydronaphthyl, benzothiazolyl, benzo[d][1,2,3]triazole, 2,3-dihydrobenzofuran and 2,3-dihydro-3,3-dimethylbenzofuran-5-yl; wherein said phenyl, pyridinyl, thiazolyl, isoxazolyl and 2,3-dihydro-3,3-dimethylbenzofuran-5-yl of $R_2$ are optionally substituted with 1 to 3 radicals independently selected from halo, isopropyl, methyl-sulfonyl, hydroxy, methyl-sulfonyl-amino, 1-(2-hydroxy-ethylamino)cyclopropyl, 3-(3-hydroxypropylamino)cyclobutyl, isopropyl-amino-cyclobutyl, 2-(2-hydroxyethylamino)propan-2-yl, 3-aminoprop-1-enyl, isopropyl-3-aminoprop-1-enyl, isopropyl-amino-propyl, isopropyl-amino-ethyl, hydroxyethyl-3-aminoprop-1-enyl, methyl-amino, 1,2-dihydroxyethyl, 2-hydroxy-ethyl, (3-hydroxyazetidin-1-yl)methyl, (3-methoxyazetidin-1-yl)methyl, 2-methyl-morpholino-methyl, (3-methoxypyrrolidin-1-yl)methyl, (2-hydroxy-2-methylpropylamino)methyl, 1-methyl-1,2,3,6-tetrahydropyridin-4-yl, 1,2,3,6-tetrahydropyridin-4-yl, piperidin-4-yl, (4-ethylpiperazin-1-yl)methyl, pyrrolidiny-1-yl-methyl, 1-(ethylamino)ethyl, 4-( 2-hydroxypropyl)-1-piperazinyl, 3-trifluoromethyl-4-methyl-1-piperazinyl, difluoro-methyl, 4-methyl-1-imidazolyl, methyl-sulfonyl-ethyl-amino-carbonyl, hydroxy-propyl-amino-carbonyl, 4-t-butoxy-carbonyl-1-piperazinyl, 4-(1-carboxyethyl)piperazin-1-yl, 4,7-diazaspiro[2.5]octan-7-yl, ethoxy, 4-(tert-butoxycarbonyl)-2-oxopiperazin-1-yl, 4-methyl-2-oxopiperazin-1-yl, 2-oxopiperazin-1-yl, methoxy, ethyl, pyrazolyl, trifluoromethyl, 2-cyanobutan-2-yl, 1-cyanocyclopropyl, 2-hydroxypropan-2-yl, difluoromethyl, 3-ethylpentan-3-yl, methyl-piperazinyl, ethyl-piperazinyl, t-butyl, t-butoxy, 1,2-dihydroxypropyl, 2-hydroxymethyl-ethyl, cyclopropyl-1-piperazinyl, 4-methyl-sulfonyl-ethyl-1-piperazinyl, 2-hydroxy-propyl-amino-methyl, (tetrahydrofuran-2-ylamino)methyl, (2,3-dihydroxypropylamino) methyl), (1,3-dihydroxypropan-2-ylamino)methyl, (1-hydroxy-2-methylpropan-2-ylamino)methyl, cyclobutyl-amino-methyl, 4-hydroxy-piperidinyl, (1-hydroxypropan-2-ylamino)methyl, dimethyl-amino-amino-methyl, methoxy-amino-methyl, hydroxy-amino-methyl, 2-hydroxy-methyl-pyrrolidin-1-yl-methyl, pyrrolidinyl-ethoxy, 3-hydroxy-pyrrolidinyl, 3-hydroxyazetidin-1-yl, 3-(methoxy-carbonyl)-4-methylpiperazin-1-yl, 4-methylpiperazin-1-yl, 4-methyl-3-hydroxymethyl-piperazin-1-yl, 4-methoxy-carbonyl-piperidinyl, 4-carboxy-piperidinyl, piperazinyl, 4-(2,2,2-trifluoroethyl)piperazin-1-yl, 2-hydroxy-cyclopent-1-yl-amino-methyl, amino-carbonyl-methyl, dimethyl-amino-propyl(methyl)-amino, (2-(dimethylamino)ethyl)(methyl) amino, methoxy-ethyl(methyl)amino, dimethyl-amino-ethoxy, nitro, 1-methyl-4-piperidinyloxy, morpholino, 2-methyl-morpholino, 4-ethyl-piperazin-1-yl-methyl, ethyl-amino-methyl, cyclopropyl-amino-methyl, diethyl-amino-ethyl, azetidin-1-ylmethyl, 3-hydroxy-pyrrolidin-1-yl-methyl, hydroxy-ethyl-amino-methyl, propyl-amino-methyl, 3-hydroxy-azetidin-1-ylmethyl, 4-methoxyethyl-1-piperazinyl, methoxy-ethyl-amino-methyl, butyl-amino-ethyl, t-butyl-amino-methyl, hydroxy-cyclohexyl-amino-methyl, amino-methyl, hydroxy-propyl-amino-methyl, hydroxy-ethyl(methyl)amino-methyl, 4-hydroxypropyl-1-piperazinyl, 4-carboxy-methyl-piperazinyl, dimethyl-amino-methyl, isopropyl-amino-methyl, 4-dimethyl-amino-carbonyl-methyl-1-piperazinyl, 4-(2-hydroxypropyl)piperazin-1-yl, hydroxy-ethyl-piperazinyl, methyl, cyclopropyl, halo, trifluoromethoxy, difluoromethoxy, 2-fluoropropan-2-yl, 2-methoxy-propan-2-yl, 1,1-difluoroethyl, 1-methyl-1-fluoroethyl, 1-methyl-1-methoxy-ethyl, 2-hydroxypropan-2-yl, 2-methoxypropan-2-yl, 2-cyanopropan-2-yl, 3-cyanopropan-2-yl, 2,3-difluoropropan-2-yl and cyano-cyclopropyl.

7. The compound of claim 1 selected from N-(4-Methyl-3-{2-methyl-4-[6-(2-morpholin-4-yl-ethylamino)-pyrimidin-4-yl]-2H-pyrazol-3-ylamino}-phenyl)-3-trifluoromethyl-benzamide, N-(4-Methyl-3-{1-methyl-4-[6-(2-morpholin-4-yl-ethylamino)-pyrimidin-4-yl]-1H-pyrazol-3-ylamino}1-phenyl)-3-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-{4-Methyl-3-[2-(6-methylamino-pyrimidin-4-yl)-2H-pyrazol-3-ylamino]-phenyl}-3-(4-methyl-piperazin-1-yl)-5-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-[4-Methyl-3-(5-methyl-2-{6-[2-(4-methyl-piperazin-1-yl)-ethylamino]-pyrimidin-4-yl}-2H-pyrazol-3-ylamino)-phenyl]-3-trifluoromethyl-benzamide, N-{3-[2-(6-Cyclopropylamino-pyrimidin-4-yl)-5-methyl-2H-pyrazol-3-ylamino]-4-methyl-phenyl}-3-trifluoromethyl-benzamide, N-{3-[4(6-Cyclopropylamino-pyrimidin-4-yl)-2-methyl-2H-pyrazol-3-ylamino]-4-methyl-phenyl}-3-trifluoromethyl-benzamide, N-[4-Methyl-3-(2-methyl-4-{6-[2-(4-methyl-piperazin-1-yl)-ethylamino]-pyrimidin-4-yl}-2H-pyrazol-3-ylamino)-phenyl]-3-trifluoromethyl-benzamide, N-(4-Methyl-3-{2-methyl-4-[6-(2-morpholin-4-yl-ethylamino)-pyrimidin-4-yl]-2H-pyrazol-3-ylamino}-phenyl)-3-trifluoromethyl-benzamide, N-{3-[4-(6-Cyclopropylamino-pyrimidin-4-yl)-1-methyl-1H-pyrazol-3-ylamino]-4-methyl-phenyl}-3-trifluoromethyl-benzamide, N-[4-Methyl-3-(1-methyl-4-{6-[2-(4-methyl-piperazin-1-yl)- ethylamino]-pyrimidin-4-yl}-1H-pyrazol-3-ylamino)-phenyl]-3-trifluoromethyl-benzamide, N-(4-Methyl-3-{1-methyl-4-[6-(2-morpholin-4-yl-ethylamino)-pyrimidin-4-yl]-1H-pyrazol-3-ylamino}-phenyl)-3-trifluoromethyl-benzamide, N-{3-[2-(6-Cyclopropylamino-pyrimidin-4-yl)-5-methyl-2H-pyrazol-3-ylamino]-4-methyl-phenyl}-3-(4-methyl-piperazin-1-yl)-5-trifluoromethyl-benzamide, N-{4-Methyl-3-[5-methyl-2-(6-methylamino-pyrimidin-4-yl)-2H-pyrazol-3-ylamino]-phenyl}-3-(4-methyl-piperazin-1-yl)-5-trifluoromethyl-benzamide, N-{3-[2-(6-Cyclopropylamino-pyrimidin-4-yl)-5-methyl-2H-pyrazol-3-ylamino]-4-methyl-phenyl}-3-(4-ethyl-piperazin-1-yl)-5-trifluoromethyl-benzamide, 3-(4-Ethyl-piperazin-1-yl)-N-{4-methyl-3-[5-methyl-2-(6-methylamino-pyrimidin-4-yl)-2H-pyrazol-3-ylamino]-phenyl}-5-trifluoromethyl-benzamide, 3-(4-Ethyl-piperazin-1-yl)-N-(4-methyl-3-{5-methyl-2-[6-(4-methyl-piperazin-1-ylamino)-pyrimidin-4-yl]-2H-pyrazol-3-ylamino}-phenyl)-5-trifluoromethyl-benzamide, N-(4-Methyl-3-{5-methyl-2-[6-(4-methyl-piperazin-1-ylamino)-pyrimidin-4-yl]-2H-pyrazol-3-ylamino}-phenyl)-3-(4-methyl-piperazin-1-yl)-5-trifluoromethyl-benzamide, N-{4-Methyl-3-[2-(6-methylamino-pyrimidin-4-yl)-2H-pyrazol-3-ylamino]-phenyl}-3-(4-methyl-piperazin-1-yl)-5-trifluoromethyl-benzamide, 3-(4-Ethyl-piperazin-1-yl)-N-{4-methyl-3-[2-(6-methylamino-pyrimidin-4-yl)-2H-pyrazol-3-ylamino]-phenyl}-5-trifluoromethyl-benzamide, N-(4-Methyl-3-{5-methyl-2-[6-(4-methyl-piperazin-1-ylamino)-pyrimidin-4-yl]-2H-pyrazol-3-ylamino}-phenyl)-3-trifluoromethyl-benzamide, 5-Methyl-6-[2-(6-methylamino-pyrimidin-4-yl)-2H-pyrazol-3-ylamino]-pyridine-2-carboxylic acid (3-trifluoromethyl-phenyl)-amide, 5-Methyl-6-[5-methyl-2-(6-methylamino-pyrimidin-4-yl)-2H-pyrazol-3-ylamino]-pyridine-2-carboxylic acid (3-trifluoromethyl-phenyl)-amide, 5-Methyl-6-{2-[6-(2-morpholin-4-yl-ethylamino)-pyrimidin-4-yl]-2H-pyrazol-3-ylamino}-pyridine-2-carboxylic acid (3-trifluoromethyl-phenyl)-amide, N-(4-Methyl-3-{2-[6-2-morpholin-4-yl-ethylamino)-pyrimidin-4-yl]-2H-pyrazol-3-ylamino}-phenyl)-3-trifluoromethyl-benzamide, N-{3-[2-(6-Cyclopropylamino-pyrimidin-4-yl)-2H-pyrazol-3-ylamino]-4-methyl-phenyl}-3-trifluoromethyl-benzamide, N-{3-[2-(6-Amino-pyrimidin-4-yl)-2H-pyrazol-3-ylamino]-4-methyl-phenyl}-3-trifluoromethyl-benzamide, N-{3-[2-(6-Cyclopropylamino-pyrimidin-4-yl)-2H-pyrazol-3-ylamino]-4-methyl-phenyl}-3-(4-methyl-piperazin-1-yl)-5-trifluoromethyl-benzamide, N-[3-(2-{6-[2-(2,6-Dimethyl-morpholin-4-yl)-ethylamino]-pyrimidin-4-yl}-5-methyl-2H-pyrazol-3-ylamino)-4-methyl-phenyl]-3-trifluoromethyl-benzamide, N-[3-(2-{6-[2-(4-Hydroxy-piperidin-1-yl)-ethylamino]-pyrimidin-4-yl}-5-methyl-2H-pyrazol-3-ylamino)-4-methyl-phenyl]-3-trifluoromethyl-benzamide, N-[4-Methyl-3-(5-methyl-2-{6-[2(4-oxo-piperazin-1-yl)-ethylamino]-pyrimidin-4-yl}-2H-pyrazol-3-ylamino)-phenyl]-3-trifluoromethyl-benzamide, N-(3-{2-[6-(2-Amino-ethylamino)-pyrimidin-4-yl]-5-methyl-2H-pyrazol-3-ylamino}-4-methyl-phenyl)-3-trifluoromethyl-benzamide, 2-tert-Butyl-N-(4-methyl-3-{2-[6-(2-morpholin-4-yl-ethylamino)-pyrimidin-4-yl]-2H-pyrazol-3-ylamino}-phenyl)-isonicotinamide, 2-tert-Butyl-N-(4-methyl-3-{5-methyl-2-[6-(2-morpholin-4-yl-ethylamino)-pyrimidin-4-yl]-2H-pyrazol-3-ylamino}-phenyl)-isonicotinamide, N-{4-Methyl-3-[4-(6-methylamino-pyrimidin-4-yl)-1H-pyrazol-3-ylamino]-phenyl}-3-trifluoromethyl-benzamide, N-{4-Methyl-3-[4-(6-methylamino-pyrimidin-4-yl)-1-(2-morpholin-4-yl-ethyl)-1H-pyrazol-3-ylamino]-phenyl}-3-trifluoromethyl-benzamide, N-{4-Methyl-3-[1-methyl-4-(6-methylamino-pyrimidin-4-yl)-1H-pyrazol-3-ylamino]-phenyl}-3-(4-methyl-piperazin-1-yl)-5-trifluoromethyl-benzamide, 3-[4-(2-Hydroxy-ethyl)-piperazin-1-yl]-N-{4-methyl-3-[1-methyl-4-(6-methylamino-pyrimidin-4-yl)-1H-pyrazol-3-ylamino]-phenyl}-5-trifluoromethyl-benzamide, N-{3-[4-6-Cyclopropylamino-pyrimidin-4-yl)-1-methyl-1H-pyrazol-3-ylamino]-4-methyl-phenyl}-3-(4-methyl-piperazin-1-yl)-5-trifluoromethyl-benzamide, N-{3-[4-(6-Cyclopropylamino-pyrimidin-4-yl)-1-methyl-1H-pyrazol-3-ylamino]-4-methyl-phenyl}-3-[4-(2-hydroxy-ethyl)-piperazin-1-yl]-5-trifluoromethyl-benzamide, N-(3-{2-[6-(2-Hydroxy-ethylamino)-pyrimidin-4-yl]-5-methyl-2H-pyrazol-3-ylamino}-4-methyl-phenyl)-3-trifluoromethyl-benzamide, N-{4-Methyl-3-[5-methyl-2-(6-methylsulfanyl-pyrimidin-4-yl)-2H-pyrazol-3-ylamino]-phenyl}-3-trifluoromethyl-benzamide, N-{3-[2-(2,3-Dihydro-imidazo[1,2-c]pyrimidin-7-yl)-5-methyl-2H-pyrazol-3-ylamino]-4-methyl-phenyl}-3-trifluoromethyl-benzamide, 2-tert-Butyl-N-(4-methyl-3-{5-methyl-2-[6-(4-methyl-piperazin-1-ylamino)-pyrimidin-4-yl]-2H-pyrazol-3-ylamino}-phenyl)-isonicotinamide, N-{3-[2-(6-Methoxy-pyrimidin-4-yl)-5-methyl-2H-pyrazol-3-ylamino]-4-methyl-phen-yl}-3-trifluoromethyl-benzamide, N-{4-Methyl-3-[5-methyl-2-(6-methylamino-pyrimidin-4-yl)-2H-pyrazol-3-ylamino]-phenyl}-3-trifluoromethyl-benzamide, N-{3-[2-(6-Amino-pyrimidin-4-yl)-5-methyl-2H-pyrazol-3-ylamino]-4-methyl-phenyl}-3-trifluoromethyl-benzamide, N-{4-Methyl-3-[2-(6-methylamino-pyrimidin-4-yl)-2H-pyrazol-3-ylamino]-phenyl}-3-trifluoromethyl-benzamide, N-{3-[2-(6-Mercapto-pyrimidin-4-yl)-5-methyl-2H-pyrazol-3-ylamino]-4-methyl-phenyl}-3-trifluoromethyl-benzamide, N-(4-Methyl-3-{5-methyl-2-[6-2-pyridin-3-yl-ethylamino)-pyrimidin-4-yl]-2H-pyrazol-3-ylamino}-phenyl)-3-trifluoromethyl-benzamide, 4-(6-{3-Methyl-5-[2-methyl-5-(3-trifluoromethyl-benzoylamino)-phenylamino]-pyrazol-1-yl}-pyrimidin-4-ylamino)-butyric acid, (6-{3-Methyl-5-[2-methyl-5-(3-trifluoromethyl-benzoylamino)-phenylamino]-pyrazol-1-yl}-pyrimidin-4-ylamino)-acetic acid, N-(3-{2-[6-(Azetidin-3-ylamino)-pyrimidin-4-yl]-5-methyl-2H-pyrazol-3-ylamino}-4-methyl-phenyl)-3-trifluoromethyl-benzamide, 3-(6-{3-Methyl-5-[2-methyl-5-(3-trifluoromethyl-benzoylamino)-phenylamino]-pyrazol-1-yl}-pyrimidin-4-ylamino)-propionic acid, N-(3-{2-[6-(3-Hydroxy-pyrrolidin-1-yl)-pyrimidin-4-yl]-5-methyl-2H-pyrazol-3-ylamino}-4-methyl-phenyl)-3-trifluoromethyl-benzamide, N-[3-(2-{6-[(Azetidin-3-ylmethyl)-amino]-pyrimidin-4-yl}-5-methyl-2H-pyrazol-3-ylamino)-4-methyl-phenyl]-3-trifluoromethyl-benzamide, N-[4-Methyl-3-(5-methyl-2-{6-[(pyridin-2-ylmethyl)-amino]-pyrimidin-4-yl}-2H-pyrazol-3-ylamino)-phenyl]-3-trifluoromethyl-benzamide, 4-Methyl-3-[5-methyl-2-(6-methylamino-pyrimidin-4-yl)-2H-pyrazol-3-ylamino]-N-[3-(4-methyl-piperazin-1-yl)-5-trifluoromethyl-phenyl]-benzamide, 5-Methyl-N-(4-methyl-3-{5-methyl-2-[6-(5-morpholin-4-ylmethyl-pyridin-2-ylamino)-pyrimidin-4-yl]-2H-pyrazol-3-ylamino}-phenyl)-nicotinamide, 3-Cyclopropyl-isoxazole-5-carboxylic acid (4-methyl-3-{5-methyl-2-[6-(5-morpholin-4-ylmethyl-pyridin-2-ylamino)-pyrimidin-4-yl]-2H-pyrazol-3-ylamino}-phenyl)-amide, 3,4-Dichloro-N-(4-methyl-3-{5-methyl-2-[6-(2-morpholin-4-yl-ethylamino)-pyrimidin-4-yl]-2H-pyrazol-3-ylamino}-phenyl)-benzamide, 3-Fluoro-N-(4-methyl-3-{5-methyl-2-[6-(2-morpholin-4-yl-ethylamino)-pyrimidin-4-yl]-2H-pyrazol-3-ylamino}-phenyl)-5-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-4-trifluoromethyl-benzamide, 3,5-Dichloro-N-(4-methyl-3-

{5-methyl-2-[6-(2-morpholin-4-yl-ethylamino)-pyrimidin-4-yl]-2H-pyrazol-3-ylamino}-phenyl)-benzamide, 4-Fluoro-N-(4-methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, N-(4-Methyl-3-{5-methyl-2-[6-(2-morpholin-4-yl-ethylamino)-pyrimidin-4-yl]-2H-pyrazol-3-ylamino}-phenyl)-3-trifluoromethoxy-benzamide, 3-Bromo-4-chloro-N-(4-methyl-3-{5-methyl-2-[6-(2-morpholin-4-yl-ethylamino)-pyrimidin-4-yl]-2H-pyrazol-3-ylamino}-phenyl)-benzamide, 3-Difluoromethoxy-N-(4-methyl-3-{5-methyl-2-[6-(2-morpholin-4-yl-ethylamino)-pyrimidin-4-yl]-2H-pyrazol-3-ylamino}-phenyl)-benzamide, 3-Chloro-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1-Hydroxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1-Methoxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 2-(Cyano-dimethyl-methyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 3-(Cyano-dimethyl-methyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1,1-Difluoro-ethyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3-(1-Cyano-cyclopropyl)-N-(4-methyl-3-{5-methyl-2-[6-(2-morpholin-4-yl-ethylamino)-pyrimidin-4-yl]-2H-pyrazol-3-ylamino}-phenyl)-benzamide, 3,3-Dimethyl-2,3-dihydrobenzofuran-5-carboxylic acid (4-methyl-3-{5-methyl-2-[6-(2-morpholin-4-yl-ethylamino)-pyrimidin-4-yl]-2H-pyrazol-3-ylamino}-phenyl)-amide, 4-Methyl-N-(4-methyl-3-{5-methyl-2-[6-(2-morpholin-4-yl-ethylamino)-pyrimidin-4-yl]-2H-pyrazol-3-ylamino}-phenyl)-3-trifluoromethyl-benzamide, 2-(Cyano-dimethyl-methyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 3-(Cyano-dimethyl-methyl)-N-(4-methyl-3-{5-methyl-2-[6-(4-methyl-piperazin-1-ylamino)-pyrimidin-4-yl]-2H-pyrazol-3-ylamino}-phenyl)-benzamide, 3-(1-Cyano-cyclopropyl)-N-(4-methyl-3-{5-methyl-2-[6-(4-methyl-piperazin-1-ylamino)-pyrimidin-4-yl]-2H-pyrazol-3-ylamino}-phenyl)-benzamide, 2-(1-Cyano-cyclopropyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 3-(1,1-Difluoro-ethyl)-N-(4-methyl-3-{5-methyl-2-[6-(4-methyl-piperazin-1-ylamino)-pyrimidin-4-yl]-2H-pyrazol-3-ylamino}-phenyl)-benzamide, 3-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-benzamide, 3-(1-Methoxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid ethyl ester, 1-(6-Cyclopropylamino-pyrimidin-4-yl)-5-[2-methyl-5-(3-trifluoromethyl-benzoylamino)-phenylamino]-1H-pyrazole-3-carboxylic acid methylamide, N-{3-[2-(6-Cyclopropylamino-pyrimidin-4-yl)-5-hydroxymethyl-2H-pyrazol-3-ylamino]-4-methyl-phenyl}-3-trifluoromethyl-benzamide, N-{3-[2-(6-Cyclopropylamino-pyrimidin-4-yl)-5-dimethylaminomethyl-2H-pyrazol-3-ylamino]-4-methyl-phenyl}-3-trifluoromethyl-benzamide, N-{3-[2-(6-Cyclopropylamino-pyrimidin-4-yl)-5-methylaminomethyl-2H-pyrazol-3-ylamino]-4-methyl-phenyl}-3-trifluoromethyl-benzamide, N-{3-[2-(6-Cyclopropylamino-pyrimidin-4-yl)-5-morpholin-4-ylmethyl-2H-pyrazol-3-ylamino]-4-methyl-phenyl}-3-trifluoromethyl-benzamide, N-(3-{2-(6-Cyclopropylamino-pyrimidin-4-yl)-5-[(2-diethylamino-ethylamino)-methyl]-2H-pyrazol-3-ylamino}-4-methyl-phenyl)-3-trifluoromethyl-benzamide, N-{3-[2-(6-Cyclopropylamino-pyrimidin-4-yl)-5-(4-methyl-piperazin-1-ylmethyl)-2H-pyrazol-3-ylamino]-4-methyl-phenyl}-3-trifluoromethyl-benzamide, N-{3-[2-(6-Cyclopropylamino-pyrimidin-4-yl)-5-1(3-dimethylamino-propylamino)-methyl]-2H-pyrazol-3-ylamino}-4-methyl-phenyl)-3-trifluoromethyl-benzamide, N-{3-[2-(6-Cyclopropylamino-pyrimidin-4-yl)-5-ethylaminomethyl-2H-pyrazol-3-ylamino]-4-methyl-phenyl}-3-trifluoromethyl-benzamide, N-(3-{2-(6-Cyclopropylamino-pyrimidin-4-yl)-5-[(2,2,2-trifluoro-ethylamino)-methyl]-2H-pyrazol-3-ylamino}-4-methyl-phenyl)-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-dimethylamino-ethyl)-amide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-piperidin-1-yl-ethyl)-amide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-morpholin-4-yl-ethyl)-amide, N-{3-[2-(6-Cyclopropylamino-pyrimidin-4-yl)-5-(morpholine-4-carbonyl)-2H-pyrazol-3-ylamino]-4-methyl-phenyl}-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid amide, 1-(6-Cyclopropylamino-pyrimidin-4-yl)-5-[2-methyl-5-(3-trifluoromethyl-benzoylamino)-phenylamino]-1H-pyrazole-3-carboxylic acid dimethylamide, N-{3-[2-(6-Cyclopropylamino-pyrimidin-4-yl)-5-(3-dimethylamino-pyrrolidine-1-carbonyl)-2H-pyrazol-3-ylamino]-4-methyl-phenyl}-3-trifluoromethyl-benzamide, 1-(6-Cyclopropylamino-pyrimidin-4-yl)-5-[2-methyl-5-(3-trifluoromethyl-benzoylamino)-phenylamino]-1H-pyrazole-3-carboxylic acid (2-methoxy-ethyl)-amide, 1-(6-Methylamino-pyrimidin-4-yl)-5-[2-methyl-5-(3-trifluoromethyl-benzoylamino)-phenylamino]-1H-pyrazole-3-carboxylic acid methylamide, N-{4-Methyl-3-[5-methylaminomethyl-2-(6-methyl amino-pyrimidin-4-yl)-2H-pyrazol-3-ylamino]-phenyl}-3-trifluoromethyl-benzamide, N-{4-Methyl-3-[2-(6-methyl amino-pyrimidin-4-yl)-5-morpholin-4-ylmethyl-2H-pyrazol-3-ylamino]-phenyl}-3-trifluoromethyl-benzamide, 1-(6-Methylamino-pyrimidin-4-yl)-5-{2-methyl-5-[3-(4-methyl-piperazin-1-yl)-5-trifluoromethyl-benzoylamino]-phenylamino}-1H-pyrazole-3-carboxylic acid methylamide, 1-(6-Methylamino-2-morpholin-4-yl-pyrimidin-4-yl)-5-[2-methyl-5-(3-trifluoromethyl-benzoylamino)-phenylamino]-1H-pyrazole-3-carboxylic acid methylamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5-{5-[3-(Cyano-dimethyl-methyl)-benzoylamino]-2-methyl-phenylamino}-1-(6-methylamino-pyrimidin-4-yl)-1H-pyrazole-3-carboxylic acid methylamide, 5-{5-[3-(1-Cyano-cyclopropyl)-benzoylamino]-2-methyl-phenylamino}-1-(6-methylamino-pyrimidin-4-yl)-1H-pyrazole-3-carboxylic acid methylamide, N-{3-[5-Cyanomethyl-2-(6-methylamino-pyrimidin-4-yl)-2H-pyrazol-3-ylamino]-4-methyl-phenyl}-3-trifluoromethyl-benzamide, 1-(6-Methylamino-pyrimidin-4-yl)-5-[2-methyl-5-(3- trifluoromethyl-benzoylamino)-phenylamino]-1H-pyrazole-3-carboxylic acid (2-morpholin-4-yl-ethyl)-amide, 1-(6-Methylamino-pyrimidin-4-yl)-5-[2-methyl-5-(3-trifluoromethyl-benzoylamino)-phenylamino]-1H-pyrazole-3-carboxylic acid cyclopropylamide, 5-tert-Butyl-N-(4-methyl-3-{5-methyl-2-[6-(2-morpholin-4-yl-ethylamino)-pyrimidin-4-yl]-2H-pyrazol-3-ylamino}-phenyl)-nicotinamide, 5-tert-Butyl-N-(4-methyl-3-{2-[6-(2-morpholin-4-yl-ethylamino)-pyrimidin-4-yl]-2H-pyrazol-3-ylamino}-phenyl)-nicotinamide, 5-tert-Butyl-N-(4-methyl-3-{5-methyl-2-[6-(4-methyl-piperazin-1-ylamino)-pyrimidin-4-yl]-2H-pyrazol-3-ylamino}-phenyl)-nicotinamide, N-[5-(1-Fluoro-1-methyl-ethyl)-pyridin-3-yl]-4-methyl-3-[5-methyl-2-(6-methylamino-pyrimidin-4-yl)-2H-pyrazol-3-ylamino]-benzamide, N-[5-(1-Methoxy-1-methyl-ethyl)-pyridin-3-yl]-4-methyl-3-[5-methyl-2-(6-methylamino-pyrimidin-4-yl)-2H-pyrazol-3-ylamino]-benzamide, N-[5-(1-Fluoro-1-methyl-ethyl)-pyridin-3-yl]-4-methyl-3-{5-methyl-2-[6-(4-methyl-piperazin-1-ylamino)-pyrimidin-4-yl]-2H-pyrazol-3-ylamino}-benzamide, N-[5-(1-Methoxy-1-methyl-ethyl)-pyridin-3-yl]-4-methyl-3-{5-methyl-2-[6-(4-methyl-piperazin-1-ylamino)-pyrimidin-4-yl]-2H-pyrazol-3-ylamino}-benzamide, 4-Methyl-3-{5-methyl-2-[6-(4-methyl-piperazin-1-ylamino)-pyrimidin-4-yl]-2H-pyrazol-3-ylamino}-N-(4-trifluoromethyl-pyridin-2-yl)-benzamide, N-(3-tert-Butyl-phenyl)-4-methyl-3-{5-methyl-2-[6-(4-methyl-piperazin-1-ylamino)-pyrimidin-4-yl]-2H-pyrazol-3-ylamino}-benzamide, N-(2-tert-Butyl-pyridin-4-yl)-4-methyl-3-[5-methyl-2-(6-methylamino-pyrimidin-4-yl)-2H-pyrazol-3-ylamino]-benzamide, N-(3-tert-Butyl-phenyl)-4-methyl-3-[5-methyl-2-(6-methylamino-pyrimidin-4-yl)-2H-pyrazol-3-ylamino]-benzamide, N-[3-(Cyano-dimethyl-methyl)-phenyl]-4-methyl-3-[5-methyl-2-(6-methylamino-pyrimidin-4-yl)-2H-pyrazol-3-ylamino]-benzamide, 4-Methyl-3-[5-methyl-2-(6-methylamino-pyrimidin-4-yl)-2H-pyrazol-3-ylamino]-N-(4-trifluoromethyl-pyridin-2-yl)-benzamide, (6-{5-[5-(6-tert-Butyl-1H-benzoimidazol-2-yl)-2-methyl-phenylamino]-3-methyl-pyrazol-1-yl}-pyrimidin-4-yl)-(4-methyl-piperazin-1-yl)-amine, (6-{3-Methyl-5-[2-methyl-5-(6-trifluoromethyl-1H-benzoimidazol-2-yl)-phenylamino]-pyrazol-1-yl}-pyrimidin-4-yl)-(4-methyl-piperazin-1-yl)-amine, N-[3-(1,1-Difluoro-ethyl)-phenyl]-4-methyl-3-{5-methyl-2-[6-(4-methyl-piperazin-1-ylamino)-pyrimidin-4-yl]-2H-pyrazol-3-ylamino}-benzamide, N-[3-(1,1-Difluoro-ethyl)-phenyl]-4-methyl-3-{5-methyl-2-[6-(4-methyl-piperazin-1-ylamino)-pyrimidin-4-yl]-2H-pyrazol-3-ylamino}-benzamide, 4-Fluoro-N-{4-methyl-3-[2-(6-methylamino-pyrimidin-4-yl)-5-morpholin-4-ylmethyl-2H-pyrazol-3-ylamino]-phenyl}-3-trifluoromethyl-benzamide, 4-Fluoro-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethyl-benzamide, 5-[5-(4-Fluoro-3-trifluoromethyl-benzoylamino)-2-methyl-phenylamino]-1-[6-(2-morpholin-4-yl-ethylamino)-pyrimidin-4-yl]-1H-pyrazole-3-carboxylic acid methylamide, 5-[5-(4-Fluoro-3-trifluoromethyl-benzoylamino)-2-methyl-phenylamino]-1-[6-(4-methyl-piperazin-1-ylamino)-pyrimidin-4-yl]-1H-pyrazole-3-carboxylic acid methylamide, 5-[5-(4-Fluoro-3-trifluoromethyl-benzoylamino)-2-methyl-phenylamino]-1-(6-methylamino-pyrimidin-4-yl)-1H-pyrazole-3-carboxylic acid (2-morpholin-4-yl-ethyl)-amide, 5-[5-(2-tert-Butyl-pyridin-4-ylcarbamoyl)-2-methyl-phenylamino]-1-[6-(4-methyl-piperazin-1-ylamino)-pyrimidin-4-yl]-1H-pyrazole-3-carboxylic acid methylamide, 5-{5-[3-(1,1-Difluoro-ethyl)-benzoylamino]-2-methyl-phenylamino}-1-[6-(4-methyl-piperazin-1-ylamino)-pyrimidin-4-yl]-1H-pyrazole-3-carboxylic acid (2-morpholin-4-yl-ethyl)-amide, N-(4-Methyl-3-{2-[6-(4-methyl-piperazin-1-ylamino)-pyrimidin-4-yl]-5-morpholin-4-ylmethyl-2H-pyrazol-3-ylamino})-3-trifluoromethyl-benzamide, 3-(1,1-Difluoro-ethyl)-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-benzamide, 3-(Cyano-dimethyl-methyl)-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-benzamide, 2-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-isonicotinamide, 5-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-nicotinamide, 2-(Cyano-dimethyl-methyl)-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-isonicotinamide, 2-(Cyano-dimethyl-methyl)-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-isonicotinamide, 3-(Cyano-dimethyl-methyl)-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-benzamide, 2-tert-Butyl-N-{3-[5-{[(2-hydroxy-ethyl)-methyl-amino]-methyl}-2-(6-methylamino-pyrimidin-4-yl)-2H-pyrazol-3-ylamino]-4-methyl-phenyl}-isonicotinamide, 2-tert-Butyl-N-{3-[5-[2-(2,6-dimethyl-piperidin-1-yl)-ethylcarbamoyl]-2-(6-methylamino-pyrimidin-4-yl)-2H-pyrazol-3-ylamino]-4-methyl-phenyl}-isonicotinamide, 2-(Cyano-dimethyl-methyl)-N-{4-methyl-3-[5-methyl-2-(6-methylamino-pyrimidin-4-yl)-2H-pyrazol-3-ylamino]-phenyl}-isonicotinamide, 3-(Cyano-dimethyl-methyl)-N-{4-methyl-3-[5-methyl-2-(6-methylamino-pyrimidin-4-yl)-2H-pyrazol-3-ylamino]-phenyl}-benzamide, 3-(1-Cyano-cyclopropyl)-N-{4-methyl-3-[5-methyl-2-(6-methylamino-pyrimidin-4-yl)-2H-pyrazol-3-ylamino]-phenyl}-benzamide, 2-(1-Cyano-cyclopropyl)-N-{4-methyl-3-[5-methyl-2-(6-methylamino-pyrimidin-4-yl)-2H-pyrazol-3-ylamino]-phenyl}-isonicotinamide, 3-(1-Cyano-1-methyl-propyl)-N-{4-methyl-3-[5-methyl-2-(6-methylamino-pyrimidin-4-yl)-2H-pyrazol-3-ylamino]-phenyl}-benzamide, 2-tert-Butyl-N-{4-methyl-3-[5-methyl-2-(6-methylamino-pyrimidin-4-yl)-2H-pyrazol-3-ylamino]-phenyl}-isonicotinamide, 3-(1,1-Difluoro-ethyl)-N-{4-methyl-3-[5-methyl-2-(6-methylamino-pyrimidin-4-yl)-2H-pyrazol-3-ylamino]-phenyl}-benzamide, 3-(1-Hydroxy-1-methyl-ethyl)-N-{4-methyl-3-[5-methyl-2-(6-methylamino-pyrimidin-4-yl)-2H-pyrazol-3-ylamino]-phenyl}-benzamide, 3-(1-Methoxy-1-methyl-ethyl)-N-{4-methyl-3-[5-methyl-2-(6-methylamino-pyrimidin-4-yl)-2H-pyrazol-3-ylamino]-phenyl}-benzamide, 5-tert-Butyl-N-{4-methyl-3-[5-methyl-2-(6-methylamino-pyrimidin-4-yl)-2H-pyrazol-3-ylamino]-phenyl}-nicotinamide, 2-tert-Butyl-N-{4-methyl-3-[5-methyl-2-(6-methylamino-pyrimidin-4-yl)-2H-pyrazol-3-ylamino]-phenyl}-isonicotinamide, 2,2-Dimethyl-2,3-dihydro-benzofuran-7-carboxylic acid {4-methyl-3-[5-methyl-2-(6-methylamino-pyrimidin-4-yl)-2H-pyrazol-3-ylamino]-phenyl}-amide, 2-(1-Fluoro-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-sonicotinamide, 2-(1-Fluoro-1-methyl-ethyl)-N-{4-methyl-3-[5-methyl-2-(6-methylamino-pyrimidin-4-yl)-2H-pyrazol-3-ylamino]-phenyl}-isonicotinamide, 2-(1-Fluoro-1-methyl-ethyl)-N-(4-methyl-3-{5-methyl-2-[6-(2- morpholin-4-yl-ethylamino)-pyrimidin-4-yl]-2H-pyrazol-3-ylamino}-phenyl)-isonicotinamide, 2-(1-Methoxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 2-(1-Methoxy-ethyl)-N-{4-methyl-3-[5-methyl-2-(6-methylamino-pyrimidin-4-yl)-2H-pyrazol-3-ylamino]-phenyl)-isonicotinamide, 2-(1-Methoxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 2-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, 2-(1-Hydroxy-1-methyl-ethyl)-N-{4-methyl-3-[5-methyl-2-(6-methylamino-pyrimidin-4-yl)-2H-pyrazol-3-ylamino]-phenyl}-isonicotinamide, 2-(1-Hydroxy-1-methyl-ethyl)-N-(4-methyl-3-{5-methyl-2-[6-(2-morpholin-4-yl-ethylamino)-pyrimidin-4-yl]-2H-pyrazol-3-ylamino}-phenyl)-isonicotinamide, 3-(1-Cyano-cyclopropyl)-N-{4-methyl-3-[2-(6-methylamino-pyrimidin-4-yl)-2H-pyrazol-3-ylamino]-phenyl}-benzamide, 3-(Cyano-dimethyl-methyl)-N-{4-methyl-3-[2-(6-methylamino-pyrimidin-4-yl)-2H-pyrazol-3-ylamino]-phenyl}-benzamide, 2-(Cyano-dimethyl-methyl)-N-{4-methyl-3-[2-(6-methylamino-pyrimidin-4-yl)-2H-pyrazol-3-ylamino]-phenyl}-isonicotinamide, 2-(1-Cyano-cyclopropyl)-N-{4-methyl-3-[2-(6-methylamino-pyrimidin-4-yl)-2H-pyrazol-3-ylamino]-phenyl}-isonicotinamide, 3-(1,1-Difluoro-ethyl)-N-{4-methyl-3-[2-(6-methylamino-pyrimidin-4-yl)-2H-pyrazol-3-ylamino]-phenyl}-benzamide, 3-(1-Methoxy-1-methyl-ethyl)-N-{4-methyl-3-[2-(6-methylamino-pyrimidin-4-yl)-2H-pyrazol-3-ylamino]-phenyl}-benzamide, 3-(1-Hydroxy-1-methyl-ethyl)-N-{4-methyl-3-[2-(6-methylamino-pyrimidin-4-yl)-2H-pyrazol-3-ylamino]-phenyl}-benzamide, 2-(1-Fluoro-1-methyl-ethyl)-N-{4-methyl-3-[2-(6-methylamino-pyrimidin-4-yl)-2H-pyrazol-3-ylamino]-phenyl}-isonicotinamide, 2-(1-Methoxy-1-methyl-ethyl)-N-{4-methyl-3-[2-(6-methylamino-pyrimidin-4-yl)-2H-pyrazol-3-ylamino]-phenyl}-isonicotinamide, 2-(1-Hydroxy-1-methyl-ethyl)-N-{4-methyl-3-[2-(6-methylamino-pyrimidin-4-yl)-2H-pyrazol-3-ylamino]-phenyl}-isonicotinamide, 5-tert-Butyl-N-{4-methyl-3-[2-(6-methylamino-pyrimidin-4-yl)-2H-pyrazol-3-ylamino]-phenyl}-nicotinamide, N-[3-(Cyano-dimethyl-methyl)-phenyl]-4-methyl-3-{5-methyl-2-[6-(4-methyl-piperazin-1-ylamino)-pyrimidin-4-yl]-2H-pyrazol-3-ylamino}-benzamide, N-(2-tert-Butyl-pyridin-4-yl)-4-methyl-3-{5-methyl-2-[6-(4-methyl-piperazin-1-ylamino)-pyrimidin-4-yl]-2H-pyrazol-3-ylamino}-benzamide, 5-(1-Fluoro-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 5-(1-Methoxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 5-(1-Hydroxy-1-methyl-ethyl)-N-(4-methyl-3-{5-methyl-2-[6-(4-methyl-piperazin-1-ylamino)-pyrimidin-4-yl]-2H-pyrazol-3-ylamino}-phenyl)-nicotinamide, 2-(1,1-Difluoro-ethyl)-N-(4-methyl-3-{5-methyl-2-[6-(4-methyl-piperazin-1-ylamino)-pyrimidin-4-yl]-2H-pyrazol-3-ylamino}-phenyl)-isonicotinamide, N-{3-[2-(6-Amino-pyrimidin-4-yl)-5-methyl-2H-pyrazol-3-ylamino]-4-methyl-phenyl}-3-(1,1-difluoro-ethyl)-benzamide, 3-(1,1-Difluoro-ethyl)-N-(4-methyl-3-{5-methyl-2-[6-(5-morpholin-4-ylmethyl-pyridin-2-ylamino)-pyrimidin-4-yl]-2H-pyrazol-3-ylamino}-phenyl)-benzamide, 3-(1,1-Difluoro-ethyl)-N-(4-methyl-3-{5-methyl-2-[6-(4-morpholin-4-ylmethyl-pyridin-2-ylamino)-pyrimidin-4-yl]-2H-pyrazol-3-ylamino}-phenyl)-benzamide, N-{3-[2-(6-Amino-pyrimidin-4-yl)-5-methyl-2H-pyrazol-3-ylamino]-4-methyl-phenyl}-2-tert-butyl-isonicotinamide, 2-tert-Butyl-N-{4-methyl-3-[2-(6-methylamino-pyrimidin-4-yl)-2H-pyrazol-3-ylamino]-phenyl}-isonicotinamide, 2-tert-Butyl-N-[3-(2-{6-[4-(2-hydroxy-ethyl)-piperazin-1-ylamino]-pyrimidin-4-yl}-5-methyl-2H-pyrazol-3-ylamino)-4-methyl-phenyl]-isonicotinamide, 5-tert-Butyl-N-[3-(2-{6-[4-(2-hydroxy-ethyl)-piperazin-1-ylamino]-pyrimidin-4-yl}-5-methyl-2H-pyrazol-3-ylamino)-4-methyl-phenyl]-nicotinamide, N-(2-tert-Butyl-pyridin-4-yl)-3-(2-{6[4-(2-hydroxy-ethyl)-piperazin-1-ylamino]-pyrimidin-4-yl}-5-methyl-2H-pyrazol-3-ylamino)-4-methyl-benzamide, N-(5-tert-Butyl-pyridin-3-yl)-4-methyl-3-{5-methyl-2-[6-(4-methyl-piperazin-1-ylamino)-pyrimidin-4-yl]-2H-pyrazol-3-ylamino}-benzamide, N-[2-(1-Methoxy-1-methyl-ethyl)-pyridin-4-yl]-4-methyl-3-{5-methyl-2-[6-(4-methyl-piperazin-1-ylamino)-pyrimidin-4-yl]-2H-pyrazol-3-ylamino}-benzamide, N-[3-(1,1-Difluoro-ethyl)-phenyl]-4-methyl-3-[5-methyl-2-(6-methylamino-pyrimidin-4-yl)-2H-pyrazol-3-ylamino]-benzamide, N-[2-(Cyano-dimethyl-methyl)-pyridin-4-yl]-4-methyl-3-[5-methyl-2-(6-methylamino-pyrimidin-4-yl)-2H-pyrazol-3-ylamino]-benzamide, 5-(1-Fluoro-1-methyl-ethyl)-N-{4-methyl-3-[2-(6-methylamino-pyrimidin-4-yl)-2H-pyrazol-3-ylamino]-phenyl}-nicotinamide, N-{3-[2-(6-Amino-pyrimidin-4-yl)-2H-pyrazol-3-ylamino]-4-methyl-phenyl}-2-tert-butyl-isonicotinamide, 3-(1,1-Difluoro-ethyl)-N-{4-methyl-3-[2-(6-methylamino-pyrimidin-4-yl)-5-morpholin-4-ylmethyl-2H-pyrazol-3-ylamino]-phenyl}-benzamide, N-[2-(1,1-Difluoro-ethyl)-pyridin-4-yl]-4-methyl-3-{5-methyl-2-[6-(2-morpholin-4-yl-ethylamino)-pyrimidin-4-yl]-2H-pyrazol-3-ylamino}-benzamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid (2-morpholin-4-yl-ethyl)-amide, 5-tert-Butyl-N-{4-methyl-3-[2-(6-methylamino-pyrimidin-4-yl)-5-(2-morpholin-4-yl-ethylcarbamoyl)-2H-pyrazol-3-ylamino]-phenyl}-nicotinamide, 5-tert-Butyl-N-(4-methyl-3-{5-methylcarbamoyl-2-[6-(4-methyl-piperazin-1-ylamino)-pyrimidin-4-yl]-2H-pyrazol-3-ylamino}-phenyl)-nicotinamide, 1-(6-Methylamino-pyrimidin-4-yl)-5-{2-methyl-5-[3-(4-methyl-piperazin-1-yl)-5-trifluoromethyl-benzoylamino]-phenylamino}-1H-pyrazole-3-carboxylic acid methylamide, 1-(6-Methylamino-2-morpholin-4-yl-pyrimidin-4-yl)-5-[2-methyl-5-(3-trifluoromethyl-benzoylamino)-phenylamino]-1H-pyrazole-3-carboxylic acid methylamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5-{5-[3-(Cyano-dimethyl-methyl)-benzoylamino]-2-methyl-phenylamino}-1-(6-methylamino-pyrimidin-4-yl)-1H-pyrazole-3-carboxylic acid methylamide, 5-{5-[3-(1-Cyano-cyclopropyl)-benzoylamino]-2-methyl-phenylamino}-1-(6-methylamino-pyrimidin-4-yl)-1H-pyrazole-3-carboxylic acid methylamide, 1-(6-Methylamino-pyrimidin-4-yl)-5-[2-methyl-5-(3-trifluoromethyl-benzoylamino)-phenylamino]-1H-pyrazole-3-carboxylic acid cyclopropylamide, 2-(Cyano-dimethyl-methyl)-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-(Cyano-dimethyl-methyl)-N-(4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, 5-{5-[3-(Cyano-dimethyl-methyl)-benzoylamino]-2-methyl-phenylamino}-1-[6-(2-morpholin-4-yl-ethylamino)- pyrimidin-4-yl]-1H-pyrazole-3-carboxylic acid methylamide, 5-{5-[3-(Cyano-dimethyl-methyl)-benzoylamino]-2-methyl-phenylamino}-1-[6-(4-methyl-piperazin-1-ylamino)-pyrimidin-4-yl]-1H-pyrazole-3-carboxylic acid methylamide, 2-tert-Butyl-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-tert-Butyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-isonicotinamide, 2-tert-Butyl-N-{4-methyl-3-[2-[6-(2-morpholin-4-yl-ethylamino)-pyrimidin-4-yl]-5-(2-morpholin-4-yl-ethylcarbamoyl)-2H-pyrazol-3-ylamino]-phenyl}-isonicotinamide, 2-tert-Butyl-N-{4-methyl-3-[2-(6-methylamino-pyrimidin-4-yl)-5-methylcarbamoyl-2H-pyrazol-3-ylamino]-phenyl}-isonicotinamide, 2-tert-Butyl-N-{4-methyl-3-[2-(6-methylamino-pyrimidin-4-yl)-5-(2-morpholin-4-yl-ethylcarbamoyl)-2H-pyrazol-3-ylamino]-phenyl}-isonicotinamide, 5-[5-(3-tert-Butyl-benzoylamino)-2-methyl-phenylamino]-1-[6-(4-methyl-piperazin-1-ylamino)-pyrimidin-4-yl]-1H-pyrazole-3-carboxylic acid methylamide, 2-Chloro-6-methoxy-N-(4-methyl-3-{5-methylcarbamoyl-2-[6-(2-morpholin-4-yl-ethylamino)-pyrimidin-4-yl]-2H-pyrazol-3-ylamino}-phenyl)-isonicotinamide, 2-Chloro-6-methoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-isonicotinamide, 2-Chloro-6-methoxy-N-{4-methyl-3-[2-[6-(2-morpholin-4-yl-ethylamino)-pyrimidin-4-yl]-5-(2-morpholin-4-yl-ethylcarbamoyl)-2H-pyrazol-3-ylamino]-phenyl}-isonicotinamide, 2-Chloro-6-methoxy-N-{4-methyl-3-[2-[6-(2-morpholin-4-yl-ethylamino)-pyrimidin-4-yl]-5-(2-morpholin-4-yl-ethylcarbamoyl)-2H-pyrazol-3-ylamino]-phenyl}-isonicotinamide, 2-Chloro-6-methoxy-N-{4-methyl-3-[2-(6-methylamino-pyrimidin-4-yl)-5-(2-morpholin-4-yl-ethylcarbamoyl)-2H-pyrazol-3-ylamino]-phenyl}-isonicotinamide, 2-Chloro-6-methoxy-N-{4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, N-(4-Methyl-3-{5-methylcarbamoyl-2-[6-(2-morpholin-4-yl-ethylamino)-pyrimidin-4-yl]-2H-pyrazol-3-ylamino}-phenyl)-6-pyrazol-1-yl-nicotinamide, N-{4-Methyl-3-[2-(6-methylamino-pyrimidin-4-yl)-5-methylcarbamoyl-2H-pyrazol-3-ylamino]-phenyl}-6-pyrazol-1-yl-nicotinamide, N-{4-Methyl-3-[2-(6-methylamino-pyrimidin-4-yl)-5-(2-morpholin-4-yl-ethylcarbamoyl)-2H-pyrazol-3-ylamino]-phenyl}-6-pyrazol-1-yl-nicotinamide, N-(4-Methyl-3-{5-methylcarbamoyl-2-[6-(4-methyl-piperazin-1-ylamino)-pyrimidin-4-yl]-2H-pyrazol-3-ylamino}-phenyl)-6-pyrazol-1-yl-nicotinamide, 5-[2-Methyl-5-(3-trifluoromethyl-benzoylamino)-phenylamino]-1-[6-(2-morpholin-4-yl-ethylamino)-pyrimidin-4-yl]-1H-pyrazole-3-carboxylic acid methylamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethyl-benzamide, 5-[2-Methyl-5-(3-trifluoromethyl-benzoylamino)-phenylamino]-1-[6-(2-morpholin-4-yl-ethylamino)-pyrimidin-4-yl]-1H-pyrazole-3-carboxylic acid (2-morpholin-4-yl-ethyl)-amide, 1-[6-(4-Methyl-piperazin-1-ylamino)-pyrimidin-4-yl]-5-[2-methyl-5-(3-trifluoromethyl-benzoylamino)-phenylamino]-1H-pyrazole-3-carboxylic acid methylamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-6-trifluoromethoxy-nicotinamide, N-{4-Methyl-3-[2-(6-methylamino-pyrimidin-4-yl)-5-(2-morpholin-4-yl-ethylcarbamoyl)-2H-pyrazol-3-ylamino]-phenyl}-6-trifluoromethoxy-nicotinamide, N-{4-Methyl-3-[2-(6-methylamino-pyrimidin-4-yl)-5-methylcarbamoyl-2H-pyrazol-3-ylamino]-phenyl}-6-trifluoromethoxy-nicotinamide, N-{4-Methyl-3-[2-(6-methylamino-pyrimidin-4-yl)-5-(2-morpholin-4-yl-ethylcarbamoyl)-2H-pyrazol-3-ylamino]-phenyl}-6-trifluoromethoxy-nicotinamide, N-(4-Methyl-3-{5-methylcarbamoyl-2-[6-(4-methyl-piperazin-1-ylamino)-pyrimidin-4-yl]-2H-pyrazol-3-ylamino}-phenyl)-6-trifluoromethoxy-nicotinamide, 2-(Cyano-dimethyl-methyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-isonicotinamide, 5-{5-[3-(1-Cyano-1-methyl-propyl)-benzoylamino]-2-methyl-phenylamino}-1-[6-(2-morpholin-4-yl-ethylamino)-pyrimidin-4-yl]-1H-pyrazole-3-carboxylic acid methylamide, 3-(1-Cyano-1-methyl-propyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5-{5-[3-(1-Cyano-1-methyl-propyl)-benzoylamino]-2-methyl-phenylamino}-1-[6-(2-morpholin-4-yl-ethylamino)-pyrimidin-4-yl]-1H-pyrazole-3-carboxylic acid methylamide, 5-{5-[3-(1-Cyano-1-methyl-propyl)-benzoylamino]-2-methyl-phenylamino}-1-[6-(4-methyl-piperazin-1-ylamino)-pyrimidin-4-yl]-1H-pyrazole-3-carboxylic acid methylamide, 5-{5-[3-(1-Methoxy-1-methyl-ethyl)-benzoylamino]-2-methyl-phenylamino}-1-[6-(2-morpholin-4-yl-ethylamino)-pyrimidin-4-yl]-1H-pyrazole-3-carboxylic acid methylamide, 3-(1-Methoxy-1-methyl-ethyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 3-(Cyano-dimethyl-methyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5-tert-Butyl-N-(4-methyl-3-{5-methylcarbamoyl-2-[6-(2-morpholin-4-yl-ethylamino)-pyrimidin-4-yl]-2H-pyrazol-3-ylamino}-phenyl)-nicotinamide, 5-tert-Butyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-nicotinamide, 5-{5-[3-(1,1-Difluoro-ethyl)-benzoylamino]-2-methyl-phenylamino}-1-[6-(2-morpholin-4-yl-ethylamino)-pyrimidin-4-yl]-1H-pyrazole-3-carboxylic acid methylamide, 3-(1,1-Difluoro-ethyl)-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 5-{5-[3-(1,1-Difluoro-ethyl)-benzoylamino]-2-methyl-phenylamino}-1-[6-(4-methyl-piperazin-1-ylamino)-pyrimidin-4-yl]-1H-pyrazole-3 1H-pyrazole-3-carboxylic acid methylamide, 2-tert-Butyl-N-(4-methyl-3-{5-methylcarbamoyl-2-[6-(4-methyl-piperazin-1-ylamino)-pyrimidin-4-yl]-2H-pyrazol-3-ylamino}-phenyl)-isonicotinamide, 4-tert-Butyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 4-tert-Butoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, 4-Methoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-3-trifluoromethyl-benzamide, 3-tert-Butoxy-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-4-trifluoromethoxy-benzamide, N-(4-Methyl-3-{2-[6-(2-morpholin-4-yl-ethylamino)-pyrimidin-4-yl]-5-morpholin-4-ylmethyl-2H-pyrazol-3-ylamino}-phenyl)-3- trifluoromethoxy-benzamide, 5-{5-[3-(1,1-Difluoro-ethyl)-benzoylamino]-2-methyl-phenylamino}-1-(6-methylamino-pyrimidin-4-yl)-1H-pyrazole-3-carboxylic acid methylamide, 5-{5-[3-(Cyano-dimethyl-methyl)-benzoylamino]-2-methyl-phenylamino}-1-(6-methylamino-pyrimidin-4-yl)-1H-pyrazole-3-carboxylic acid (2-morpholin-4-yl-ethyl)-amide, 5-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-nicotinamide, 2-tert-Butyl-N-(4-methyl-3-{2-[6-(4-methyl-piperazin-1-ylamino)-pyrimidin-4-yl]-5-morpholin-4-ylmethyl-2H-pyrazol-3-ylamino}-phenyl)-isonicotinamide, 5-tert-Butyl-N-{4-methyl-3-[2-(6-methylamino-pyrimidin-4-yl)-5-morpholin-4-ylmethyl-2H-pyrazol-3-ylamino]-phenyl}-nicotinamide, 1-Isopropyl-1H-benzotriazole-5-carboxylic acid {4-methyl-3-[2-(6-methylamino-pyrimidin-4-yl)-5-morpholin-4-ylmethyl-2H-pyrazol-3-ylamino]-phenyl}-amide, 5,5,8,8-Tetramethyl-5,6,7,8-tetrahydro-naphthalene-2-carboxylic acid {4-methyl-3-[2-(6-methylamino-pyrimidin-4-yl)-5-morpholin-4-ylmethyl-2H-pyrazol-3-ylamino]-phenyl}-amide, 2-Methyl-benzothiazole-5-carboxylic acid {4-methyl-3-[2-(6-methylamino-pyrimidin-4-yl)-5-morpholin-4-ylmethyl-2H-pyrazol-3-ylamino]-phenyl}-amide, N-{3-[5-(3-Dimethylamino-pyrrolidin-1-ylmethyl)-2-(6-methylamino-pyrimidin-4-yl)-2H-pyrazol-3-ylamino]-4-methyl-phenyl}-3-trifluoromethyl-benzamide, N-{3-[5-(2,6-Dimethyl-morpholin-4-ylmethyl)-2-(6-methylamino-pyrimidin-4-yl)-2H-pyrazol-3-ylamino]-4-methyl-phenyl}-3-trifluoromethyl-benzamide, N-{3-[5-(2,6-Dimethyl-morpholin-4-ylmethyl)-2-(6-methylamino-pyrimidin-4-yl)-2H-pyrazol-3-ylamino]-4-methyl-phenyl}-3-trifluoromethyl-benzamide, N-[4-Methyl-3-(2-(6-methylamino-pyrimidin-4-yl)-5-{[methyl-(1-methyl-piperidin-4-yl)-amino]-methyl}-2H-pyrazol-3-ylamino)-phenyl]-3-trifluoromethyl-benzamide, N-{3-[5-((1,1-dioxothiomorpholin-4-yl)methyl)-2-(6-methylamino-pyrimidin-4-yl)-2H-pyrazol-3-ylamino]-4-methyl-phenyl}-3-trifluoromethyl-benzamide; N-{4-Methyl-3-[2-(6-methylamino-pyrimidin-4-yl)-5-thiomorpholin-4-ylmethyl-2H-pyrazol-3-ylamino]-phenyl}-3-trifluoromethyl-benzamide, 5-tert-butyl-N-(3-(3-(((2-hydroxyethyl)(methyl)amino)methyl)-1-(6-(methylamino)pyrimidin-4-yl)-1H-pyrazol-5-ylamino)-4-methylphenyl)nicotinamide, -(2-(2-fluoropropan-2-yl)pyridin-4-yl)-4-methyl-3-(3-methyl-1-(6-(methylamino)pyrimidin-4-yl)-1H-pyrazol-5-ylamino)benzamide, 5-tert-butyl-N-(3-(3-(((2-hydroxyethyl)(methyl)aminomethyl)-1-(6-(methylamino)pyrimidin-4-yl)-1H-pyrazol-5-ylamino)-4-methylphenyl)nicotinamide, 5-tert-butyl-N-(3-(3-(2-(2,6-dimethylpiperidin-1-yl)ethylcarbamoyl)-1-(6-(methylamino)pyrimidin-4-yl)-1H-pyrazol-5-ylamino)-4-methylphenyl)nicotinamide, 5-(2-methoxypropan-2-yl)-N-(4-methyl-3-(3-methyl-1-(6-(methylamino)pyrimidin-4-yl)-1H-pyrazol-5-ylamino)phenyl)nicotinamide, 5-(2-fluoropropan-2-yl)-N-(4-methyl-3-(3-methyl-1-(6-(methylamino)pyrimidin-4-yl)-1H-pyrazol-5-ylamino)phenyl)nicotinamide, N-(4-tert-butylthiazol-2-yl)-4-methyl-3-(3-methyl-1-(6-(methylamino)pyrimidin-4-yl)-1H-pyrazol-5-ylamino)benzamide, N-(4-(2-fluoropropan-2-yl)pyridin-2-yl)-4-methyl-3-(3-methyl-1-(6-(4-methylpiperazin-1-ylamino)pyrimidin-4-yl)-1H-pyrazol-5-ylamino)benzamide, 5-(5-(2-tert-butylpyridin-4-ylcarbamoyl)-2-methylphenylamino)-1-(6-(isopropylamino)pyrimidin-4-yl)-N-methyl-1H-pyrazole-3-carboxamide, 5-(5-(2-tert-butylpyridin-4-ylcarbamoyl)-2-methylphenylamino)-N-methyl-1-(6-(methylamino)pyrimidin-4-yl)-1H-pyrazole-3-carboxamide, N-(2-tert-butylpyridin-4-yl)-4-methyl-3-(1-(6-(methylamino)pyrimidin-4-yl)-3-(morpholinomethyl)-1H-pyrazol-5-ylamino)benzamide, N-(2-tert-Butyl-pyridin-4-yl)-3-[5-((1,1-dioxothiomorpholin-4-yl)methyl)-2-(6-methylamino-pyrimidin-4-yl)-2H-pyrazol-3-ylamino]-4-methyl-benzamide, 2-tert-butyl-N-(3-(1-(6-(isopropylamino)pyrimidin-4-yl)-3-(methylcarbamoyl)-1H-pyrazol-5-ylamino)-4-methylphenyl)isonicotinamide, N-(2-tert-butylpyridin-4-yl)-3-(1-(6-(isopropylamino)pyrimidin-4-yl)-3-(morpholinomethyl)-1H-pyrazol-5-ylamino)-4-methylbenzamide, N-(2-tert-Butyl-pyridin-4-yl)-3-[5-((1,1-dioxothiomorpholin-4-yl)methyl)-2-(6-isopropylamino-pyrimidin-4-yl)-2H-pyrazol-3-ylamino]-4-methyl-benzamide, 2-tert-butyl-N-(3-(1-(6-(isopropylamino)pyrimidin-4-yl)-3-(morpholinomethyl)-1H-pyrazol-5-ylamino)-4-methylphenyl)isonicotinamide, N-(4-(2-fluoropropan-2-yl)pyridin-2-yl)-4-methyl-3-(3-methyl-1-(6-(methylamino)pyrimidin-4-yl)-1H-pyrazol-5-ylamino)benzamide, N-(5-tert-butyl-4-methylthiazol-2-yl)-4-methyl-3-(3-methyl-1-(6-(methylamino)pyrimidin-4-yl)-1H-pyrazol-5-ylamino)benzamide, N-(5-tert-butyl-4-methylthiazol-2-yl)-4-methyl-3-(3-methyl-1-(6-(4-methylpiperazin-1-ylamino)pyrimidin-4-yl)-1H-pyrazol-5-ylamino)benzamide, N-(4-(2-cyanopropan-2-yl)pyridin-2-yl)-4-methyl-3-(3-methyl-1-(6-(methylamino)pyrimidin-4-yl)-1H-pyrazol-5-ylamino)benzamide, N-(2-(2-methoxypropan-2-yl)pyridin-4-yl)-4-methyl-3-(3-methyl-1-(6-(methylamino)pyrimidin-4-yl)-1H-pyrazol-5-ylamino)benzamide, N-(4-tert-butylthiazol-2-yl)-4-methyl-3-(3-methyl-1-(6-(2-morpholinoethylamino)pyrimidin-4-yl)-1H-pyrazol-5-ylamino)benzamide, N-(5-tert-butyl-4-methylthiazol-2-yl)-4-methyl-3-(3-methyl-1-(6-(2-morpholinoethylamino)pyrimidin-4-yl)-1H-pyrazol-5-ylamino)benzamide, -(4-(1,1-difluoroethyl)pyridin-2-yl)-4-methyl-3-(3-methyl-1-(6-(methylamino)pyrimidin-4-yl)-1H-pyrazol-5-ylamino)benzamide, N-(4-(1,1-difluoroethyl)pyridin-2-yl)-4-methyl-3-(3-methyl-1-(6-(4-methylpiperazin-1-ylamino)pyrimidin-4-yl)-1H-pyrazol-5-ylamino)benzamide, N-(4-tert-butylpyridin-2-yl)-4-methyl-3-(3-methyl-1-(6-(methylamino)pyrimidin-4-yl)-1H-pyrazol-5-ylamino)benzamide, N-(4-tert-butylpyridin-2-yl)-4-methyl-3-(3-methyl-1-(6-(4-methylpiperazin-1-ylamino)pyrimidin-4-yl)-1H-pyrazol-5-ylamino)benzamide, 3-(1-(6-aminopyrimidin-4-yl)-1H-pyrazol-5-ylamino)-N-(5-tert-butyl-4-methylthiazol-2-yl)-4-methylbenzamide, 3-(1-(6-aminopyrimidin-4-yl)-1H-pyrazol-5-ylamino)-N-(4-tert-butylthiazol-2-yl)-4-methylbenzamide, N-(4-(2-methoxypropan-2-yl)pyridin-2-yl)-4-methyl-3-(3-methyl-1-(6-(methylamino)pyrimidin-4-yl)-1H-pyrazol-5-ylamino)benzamide, N-(4-(2-methoxypropan-2-yl)pyridin-2-yl)-4-methyl-3-(3-methyl-1-(6-(4-methylpiperazin-1-ylamino)pyrimidin-4-yl)-1H-pyrazol-5-ylamino)benzamide, N-(6-methyl-5-(3-methyl-1-(6-(4-methylpiperazin-1-ylamino)pyrimidin-4-yl)-1H-pyrazol-5-ylamino)pyridin-3-yl)-3-(trifluoromethyl)benzamide, N-(6-methyl-5-(3-methyl-1-(6-(methylamino)pyrimidin-4-yl)-1H-pyrazol-5-ylamino)pyridin-3-yl)-3-(trifluoromethyl)benzamide, 2-tert-butyl-N-(6-methyl-5-(3-methyl-1-(6-(methylamino)pyrimidin-4-yl)-1H-pyrazol-5-ylamino)pyridin-3-yl)isonicotinamide, 2-tert-butyl-N-(6-methyl-5-(3-methyl-1-(6-(4-methylpiperazin-1-ylamino)pyrimidin-4-yl)-1H-pyrazol-5-ylamino)pyridin-3-yl)isonicotinamide, N-(4-methyl-3-(1-(6-(methylamino)pyrimidin-4-yl)-3-(1-oxo-thiomorpholinomethyl)-1H-pyrazol-5-ylamino)phenyl)-3-(trifluoromethyl)benzamide, N-(3-(1-(6-aminopyrimidin-4-yl)-3-methyl-1H-pyrazol-5-ylamino)-4-methylphenyl)-3-(4-hydroxypiperidin-1-yl)-5-(trifluoromethyl)benzamide, 3-(4-hydroxypiperidin-1-yl)-N-(4-methyl-3-(1-(6-(methylamino)pyrimidin-4-yl)-1H- pyrazol-5-ylamino)phenyl)-5-(trifluoromethyl)benzamide, 3-(4-hydroxypiperidin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-(2-hydroxyethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-morpholino-5-(trifluoromethyl)benzamide, (S)-N-(4-methyl-3-(3-methyl-1-(6-(methylamino)pyrimidin-4-yl)-1H-pyrazol-5-ylamino)phenyl)-3-(2-methylmorpholino)-5-(trifluoromethyl)benzamide, (R)-N-(4-methyl-3-(3-methyl-1-(6-(methylamino)pyrimidin-4-yl)-1H-pyrazol-5-ylamino)phenyl)-3-(2-methylmorpholino)-5-(trifluoromethyl)benzamide, 1-(4-methyl-3-(3-methyl-1-(6-(methylamino)pyrimidin-4-yl)-1H-pyrazol-5-ylamino)phenyl)-3-(3-(trifluoromethyl)phenyl)urea, 1-(4-fluoro-3-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(4-methyl-3-(3-methyl-1-(6-(methylamino)pyrimidin-4-yl)-1H-pyrazol-5-ylamino)phenyl)urea, 1-(3-(4-ethylpiperazin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, N-(4-methyl-3-(3-methyl-1-(6-(methylamino)pyrimidin-4-yl)-1H-pyrazol-5-ylamino)phenyl)-3-(1,1-dioxo-thiomorpholino)-5-(trifluoromethyl)benzamide, (R)-3-(3,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(3,4-dimethylpiperazin-1-yl)-N-(4-methyl-3-(1-(6-(methylamino)pyrimidin-4-yl)-1H-pyrazol-5-ylamino)phenyl)-5-(trifluoromethyl)benzamide, N-(3-(4-hydroxypiperidin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-(3-hydroxypyrrolidin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-(3-hydroxyazetidin-1-yl)-5-(trifluoromethyl)phenyl)-4-methyl-3-(3-methyl-1-(6-(methylamino)pyrimidin-4-yl)-1H-pyrazol-5-ylamino)benzamide, 2-(1,1-difluoroethyl)-N-(4-methyl-3-(3-methyl-1-(6-(methylamino)pyrimidin-4-yl)-1H-pyrazol-5-ylamino)phenyl)isonicotinamide, N-(3-((2-methoxyethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide, 3-(1,1-difluoroethyl)-N-(3-(3-(hydroxymethyl)-1-(6-(methylamino)pyrimidin-4-yl)-1H-pyrazol-5-ylamino)-4-methylphenyl)benzamide, N-(3-(3-(hydroxymethyl)-1-(6-(methylamino)pyrimidin-4-yl)-1H-pyrazol-5-ylamino)-4-methylphenyl)-3-(4-hydroxypiperidin-1-yl)-5-(trifluoromethyl)benzamide, 4-methyl-3-(1-(6-(methylamino)pyrimidin-4-yl)-3-(trifluoromethyl)-1H-pyrazol-5-ylamino)-N-(3-(4-methylpiperazin-1-yl)-5-(trifluoromethyl)phenyl)benzamide, N-(3-(3-(hydroxymethyl)-4-methylpiperazin-1-yl)-5-(trifluoromethyl)phenyl)-4-methyl-3-(3-methyl-1-(6-(methylamino)pyrimidin-4-yl)-1H-pyrazol-5-ylamino)benzamide, N-(3-((2-hydroxyethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide, N-(3-(4-(hydroxymethyl)piperidin-1-yl)-5-(trifluoromethyl)phenyl)-4-methyl-3-(3-methyl-1-(6-(methylamino)pyrimidin-4-yl)-1H-pyrazol-5-ylamino)benzamide, 1-(3-(1,1-difluoroethyl)phenyl)-3-(4-methyl-3-(3-methyl-1-(6-(methylamino)pyrimidin-4-yl)-1H-pyrazol-5-ylamino)phenyl)urea, 1-(2-(1,1-difluoroethyl)pyridin-4-yl)-3-(4-methyl-3-(3-methyl-1-(6-(methylamino)pyrimidin-4-yl)-1H-pyrazol-5-ylamino)phenyl)urea, 1-(3-(4-hydroxypiperidin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, N-(3-fluoro-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-(methylsulfonamido)-5-(trifluoromethyl)phenyl)benzamide, 2-methoxy-N-(4-methyl-3-(3-methyl-1-(6-(methylamino)pyrimidin-4-yl)-1H-pyrazol-5-ylamino)phenyl)-6-(trifluoromethyl)isonicotinamide, 4-methyl-3-(3-methyl-1-(6-(methylamino)pyrimidin-4-yl)-1H-pyrazol-5-ylamino)-N-(3-(trifluoromethyl)phenyl)benzamide, N-(4-chloro-3-(trifluoromethyl)phenyl)-4-methyl-3-(3-methyl-1-(6-(methylamino)pyrimidin-4-yl)-1H-pyrazol-5-ylamino)benzamide, N-(4-fluoro-3-(trifluoromethyl)phenyl)-4-methyl-3-(3-methyl-1-(6-(methylamino)pyrimidin-4-yl)-1H-pyrazol-5-ylamino)benzamide, N-(4-methyl-3-(3-methyl-1-(6-(methylamino)pyrimidin-4-yl)-1H-pyrazol-5-ylamino)phenyl)-3-nitro-5-(trifluoromethyl)benzamide, 3-amino-N-(4-methyl-3-(3-methyl-1-(6-(methylamino)pyrimidin-4-yl)-1H-pyrazol-5-ylamino)phenyl)-5-(trifluoromethyl)benzamide, 3-((2-methoxyethyl)(methyl)amino)-N-(4-methyl-3-(3-methyl-1-(6-(methylamino)pyrimidin-4-yl)-1H-pyrazol-5-ylamino)phenyl)-5-(trifluoromethyl)benzamide, 1-(4-bromo-3-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(6-methyl-5-(3-methyl-1-(6-(methylamino)pyrimidin-4-yl)-1H-pyrazol-5-ylamino)pyridin-3-yl)urea, 1-(3-(4-(2-hydroxyethyl)piperazin-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(3-(3-(hydroxymethyl)-1-(6-(methylamino)pyrimidin-4-yl)-1H-pyrazol-5-ylamino)-4-methylphenyl)urea, 3-hydroxy-N-(4-methyl-3-(3-methyl-1-(6-(methylamino)pyrimidin-4-yl)-1H-pyrazol-5-ylamino)phenyl)-5-(trifluoromethyl)benzamide, 3-(1-(6-(2-(dimethylamino)ethylamino)pyrimidin-4-yl)-3-methyl-1H-pyrazol-5-ylamino)-4-methyl-N-(3-(trifluoromethyl)phenyl)benzamide, 1-(4-chloro-3-(trifluoromethyl)phenyl)-3-(3-(1-(6-(2-(dimethylamino)ethylamino)pyrimidin-4-yl)-3-methyl-1H-pyrazol-5-ylamino)-4-methylphenyl)urea, 1-(4-chloro-3-(trifluoromethyl)phenyl)-3-(4-methyl-3-(3-methyl-1-(6-(2-morpholinoethylamino)pyrimidin-4-yl)-1H-pyrazol-5-ylamino)phenyl)urea, 3-(1-(6-(3-hydroxypropylamino)pyrimidin-4-yl)-3-methyl-1H-pyrazol-5-ylamino)-4-methyl-N-(3-(trifluoromethyl)phenyl)benzamide, 3-(difluoromethyl)-N-(4-methyl-3-(3-methyl-1-(6-(methylamino)pyrimidin-4-yl)-1H-pyrazol-5-ylamino)phenyl)benzamide, 3-(difluoromethyl)-N-(3-(3-(hydroxymethyl)-1-(6-(methylamino)pyrimidin-4-yl)-1H-pyrazol-5-ylamino)-4-methylphenyl)benzamide, 1-(3-(4-methyl-1H-imidazol-1-yl)-5-(trifluoromethyl)phenyl)-3-(4-methyl-3-(3-methyl-1-(6-(methylamino)pyrimidin-4-yl)-1H-pyrazol-5-ylamino)phenyl)urea, 3-(4-methyl-1H-imidazol-1-yl)-N-(4-methyl-3-(3-methyl-1-(6-(methylamino)pyrimidin-4-yl)-1H-pyrazol-5-ylamino)phenyl)-5-(trifluoromethyl)benzamide, 4-methyl-3-(3-methyl-1-(6-(methylamino)pyrimidin-4-yl)-1H-pyrazol-5-ylamino)-N-(3-(4-methyl-1H-imidazol-1-yl)-5-(trifluoromethyl)phenyl)benzamide, N-(3-methoxy-5-(trifluoromethyl)phenyl)-4-methyl-3-(3-methyl-1-(6-(methylamino)pyrimidin-4-yl)-1H-pyrazol-5-ylamino)

benzamide, 4-methyl-3-(3-methyl-1-(6-(methylamino)pyrimidin-4-yl)-1H-pyrazol-5-ylamino)-N-(2-methyl-5-(trifluoromethyl)phenyl)benzamide, 1-(3-(1,1-difluoroethyl)phenyl)-3-(3-(3-(hydroxymethyl)-1-(6-(methylamino)pyrimidin-4-yl)-1H-pyrazol-5-ylamino)-4-methylphenyl)urea, 4-methyl-3-(3-methyl-1-(6-(methylamino)pyrimidin-4-yl)-1H-pyrazol-5-ylamino)-N-(3-methyl-5-(trifluoromethyl)phenyl)benzamide, 1-(3-((2-methoxyethyl)(methyl)amino)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(3-((2-(dimethylamino)ethyl)(methyl)amino)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-chloro-3-(trifluoromethyl)phenyl)-3-(4-methyl-3-(1-(6-(methylamino)pyrimidin-4-yl)-3-(morpholinomethyl)-1H-pyrazol-5-ylamino)phenyl)urea, 1-(4-chloro-3-(trifluoromethyl)phenyl)-3-(3-(3-((dimethylamino)methyl)-1-(6-(methylamino)pyrimidin-4-yl)-1H-pyrazol-5-ylamino)-4-methylphenyl)urea, 3-bromo-5-(1,1-difluoroethyl)-N-(4-methyl-3-(3-methyl-1-(6-(methylamino)pyrimidin-4-yl)-1H-pyrazol-5-ylamino)phenyl)benzamide, (R)-1-(4-chloro-3-(trifluoromethyl)phenyl)-3-(4-methyl-3-(1-(6-(methylamino)pyrimidin-4-yl)-3-((2-methylmorpholino)methyl)-1H-pyrazol-5-ylamino)phenyl)urea, N-(4-methyl-3-(3-methyl-1-(6-(methylamino)pyrimidin-4-yl)-1H-pyrazol-5-ylamino)phenyl)-3-(piperazin-1-yl)-5-(trifluoromethyl)benzamide, N-(4-methyl-3-(3-methyl-1-(6-(methylamino)pyrimidin-4-yl)-1H-pyrazol-5-ylamino)phenyl)-3-(4-(2,2,2-trifluoroethyl)piperazin-1-yl)-5-(trifluoromethyl)benzamide, 3-(4-(3-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-(2-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-cyclopropylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(4,7-diazaspho[2.5]octan-7-yl)-5-(trifluoromethyl)benzamide, 2-ethoxy-N-(4-methyl-3-(3-methyl-1-(6-(methylamino)pyrimidin-4-yl)-1H-pyrazol-5-ylamino)phenyl)-6-(trifluoromethyl)isonicotinamide, N-(4-methyl-3-(3-methyl-1-(6-(methylamino)pyrimidin-4-yl)-1H-pyrazol-5-ylamino)phenyl)-3-(trifluoromethyl)-5-(3-(trifluoromethyl)piperazin-1-yl)benzamide, N-(4-methyl-3-(3-methyl-1-(6-(methylamino)pyrimidin-4-yl)-1H-pyrazol-5-ylamino)phenyl)-3-(4-methyl-4,7-diazaspho[2.5]octan-7-yl)-5-(trifluoromethyl)benzamide, N-(4-methyl-3-(3-methyl-1-(6-(methylamino)pyrimidin-4-yl)-1H-pyrazol-5-ylamino)phenyl)-2-(methylamino)-6-(trifluoromethyl)isonicotinamide, N-(4-methyl-3-(3-methyl-1-(6-(methylamino)pyrimidin-4-yl)-1H-pyrazol-5-ylamino)phenyl)-3-(4-methyl-3-(trifluoromethyl)piperazin-1-yl)-5-(trifluoromethyl)benzamide, 2-(2-hydroxyethylamino)-N-(4-methyl-3-(3-methyl-1-(6-(methylamino)pyrimidin-4-yl)-1H-pyrazol-5-ylamino)phenyl)-6-(trifluoromethyl)isonicotinamide, 3-(4-hydroxypiperidin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(4-(2-hydroxypropyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, N-(3-((4-ethylpiperazin-1-yl)methyl)-5-(trifluoromethyl)phenyl)-4-methyl-3-(3-methyl-1-(6-(methylamino)pyrimidin-4-yl)-1H-pyrazol-5-ylamino)benzamide, 4-methyl-3-(3-methyl-1-(6-(methylamino)pyrimidin-4-yl)-1H-pyrazol-5-ylamino)-N-(3-(pyrrolidin-1-ylmethyl)-5-(trifluoromethyl)phenyl)benzamide, N-(3-((dimethylamino)methyl)-5-(trifluoromethyl)phenyl)-4-methyl-3-(3-methyl-1-(6-(methylamino)pyrimidin-4-yl)-1H-pyrazol-5-ylamino)benzamide, 3-((dimethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(pyrrolidin-1-ylmethyl)-5-(trifluoromethyl)benzamide, 3-((isopropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-((methylamino)methyl)-5-(trifluoromethyl)benzamide, 1-(3-((dimethylamino)methyl)-5-(trifluoromethyl)phenyl)-3-(4-methyl-3-(3-methyl-1-(6-(methylamino)pyrimidin-4-yl)-1H-pyrazol-5-ylamino)phenyl)urea, 1-(4-methyl-3-(3-methyl-1-(6-(methylamino)pyrimidin-4-yl)-1H-pyrazol-5-ylamino)phenyl)-3-(3-(pyrrolidin-1-ylmethyl)-5-(trifluoromethyl)phenyl)urea, 1-(3-((4-ethylpiperazin-1-yl)methyl)-5-(trifluoromethyl)phenyl)-3-(4-methyl-3-(3-methyl-1-(6-(methylamino)pyrimidin-4-yl)-1H-pyrazol-5-ylamino)phenyl)urea, 3-((ethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((cyclopropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,1-difluoroethyl)-5-((isopropylamino)methyl)-N-(4-methyl-3-(1-(6-(methylamino)pyrimidin-4-yl)-1H-pyrazol-5-ylamino)phenyl)benzamide, 3-(1,1-difluoroethyl)-5-((isopropylamino)methyl)-N-(4-methyl-3-(3-methyl-1-(6-(methylamino)pyrimidin-4-yl)-1H-pyrazol-5-ylamino)phenyl)benzamide, 3-((diethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(azetidin-1-ylmethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(azetidin-1-ylmethyl)-N-(4-methyl-3-(1-(6-(methylamino)pyrimidin-4-yl)-1H-pyrazol-5-ylamino)phenyl)-5-(trifluoromethyl)benzamide, 3-((3-hydroxyazetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3-hydroxypyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((2-hydroxyethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-((propylamino)methyl)-5-(trifluoromethyl)benzamide, 3-(1,1-difluoroethyl)-5-((dimethylamino)methyl)-N-(4-methyl-3-(3-methyl-1-(6-(methylamino)pyrimidin-4-yl)-1H-pyrazol-5-ylamino)phenyl)benzamide, 3-((cyclopropylamino)methyl)-5-(1,1-difluoroethyl)-N-(4-methyl-3-(3-methyl-1-(6-(methylamino)pyrimidin-4-yl)-1H-pyrazol-5-ylamino)phenyl)benzamide, 3-((3-hydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,1-difluoroethyl)-5-((ethylamino)methyl)-

N-(4-methyl-3-(3-methyl-1-(6-(methylamino)pyrimidin-4-yl)-1H-pyrazol-5-ylamino)phenyl)benzamide, 3-((2-methoxyethylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((butylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((tert-butylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,1-difluoroethyl)-5-((4-hydroxycyclohexylamino)methyl)-N-(4-methyl-3-(3-methyl-1-(6-(methylamino)pyrimidin-4-yl)-1H-pyrazol-5-ylamino)phenyl)benzamide, 3-((cyclopropylamino)methyl)-5-(1,1-difluoroethyl)-N-(4-methyl-3-(1-(6-(methylamino)pyrimidin-4-yl)-1H-pyrazol-5-ylamino)phenyl)benzamide, 3-(aminomethyl)-N-(4-methyl-3-(3-methyl-1-(6-(methylamino)pyrimidin-4-yl)-1H-pyrazol-5-ylamino)phenyl)-5-(trifluoromethyl)benzamide, 2-((dimethylamino)methyl)-N-(4-methyl-3-(3-methyl-1-(6-(methylamino)pyrimidin-4-yl)-1H-pyrazol-5-ylamino)phenyl)-6-(trifluoromethyl)isonicotinamide, 3-(((2-hydroxyethyl)(methyl)amino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,2-dihydroxyethyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1-hydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1-hydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((2,2-dimethylhydrazinyl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((methoxyamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((hydroxyamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-((2-(hydroxymethyl)pyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-((2-hydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (R)-N-(4-methyl-3-(3-methyl-1-(6-(methylamino)pyrimidin-4-yl)-1H-pyrazol-5-ylamino)phenyl)-3-(((tetrahydrofuran-2-yl)methylamino)methyl)-5-(trifluoromethyl)benzamide, (R)-3-((2,3-dihydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-((2,3-dihydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1,3-dihydroxypropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((1-hydroxy-2-methylpropan-2-ylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((cyclobutylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((dimethylamino)methyl)-N-(4-methyl-3-(1-(6-(methylamino)pyrimidin-4-yl)-1H-pyrazol-5-ylamino)phenyl)-5-(trifluoromethyl)benzamide, 3-(((2-methoxyethyl)(methyl)amino)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-(((1S,2R)-2-hydroxycyclopentylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, (S)-N-(4-methyl-3-(3-methyl-1-(6-(methylamino)pyrimidin-4-yl)-1H-pyrazol-5-ylamino)phenyl)-3-(((tetrahydrofuran-2-yl)methylamino)methyl)-5-(trifluoromethyl)benzamide, (R)-3-((2-hydroxypropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(morpholinomethyl)-5-(trifluoromethyl)benzamide, 3-((3-methoxy azetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide 3-((3-methoxypyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3-hydroxyazetidin-1-yl)methyl)-N-(4-methyl-3-(1-(6-(methylamino)pyrimidin-4-yl)-1H-pyrazol-5-ylamino)phenyl)-5-(trifluoromethyl)benzamide, N-(4-chloro-3-(3-methyl-1-(6-(methylamino)pyrimidin-4-yl)-1H-pyrazol-5-ylamino)phenyl)-3-((dimethylamino)methyl)-5-(trifluoromethyl)benzamide, N-(4-chloro-3-(3-methyl-1-(6-(methylamino)pyrimidin-4-yl)-1H-pyrazol-5-ylamino)phenyl)-3-((isopropylamino)methyl)-5-(trifluoromethyl)benzamide, N-(4-chloro-3-(3-methyl-1-(6-(methylamino)pyrimidin-4-yl)-1H-pyrazol-5-ylamino)phenyl)-3-(pyrrolidin-1-ylmethyl)-5-(trifluoromethyl)benzamide, 3-((isopropylamino)methyl)-N-(4-methyl-3-(1-(6-(methylamino)pyrimidin-4-yl)-1H-pyrazol-5-ylamino)phenyl)-5-(trifluoromethyl)benzamide, N-(4-methyl-3-(1-(6-(methylamino)pyrimidin-4-yl)-1H-pyrazol-5-ylamino)phenyl)-3-(pyrrolidin-1-ylmethyl)-5-(trifluoromethyl)benzamide, 3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)-N-(4-methyl-3-(3-methyl-1-(6-(methylamino)pyrimidin-4-yl)-1H-pyrazol-5-ylamino)phenyl)-3-((2-methylmorpholino)methyl)-5-(trifluoromethyl)benzamide, (R)-N-(4-methyl-3-(3-methyl-1-(6-(methylamino)pyrimidin-4-yl)-1H-pyrazol-5-ylamino)phenyl)-3-((2-methylmorpholino)methyl)-5-(trifluoromethyl)benzamide, 3-((2-hydroxy-2-methylpropylamino)methyl)-N-(4-methyl-3-(3-methyl-1-(6-(methylamino)pyrimidin-4-yl)-1H-pyrazol-5-ylamino)phenyl)-5-(trifluoromethyl)benzamide, N-(4-methyl-3-(3-methyl-1-(6-(methylamino)pyrimidin-4-yl)-1H-pyrazol-5-ylamino)phenyl)-3-(1,2,3,6-tetrahydropyridin-4-yl)-5-(trifluoromethyl)benzamide, N-(4-methyl-3-(3-methyl-1-(6-(methylamino)pyrimidin-4-yl)-1H-pyrazol-5-ylamino)phenyl)-3-(piperidin-4-yl)-5-(trifluoromethyl)benzamide, 3-(1-methyl-1,2,3,6-tetrahydropyridin-4-yl)-N-(4-methyl-3-(3-methyl-1-(6-(methylamino)pyrimidin-4-yl)-1H-pyrazol-5-ylamino)phenyl)-5-(trifluoromethyl)benzamide, 3-(1,2-dihydroxyethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1-hydroxyethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(2-hydroxyethylamino)cyclobutyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(isopropylamino)cyclobutyl)-N-(4-methyl- 3-(3-methyl-1-(6-(methylamino)pyrimidin-4-yl)-1H-pyrazol-5-ylamino)phenyl)-5-(trifluoromethyl)benzamide, (E)-3-(3-aminoprop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, (E)-3-(3-(isopropylamino)prop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, (E)-3-(3-(2-hydroxyethylamino)prop-1-enyl)-N-(4-methyl-3-(3-methyl-1-(6-(methylamino)pyrimidin-4-yl)-1H-pyrazol-5-ylamino)phenyl)-5-(trifluoromethyl)benzamide, 3-(3-(isopropylamino)propyl)-N-(4-methyl-3-(3-methyl-1-(6-(methylamino)pyrimidin-4-yl)-1H-pyrazol-5-ylamino)phenyl)-5-(trifluoromethyl)benzamide, 3-(2-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(2-(2-hydroxyethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(1-((2-hydroxyethyl)amino)cyclopropyl)-N-(4-methyl-3-(3-methyl-1-(6-(methylamino)pyrimidin-4-yl)-1H-pyrazol-5-ylamino)phenyl)-5-(trifluoromethyl)benzamide, 3-(2-((2-hydroxyethyl)amino)propan-2-yl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(ethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(dimethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(1-(dimethylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (S)-N-(4-methyl-3-(3-methyl-1-(6-(methylamino)pyrimidin-4-yl)-1H-pyrazol-5-ylamino)phenyl)-3-(1-(pyrrolidin-1-yl)ethyl)-5-(trifluoromethyl)benzamide, (R)-N-(4-methyl-3-(3-methyl-1-(6-(methylamino)pyrimidin-4-yl)-1H-pyrazol-5-ylamino)phenyl)-3-(1-(pyrrolidin-1-yl)ethyl)-5-(trifluoromethyl)benzamide, (S)-3-(1-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(1-(isopropylamino)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-(4-(2,2-difluoroethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-chloro-5-(4-(2-methoxyethyl)piperazin-1-yl)-N-(4-methyl-3-(3-methyl-1-(6-(methylamino)pyrimidin-4-yl)-1H-pyrazol-5-ylamino)phenyl)benzamide, 3-chloro-5-(4-(2-ethoxyethyl)piperazin-1-yl)-N-(4-methyl-3-(3-methyl-1-(6-(methylamino)pyrimidin-4-yl)-1H-pyrazol-5-ylamino)phenyl)benzamide, 3-chloro-N-(4-methyl-3-(3-methyl-1-(6-(methylamino)pyrimidin-4-yl)-1H-pyrazol-5-ylamino)phenyl)-5-(4-methylpiperazin-1-yl)benzamide, (S)-3-(4-(2-methoxyethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2-methoxyethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(2,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, (S)-3-(2,4-dimethylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, 3-((3,3-difluoroazetidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, 3-((3,3-difluoropyrrolidin-1-yl)methyl)-N-(4-methyl-3-(3-methyl-1-(6-(methylamino)pyrimidin-4-yl)-1H-pyrazol-5-ylamino)phenyl)-5-(trifluoromethyl)benzamide, (R)-3-(4-(2,2-difluoroethyl)-2-methylpiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide, rac-3-(2-(3,3-difluoropyrrolidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide, rac-3-(2-(3,3-difluoroazetidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide, 3-((2,2-difluoroethyl)methyl)-N-(4-methyl-3-(3-methyl-1-(6-(methylamino)pyrimidin-4-yl)-1H-pyrazol-5-ylamino)phenyl)-5-(trifluoromethyl)benzamide and 3-(((2,2-difluoroethyl)amino)methyl)-N-(4-methyl-3-(3-methyl-1-(6-(methylamino)pyrimidin-4-yl)-1H-pyrazol-5-ylamino)phenyl)-5-(trifluoromethyl)benzamide.

8. A pharmaceutical composition comprising a therapeutically effective amount of a compound of claim 1 in combination with a pharmaceutically acceptable excipient.

9. A compound selected from:
N-[3-(2-(6-Cyclopropylamino-pyrimidin-4-yl)-5-{[2-(4-methyl-piperazin-1-yl)-ethylamino]-methyl}-2H-pyrazol-3-ylamino)-4-methyl-phenyl]-3-trifluoromethyl-benzamide;
2-tert-Butyl-N-(3-{2-[6-(2-dimethylamino-acetylamino)-pyrimidin-4-yl]-2H-pyrazol-3-ylamino}-4-methyl-phenyl)-isonicotinamide;
4-Methanesulfonyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide;
4-Chloro-3-methanesulfonyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide;
3-Methanesulfonyl-N-(4-methyl-3-{2-[6-(2-morpholin-4-yl-ethylamino)-pyrimidin-4-yl]-5-morpholin-4-ylmethyl-2H-pyrazol-3-ylamino}-phenyl)-benzamide;
3-(1,1-Diethyl-propyl)-N-{4-methyl-3-[2-(6-methylamino-pyrimidin-4-yl)-5-morpholin-4-ylmethyl-2H-pyrazol-3-ylamino]-phenyl}-benzamide;
N-{3-[5-[4-(2-Methoxy-ethyl)-piperazin-1-ylmethyl]-2-(6-methylamino-pyrimidin-4-yl)-2H-pyrazol-3-ylamino]-4-methyl-phenyl}-3-trifluoromethyl-benzamide;
N-(4-methyl-3-(3-methyl-1-(6-(methylamino)pyrimidin-4-yl)-1H-pyrazol-5-ylamino)phenyl)-3-(1-methylpiperidin-4-yloxy)-5-(trifluoromethyl)benzamide;
N-(3-(2-(dimethylamino)ethoxy)-5-(trifluoromethyl)phenyl)-4-methyl-3-(3-methyl-1-(6-(methylamino)pyrimidin-4-yl)-1H-pyrazol-5-ylamino)benzamide;
4-methyl-3-(3-methyl-1-(6-(methylamino)pyrimidin-4-yl)-1H-pyrazol-5-ylamino)-N-(3-(2-(pyrrolidin-1-yl)ethoxy)-5-(trifluoromethyl)phenyl)benzamide;
methyl 1-methyl-4-(3-(4-methyl-3-(3-methyl-1-(6-(methylamino)pyrimidin-4-yl)-1H-pyrazol-5-ylamino)benzamido)-5-(trifluoromethyl)phenyl)piperazine-2-carboxylate;

N-(3-((2-(dimethylamino)ethyl)(methyl)amino)-5-(trifluoromethyl)phenyl)-4-methyl-3-(3-methyl-1-(6-(methylamino)pyrimidin-4-yl)-1H-pyrazol-5-ylamino)benzamide;

methyl 1-(3-(4-methyl-3-(3-methyl-1-(6-(methylamino)pyrimidin-4-yl)-1H-pyrazol-5-ylamino)benzamido)-5-(trifluoromethyl)phenyl)piperidine-4-carboxylate, 1-(3-(4-methyl-3-(3-methyl-1-(6-(methylamino)pyrimidin-4-yl)-1H-pyrazol-5-ylamino)benzamido)-5-(trifluoromethyl)phenyl)piperidine-4-carboxylic acid;

3-((3-(dimethylamino)propyl)(methyl)amino)-N-(4-methyl-3-(3-methyl-1-(6-(methylamino)pyrimidin-4-yl)-1H-pyrazol-5-ylamino)phenyl)-5-(trifluoromethyl)benzamide;

3-((2-(dimethylamino)ethyl)(methyl)amino)-N-(4-methyl-3-(3-methyl-1-(6-(methylamino)pyrimidin-4-yl)-1H-pyrazol-5-ylamino)phenyl)-5-(trifluoromethyl)benzamide;

methyl 3-(4-methyl-3-(3-methyl-1-(6-(methylamino)pyrimidin-4-yl)-1H-pyrazol-5-ylamino)benzamido)-5-(trifluoromethyl)benzoate;

3-(2-(dimethylamino)ethoxy)-N-(4-methyl-3-(3-methyl-1-(6-(methylamino)pyrimidin-4-yl)-1H-pyrazol-5-ylamino)phenyl)-5-(trifluoromethyl)benzamide;

3-(3-(dimethylamino)propoxy)-N-(4-methyl-3-(3-methyl-1-(6-(methylamino)pyrimidin-4-yl)-1H-pyrazol-5-ylamino)phenyl)-5-(trifluoromethyl)benzamide;

4-methyl-3-(3-methyl-1-(6-(methylamino)pyrimidin-4-yl)-1H-pyrazol-5-ylamino)-N-(3-(2-(methylsulfonyl)ethylcarbamoyl)-5-(trifluoromethyl)phenyl)benzamide;

N-(3-(3-hydroxypropylcarbamoyl)-5-(trifluoromethyl)phenyl)-4-methyl-3-(3-methyl-1-(6-(methylamino)pyrimidin-4-yl)-1H-pyrazol-5-ylamino)benzamide;

tert-butyl 4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)piperazine-1-carboxylate;

3-(4-(2-amino-2-oxoethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide;

3-(4-(2-methoxyethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide;

2-(4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)piperazin-1-yl)acetic acid;

3-(4-(2-(dimethylamino)-2-oxoethyl)piperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide;

N-(4-methyl-3-(3-methyl-1-(6-(methylamino)pyrimidin-4-yl)-1H-pyrazol-5-ylamino)phenyl)-3-(4-(2-(methylsulfonyl)ethyl)piperazin-1-yl)-5-(trifluoromethyl)benzamide;

(S)-2-(4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)piperazin-1-yl)propanoic acid;

tert-butyl 4-(3-(4-methyl-3-(3-methyl-1-(6-(methylamino)pyrimidin-4-yl)-1H-pyrazol-5-ylamino)phenylcarbamoyl)-5-(trifluoromethyl)phenyl)-3-oxopiperazine-1-carboxylate;

N-(4-methyl-3-(3-methyl-1-(6-(methylamino)pyrimidin-4-yl)-1H-pyrazol-5-ylamino)phenyl)-3-(2-oxopiperazin-1-yl)-5-(trifluoromethyl)benzamide;

3-(4-methyl-2-oxopiperazin-1-yl)-N-(4-methyl-3-(3-methyl-1-(6-(methylamino)pyrimidin-4-yl)-1H-pyrazol-5-ylamino)phenyl)-5-(trifluoromethyl)benzamide;

2-(2-(dimethylamino)ethylamino)-N-(4-methyl-3-(3-methyl-1-(6-(methylamino)pyrimidin-4-yl)-1H-pyrazol-5-ylamino)phenyl)-6-(trifluoromethyl)isonicotinamide;

3-(1-(3,3-difluoropyrrolidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide, and 3-(1-(3,3-difluoroazetidin-1-yl)ethyl)-N-(4-methyl-3-(3-methyl-1-(6-(methylamino)pyrimidin-4-yl)-1H-pyrazol-5-ylamino)phenyl)-5-(trifluoromethyl)benzamide.

\* \* \* \* \*